US010280468B2

(12) United States Patent
Harkin et al.

(10) Patent No.: US 10,280,468 B2

(45) Date of Patent: May 7, 2019

(54) MOLECULAR DIAGNOSTIC TEST FOR PREDICTING RESPONSE TO ANTI-ANGIOGENIC DRUGS AND PROGNOSIS OF CANCER

(71) Applicant: Almac Diagnostics Limited, Craigavon (GB)

(72) Inventors: Denis Paul Harkin, Dromore (GB); Richard Kennedy, Belfast (GB); Katherine E. Keating, Magherafelt (GB); Andrena McCavigan, Derryadd Lurgan (GB); Laura A. Hill, Lisburn (GB); Steve Deharo, Belfast (GB); Timothy Davison, Hillsborough (GB); Fionnuala Patterson, Hauxton (GB); Sinead Donegan, Belfast (GB); Gera Jellema, Portadown (GB); Charlie Gourley, Dumfermline (GB)

(73) Assignee: Almac Diagnostics Limited, Craigavon (GB)

( * ) Notice: Subject to any disclaimer, the term of this patent is extended or adjusted under 35 U.S.C. 154(b) by 0 days.

(21) Appl. No.: 15/116,641

(22) PCT Filed: Feb. 9, 2015

(86) PCT No.: PCT/GB2015/050352

§ 371 (c)(1),
(2) Date: Aug. 4, 2016

(87) PCT Pub. No.: WO2015/118353

PCT Pub. Date: Aug. 13, 2015

(65) Prior Publication Data

US 2017/0073761 A1 Mar. 16, 2017

Related U.S. Application Data

(60) Provisional application No. 61/937,224, filed on Feb. 7, 2014.

(30) Foreign Application Priority Data

May 28, 2014 (GB) .................................. 1409479.1

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,143,854 | A | 9/1992 | Pirrung et al. |
| 5,288,644 | A | 2/1994 | Beavis et al. |
| 5,324,633 | A | 6/1994 | Fodor et al. |
| 5,432,049 | A | 7/1995 | Fischer et al. |
| 5,470,710 | A | 11/1995 | Weiss et al. |
| 5,492,806 | A | 2/1996 | Drmanac et al. |
| 5,503,980 | A | 4/1996 | Cantor |
| 5,510,270 | A | 4/1996 | Fodor et al. |
| 5,525,464 | A | 6/1996 | Drmanac et al. |
| 5,547,839 | A | 8/1996 | Dower et al. |
| 5,580,732 | A | 12/1996 | Grossman et al. |
| 5,661,028 | A | 8/1997 | Foote |
| 5,800,992 | A | 9/1998 | Fodor et al. |
| 2005/0186208 | A1 | 8/2005 | Fyfe et al. |
| 2006/0127928 | A1 | 6/2006 | Bacus et al. |
| 2006/0134663 | A1 | 6/2006 | Harkin et al. |
| 2008/0199855 | A1 | 8/2008 | Nister et al. |
| 2008/0286771 | A1 | 11/2008 | Hudson et al. |
| 2008/0305962 | A1 | 12/2008 | Wirtz |
| 2009/0023149 | A1 | 1/2009 | Knudsen |

(Continued)

FOREIGN PATENT DOCUMENTS

| | | | |
|---|---|---|---|
| CA | 2 726 811 | A1 | 12/2009 |
| CA | 2 747 937 | A1 | 7/2010 |

(Continued)

OTHER PUBLICATIONS

Aghajanian et al., "Oceans: A Randomized, Double-Blind, Placebo Controlled Phase III Trial of Chemotherapy With or Without Bevacizumab in Patients With Platinum-Sensitive Recurrent Epithelial Ovarian, Primary Peritoneal, or Fallopian Tube Cancer", J Clin Oncol, 30:2039-2045, (2012).

(Continued)

*Primary Examiner* — Lei Yao

(74) *Attorney, Agent, or Firm* — Finnegan, Henderson, Farabow, Garrett & Dunner, LLP

(57) ABSTRACT

Methods for selecting whether to administer an anti-angiogenic therapeutic agent to a subject include steps of measuring the expression levels of one or more biomarkers selected from Table 2 or Table 3 in a sample from the subject; assessing from the expression levels of the one or more biomarkers whether the sample from the subject is positive or negative for a biomarker signature, wherein if the sample is positive for the biomarker signature an anti-angiogenic therapeutic agent is contraindicated. Related prognostic methods and treatment methods are also provided. The invention is particularly applicable in ovarian and colorectal cancers.

4 Claims, 25 Drawing Sheets

Specification includes a Sequence Listing.

(56) References Cited

U.S. PATENT DOCUMENTS

| | | | |
|---|---|---|---|
| 2009/0082218 A1 | 3/2009 | Harkin et al. | |
| 2009/0304594 A1 | 12/2009 | Fantin et al. | |
| 2010/0196366 A1 | 8/2010 | Bunn et al. | |
| 2010/0304989 A1 | 12/2010 | Von Hoff et al. | |
| 2014/0342924 A1 | 11/2014 | Harkin et al. | |
| 2016/0002732 A1* | 1/2016 | Harkin ................. | C12Q 1/6886 506/9 |

FOREIGN PATENT DOCUMENTS

| | | | |
|---|---|---|---|
| EP | 0 785 280 B1 | 4/2003 |
| EP | 0 373 203 B2 | 2/2007 |
| JP | 2007-517058 A | 6/2007 |
| JP | 2007-532113 A | 11/2007 |
| JP | 2009-524438 A | 7/2009 |
| JP | A-2010-504530 | 2/2010 |
| JP | A-2012-513422 | 6/2012 |
| JP | A-2012-525159 | 10/2012 |
| WO | WO 95/21265 A1 | 8/1995 |
| WO | WO 96/31622 A1 | 10/1996 |
| WO | WO 97/10365 A1 | 3/1997 |
| WO | WO 97/27317 A1 | 7/1997 |
| WO | WO2012/167278 * | 12/2002 |
| WO | WO 03/095977 A2 | 11/2003 |
| WO | WO 2004/108896 A2 | 12/2004 |
| WO | WO 2005/066371 A2 | 7/2005 |
| WO | WO 2005/100606 A2 | 10/2005 |
| WO | WO 2007/090076 A2 | 8/2007 |
| WO | WO 2008/082730 A2 | 7/2008 |
| WO | WO 2009/022129 A1 | 2/2009 |
| WO | WO 2009/061800 A2 | 5/2009 |
| WO | WO 2009/149297 A1 | 12/2009 |
| WO | WO 2009/149359 A3 | 12/2009 |
| WO | WO 2010/009337 A2 | 1/2010 |
| WO | WO 2010/010153 A1 | 1/2010 |
| WO | WO 2010/072348 A1 | 7/2010 |
| WO | WO 2010/088688 A2 | 8/2010 |
| WO | WO 2010/127322 A1 | 11/2010 |
| WO | WO 2011/005273 A1 | 1/2011 |
| WO | WO 2011/033006 A1 | 3/2011 |
| WO | WO 2012/037378 A2 | 3/2012 |
| WO | WO2014/087156 * | 3/2012 |
| WO | WO 2012/092336 A2 | 7/2012 |
| WO | WO 2012/167278 A1 | 12/2012 |
| WO | WO 2013/106765 A1 | 7/2013 |
| WO | WO 2014/087156 A1 | 6/2014 |

OTHER PUBLICATIONS

Ahdesmäki et al., "Feature Selection in Omics Prediction Problems Using Cat Scores and False Nondiscovery Rate Control", The Annals of Applied Statistics, 4(1):503-519, (2010).

Bagri et al., "Effects of anti-VEGF Treatment Duration on Tumor Growth, Tumor Regrowth, and Treatment Efficacy", Clin Cancer Res, 16(15):3887-3900, (2010).

Bauerschlag et al., "Evaluation of Potentially Predictive Markers for Anti-Angiogenic Therapy with Sunitinib in Recurrent Ovarian Cancer Patients", Translational Oncology, 6:305-310, (2013).

Breiman, "Random Forests", Machine Learning, 45:5-32, (2001).

Burger et al., "Phase II Trial of Bevacizumab in Persistent or Recurrent Epithelial Ovarian Cancer or Primary Peritoneal Cancer: A Gynecologic Oncology Group Study", J Clin Oncol, 25:5165-5171, (2007).

Burlingame et al., "Mass spectrometry", Anal Chem, 70(16):647R-716R, (1998).

Dejong, "SIMPLS: An alternative approach to partial least-squares regression", Chemometr Intell Lab, 18:251-263, (1993).

Dudoit et al., "Comparison of Discrimination Methods for the Classification of Tumors Using Gene Expression Data", Journal of the American Statistical Association, 97(457):77-87, (2002).

Ebos et al., "Accelerated Metastasis after Short-Term Treatment with a Potent Inhibitor of Tumor Angiogenesis", Cancer Cell, 15:232-239, (2009).

Escudier et al., "Phase III Trial of Bevacizumab Plus Interferon Alfa-2a in Patients with Metastatic Renal Cell Carcinoma (AVOREN): Final Analysis of Overall Survival", J Clin Oncol, 28:2144-2150, (2010).

Freedman, "Tables of the number of patients required in clinical trials using the logrank test", Stat Med, 1(2):121-129,(1982).

Friedman et al., "Bevacizumab Alone and in Combination With Irinotecan in Recurrent Glioblastoma", J Clin Oncl, 27:4733-4740, (2009).

Grambsch et al., "Proportional hazards tests and diagnostics based on weighted residuals", Biometrika, 81(3):515-526, (1994).

Grepin et al., "Acceleration of clear cell renal cell carcinoma growth in mice following bevacizumab/Avastin treatment: the role of CXCL cytokines", Oncogene, 29:31(13), (2012).

Hurwitz et al., "Bevacizumab plus Irinotecan, Fluorouracil, and Leucovorin for Metastatic Colorectal Cancer", N Engl J Med, 350:2335-2342, (2004).

Italiano et al., "Patterns of Deregulation of Insulin Growth Factor Signaling Pathway in Pediatric and Adult Gastrointestinal Stromal Tumors", Eur J Cancer, 48(17):3215-3222, (2012).

Jorissen et al., "Metastasis-Associated Gene Expression Changes Predict Poor Outcomes in Patients with Dukes Stage B and C Colorectal Cancer", Clin Cancer Res, 15(24);7642-7651, (2009).

Li et al., "Possible angiogenic roles for claudin-4 in ovarian cancer", Cancer Biology & Therapy, 8(19):1806-1814, (2009).

Liu et al., "Vascular gene expression patterns are conserved in primary and metastatic brain tumors", J Neurooncol, 99(1):13-24, (2010).

Lu et al., "Insulin-like growth factor-I receptor signaling and resistance to trastuzumab (Herceptin)", J Natl Cancer Inst, 93(24):1852-1857, (2001).

Ma et al., "Pharmacodynamic-mediated Reduction of Temozolomide Tumor Concentrations by the Angiogenesis Inhibitor TNP-470", Cancer Res, 61:5491-5498, (2001).

Marisa et al., "Gene Expression Classification of Colon Cancer into Molecular Subtypes: Characterization, Validation, and Prognostic Value", PLoS Medicine, 10(5):e1001453, (2013).

McCluggage, "Morphological subtypes of ovarian carcinoma: a review with emphasis on new developments and pathogenesis", Pathology, 43(5);420-432, (2011).

Miller et al., "Paclitaxel plus Bevacizumab versus Paclitaxel Alone for Metastatic Breast Cancer", N Engl J Med, 357:2666-2676, (2007).

Miller et al., "Randomized Phase III Trial of Capecitabine Compared With Bevacizumab Plus Capecitabine in Patients With Previously Treated Metastatic Breast Cancer", J Clin Oncol, 23(4):792-799 (2005).

Nguyen et al., "Tumor classification by partial least squares using microarray gene expression data", Bioinformatics, 18(1):39-50, (2002).

O'Shaughnessy et al., "A meta-analysis of overall survival data from three randomized trials of bevacizumab (BV) and first-line chemotherapy as treatment for patients with metastatic breast cancer (MBC)", J Clin Oncol, 28 (suppl) (abstr 1005), (2010).

Perren et al., "A Phase 3 Trial of Bevacizumab in Ovarian Cancer", N Engl J Med 365:2484-2496, (2011).

Quackenbush, "Microarray Analysis and Tumor Classification", N Engl J Med, 354:2463-2472, (2006).

Reck et al., "Phase III Trial of Cisplatin Plus Gemcitabine With Either Placebo or Bevacizumab as First-Line Therapy for Nonsquamous Non-Small-Cell Lung Cancer: AVAil", J Clin Oncol, 27:1227-1234, (2009).

Reinmuth et al., "Current data on predictive markers for anti-angiogenic therapy in thoracic tumours", Eur Respir J, 36:915-924, (2010).

Rini et al., "Bevacizumab Plus Interferon Alfa Compared With Interferon Alfa Monotherapy in Patients With Metastatic Renal Cell Carcinoma: CALGB 90206", J Clin Oncol, 26:5422-5428, (2008).

Royston et al., "The use of restricted mean survival time to estimate the treatment effect in randomized clinical trials when the proportional hazards assumption is in doubt", Stat Med, 30(19):2409-2421, (2011).

(56) References Cited

OTHER PUBLICATIONS

Sandler et al., "Paclitaxel-Carboplatin Alone or with Bevacizumab for Non-Small-Cell Lung Cancer", N Engl J Med, 355:2542-2550, (2006).
Schmoor et al., "Sample size considerations for the evaluation of prognostic factors in survival analysis", Statist Med, 19:441-452, (2000).
Schena et al., "Parallel human genome analysis: Microarray-based expression monitoring of 1000 genes", Proc Natl Acad Sci USA, 93:10614-10619, (1996).
Ståhle et al., "Partial least squares analysis with cross-validation for the two-class problem: A Monte Carlo study", Journal of Chemometrics, 1(3):185-196, (1987).
Tibshirani et al., "Diagnosis of multiple cancer types by shrunken centroids of gene expression", Proc Natl Acad Sci USA, 99(10):6567-6572, (2002).
Tothill et al., "Novel Molecular Subtypes of Serous and Endometrioid Ovarian Cancer Linked to Clinical Outcome", Clin Cancer Res, 14:5198-5208, (2008).
Willett et al., "Direct evidence that the VEGF-specific antibody bevacizumab has antivascular effects in human rectal cancer", Nat Med, 10(2):145-147, (2004).
Wold, "Pattern recognition by means of disjoint principal components models", Pattern Recognition, 8(3):127-139, (1976).
Wolmark et al., "A phase III trial comparing mFOLFOX6 to mFOLFOX6 plus bevacizumab in stage II or III carcinoma of the colon: Results of NSABP protocol C-08", J Clin Oncol, 27:18s (suppl; abstr LBA4), (2009).
Yang et al., "A Randomized Trial of Bevacizumab, an Anti-Vascular Endothelial Growth Factor Antibody, for Metastatic Renal Cancer", N Engl J Med, 349:427-434, (2003).
Yang et al., "Gene Expression Profile and Angiogenic Markers Correlate with Response to Neoadjuvant Bevacizumab Followed by Bevacizumab plus Chemotherapy in Breast Cancer", Clin Cancer Res, 14(18):5893-5899, (2008).
Communication Pursuant to Rules 161(1) and 162 EPC for Application No. 15705693.8-1403, dated Sep. 16, 2016.
Database Geneseq [Online], "Human Expression Signature Biomarker DNA, SEQ ID: 853", retrieved from EBI Accession No. GSN: BAH85778, Database Accession No. BAH85778 Sequence.
International Search Report for International Application No. PCT/US2012/040805, dated Oct. 5, 2012. (U.S. Appl. No. 14/123,406).
International Search Report for International Application No. PCT/GB2013/053202, dated Apr. 24, 2014. (U.S. Appl. No. 14/649,421).
International Search Report for International Application No. PCT/GB2015/050352, dated Jul. 5, 2015. (U.S. Appl. No. 15/116,641).
Written Opinion of the International Searching Authority for International Application No. PCT/US2012/040805, dated Oct. 5, 2012. (U.S. Appl. No. 14/123,406).
Written Opinion of the International Searching Authority for International Application No. PCT/GB2013/053202, dated Apr. 24, 2014. (U.S. Appl. No. 14/649,421).
Written Opinion of the International Searching Authority for International Application No. PCT/GB2015/050352, dated Jul. 5, 2015. (U.S. Appl. No. 15/116,641).
Co-pending U.S. Appl. No. 14/123,406.
Co-pending U.S. Appl. No. 14/649,421.
Azad et al., "Correlative studies of a phase I trial of combination anti-vascular endothelial growth factor (VEGF) therapy with sorafenib and bevacizumab," Developmental Therapeutics: Molecular Therapeutics, Abstract 3545, (2008).
Garcia et al., "Phase II clinical trial of bevacizumab and low-dose metronomic oral cyclophosphamide in recurrent ovarian cancer: a trial of the California, Chicago, and Princess Margaret Hospital phase II consortia," J Clin Oncol, 26(1):76-82, (2008).
Gerger et al., "Molecular predictors of response to antiangiogenesis therapies," Cancer J, 17(2):134-141, (2011).
Jubb et al., "Impact of vascular endothelial growth factor-A expression, thrombospondin-2 expression, and microvessel density on the treatment effect of bevacizumab in metastatic colorectal cancer," J Clin Oncol, 24(2):217-227, (2006).
Jubb et al., "Biomarkers to predict the clinical efficacy of bevacizumab in cancer," Lancet Oncol, 11(12):1172-1183, (2010).
Tothill et al., "Novel molecular subtypes of serous and endometroid ovarian cancer linked to clinical outcome," Clin Cancer Res, 14(16):5198-5208, (2008).
Communication pursuant to Article 94(3) EPC for Application No. 15 705 693.8-1111, dated Feb. 11, 2019.
Mehrmohamadi et al., "Molecular features that predict the response to antimetabolite chemotherapies," Cancer Metab, 5:8 (2017).

* cited by examiner

A)

B)

A)

B)

A)

B)

A)

B)

A)

B)

A)

B)

MOLECULAR DIAGNOSTIC TEST FOR PREDICTING RESPONSE TO ANTI-ANGIOGENIC DRUGS AND PROGNOSIS OF CANCER

CROSS REFERENCE TO RELATED APPLICATIONS

This application is the national stage entry under 35 U.S.C. § 371 of International Application No. PCT/GB2015/050352, filed Feb. 9, 2015, which claims priority to U.S. Provisional Application No. 61/937,224, filed Feb. 7, 2014, and Great Britain Application No. 1409479.1, filed May 28, 2014. The contents of these applications are each incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 3, 2016, is named SequenceListing.txt and is 261,549 bytes in size.

FIELD OF THE INVENTION

The present invention relates to a molecular diagnostic test useful for providing a prognosis and directing treatment of cancers from different anatomical sites. The invention includes the derivation of a gene classification model from gene expression levels. One application is the selection of whether to administer certain therapeutics, such as anti-angiogeneic therapeutics, to subjects receiving a standard of care cancer therapy. Another application is the stratification of cancer patients into those that have a good clinical prognosis or poor clinical prognosis. The present invention provides a test that can guide therapy selection as well as selecting patient groups for enrichment strategies during clinical trial evaluation of novel therapeutics. The invention can be used as a prognostic indicator for certain cancers including ovarian cancer, breast cancer, colon, prostate, lung and glioblastoma. The angiogenesis subtype can be identified from fresh/frozen (FF) or formalin fixed paraffin embedded FFPE patient samples.

BACKGROUND

The pharmaceutical industry continuously pursues new drug treatment options that are more effective, more specific or have fewer adverse side effects than currently administered drugs. Drug therapy alternatives are constantly being developed because genetic variability within the human population results in substantial differences in the effectiveness of many established drugs. Therefore, although a wide variety of drug therapy options are currently available, more therapies are always needed in the event that a patient fails to respond.

Traditionally, the treatment paradigm used by physicians has been to prescribe a first-line drug therapy that results in the highest success rate possible for treating a disease. Alternative drug therapies are then prescribed if the first is ineffective. This paradigm is clearly not the best treatment method for certain diseases. For example, in diseases such as cancer, the first treatment is often the most important and offers the best opportunity for successful therapy, so there exists a heightened need to choose an initial drug that will be the most effective against that particular patient's disease.

Ovarian cancer is the leading cause of death among all gynecological cancers in western countries. This high death rate is due to the diagnosis at an advanced stage in most patients. Epithelial ovarian cancer (EOC) constitutes 90% of ovarian malignancies and is classified into distinct histologic categories including serous, mucinous, endometrioid, clear cell, transitional, mixed, and undifferentiated subtypes. There is increasing evidence that these differed histologies arise from different aetiologies. There have been recent advances in the methodology used to classify epithelial ovarian cancer (McCluggage, W. G. "Morphological subtypes of ovarian carcinoma: a review with emphasis on new developments and pathogenesis," Pathology 2011 August; 43(5):420-32). One of the consequences of this is that many tumors that would previously been classified as endometrioid are now being classified as serous.

The current standard treatment for ovarian cancer is debulking surgery and standard platinum taxane based cytotoxic chemotherapy. However, not all patients respond to this, and of those that do, approximately 70% will experience a recurrence. Specific targeted therapies for ovarian cancer based on histological or molecular classification have not yet reached the marketplace. Similarly for other types of cancer, there is still no accurate way of selecting appropriate cytotoxic chemotherapeutic agents.

The advent of microarrays and molecular genomics has the potential for a significant impact on the diagnostic capability and prognostic classification of disease, which may aid in the prediction of the response of an individual patient to a defined therapeutic regimen. Microarrays provide for the analysis of large amounts of genetic information, thereby providing a genetic fingerprint of an individual. There is much enthusiasm that this technology will ultimately provide the necessary tools for custom-made drug treatment regimens.

Currently, healthcare professionals have few mechanisms to help them identify cancer patients who will benefit from chemotherapeutic agents. Identification of the optimal first-line drug has been difficult because methods are not available for accurately predicting which drug treatment would be the most effective for a particular cancer's physiology. This deficiency results in relatively poor single agent response rates and increased cancer morbidity and death. Furthermore, patients often needlessly undergo ineffective, toxic drug therapy.

Angiogenesis is a key component of neo-vascularisation of tumors and essential to tumorigenesis and metastatsis. As such, it is a key area for therapeutic intervention and has been correlated to poor prognosis and reduced survival. This has promoted the development of a number of agents that target angiogenesis related processes and pathways, including the market leader and first FDA-approved anti-angiogenic, bevacizumab (Avastin), produced by Genentech/Roche.

Treatment regimens that include bevacizumab have demonstrated broad clinical activity[1-10]. However, no overall survival (OS) benefit has been shown after the addition of bevacizumab to cytotoxic chemotherapy in most cancers[8, 12-13]. This suggests that a substantial proportion of tumours are either initially resistant or quickly develop resistance to VEGF blockade (the mechanism of action of bevacizumab). In fact, 21% of ovarian, 10% of renal and 33% of rectal cancer patients show partial regression when receiving bevacizumab monotherapy, suggesting that bevacizumab may be active in small subgroups of patients, but that such incremental benefits do not reach significance in unselected patients.[15-18] As such, the use of a biomarker of response to bevacizumab would improve assessment of treatment outcomes and thus enable the identification of patient subgroups that would receive the most clinical benefit from bevacizumab treatment. This would be particularly relevant in the case of metastatic breast cancer, where the absence of a clinically beneficial biomarker has undermined the use of bevacizumab. Thus far, no such biomarker has been clinically validated to predict bevacizumab efficacy. Hypertension and VEGF polymorphisms are so far the only biomarkers to show potential, but important questions remain about their use in a clinical setting.

Another approach to anti-angiogenic therapy is simultaneous targeting of multiple angiogenic pathways rather than selective targeting of the VEGF pathway. Theoretically, multitargeted anti-angiogenic agents should more completely inhibit angiogenesis than agents such as bevacizumab and thus may produce greater therapeutic benefit. It has been postulated that in some tumors, angiogenesis may require VEGF only in the early stages of disease but is driven by additional angiogenic pathways as the disease progresses. Therefore, by targeting multiple pathways, it may be possible to counteract compensatory escape mechanisms that could lead to resistance to VEGF inhibition.

As for other types of cancer there is still no accurate way of selecting which patients will or will not respond to standard of care with an anti-angiogenic therapeutic or single agent anti-angiogenic therapy.

What is therefore needed is a molecular diagnostic test that would facilitate the stratification of patients based upon their predicted response to anti-angiogenic therapeutics, either in combination with standard of care or as a single-agent therapeutic. This would allow for the rapid identification of those patients who should receive alternative therapies. Such a molecular diagnostic test should be predictive of therapeutic responsiveness across different cancer types with sufficient accuracy.

SUMMARY OF THE INVENTION

Disclosed are methods of using one or more biomarkers, or a collection of biomarkers expressed in cancer that identify a subtype of cancer that is associated with an up-regulation in molecular signaling related to immune response and a down-regulation in molecular signaling related to angiogenesis and vasculature development, referred to herein as a "non-angiogenesis" or "immune" subtype. The collection of biomarkers may be defined by an expression signature, and the expression signature is used to assign a cumulative score to the measured expression values of the collection of biomarkers. In different aspects, the biomarkers and expression signatures may form the basis of a single parameter or multiparametric predictive test that could be delivered using methods known in the art such as microarray, next generation sequencing (NGS), Q-PCR, immunohistochemistry, ELISA or other technologies that can quantify mRNA or protein expression.

In addition, the cancer subtypes described herein are common to many types of cancer and are not limited to a single cancer disease type. Accordingly, the expression signatures of the present invention are not limited to a single cancer type. In certain example embodiments, the non-angiogenesis expression signature comprises two or more biomarkers selected from the biomarkers listed in Tables 1. In another example embodiment, the non-angiogenesis expression signature comprises two or more biomarkers listed in Table 2 or 3. In certain other example embodiments, the expression signature comprises one or more of IGF2, SOX11, INS, CXCL17, SLC5A1, TMEM45A, CXCR2PA, MFAP2, MATN3, or RTP4. In another example embodiment, the expression signature comprises one or more of IGF2, CDR1, COL3A1, SPARC, TIMP3, INS, COL8A1, NUAK1, MATN3, and TMEM45A. In another example embodiment, the expression signature comprises one or more of INS, SPARC, COL8A1, COL3A1, CDR1, NUAK1, TIMP3, and MMP14. In another example embodiment, the non-angiogenesis signature comprises the biomarkers listed in Table 2 and their corresponding weights as determined using a PLS classifier. In another example embodiment, the non-angiogenesis signature comprises the biomarkers listed in Table 3 and their corresponding ranks within a decision function.

In one aspect the invention provides a method for selecting whether to administer an anti-angiogenic therapeutic agent to a subject, comprising: measuring the expression level(s) of one or more biomarkers selected from Table 2 or Table 3 in a sample from the subject; assessing from the expression level(s) of the one or more biomarkers whether the sample from the subject is positive or negative for a biomarker signature, wherein if the sample is positive for the biomarker signature an anti-angiogenic therapeutic agent is contraindicated. In certain embodiments assessing whether the sample is positive or negative for the biomarker signature comprises: determining a sample expression score for the one or more biomarkers; comparing the sample expression score to a threshold score; and determining whether the sample expression score is above or equal to the threshold expression score, wherein if the sample expression score is above or equal to the threshold score the sample is positive for the biomarker signature. In further embodiments the subject is receiving or has received treatment with a chemotherapeutic agent.

In a further aspect the invention provides a method of treating cancer comprising administering a chemotherapeutic agent and not administering an anti-angiogenic therapeutic agent to a subject wherein the subject is selected for treatment on the basis of a method as described herein and the subject is positive for the biomarker signature. According to a further aspect of the invention there is provided a method of treating cancer comprising administering a chemotherapeutic agent and not administering an anti-angiogenic therapeutic agent to a subject wherein the subject is selected for treatment by measuring the expression level(s) of one or more biomarkers selected from Table 2 or Table 3 in a sample from the subject; assessing from the expression levels of the biomarkers whether the sample from the subject is positive or negative for a biomarker signature, wherein if the sample is positive for the biomarker signature the subject is selected for treatment. In yet a further aspect, the present invention relates to a chemotherapeutic agent for use in treating cancer in a subject wherein the subject is selected for treatment on the basis of a method as described herein and is positive for the biomarker signature and wherein the subject is not treated with an anti-angiogenic therapeutic agent. The invention also relates to a chemotherapeutic agent for use in treating cancer in a subject wherein the subject is selected for treatment by measuring the expression level(s) of one or more biomarkers selected from Table 2 or Table 3 in a sample from the subject; assessing from the expression levels of the biomarkers whether the sample from the subject is positive or negative for a biomarker signature, wherein if the sample is positive for the biomarker signature the subject is selected for treatment and wherein the subject is not treated with an anti-angiogenic therapeutic agent. In a further aspect, the present invention relates to a method of treating cancer comprising administering a chemotherapeutic agent to a subject wherein the subject is positive for a biomarker signature defined by the expression levels of one or more biomarkers selected from Table 2 or Table 3 and wherein an anti-angiogenic therapeutic agent is not administered. In yet a further aspect, the present invention relates to a chemotherapeutic agent for use in treating cancer in a subject wherein the subject is positive for a biomarker signature defined by the expression levels of one or more biomarkers selected from Table 2 or Table 3 and wherein the subject is not treated with an anti-angiogenic therapeutic agent. In certain embodiments the chemotherapeutic agent comprises a platinum-based chemotherapeutic agent, an alkylating agent, an anti-metabolite (such as 5FU), an anti-tumor antibiotic, a topoisomerase inhibitor, a mitotic inhibitor, or a combination thereof. The chemotherapeutic agent may comprise a platinum based-chemotherapeutic agent, a mitotic inhibitor, or a combination thereof. In specific embodiments the chemotherapeutic agent comprises carboplatin and/or paclitaxel. The chemotherapeutic agent may reflect the standard of care treatment for the cancer. The standard of care treatment may differ for different types of cancer—for example carboplatin in ovarian cancer, 5FU in colorectal cancer, platinum in head and neck cancer. According to all aspects of the invention assessing whether the sample is positive or negative for the biomarker signature may comprise determining a sample expression score for the one or more biomarkers; comparing the sample expression score to a threshold score; and determining whether the sample expression score is above or equal to the threshold expression score, wherein if the sample expression score is above or equal to the threshold score the sample is positive for the biomarker signature. According to all aspects of the invention the subject may be suffering from cancer. The cancer may be ovarian cancer, optionally high grade serous ovarian cancer. Herein "administering" an agent is used interchanging with "treating with" an agent.

According to a further aspect of the invention there is provided a method for determining clinical prognosis of a subject with cancer, comprising: measuring the expression level(s) of one or more biomarkers selected from Table 2 or Table 3 in a sample from the subject; assessing from the expression level(s) of the one or more biomarkers whether the sample from the subject is positive or negative for a biomarker signature, wherein if the sample is positive for the biomarker signature the subject has a good prognosis. Assessing whether the sample is positive or negative for the biomarker signature may comprise: determining a sample expression score for the biomarkers; comparing the sample expression score to a threshold score; and determining whether the sample expression score is above or equal to the threshold expression score, wherein if the sample expression score is above or equal to the threshold score the sample is positive for the biomarker signature. In certain embodiments the good prognosis indicates increased progression free survival or overall survival rates compared to samples that are negative for the biomarker signature, optionally compared to samples with a sample expression score below the threshold score. In certain embodiments the subject is receiving, has received and/or will receive chemotherapeutic treatment and/or will not receive treatment with an anti-angiogenic therapeutic agent. The chemotherapeutic treatment may comprise administration of a platinum-based chemotherapeutic agent, an alkylating agent, an anti-metabolite, an anti-tumor antibiotic, a topoisomerase inhibitor, a mitotic inhibitor, or a combination thereof. The chemotherapeutic treatment may comprise administration of a platinum-based chemotherapeutic agent, a mitotic inhibitor, or a combination thereof. In specific embodiments the chemotherapeutic treatment comprises administration of paclitaxel and carboplatin. The cancer may be ovarian cancer or colorectal cancer In a further aspect the present invention relates to a method for selecting whether to administer Bevacizumab to a subject, comprising: in a test sample obtained from a subject suffering from ovarian cancer, which subject is being, has been and/or will be treated using a platinum-based chemotherapeutic agent and/or a mitotic inhibitor; measuring expression levels of one, two or more, up to all of the, biomarkers selected from Table 2; assessing from the expression level(s) of the one, two or more biomarkers whether the sample from the subject is positive or negative for a biomarker signature, selecting a treatment based on whether the sample is positive for the biomarker signature, wherein is the sample is positive for the biomarker signature Bevacizumab is contraindicated. In certain embodiments assessing whether the sample is positive or negative for the biomarker signature comprises determining a sample expression score for the one, two or more biomarkers; comparing the sample expression score to a threshold score; and determining whether the sample expression score is above or equal to the threshold expression score, wherein if the sample expression score is above or equal to the threshold score the sample is positive for the biomarker signature.

The invention also relates to a method for determining clinical prognosis of a subject, comprising: (a) in a test sample obtained from a subject suffering from ovarian cancer, which subject is being, has been and/or will be treated using a platinum-based chemotherapeutic agent and/or a mitotic inhibitor; (b) measuring expression levels of one or more, up to all of the, biomarkers selected from Table 2 or Table 3; (c) assessing from the expression level(s) of the one or more biomarkers whether the sample from the subject is positive or negative for a biomarker signature, wherein if the sample is positive for the biomarker signature the subject has a good prognosis. Assessing whether the sample is positive or negative for the biomarker signature may comprise: (i) determining a sample expression score for the one or more biomarkers; (ii) comparing the sample expression score to a threshold score; and (iii) determining whether the sample expression score is above or equal to the threshold expression score, wherein if the sample expression score is above or equal to the threshold score the sample is positive for the biomarker signature. In certain embodiments the good prognosis indicates increased progression free survival or overall survival rates compared to samples that are negative for the biomarker signature, optionally compared to samples with a sample expression score below the threshold score.

According to all aspects of the invention the expression level(s) of two or more biomarkers selected from Table 2 or Table 3 may be measured in a sample from the subject. The expression level(s) of five or more biomarkers selected from Table 2 or Table 3 may be measured in a sample from the subject. Assessing whether the sample is positive or negative for the biomarker signature may comprise the use of classification trees or random forests. Classification trees (Breiman, Leo; Friedman, J. H.; Olshen, R. A.; Stone, C. J. (1984). Classification and regression trees. Monterey, Calif.: Wadsworth & Brooks/Cole Advanced Books & Software. ISBN 978-0-412-04841-8) provide a means of predicting outcomes based on logic and rules. A classification tree is built through a process called binary recursive partitioning, which is an iterative procedure of splitting the data into partitions/branches. The goal is to build a tree that distinguishes among pre-defined classes. Each node in the tree corresponds to a variable. To choose the best split at a node, each variable is considered in turn, where every possible split is tried and considered, and the best split is the one which produces the largest decrease in diversity of the classification label within each partition. This is repeated for all variables, and the winner is chosen as the best splitter for that node. The process is continued at the next node and in this manner, a full tree is generated. One of the advantages of classification trees over other supervised learning approaches such as discriminant analysis, is that the variables that are used to build the tree can be either categorical, or numeric, or a mix of both. In this way it is possible to generate a classification tree for predicting outcomes based on say the directionality of gene expression. Random forest algorithms (Breiman, Leo (2001). "Random Forests". Machine Learning 45 (1): 5-32. doi:10.1023/A:1010933404324) provide a further extension to classification trees, whereby a collection of classification trees are randomly generated to form a "forest" and an average of the predicted outcomes from each tree is used to make inference with respect to the outcome.

In one aspect, a method for selecting whether to administer an anti-angiogenic therapeutic agent to a subject using the expression signatures disclosed herein is provided, the method comprising obtaining a test sample from the subject, measuring expression levels of a biomarker panel from the test sample, determining a sample expression score for the biomarker panel, comparing the sample expression score to a threshold score, and selecting a treatment based on whether the expression score is equal to or above the threshold score. In certain example embodiments, a sample expression score is equal to or above the threshold score indicates an anti-angiogenic agent is contraindicated and should not be administered to the subject. In certain example embodiments, a sample expression score below the threshold score indicates an anti-angiogenic agent is not contraindicated and can be administered to the subject. A therapeutic agent is "contraindicated" or "detrimental" to a patient if the cancer's rate of growth is accelerated as a result of contact with the therapeutic agent, compared to its growth in the absence of contact with the therapeutic agent. Growth of a cancer can be measured in a variety of ways. For instance, the size of a tumor, or measuring the expression of tumor markers appropriate for that tumor type. A therapeutic agent can also be considered "contraindicated" or "detrimental" if the patient's overall prognosis (progression free survival and overall survival) is reduced by the administration of the therapeutic agent. In one example embodiment, the expression signature disclosed herein may determine a patient's clinical prognosis upon administration of an anti-angiogeneic agent following standard cancer therapy.

In certain example embodiments, the subject suffers from cancer. The cancer may include, but is not limited to, ovarian cancer, breast cancer, colon cancer, colorectal cancer, glioblastoma, kidney cancer, including renal cell carcinoma, heatocelluar cancer, thyroid cancer, pancreatic cancer, neuroendocrine cancer, esophageal cancer, gastrointestinal stromal tumors (GIST), gastric cancer, liver cancer, including adult primary liver cancer, lymphoma, melanoma, or multiple myeloma. In certain example embodiments, the cancer is ovarian cancer. In certain other example embodiments, the ovarian cancer is high grade serous ovarian cancer. In certain example embodiments, the patient may have received, is receiving and/or will receive a treatment which may be a standard of care treatment for the cancer type of the subject. In certain example embodiments, that treatment which may be a standard of care treatment may include treatment with a chemotherapeutic agent. The chemotherapeutic treatment may include administration of a platinum-based chemotherapeutic agent, an alkylating agent, an anti-metabolite, an anti-tumor antibiotic, a topoisomerase inhibitor, a mitotic inhibitor, or a combination thereof. In certain example embodiments, the chemotherapeutic treatment comprises administration of a platinum-based chemotherapeutic agent, a mitotic inhibitor, or a combination thereof. In certain other example embodiments, the chemotherapeutic treatment comprises administration of carboplatin and paclitaxel. In one example embodiment, the subject has high grade serous ovarian cancer and has previously received a platinum-based chemotherapeutic agent and a mitotic inhibitor. In another example embodiment, the subject has high grade serous ovarian cancer and has previously received carboplatin and paclitaxel. The anti-angiogenic therapeutic agent may be a VEGF-pathway-targeted therapeutic agent (such as bevacizumab or aflibercept), an angiopoietin-TIE2 pathway inhibitor, an endogenous angiogenic inhibitor, or an immunomodulatory agent. In one example embodiment, the anti-angiogenic therapeutic agent is a VEGF-pathway-targeted therapeutic agent. In another example embodiment, the anti-angiogenic therapeutic agent is bevacizumab.

In another aspect, a method for determining a clinical prognosis of a subject using the expression signatures disclosed herein is provided, the method comprising obtaining a test sample from the subject, measuring expression levels of a biomarker panel from the test sample, determining a sample expression score for the biomarker panel, comparing the sample expression score to the threshold expression score, wherein if the expression score is equal to or above the threshold expression score the clinical prognosis is a good prognosis. In certain example embodiments, a good prognosis indicates increased survival rates compared to a subject with an expression score below the threshold score. In certain example embodiments, the subject suffers from cancer. The cancer may include, but is not limited to, ovarian cancer, breast cancer, colon cancer, colorectal cancer, or glioblastoma. In certain example embodiments, the cancer is ovarian cancer. In certain other example embodiments, the ovarian cancer is high grade serous ovarian cancer. In certain example embodiments, the subject may receive, has received and/or will receive a chemotherapeutic treatment. The chemotherapeutic treatment may include administration of a platinum-based chemotherapeutic agent, an alkylating agent, an anti-metabolite, an anti-tumor antibiotic, a topoisomerase inhibitor, a mitotic inhibitor, or a combination thereof. In certain example embodiments, the chemotherapeutic treatment comprises administration of a platinum-based chemotherapeutic agent, a mitotic inhibitor, or a combination thereof. In certain other example embodiments, the chemotherapeutic treatment comprises administration of carboplatin and paclitaxel. In one example embodiment, the subject has high grade serous ovarian cancer and may receive, has received and/or will receive a platinum-based chemotherapeutic agent and a mitotic inhibitor, such as taxane. In another example embodiment, the subject has high grade serous ovarian cancer and is may receive, has received, and/or will receive carboplatin and paclitaxel.

In another aspect, the present invention relates to kits for conventional diagnostic uses listed above such as qPCR, NGS, microarray, and immunoassays such as immunohistochemistry, ELISA, Western blot and the like. Such kits include appropriate reagents and directions to assay the expression of the genes or gene products and quantify mRNA or protein expression.

Also disclosed are methods for identifying human tumors with or without the non-angiogenesis phenotype. In certain example embodiments, such methods may be used to identify patients that are sensitive to and respond to drugs that inhibit, either directly or indirectly, processes relating to angiogenesis. In certain other example embodiments, such methods may be used to identify patients that are resistant to or do not respond or will respond in adverse fashion to drugs that inhibit, either directly or indirectly, processes relating to angiogenesis.

This invention also relates to guiding effective treatment of patients. Further, methods relating to selection of patient treatment regimens and selecting patients for clinical trials of current, or developmental stage drugs that directly or indirectly affect angiogenesis are provided.

In addition, methods that accommodate the use of archived formalin fixed paraffin-embedded (FFPE) biopsy material, as well as fresh/frozen (FF) tissue, for assay of all transcripts, and are therefore compatible with the most widely available type of biopsy material, are described herein. A biomarker expression level may be determined using RNA obtained from FFPE tissue, fresh frozen tissue or fresh tissue that has been stored in solutions such as RNAlater®.

DETAILED DESCRIPTION OF THE INVENTION

Figure 1:
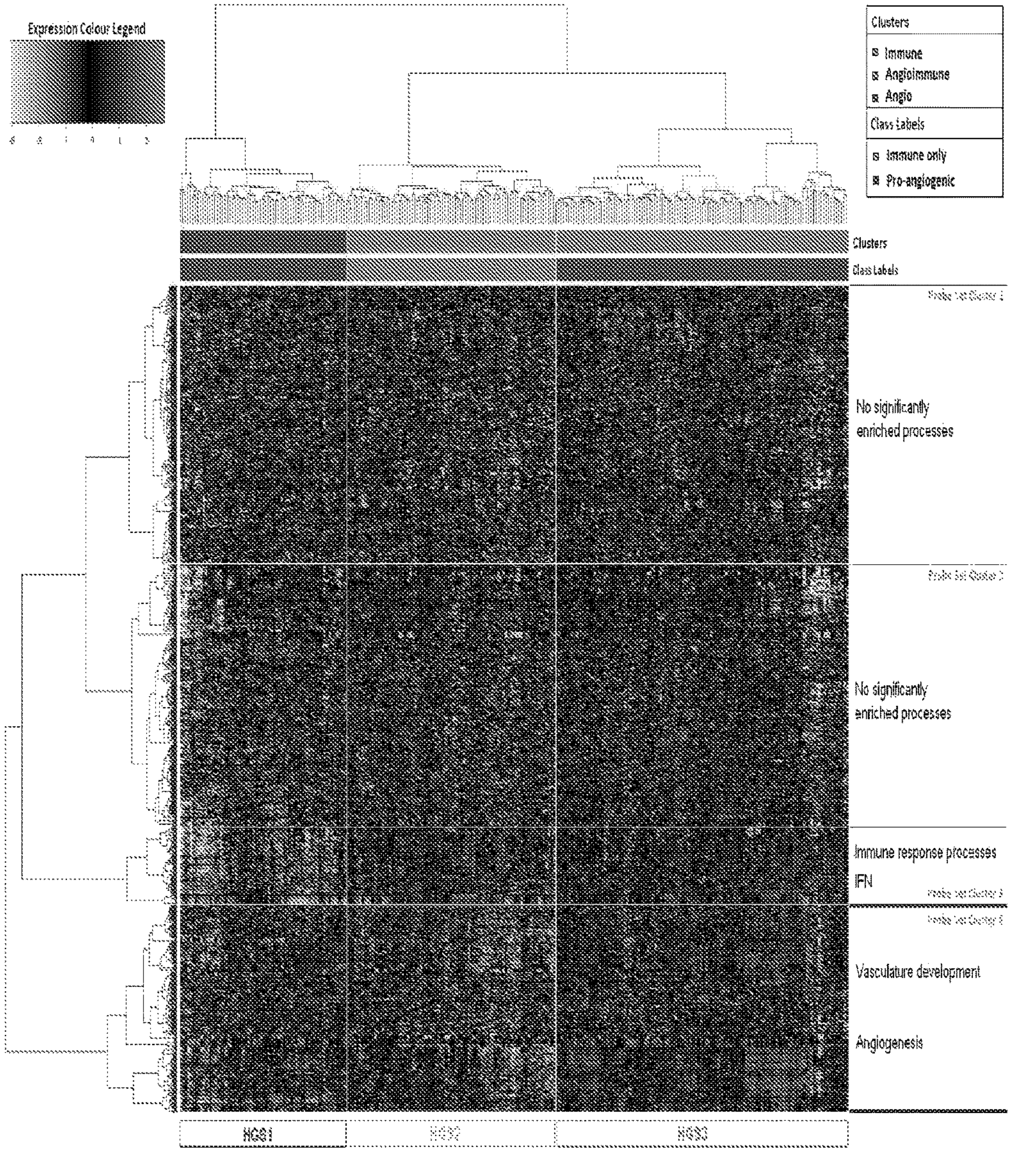
FIG. 1 provides a heat map showing unsupervised hierarchical clustering of gene expression data in 265 high grade serous ovarian carcinomas. Each column represents the expression of these probe sets in one tumor. Probe set expression across all clusters is represented horizontally. The bar above the heat map is color-coded by cluster as described in the legend box. The second bar is color-coded for class label as described in the legend box. Functional processes corresponding to each probe set cluster are labeled to the right of the figure.

Unless defined otherwise, technical and scientific terms used herein have the same meaning as commonly understood by one of ordinary skill in the art to which this disclosure belongs. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992).

The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

As used herein terms "biomarker panel," "expression classifier," "classifier," "expression signature," or "signature" may be used interchangeably. The panel typically includes a plurality of biomarkers but may include only a single biomarker where that biomarker is useful individually in the methods of the invention.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

Overview

A major goal of current research efforts in cancer is to increase the efficacy of perioperative systemic therapy in patients by incorporating molecular parameters into clinical therapeutic decisions. Pharmacogenetics/genomics is the study of genetic/genomic factors involved in an individuals' response to a foreign compound or drug. Agents or modulators which have a stimulatory or inhibitory effect on expression of a biomarker of the invention can be administered to individuals to treat (prophylactically or therapeutically) cancer in the patient. It is ideal to also consider the pharmacogenomics of the individual in conjunction with such treatment. Differences in metabolism of therapeutics may possibly lead to severe toxicity or therapeutic failure by altering the relationship between dose and blood concentration of the pharmacologically active drug. Thus, understanding the pharmacogenomics of an individual permits the selection of effective agents (e.g., drugs) for prophylactic or therapeutic treatments. Such pharmacogenomics can further be used to determine appropriate dosages and therapeutic regimens. Accordingly, the level of expression of a biomarker of the invention in an individual can be determined to thereby select appropriate agent(s) for therapeutic or prophylactic treatment of the individual.

The present invention relates to a molecular diagnostic tests useful for diagnosing cancers from different anatomical sites that includes the use of one or more common subtypes related to angiogenesis. The invention includes expression signatures that identify a subject as having a good or poor clinical prognosis, and expression signatures that indicate whether to administer an anti-angiogenic therapeutic agent to a subject. The expression signature is derived by obtaining the expression profiles of samples from a sample set of known pathology and/or clinical outcome. The samples may originate from the same sample tissue type or different tissue types. As used herein an "expression profile" comprises a set of values representing the expression level for each biomarker analyzed from a given sample.

The expression profiles from the sample set are then analyzed using a mathematical model. Different mathematical models may be applied and include, but are not limited to, models from the fields of pattern recognition (Duda et al. Pattern Classification, $2^{nd}$ ed., John Wiley, New York 2001), machine learning (Scholkopf et al. Learning with Kernels, MIT Press, Cambridge 2002, Bishop, Neural Networks for Pattern Recognition, Clarendon Press, Oxford 1995), statistics (Hastie et al. The Elements of Statistical Learning, Springer, New York 2001), bioinformatics (Dudoit et al., 2002, J. Am. Statist. Assoc. 97:77-87, Tibshirani et al., 2002, Proc. Natl. Acad. Sci. USA 99:6567-6572) or chemometrics (Vandeginste, et al., Handbook of Chemometrics and Qualimetrics, Part B, Elsevier, Amsterdam 1998). The mathematical model identifies one or more biomarkers expressed in the sample set that are most predictive of a given disease phenotype. These one or more biomarkers define an expression signature. Accordingly, an expression signature includes the biomarkers identified as most predictive of a given disease phenotype. In certain example embodiments, the mathematical model defines a variable, such as a weight, for each identified biomarker. In certain example embodiments, the mathematical model defines a decision function. The decision function may further define a threshold score which separates the sample set into two disease phenotypes such as, but not limited to, samples that have a good and poor clinical prognosis. In one example embodiment, the decision function and expression signature are defined using a linear classifier.

To classify new samples using a defined expression signature, the biomarkers defined by the expression signature, also referred to as a biomarker panel, are isolated and an expression profile of the biomarker panel determined. The new sample biomarker panel expression profile is analyzed with the same mathematical model used to define the expression signature. The biomarker panel may comprise one or more of the biomarkers defined by the expression signature. The biomarker panel may comprise one or more of the biomarkers defined by the expression signature. In certain example embodiments, the biomarker panel comprises one or more of the biomarkers listed in Table 2. In certain other example embodiments, the biomarker panel comprises all of the biomarkers listed in Table 2. In certain example embodiments, the biomarker panel comprises one or more of the biomarkers listed in Table 2. In certain other example embodiments, the biomarker panel comprises all of the biomarkers listed in Table 2. In certain example embodiments, the mathematical model defines an expression score for the new sample. The expression score may be determined by combining the expression values of the biomarkers with corresponding scalar weights using non-linear, algebraic, trigonometric or correlative means to derive a single scalar value. The expression score is compared to the threshold score and the sample classified based on whether the expression score is greater than, or equal to, or less than the threshold score. In certain example embodiments, a sample expression score equal to or greater than the threshold score indicates a subject has a good clinical prognosis, and a sample expression score below the threshold score indicates a subject has a poor clinical prognosis. In certain example embodiments, a sample expression score equal to or greater than the threshold score indicates a subject has the signature. This may indicate a good clinical prognosis. A sample expression score below the threshold score indicates a subject does not have the signature. This may indicate a poor clinical prognosis.

One application of the expression signatures disclosed herein is the identification of patients with a good and poor clinical prognosis. The good or poor prognosis may be determined in the context of a certain treatment background (such as carboplatin/paclitaxel therapy as discussed herein). For example, the subject may be receiving or have received a standard chemotherapeutic treatment for the subject's cancer type. Given a treatment background, the expression signatures disclosed herein may also be used to determine whether an additional therapeutic agent, such as an anti-angiogenic therapeutic agent, should be administered to the patient. By examining the expression of at least one, optionally a collection of the identified biomarkers in a tumor, it is possible to determine the likely clinical outcomes of a patient. By examining the expression of at least one, optionally a collection of biomarkers, it is therefore possible to identify those patients in most need of more aggressive therapeutic regimens and likewise eliminate unnecessary therapeutic treatments or those unlikely to significantly improve or possibly harm a patient's clinical outcome. The present invention relates to prediction of clinical prognosis using at least progression free survival or overall survival rates. Accordingly, a "good prognosis" indicates a subject population with a cancer subtype that demonstrates an increased survival rate compared to other cancer subtypes, whereas a "poor prognosis" or "bad prognosis" indicates a subject population with a cancer subtype that demonstrates decreased survival rate compared to other cancer subtypes. Additional prognostic factors that may be considered are ethnicity and race, age, stage of disease, histology, tumor grade, tumor makers (for example, CA125), site-specific surgical treatment, size of residual disease, and tumor response. In certain example embodiments, a subject with an expression score equal to or above the threshold score is classified as having the non-angiogenesis subtype. In another example embodiment, a subject with a sample expression score above the threshold score is classified as having a good clinical prognosis. In yet another example embodiment, a subject with a sample expression score above or equal to the threshold score indicates the subject will likely experience a detrimental effect, or have a poorer clinical prognosis, if administered an anti-angiogenic therapeutic agent.

In certain example embodiments, the determination of a subject's clinical prognosis or selection of an additional therapeutic agent may be made in the context of past, current, or planned chemotherapeutic treatment. For example, the subject may set to start, be currently receiving, or have just completed, a standard of care chemotherapeutic treatment for the cancer type of the subject. In certain example embodiments, the chemotherapeutic treatment may include administration of an alkylating agent, an anti-metabolite, a platinum-based drug, an anti-tumor antibiotic, a topoisomerase inhibitor, a mitotic inhibitor, a corticosteroid, a hormone based therapeutic, or a combination thereof. Example alkylating agents include nitrogen mustards, nitrosureas, alkyl sulfonates, triazines, and ethylenimines. Example platinum drugs include cisplatin, carboplatin, and oxalaplatin. Example anti-metabolites include 5-fluoruracil, 6-mercaptopurine, capecitabine, cladribine, clofarabine, cytarabine, floxuridine, fludarabine, gemcitabine, hydroxyurea, methotrexate, pemetrexed, pentostatin, and thioguanine. Example anti-tumor antibiotics include daunorubicin, doxorubicin, epirubicin, idarubicin, actinomocyin-D, bleomycin, mitomycin-C, and mitoxantrone. Example topoisomerase inhibitors include topotecan, irinotecan, etoposide, and teniposide. Example mitotic inhibitors include taxanes, epothilones, vinca alkaloids, and estramustine. Example corticosteroids include predisone, methylprednisolone, and dexamethasone. In certain example embodiments the chemotherapy may include treatment with L-asparaginase, imatinib, gefitinib, sunitinib, bortezomib, retinoids, tretinoin, bexaroten, arsenic trioxide, fluvestrant, tamoxifen, toremifene, anastrozole, exemestane, letrozole, progestins, estrogens, bicalutamide, flutamide, nilutamide, gonadotropoin-releasing hormone agonists or analogs, rituximab, alemtuzumab, BCG, interleukin-2, interferon-alfa, thalidomide, and lenalidomide.

In certain example embodiments the chemotherapeutic treatment may comprise a cyclosphoshamide, methotrexate, and fluorouracil (CMF) treatment regimen, a cyclophosphamide, doxorubicin, and fluorouracil (CAF) treatment regimen, an epirubicin and cyclophosphamide (EC) treatment regimen, a fluorouracil, epirubicin, and cyclophosphamide (FEC) treatment regimen, a paclitaxel and cyclophosphamide treatment regimen, a paclitaxel and carboplatin treatment regiment, a doxorubicin and cyclophosphamide treatment regiment, or a doxorubicin and paclitaxel treatment regimen. In one example embodiment, the neoadjuvant cancer therapy comprises a platinum based chemotherapy treatment regimen. In one example embodiment, the platinum-based chemotherapy treatment regimen comprises paclitaxel and carboplatin.

Another application of the expression signatures disclosed herein is the stratification of response to, and selection of patients for therapeutic drug classes that encompass anti-angiogenic therapies. By examining the expression of a collection of the identified biomarkers in a tumor, it is possible to determine which therapeutic agent or combination of agents will be most likely to reduce the growth rate of a cancer. It is also possible to determine which therapeutic agent or combination of agents will be the least likely to reduce the growth rate of a cancer and/or which may cause adverse affects and thus be contra-indicated. By examining the expression of a collection of biomarkers, it is therefore possible to eliminate ineffective or inappropriate therapeutic agents. Importantly, in certain embodiments, these determinations can be made on a patient-by-patient basis or on an agent-by-agent basis. Thus, one can determine whether or not a particular therapeutic regimen is likely to benefit a particular patient or type of patient, and/or whether a particular regimen should be continued. The present invention provides a test that can guide therapy selection as well as selecting patient groups for enrichment strategies during clinical trial evaluation of novel therapeutics. For example, when evaluating a putative anti-angiogeneic agent or treatment regime, the expression signatures and methods disclosed herein may be used to select individuals for clinical trials that have cancer subtypes that are responsive to anti-angiogenic agents.

A cancer is "responsive" to a therapeutic agent if its rate of growth is inhibited as a result of contact with the therapeutic agent, compared to its growth in the absence of contact with the therapeutic agent. Growth of a cancer can be measured in a variety of ways. For instance, the size of a tumor or measuring the expression of tumor markers appropriate for that tumor type. In one example embodiment, the expression signature disclosed herein may determine a patient's clinical prognosis upon administration of an anti-angiogeneic agent following standard of care chemotherapeutic therapy for the cancer type of the patient.

A cancer is "non-responsive" to a therapeutic agent if its rate of growth is not inhibited, or inhibited to a very low degree, as a result of contact with the therapeutic agent when compared to its growth in the absence of contact with the therapeutic agent. As stated above, growth of a cancer can be measured in a variety of ways, for instance, the size of a tumor or measuring the expression of tumor markers appropriate for that tumor type. The quality of being non-responsive to a therapeutic agent is a highly variable one, with different cancers exhibiting different levels of "non-responsiveness" to a given therapeutic agent, under different conditions. Still further, measures of non-responsiveness can be assessed using additional criteria beyond growth size of a tumor such as, but not limited to, patient quality of life, and degree of metastases.

The angiogenesis subtype can be identified from a fresh/frozen (FF) or formalin fixed paraffin embedded (FFPE) patient sample. In one example embodiment, the cancer type is ovarian cancer, breast cancer, colon cancer, colorectal cancer, lung cancer, prostate cancer, or glioblastoma. In another example embodiment, the cancer type is an ovarian cancer. In a further example embodiment, the cancer type is breast cancer. In another example embodiment, the cancer type is lung cancer. In another example embodiment, the cancer type is colon cancer. In another example embodiment, the cancer type is prostate cancer. In another example embodiment, the cancer type is glioblastoma.

Identifying Expression Signatures

The expression signatures of the present invention are identified by analyzing the expression profiles of certain biomarkers in a patient sample set. Biomarkers suitable for use in the present invention include DNA, RNA, and proteins. In one example embodiment, biomarkers suitable for use in the present invention include RNA and cDNA. The biomarkers are isolated from a patient sample and their expression levels determined to derive a set of expression profiles for each sample analyzed in the patient sample set. In certain example embodiments the expression signature identifies a non-angiogenesis phenotype observed in cancer tissues, identified as a signature score for a combination of biomarkers above or equal to a threshold, the phenotype characterized by an up-regulation of immune response related genes and a down-regulation of genes associated with angiogeneisis or vasculature development related processes.

a. Expression Profiles

In certain embodiments, the expression profile obtained is a genomic or nucleic acid expression profile, where the amount or level of one or more nucleic acids in the sample is determined. In these embodiments, the sample that is assayed to generate the expression profile employed in the diagnostic or prognostic methods is a nucleic acid sample. The nucleic acid sample includes a population of nucleic acids that includes the expression information of the phenotype determinative biomarkers of the cell or tissue being analyzed. In some embodiments, the nucleic acid may include RNA or DNA nucleic acids, e.g., mRNA, cRNA, cDNA etc., so long as the sample retains the expression information of the host cell or tissue from which it is obtained. The sample may be prepared in a number of different ways, as is known in the art, e.g., by mRNA isolation from a cell, where the isolated mRNA is used as isolated, amplified, or employed to prepare cDNA, cRNA, etc., as is known in the field of differential gene expression. Accordingly, determining the level of mRNA in a sample includes preparing cDNA or cRNA from the mRNA and subsequently measuring the cDNA or cRNA. The sample is typically prepared from a cell or tissue harvested from a subject in need of treatment, e.g., via biopsy of tissue, using standard protocols, where cell types or tissues from which such nucleic acids may be generated include any tissue in which the expression pattern of the to be determined phenotype exists, including, but not limited to, disease cells or tissue, body fluids, etc.

The expression profile may be generated from the initial nucleic acid sample using any convenient protocol. While a variety of different manners of generating expression profiles are known, such as those employed in the field of differential gene expression/biomarker analysis, one representative and convenient type of protocol for generating expression profiles is array-based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of a signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the biomarkers whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acids provides information regarding expression for each of the biomarkers that have been probed, where the expression information is in terms of whether or not the gene is expressed and, typically, at what level, where the expression data, i.e., expression profile, may be both qualitative and quantitative.

b. Diseases and Sample Tissue Sources

In certain example embodiments, the patient sample comprises a cancer tissue samples, such as an archived sample. The patient sample is preferably derived from cancer tissue and may be from a sample having been characterized by prognosis, likelihood of recurrence, long term survival, clinical outcome, treatment response, diagnosis, cancer classification, or personalized genomics profile. As used herein cancer includes, but is not limited to, leukemia, brain cancer, prostate cancer, liver cancer, ovarian cancer, stomach cancer, colorectal cancer, throat cancer, breast cancer, skin cancer, melanoma, lung cancer, sarcoma, cervical cancer, testicular cancer, bladder cancer, endocrine cancer, endometrial cancer, esophageal cancer, glioma, lymphoma, neuroblastoma, osteosarcoma, pancreatic cancer, pituitary cancer, renal cancer, and the like. As used herein, colorectal cancer encompasses cancers that may involve cancer in tissues of both the rectum and other portions of the colon as well as cancers that may be individually classified as either colon cancer or rectal cancer. In one embodiment, the methods described herein refer to cancers that are treated with anti-angiogenic agents, anti-angiogenic targeted therapies, inhibitors of angiogenesis signaling, but not limited to these classes. These cancers also include subclasses and subtypes of these cancers at various stages of pathogenesis. In certain example embodiments, the patient sample comprises an ovarian cancer sample. In certain example embodiments, the ovarian cancer sample is a serous ovarian cancer sample such as a high grade serous ovarian cancer sample. In another example embodiment, the patient sample comprises a breast cancer sample. In yet another example embodiment, the patient sample comprises a glioblastoma sample.

"Biological sample", "sample", and "test sample" are used interchangeably herein to refer to any material, biological fluid, tissue, or cell obtained or otherwise derived from an individual. This includes blood (including whole blood, leukocytes, peripheral blood mononuclear cells, buffy coat, plasma, and serum), sputum, tears, mucus, nasal washes, nasal aspirate, breath, urine, semen, saliva, meningeal fluid, amniotic fluid, glandular fluid, lymph fluid, nipple aspirate, bronchial aspirate, synovial fluid, joint aspirate, ascites, cells, a cellular extract, and cerebrospinal fluid. This also includes experimentally separated fractions of all of the preceding. For example, a blood sample can be fractionated into serum or into fractions containing particular types of blood cells, such as red blood cells or white blood cells (leukocytes). If desired, a sample can be a combination of samples from an individual, such as a combination of a tissue and fluid sample. The term "biological sample" also includes materials containing homogenized solid material, such as from a stool sample, a tissue sample, or a tissue biopsy, for example. The term "biological sample" also includes materials derived from a tissue culture or a cell culture, including tissue resection and biopsy samples. Any suitable methods for obtaining a biological sample can be employed; example methods include, e.g., phlebotomy, swab (e.g., buccal swab), and a fine needle aspirate biopsy procedure. Samples can also be collected, e.g., by micro dissection (e.g., laser capture micro dissection (LCM) or laser micro dissection (LMD)), bladder wash, smear (e.g., a PAP smear), or ductal lavage. A "biological sample" obtained or derived from an individual includes any such sample that has been processed in any suitable manner after being obtained from the individual, for example, fresh frozen or formalin fixed and/or paraffin embedded. The methods of the invention as defined herein may begin with an obtained sample and thus do not necessarily incorporate the step of obtaining the sample from the patient. The methods may be in vitro methods performed on an isolated sample.

As used herein, the term "patient" includes human and non-human animals. The preferred patient for treatment is a human. "Patient," "individual" and "subject" are used interchangeably herein.

c. Biomarkers

As used herein, the term "biomarker" can refer to a gene, an mRNA, cDNA, an antisense transcript, a miRNA, a polypeptide, a protein, a protein fragment, or any other nucleic acid sequence or polypeptide sequence that indicates either gene expression levels or protein production levels. When a biomarker indicates or is a sign of an abnormal process, disease or other condition in an individual, that biomarker is generally described as being either over-expressed or under-expressed as compared to an expression level or value of the biomarker that indicates or is a sign of a normal process, an absence of a disease or other condition in an individual. "Up-regulation", "up-regulated", "over-expression", "over-expressed", and any variations thereof are used interchangeably to refer to a value or level of a biomarker in a biological sample that is greater than a value or level (or range of values or levels) of the biomarker that is typically detected in similar biological samples from healthy or normal individuals. The terms may also refer to a value or level of a biomarker in a biological sample that is greater than a value or level (or range of values or levels) of the biomarker that may be detected at a different stage of a particular disease.

"Down-regulation", "down-regulated", "under-expression", "under-expressed", and any variations thereof are used interchangeably to refer to a value or level of a biomarker in a biological sample that is less than a value or level (or range of values or levels) of the biomarker that is typically detected in similar biological samples from healthy or normal individuals. The terms may also refer to a value or level of a biomarker in a biological sample that is less than a value or level (or range of values or levels) of the biomarker that may be detected at a different stage of a particular disease.

Further, a biomarker that is either over-expressed or under-expressed can also be referred to as being "differentially expressed" or as having a "differential level" or "differential value" as compared to a "normal" expression level or value of the biomarker that indicates or is a sign of a normal process or an absence of a disease, disease subtype, or other condition in an individual. Thus, "differential expression" of a biomarker can also be referred to as a variation from a "normal" expression level of the biomarker.

The terms "differential biomarker expression" and "differential expression" are used interchangeably to refer to a biomarker whose expression is activated to a higher or lower level in a subject suffering from a specific disease, relative to its expression in a normal subject, or relative to its expression in a patient that responds differently to a particular therapy or has a different prognosis. The terms also include biomarkers whose expression is activated to a higher or lower level at different stages of the same disease. It is also understood that a differentially expressed biomarker may be either activated or inhibited at the nucleic acid level or protein level, or may be subject to alternative splicing to result in a different polypeptide product. Such differences may be evidenced by a variety of changes including mRNA levels, miRNA levels, antisense transcript levels, or protein surface expression, secretion or other partitioning of a polypeptide. Differential biomarker expression may include a comparison of expression between two or more genes or their gene products; or a comparison of the ratios of the expression between two or more genes or their gene products; or even a comparison of two differently processed products of the same gene, which differ between normal subjects and subjects suffering from a disease; or between various stages of the same disease. Differential expression includes both quantitative, as well as qualitative, differences in the temporal or cellular expression pattern in a biomarker among, for example, normal and diseased cells, or among cells which have undergone different disease events or disease stages.

In certain example embodiments, the biomarker is an RNA transcript. As used herein "RNA transcript" refers to both coding and non-coding RNA, including messenger RNAs (mRNA), alternatively spliced mRNAs, ribosomal RNA (rRNA), transfer RNA (tRNA), small nuclear RNAs (snRNA), and antisense RNA. Measuring mRNA in a biological sample may be used as a surrogate for detection of the level of the corresponding protein and gene in the biological sample. Thus, any of the biomarkers or biomarker panels described herein can also be detected by detecting the appropriate RNA. Methods of biomarker expression profiling include, but are not limited to quantitative PCR, NGS, northern blots, southern blots, microarrays, SAGE, immunoassays (ELISA, EIA, agglutination, nephelometry, turbidimetry, Western blot, immunoprecipitation, immunocytochemistry, flow cytometry, Luminex assay), and mass spectrometry. The overall expression data for a given sample may be normalized using methods known to those skilled in the art in order to correct for differing amounts of starting material, varying efficiencies of the extraction and amplification reactions.

In certain example embodiments, biomarkers useful for distinguishing between cancer subtypes that demonstrate a good clinical prognosis and a poor clinical prognosis and can be determined by identifying biomarkers exhibiting the highest degree of variability between samples in the patient data set as determined using the expression detection methods and patient sample sets discussed above. Standard statistical methods known in the art for identifying highly variable data points in expression data may be used to identify the highly variable biomarkers. For example, a combined background and variance filter to the patient data set. The background filter is based on the selection of probe sets with expression E and expression variance $var_E$ above the thresholds defined by background standard deviation σBg (from the Expression Console software) and quantile of the standard normal distribution $z_a$ at a specified significance a probe sets were kept if:

$$E>\log_2((z_a\sigma_{Bg}));\log_2((\mathrm{var}_E)>2[\log_2(\sigma_{Bg})-E-\log_2(\log(2))]$$

where a defines a significance threshold. In certain example embodiment, the significance threshold is $6.3\cdot10^{-5}$. In another example embodiment, the significance threshold may be between $1.0\cdot10^{-7}$ to $1.0\cdot10^{-3}$.

In certain example embodiments, the highly variable biomarkers may be further analyzed to group samples in the patient data set into subtypes or clusters based on similar gene expression profiles. For examples, biomarkers may be clustered based on how highly correlated the up-regulation or down-regulation of their expression is to one another. Various clustering analysis techniques known in the art may be used. In one example embodiment, hierarchical agglomerative clustering is used to identify the cancer subtypes. To determine the biological relevance of each subtype, the biomarkers within each cluster may be further mapped to their corresponding genes and annotated by cross-reference to one or more gene ontology databases containing information on biological activity and biological pathways associated with the gene. In another example embodiment, biomarkers in clusters that are up regulated and enriched for immune response general functional terms are grouped into a putative non-angiongenesis sample group and used for expression signature generation. In another example embodiment, biomarkers in clusters that are down regulated and enriched for angiogenesis and vasculature development and are up regulated and enriched for immune response general functional terms are grouped into a putative non-angiongenesis sample group and used for expression signature generation. Further details for conducting functional analysis of biomarker clusters is provided in the Examples section below.

In one example embodiment, the biomarkers useful in deriving an expression signature for use in the present invention are those biomarkers listed in Table 1. These biomarkers are identified as having predictive value to determine a patient response to a therapeutic agent and/or a prognostice value in identifying individuals with a good or poor clinical prognosis.

In certain example embodiments, the expression of the biomarkers disclosed herein correlates with whether a patient will experience a detrimental or beneficial effect from administration of an anti-angiogenic therapeutic agent. By examining the expression of a collection of biomarkers, it is therefore possible to eliminate ineffective or inappropriate therapeutic agents. Importantly, in certain embodiments, these determinations can be made on a patient-by-patient basis or on an agent-by-agent basis. Thus, one can determine whether or not a particular therapeutic regimen is likely to benefit a particular patient or type of patient, and/or whether a particular regimen should be continued.

In certain other example embodiments, the expression of the biomarkers disclosed herein correlate with a patient's overall clinical prognosis. By examining the expression of a collection of biomarkers identified in a tumor, it is possible to determine whether the individual has a cancer subtype associated with good clinical prognosis or poor clinical prognosis. Importantly, in certain embodiments, these determinations can be made on a patient-by-patient basis. Thus, one of ordinary skill in the art can use predicted prognosis to help select appropriate treatment regimens to treat the underlying disease while eliminating those treatment regimens most likely to produce undesired or medically unwarranted adverse side effects.

The SEQ ID NOs listed in Table 1 refer to probe set identifiers used to measure the expression levels of the genes on an example transcriptome array. Expression signatures of the present invention have been cross-validated using expression data from different arrays with different probe sets as detailed further in the Examples section below. Accordingly, the expression signatures and methods disclosed herein are not limited to expression values measured using the probe sets disclosed herein.

TABLE 1

Genes in Clusters of FIG. 1

| SEQ NO: | Orientation | Gene Symbol |
|---|---|---|
| 1 | Sense (Fully Exonic) | PDGFC |
| 2 | Sense (Fully Exonic) | TGFB3 |
| 3 | Sense (Fully Exonic) | RAC2 |
| 4 | Sense (Fully Exonic) | MARCKS |
| 5 | Sense (Fully Exonic) | ALOX5 |
| 6 | Sense (Fully Exonic) | COL8A1 |
| 7 | Sense (Fully Exonic) | KCNAB2 |
| 8 | Sense (Fully Exonic) | THBS1 |
| 9 | Sense (Fully Exonic) | CTGF |
| 10 | Sense (Fully Exonic) | CTGF |
| 11 | Sense (Fully Exonic) | VCAN |
| 12 | Sense (Fully Exonic) | IGKC |
| 13 | Sense (Fully Exonic) | IGKC |
| 14 | Sense (includes Intronic) | NFATC1 |
| 15 | Sense (Fully Exonic) | HMHA1 |
| 16 | Sense (Fully Exonic) | FCGR1B |
| 17 | Sense (Fully Exonic) | EDA2R |
| 18 | Sense (Fully Exonic) | COL8A1 |
| 19 | Sense (Fully Exonic) | COL12A1 |
| 20 | Sense (Fully Exonic) | HLA-B |
| 21 | Sense | HLA-F |
| 22 | Sense (Fully Exonic) | EGR1 |
| 23 | Sense (Fully Exonic) | SULF2 |
| 24 | Sense (Fully Exonic) | CERCAM |
| 25 | Sense (Fully Exonic) | ATF3 |
| 26 | Sense (Fully Exonic) | MIR21 |
| 27 | Sense (Fully Exonic) | IFIT2 |
| 28 | Sense (Fully Exonic) | IGLC3 |
| 29 | Sense (Fully Exonic) | IGLC3 |
| 30 | Sense (Fully Exonic) | IGLC3 |
| 31 | Sense (Fully Exonic) | IGLC3 |
| 32 | Sense (Fully Exonic) | IGLC3 |
| 33 | Sense (Fully Exonic) | IGLC3 |
| 34 | Sense (Fully Exonic) | ANGPTL2 |
| 35 | Sense (Fully Exonic) | COL5A2 |
| 36 | Sense (Fully Exonic) | THY1 |

TABLE 1-continued

Genes in Clusters of FIG. 1

| SEQ NO: | Orientation | Gene Symbol |
|---|---|---|
| 37 | Sense (Fully Exonic) | NDN |
| 38 | Sense (Fully Exonic) | RGS2 |
| 39 | Sense (Fully Exonic) | MEIS3P2 |
| 40 | Sense (Fully Exonic) | GBP2 |
| 41 | Sense (Fully Exonic) | FAT1 |
| 42 | Sense (Fully Exonic) | COL1A1 |
| 43 | Sense (Fully Exonic) | MMP11 |
| 44 | Sense (Fully Exonic) | GADD45B |
| 45 | Sense (Fully Exonic) | MMP14 |
| 46 | Sense (Fully Exonic) | IGHG4 |
| 47 | Sense (Fully Exonic) | HCLS1 |
| 48 | No Transcript match | |
| 49 | Sense (Fully Exonic) | JAM3 |
| 50 | Sense (Fully Exonic) | TMEM49 |
| 51 | Sense (Fully Exonic) | LTBP2 |
| 52 | Sense (Fully Exonic) | IRS1 |
| 53 | Sense (Fully Exonic) | C17orf91 |
| 54 | Sense (Fully Exonic) | GPNMB |
| 55 | Sense (Fully Exonic) | FAM198B |
| 56 | Sense (Fully Exonic) | CHST15 |
| 57 | Sense (Fully Exonic) | DCN |
| 58 | Sense (Fully Exonic) | VCAM1 |
| 59 | Sense (Fully Exonic) | CIITA |
| 60 | Sense (Fully Exonic) | GAS7 |
| 61 | Sense (Fully Exonic) | COL3A1 |
| 62 | Sense (Fully Exonic) | ITGB2 |
| 63 | Sense (Fully Exonic) | ELN |
| 64 | Sense (Fully Exonic) | CMTM3 |
| 65 | Sense (Fully Exonic) | ANTXR1 |
| 66 | Sense (Fully Exonic) | IL4I1 |
| 67 | Sense (Fully Exonic) | ANTXR2 |
| 68 | Sense (Fully Exonic) | IGLC2 /// IGLC3 |
| 69 | Sense (Fully Exonic) | IGLC3 |
| 70 | Sense (Fully Exonic) | BST2 |
| 71 | Sense (Fully Exonic) | COL10A1 |
| 72 | Sense (Fully Exonic) | IGLC3 |
| 73 | Sense (Fully Exonic) | FBP1 |
| 74 | Sense (Fully Exonic) | RHOBTB3 |
| 75 | Sense (Fully Exonic) | CD74 |
| 76 | Sense (Fully Exonic) | ISM1 |
| 77 | Sense (Fully Exonic) | CSRNP1 |
| 78 | Sense (Fully Exonic) | DCN |
| 79 | Sense (Fully Exonic) | IGFBP4 |
| 80 | Sense (Fully Exonic) | CCDC80 |
| 81 | Sense (Fully Exonic) | COL3A1 |
| 82 | Sense (Fully Exonic) | ZFP36 |
| 83 | Sense (Fully Exonic) | MMP11 |
| 84 | Sense (Fully Exonic) | COL1A2 |
| 85 | Sense (Fully Exonic) | HLA-DPA1 |
| 86 | Sense (Fully Exonic) | TWIST1 |
| 87 | Sense (Fully Exonic) | ZNF154 |
| 88 | Sense (Fully Exonic) | IGLC3 |
| 89 | Sense (Fully Exonic) | IGKC |
| 90 | Sense (Fully Exonic) | IGHG1 |
| 91 | Sense (Fully Exonic) | COL1A2 |
| 92 | Sense (Fully Exonic) | APOC1 |
| 93 | AntiSense | EGR1 |
| 94 | Sense (Fully Exonic) | KIAA0146 |
| 95 | Sense (Fully Exonic) | TPM1 |
| 96 | Sense (includes Intronic) | DMD |
| 97 | No Transcript match | |
| 98 | Sense (Fully Exonic) | DUSP1 |
| 99 | Sense (Fully Exonic) | GBP1 |
| 100 | Sense (includes Intronic) | PDGFC |
| 101 | Sense (includes Intronic) | MSN |
| 102 | Sense (includes Intronic) | TPM1 |
| 103 | Sense (Fully Exonic) | EMB |
| 104 | Sense (Fully Exonic) | FOS |
| 105 | Sense (includes Intronic) | DPYSL3 |
| 106 | AntiSense | EGR1 |
| 107 | AntiSense | NRP2 |
| 108 | Sense (Fully Exonic) | MMP2 |
| 109 | Sense (Fully Exonic) | CTGF |
| 110 | Sense (Fully Exonic) | ACTA2 |
| 111 | Sense (Fully Exonic) | LOXL1 |
| 112 | Sense (Fully Exonic) | CDH11 |

TABLE 1-continued

Genes in Clusters of FIG. 1

| SEQ NO: | Orientation | Gene Symbol |
|---|---|---|
| 113 | Sense (Fully Exonic) | LUM |
| 114 | Sense (Fully Exonic) | NNMT |
| 115 | Sense (Fully Exonic) | GJA1 |
| 116 | AntiSense | CTHRC1 |
| 117 | Sense (Fully Exonic) | CTSB |
| 118 | Sense (Fully Exonic) | PLAU |
| 119 | Sense (Fully Exonic) | PDGFRA |
| 120 | Sense (Fully Exonic) | VCAN |
| 121 | AntiSense | — |
| 122 | Sense (Fully Exonic) | IGHG4 /// IGHG2 /// IGHG1 ///I GHGP |
| 123 | Sense (Fully Exonic) | IGHG2 |
| 124 | Sense (includes Intronic) | C3orf26 |
| 125 | AntiSense | ATF3 |
| 126 | AntiSense | ATF3 |
| 127 | Sense (Fully Exonic) | FN1 |
| 128 | AntiSense | CALD1 |
| 129 | AntiSense | CALD1 |
| 130 | AntiSense | EGR1 |
| 131 | AntiSense | TWIST1 |
| 132 | AntiSense | TWIST1 |
| 133 | AntiSense | BATF2 |
| 134 | AntiSense | NFKBIZ |
| 135 | Sense (includes Intronic) | C3orf26 |
| 136 | AntiSense | LOXL1 |
| 137 | Sense (includes Intronic) | — |
| 138 | AntiSense | FN1 |
| 139 | AntiSense | COL1A1 |
| 140 | Sense (Fully Exonic) | TREH |
| 141 | AntiSense | APOL1 |
| 142 | Sense (Fully Exonic) | COL10A1 |
| 143 | Sense (Fully Exonic) | GAL3ST4 |
| 144 | Sense (Fully Exonic) | TAGLN |
| 145 | Sense (Fully Exonic) | TWIST1 |
| 146 | Sense (Fully Exonic) | HCLS1 |
| 147 | Sense (Fully Exonic) | ITGB2 |
| 148 | Sense (Fully Exonic) | HLA-B |
| 149 | Sense (Fully Exonic) | C17orf91 |
| 150 | Sense (Fully Exonic) | FBLIM1 |
| 151 | Sense (Fully Exonic) | COL15A1 |
| 152 | Sense (Fully Exonic) | AQP7P3 |
| 153 | AntiSense | IGFBP5 |
| 154 | Sense (Fully Exonic) | FANK1 |
| 155 | AntiSense | INS |
| 156 | Sense (Fully Exonic) | COL27A1 |
| 157 | Sense (Fully Exonic) | COL5A1 |
| 158 | Sense (Fully Exonic) | PRICKLE2 |
| 159 | Sense (Fully Exonic) | N/A |
| 160 | Sense (Fully Exonic) | GXYLT2 |
| 161 | Sense (includes Intronic) | KLF12 |
| 162 | No Transcript match | |
| 163 | Sense (Fully Exonic) | FBXO32 |
| 164 | No Transcript match | |
| 165 | Sense (Fully Exonic) | ASAH2B |
| 166 | AntiSense | PPFIBP1 |
| 167 | AntiSense | XIST |
| 168 | Sense (Fully Exonic) | IGFBP6 |
| 169 | Sense (Fully Exonic) | ROBO1 |
| 170 | Sense (Fully Exonic) | TPM1 |
| 171 | AntiSense | N/A |
| 172 | AntiSense | PLEKHG1 |
| 173 | Sense (Fully Exonic) | NR2F1 |
| 174 | Sense (Fully Exonic) | NPDC1 |
| 175 | AntiSense | INS |
| 176 | Sense (Fully Exonic) | TRAF5 |
| 177 | Sense (Fully Exonic) | CALD1 |
| 178 | Sense (includes Intronic) | CHRM3 |
| 179 | Sense (Fully Exonic) | AMOTL1 |
| 180 | Sense (includes Intronic) | COL12A1 |
| 181 | Sense (Fully Exonic) | PLXNA4 |
| 182 | Sense (includes Intronic) | TMEM43 |
| 183 | Sense (includes Intronic) | RORA |
| 184 | AntiSense | INS |
| 185 | Sense (Fully Exonic) | TSPAN18 |
| 186 | No Transcript match | |
| 187 | Sense (Fully Exonic) | TNC |

TABLE 1-continued

| Genes in Clusters of FIG. 1 | | |
|---|---|---|
| SEQ NO: | Orientation | Gene Symbol |
| 188 | Sense (Fully Exonic) | TYRO3 |
| 189 | AntiSense | EFNA5 |
| 190 | Sense (Fully Exonic) | MYL9 |
| 191 | Sense (Fully Exonic) | MIR198 |
| 192 | Sense (includes Intronic) | N/A |
| 193 | Sense (includes Intronic) | PLA2R1 |
| 194 | Sense (Fully Exonic) | COL14A1 |
| 195 | Sense (Fully Exonic) | NRP1 |
| 196 | Sense (Fully Exonic) | FSCN1 |
| 197 | Sense (includes Intronic) | PDGFD |
| 198 | No Transcript match | |
| 199 | Sense (includes Intronic) | DOCK4 |
| 200 | Sense (Fully Exonic) | TRIM13 |
| 201 | Sense (Fully Exonic) | IGFBP5 |
| 202 | Sense (Fully Exonic) | C19orf63 |
| 203 | AntiSense | KLF6 |
| 204 | AntiSense | TRIO |
| 205 | Sense (Fully Exonic) | COL4A1 |
| 206 | Sense (Fully Exonic) | EPDR1 |
| 207 | Sense (Fully Exonic) | FNDC1 |
| 208 | Sense (Fully Exonic) | IL1R1 |
| 209 | Sense (Fully Exonic) | CES4 |
| 210 | Sense (Fully Exonic) | GPR176 |
| 211 | Sense (includes Intronic) | GXYLT2 |
| 212 | AntiSense | WHSC1L1 |
| 213 | Sense (Fully Exonic) | N/A |
| 214 | Sense (Fully Exonic) | RGN |
| 215 | Sense (includes Intronic) | CA3 |
| 216 | Sense (Fully Exonic) | TIMP3 |
| 217 | Sense (Fully Exonic) | EFNA5 |
| 218 | Sense (Fully Exonic) | RASGRF2 |
| 219 | Sense (includes Intronic) | RELL1 |
| 220 | AntiSense | ACSS3 |
| 221 | Sense (Fully Exonic) | STMN3 |
| 222 | Sense (Fully Exonic) | N/A |
| 223 | AntiSense | C7orf29 |
| 224 | Sense (Fully Exonic) | HOXC6 |
| 225 | Sense (Fully Exonic) | KLF8 |
| 226 | Sense (includes Intronic) | SERINC5 |
| 227 | Sense (Fully Exonic) | AKT3 |
| 228 | Sense (Fully Exonic) | TGFB2 |
| 229 | AntiSense | WNT5A |
| 230 | No Transcript match | |
| 231 | No Transcript match | |
| 232 | AntiSense | IGFBP7 |
| 233 | No Transcript match | |
| 234 | Sense (includes Intronic) | SULT1C4 |
| 235 | Sense (Fully Exonic) | AASS |
| 236 | Sense (Fully Exonic) | HEPH |
| 237 | Sense (Fully Exonic) | ADH5 |
| 238 | Sense (Fully Exonic) | TIMP2 |
| 239 | Sense (Fully Exonic) | EMP1 |
| 240 | Sense (Fully Exonic) | CXCL14 |
| 241 | Sense (Fully Exonic) | ZNF548 |
| 242 | Sense (Fully Exonic) | SGCB |
| 243 | Sense (includes Intronic) | ASH2L |
| 244 | Sense (includes Intronic) | SERINC5 |
| 245 | No Genome match | |
| 246 | Sense (Fully Exonic) | TMEM159 |
| 247 | Sense (includes Intronic) | RBMS3 |
| 248 | Sense (Fully Exonic) | TMEM49 |
| 249 | Sense (includes Intronic) | RORA |
| 250 | No Transcript match | |
| 251 | AntiSense | ZNF608 |
| 252 | No Genome match | |
| 253 | Sense (Fully Exonic) | ADAMTS2 |
| 254 | Sense (Fully Exonic) | APCDD1 |
| 255 | AntiSense | GXYLT2 |
| 256 | Sense (Fully Exonic) | XIST |
| 257 | Sense (Fully Exonic) | MBNL2 |
| 258 | Sense (Fully Exonic) | SHF |
| 259 | Sense (includes Intronic) | APBB2 |
| 260 | No Transcript match | |
| 261 | Sense (Fully Exonic) | COL14A1 |
| 262 | Sense (Fully Exonic) | IGFBP5 |
| 263 | Sense (Fully Exonic) | CREB5 |

TABLE 1-continued

| Genes in Clusters of FIG. 1 | | |
|---|---|---|
| SEQ NO: | Orientation | Gene Symbol |
| 264 | AntiSense | INS |
| 265 | Sense (Fully Exonic) | BAHCC1 |
| 266 | Sense (Fully Exonic) | RFXAP |
| 267 | Sense (Fully Exonic) | INS |
| 268 | Sense (Fully Exonic) | DDR2 |
| 269 | Sense (Fully Exonic) | CA12 |
| 270 | Sense (Fully Exonic) | RHOB |
| 271 | Sense (Fully Exonic) | N/A |
| 272 | Sense (Fully Exonic) | SNORD116-4 |
| 273 | Sense (Fully Exonic) | MEG3 |
| 274 | Sense (Fully Exonic) | WNT4 |
| 275 | Sense (Fully Exonic) | FBLN2 |
| 276 | AntiSense | DAAM1 |
| 277 | No Transcript match | |
| 278 | Sense (Fully Exonic) | CHN1 |
| 279 | Sense (includes Intronic) | APBB2 |
| 280 | Sense (Fully Exonic) | PTRF |
| 281 | AntiSense | IGF1 |
| 282 | Sense (Fully Exonic) | UST |
| 283 | Sense (Fully Exonic) | SMARCA1 |
| 284 | Sense (includes Intronic) | N/A |
| 285 | Sense (Fully Exonic) | IGLC3 |
| 286 | AntiSense | INS |
| 287 | Sense (Fully Exonic) | KANK4 |
| 288 | AntiSense | IGF1 |
| 289 | Sense (Fully Exonic) | CYP27A1 |
| 290 | AntiSense | EIF2B5 |
| 291 | No Transcript match | |
| 292 | Sense (Fully Exonic) | SNRNP25 |
| 293 | Sense (Fully Exonic) | SETD7 |
| 294 | Sense (Fully Exonic) | MSX1 |
| 295 | Sense (Fully Exonic) | HOPX |
| 296 | Sense (Fully Exonic) | NID2 |
| 297 | Sense (Fully Exonic) | IGF1 |
| 298 | Sense (Fully Exonic) | PSD3 |
| 299 | Sense (Fully Exonic) | FGFR1 |
| 300 | Sense (Fully Exonic) | ETV1 |
| 301 | Sense (Fully Exonic) | ZNF655 |
| 302 | No Genome match | |
| 303 | AntiSense | INS |
| 304 | Sense (Fully Exonic) | SFRP2 |
| 305 | Sense (Fully Exonic) | SPAG16 |
| 306 | AntiSense | NR2F2 |
| 307 | Sense (includes Intronic) | SYNPO2 |
| 308 | Sense (Fully Exonic) | FAM101B |
| 309 | AntiSense | IGF2 |
| 310 | Sense (Fully Exonic) | CA3 |
| 311 | Sense (Fully Exonic) | XIST |
| 312 | No Transcript match | |
| 313 | Sense (Fully Exonic) | WNT7A |
| 314 | Sense (includes Intronic) | N/A |
| 315 | Sense (Fully Exonic) | FGFR1 |
| 316 | AntiSense | FXYD6 |
| 317 | Sense (Fully Exonic) | FGFR1 |
| 318 | Sense (includes Intronic) | IGFBP7 |
| 319 | Sense (Fully Exonic) | TIMP2 |
| 320 | Sense (Fully Exonic) | DUSP1 |
| 321 | Sense (includes Intronic) | SERINC5 |
| 322 | No Transcript match | |
| 323 | Sense (Fully Exonic) | ABLIM1 |
| 324 | Sense (Fully Exonic) | ARL4A |
| 325 | AntiSense | SH3TC2 |
| 326 | AntiSense | NR2F2 |
| 327 | Sense (Fully Exonic) | ENG |
| 328 | Sense (Fully Exonic) | MGP |
| 329 | Sense (Fully Exonic) | MEG3 |
| 330 | AntiSense | FAM115A |
| 331 | Sense (Fully Exonic) | EGR1 |
| 332 | Sense (Fully Exonic) | SNORD116-3 |
| 333 | Sense (Fully Exonic) | AEBP1 |
| 334 | Sense (includes Intronic) | SDK1 |
| 335 | Sense (Fully Exonic) | ENC1 |
| 336 | Sense (Fully Exonic) | SNORD116-7 |
| 337 | Sense (Fully Exonic) | N/A |
| 338 | Sense (Fully Exonic) | APOD |
| 339 | AntiSense | N/A |

TABLE 1-continued

| Genes in Clusters of FIG. 1 | | |
|---|---|---|
| SEQ NO: | Orientation | Gene Symbol |
| 340 | AntiSense | GAS1 |
| 341 | Sense (Fully Exonic) | VPS36 |
| 342 | No Transcript match | |
| 343 | Sense (Fully Exonic) | SPHK2 |
| 344 | Sense (Fully Exonic) | SNORD116-8 |
| 345 | Sense (Fully Exonic) | MYO10 |
| 346 | Sense (Fully Exonic) | HOXC6 |
| 347 | Sense (Fully Exonic) | RNF149 |
| 348 | Sense (Fully Exonic) | BTG2 |
| 349 | Sense (includes Intronic) | MAP3K1 |
| 350 | Sense (Fully Exonic) | SNORD116-23 |
| 351 | Sense (includes Intronic) | ACSL4 |
| 352 | Sense (Fully Exonic) | CYP27C1 |
| 353 | Sense (includes Intronic) | COL12A1 |
| 354 | Sense (Fully Exonic) | IGFBP5 |
| 355 | Sense (Fully Exonic) | DUSP4 |
| 356 | Sense (Fully Exonic) | PFKFB3 |
| 357 | Sense (Fully Exonic) | SDC2 |
| 358 | AntiSense | FXYD6 |
| 359 | Sense (Fully Exonic) | COL5A1 |
| 360 | Sense (Fully Exonic) | MARCKS |
| 361 | Sense (Fully Exonic) | IRS2 |
| 362 | Sense (Fully Exonic) | N/A |
| 363 | AntiSense | FSCN1 |
| 364 | Sense (Fully Exonic) | FYN |
| 365 | Sense (Fully Exonic) | IGFBP5 |
| 366 | Sense (Fully Exonic) | NUDT4P1 |
| 367 | Sense (Fully Exonic) | NFKBIZ |
| 368 | Sense (Fully Exonic) | N/A |
| 369 | Sense (Fully Exonic) | C7orf41 |
| 370 | Sense (Fully Exonic) | MEG3 |
| 371 | Sense (Fully Exonic) | N/A |
| 372 | Sense (Fully Exonic) | PLEKHG1 |
| 373 | Sense (Fully Exonic) | ZNF827 |
| 374 | Sense (Fully Exonic) | ZNF175 |
| 375 | Sense (Fully Exonic) | XIST |
| 376 | Sense (includes Intronic) | GSN |
| 377 | Sense (includes Intronic) | RORA |
| 378 | Sense (Fully Exonic) | CA13 |
| 379 | AntiSense | TMX4 |
| 380 | Sense (Fully Exonic) | KIT |
| 381 | Sense (includes Intronic) | WDR78 |
| 382 | Sense (Fully Exonic) | ECEL1 |
| 383 | Sense (Fully Exonic) | XIST |
| 384 | Sense (Fully Exonic) | PROCR |
| 385 | Sense (Fully Exonic) | C9orf167 |
| 386 | Sense (Fully Exonic) | MUC6 |
| 387 | Sense (includes Intronic) | P4HA2 |
| 388 | Sense (Fully Exonic) | FAM69C |
| 389 | Sense (Fully Exonic) | NOX4 |
| 390 | Sense (includes Intronic) | N/A |
| 391 | No Transcript match | |
| 392 | Sense (Fully Exonic) | SMOX |
| 393 | Sense (Fully Exonic) | KIAA0922 |
| 394 | No Transcript match | |
| 395 | Sense (Fully Exonic) | XIST |
| 396 | Sense (Fully Exonic) | NPAS2 |
| 397 | Sense (Fully Exonic) | NAV1 |
| 398 | Sense (includes Intronic) | N/A |
| 399 | Sense (Fully Exonic) | HLA-A |
| 400 | Sense (Fully Exonic) | FAM46C |
| 401 | Sense (Fully Exonic) | N/A |
| 402 | Sense (Fully Exonic) | SLAMF7 |
| 403 | Sense (Fully Exonic) | FCER1G |
| 404 | Sense (Fully Exonic) | C1S |
| 405 | Sense (Fully Exonic) | NUPR1 |
| 406 | AntiSense | C1QC |
| 407 | AntiSense | SAT1 |
| 408 | Sense (Fully Exonic) | SOD2 |
| 409 | Sense (Fully Exonic) | IRF1 |
| 410 | Sense (Fully Exonic) | SFN |
| 411 | AntiSense | LTB |
| 412 | Sense (Fully Exonic) | ARID5A |
| 413 | Sense (Fully Exonic) | BST2 |
| 414 | Sense (Fully Exonic) | HLA-F |
| 415 | Sense (Fully Exonic) | XAF1 |

TABLE 1-continued

| Genes in Clusters of FIG. 1 | | |
|---|---|---|
| SEQ NO: | Orientation | Gene Symbol |
| 416 | Sense (Fully Exonic) | TCOF1 |
| 417 | Sense (Fully Exonic) | RPL23AP1 |
| 418 | Sense (Fully Exonic) | IL1RN |
| 419 | Sense (Fully Exonic) | IFIT5 |
| 420 | Sense (Fully Exonic) | B2M |
| 421 | AntiSense | GBP1 |
| 422 | Sense (Fully Exonic) | HLA-F |
| 423 | Sense (Fully Exonic) | DGKA |
| 424 | Sense (Fully Exonic) | XBP1 |
| 425 | Sense (Fully Exonic) | PLCG2 |
| 426 | Sense (Fully Exonic) | FAM46C |
| 427 | No Genome match | |
| 428 | Sense (Fully Exonic) | TREM2 |
| 429 | Sense (Fully Exonic) | LGALS9 |
| 430 | Sense (Fully Exonic) | HLA-DPB1 |
| 431 | AntiSense | ODF3B |
| 432 | Sense (Fully Exonic) | MX1 |
| 433 | Sense (Fully Exonic) | STAT1 |
| 434 | Sense (Fully Exonic) | CTSB |
| 435 | Sense (Fully Exonic) | FAM26F |
| 436 | Sense (includes Intronic) | PARP14 |
| 437 | AntiSense | SAT1 |
| 438 | Sense (Fully Exonic) | CTSS |
| 439 | No Transcript match | |
| 440 | Sense (Fully Exonic) | CTSB |
| 441 | Sense (Fully Exonic) | ADAM8 |
| 442 | Sense (includes Intronic) | B2M |
| 443 | Sense (Fully Exonic) | FLVCR2 |
| 444 | Sense (Fully Exonic) | TYROBP |
| 445 | AntiSense | SAMD9L |
| 446 | Sense (Fully Exonic) | SAMD9L |
| 447 | Sense (Fully Exonic) | SIGLEC1 |
| 448 | Sense (Fully Exonic) | MMP7 |
| 449 | Sense (Fully Exonic) | APOL1 |
| 450 | Sense (Fully Exonic) | CYLD |
| 451 | Sense (Fully Exonic) | HLA-B |
| 452 | Sense (Fully Exonic) | SAT1 |
| 453 | Sense (Fully Exonic) | C1QB |
| 454 | Sense (Fully Exonic) | HLA-DMB |
| 455 | Sense (Fully Exonic) | NLRC5 |
| 456 | Sense (Fully Exonic) | FAM20A |
| 457 | AntiSense | N/A |
| 458 | Sense (Fully Exonic) | STAT1 |
| 459 | Sense (includes Intronic) | STAT1 |
| 460 | Sense (Fully Exonic) | STAT1 |
| 461 | AntiSense | N/A |
| 462 | Sense (Fully Exonic) | DERL3 |
| 463 | Sense (Fully Exonic) | HLA-F |
| 464 | Sense (Fully Exonic) | MAFB |
| 465 | Sense (Fully Exonic) | CD4 |
| 466 | Sense (Fully Exonic) | HLA-A |
| 467 | Sense (Fully Exonic) | UBE2L6 |
| 468 | Sense (Fully Exonic) | C1QC |
| 469 | Sense (Fully Exonic) | CD163 |
| 470 | Sense (Fully Exonic) | LRMP |
| 471 | Sense (Fully Exonic) | C11orf17 |
| 472 | Sense (Fully Exonic) | XAF1 |
| 473 | Sense (Fully Exonic) | GLRX |
| 474 | Sense (Fully Exonic) | IFIH1 |
| 475 | Sense (Fully Exonic) | CD44 |
| 476 | Sense (Fully Exonic) | LITAF |
| 477 | Sense (Fully Exonic) | CCDC69 |
| 478 | Sense (Fully Exonic) | GBP5 |
| 479 | Sense (Fully Exonic) | PML |
| 480 | Sense (Fully Exonic) | SAMD9 |
| 481 | Sense (Fully Exonic) | CBR3 |
| 482 | Sense (Fully Exonic) | RASGRP2 |
| 483 | Sense (Fully Exonic) | FCGR2A |
| 484 | Sense (Fully Exonic) | BST2 |
| 485 | Sense (Fully Exonic) | HLA-A |
| 486 | Antisense | COL1A1 |
| 487 | No Genome Match | |
| 488 | No Genome Match | |

In certain example embodiments, all or a portion of the biomarkers recited in Table 1 may be used in an expression signature. For example, expression signatures comprising the biomarkers in Table 1 can be generated using the methods provided herein and can comprise between one, and all of the markers set forth in Tables 1 and each and every combination in between (e.g., four selected markers, 16 selected markers, 74 selected markers, etc.). In some embodiments, the expression signature comprises at least 5, 10, 20, 40, 60, 100, 150, 200, or 300 or more markers. In other embodiments, the predictive biomarker panel comprises no more than 5, 10, 20, 40, 60, 100, 150, 200, 300, 400, 500, 600 or 700 markers. In one example embodiment, the expression signature includes a plurality of markers listed in Table 1. In some embodiments the expression signature includes at least about 1%, about 5%, about 10%, about 20%, about 30%, about 40%, about 50%, about 60%, about 70%, about 80%, about 90%, about 95%, about 96%, about 97%, about 98%, or about 99% of the markers listed in Table 1. Selected expression signatures can be assembled from the biomarkers provided using methods described herein and analogous methods known in the art. In one embodiment, the expression signature contains all genes or gene products in Table 1.

4. Mathematical Models

The following methods may be used to derive expression signatures for distinguishing between subjects that are responsive or non-responsive to anti-angiogenic therapeutics, or as prognostic indicators of certain cancer types, including expression signatures derived from the biomarkers disclosed above. In certain other example embodiments, the expression signature is derived using a decision tree (Hastie et al. The Elements of Statistical Learning, Springer, New York 2001), a random forest (Breiman, 2001 Random Forests, Machine Learning 45:5), a neural network (Bishop, Neural Networks for Pattern Recognition, Clarendon Press, Oxford 1995), discriminant analysis (Duda et al. Pattern Classification, 2nd ed., John Wiley, New York 2001), including, but not limited to linear, diagonal linear, quadratic and logistic discriminant analysis, a Prediction Analysis for Microarrays (PAM, (Tibshirani et al., 2002, Proc. Natl. Acad. Sci. USA 99:6567-6572)) or a Soft Independent Modeling of Class Analogy analysis. (SIMCA, (Wold, 1976, Pattern Recogn. 8:127-139)).

Biomarker expression values may be defined in combination with corresponding scalar weights on the real scale with varying magnitude, which are further combined through linear or non-linear, algebraic, trigonometric or correlative means into a single scalar value via an algebraic, statistical learning, Bayesian, regression, or similar algorithms which together with a mathematically derived decision function on the scalar value provide a predictive model by which expression profiles from samples may be resolved into discrete classes of responder or non-responder, resistant or non-resistant, to a specified drug, drug class, molecular subtype, or treatment regimen. Such predictive models, including biomarker membership, are developed by learning weights and the decision threshold, optimized for sensitivity, specificity, negative and positive predictive values, hazard ratio or any combination thereof, under cross-validation, bootstrapping or similar sampling techniques, from a set of representative expression profiles from historical patient samples with known drug response and/or resistance.

In one embodiment, the biomarkers are used to form a weighted sum of their signals, where individual weights can be positive or negative. The resulting sum ("expression score") is compared with a pre-determined reference point or value. The comparison with the reference point or value may be used to diagnose, or predict a clinical condition or outcome.

As described above, one of ordinary skill in the art will appreciate that the biomarkers included in the classifier provided in Tables 1 will carry unequal weights in a classifier for determining clinical prognosis. Therefore, while as few as one biomarker may be used to diagnose or predict an clinical prognosis or response to a therapeutic agent, the specificity and sensitivity or diagnosis or prediction accuracy may increase using more biomarkers.

As used herein, the term "weight" refers to the absolute magnitude of an item in a statistical calculation. The weight of each biomarker in a gene expression classifier may be determined on a data set of patient samples using learning methods known in the art. As used herein the term "bias" or "offset" refers to a constant term derived using the mean expression of the signatures genes in a training set and is used to mean-center the each gene analyzed in the test dataset.

In certain example embodiments, the expression signature is defined by a decision function. A decision function is a set of weighted expression values derived using a linear classifier. All linear classifiers define the decision function using the following equation:

$$f(x)=w'\cdot x\ b=\Sigma w_i\cdot x_i+b \quad (1)$$

All measurement values, such as the microarray gene expression intensities $x_i$, for a certain sample are collected in a vector x. Each intensity is then multiplied with a corresponding weight $w_i$ to obtain the value of the decision function $f(x)$ after adding an offset term b. In deriving the decision function, the linear classifier will further define a threshold value that splits the gene expression data space into two disjoint sections. Example linear classifiers include but are not limited to partial least squares (PLS), (Nguyen et al., Bioinformatics 18 (2002) 39-50), support vector machines (SVM) (Schölkopf et al., Learning with Kernels, MIT Press, Cambridge 2002), and shrinkage discriminant analysis (SDA) (Ahdesmäki et al., Annals of applied statistics 4, 503-519 (2010)). In one example embodiment, the linear classifier is a PLS linear classifier.

The decision function is empirically derived on a large set of training samples, for example from patients showing a good or poor clinical prognosis. The threshold separates a patient group based on different characteristics such as, but not limited to, clinical prognosis before or after a given therapeutic treatment. The interpretation of this quantity, i.e. the cut-off threshold, is derived in the development phase ("training") from a set of patients with known outcome. The corresponding weights and the responsiveness/resistance cut-off threshold for the decision score are fixed a priori from training data by methods known to those skilled in the art. In one example embodiment, Partial Least Squares Discriminant Analysis (PLS-DA) is used for determining the weights. (L. Ståhle, S. Wold, J. Chemom. 1 (1987) 185-196; D. V. Nguyen, D. M. Rocke, Bioinformatics 18 (2002) 39-50).

Effectively, this means that the data space, i.e. the set of all possible combinations of biomarker expression values, is split into two mutually exclusive groups corresponding to different clinical classifications or predictions, for example, one corresponding to good clinical prognosis and poor clinical prognosis. In the context of the overall classifier, relative over-expression of a certain biomarker can either increase the decision score (positive weight) or reduce it (negative weight) and thus contribute to an overall decision of, for example, a good clinical prognosis.

In certain example embodiments of the invention, the data is transformed non-linearly before applying a weighted sum as described above. This non-linear transformation might include increasing the dimensionality of the data. The non-linear transformation and weighted summation might also be performed implicitly, for example, through the use of a kernel function. (Schölkopf et al. Learning with Kernels, MIT Press, Cambridge 2002).

In certain example embodiments, the patient training set data is derived by isolated RNA from a corresponding cancer tissue sample set and determining expression values by hybridizing the isolated RNA to a microarray. In certain example embodiments, the microarray used in deriving the expression signature is a transcriptome array. As used herein a "transcriptome array" refers to a microarray containing probe sets that are designed to hybridize to sequences that have been verified as expressed in the diseased tissue of interest. Given alternative splicing and variable poly-A tail processing between tissues and biological contexts, it is possible that probes designed against the same gene sequence derived from another tissue source or biological context will not effectively bind to transcripts expressed in the diseased tissue of interest, leading to a loss of potentially relevant biological information. Accordingly, it is beneficial to verify what sequences are expressed in the disease tissue of interest before deriving a microarray probe set. Verification of expressed sequences in a particular disease context may be done, for example, by isolating and sequencing total RNA from a diseased tissue sample set and cross-referencing the isolated sequences with known nucleic acid sequence databases to verify that the probe set on the transcriptome array is designed against the sequences actually expressed in the diseased tissue of interest. Methods for making transcriptome arrays are described in United States Patent Application Publication No. 2006/0134663, which is incorporated herein by reference. In certain example embodiments, the probe set of the transcriptome array is designed to bind within 300 nucleotides of the 3' end of a transcript. Methods for designing transcriptome arrays with probe sets that bind within 300 nucleotides of the 3' end of target transcripts are disclosed in United States Patent Application Publication No. 2009/0082218, which is incorporated by reference herein. In certain example embodiments, the microarray used in deriving the gene expression profiles of the present invention is the Almac Ovarian Cancer DSA™ microarray (Almac Group, Craigavon, United Kingdom).

An optimal linear classifier can be selected by evaluating a linear classifier's performance using such diagnostics as "area under the curve" (AUC). AUC refers to the area under the curve of a receiver operating characteristic (ROC) curve, both of which are well known in the art. AUC measures are useful for comparing the accuracy of a classifier across the complete data range. Linear classifiers with a higher AUC have a greater capacity to classify unknowns correctly between two groups of interest (e.g., ovarian cancer samples and normal or control samples). ROC curves are useful for plotting the performance of a particular feature (e.g., any of the biomarkers described herein and/or any item of additional biomedical information) in distinguishing between two populations (e.g., individuals responding and not responding to a therapeutic agent). Typically, the feature data across the entire population (e.g., the cases and controls) are sorted in ascending order based on the value of a single feature. Then, for each value for that feature, the true positive and false positive rates for the data are calculated. The true positive rate is determined by counting the number of cases above the value for that feature and then dividing by the total number of positive cases. The false positive rate is determined by counting the number of controls above the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to provide a single sum value, and this single sum value can be plotted in a ROC curve. Additionally, any combination of multiple features, in which the combination derives a single output value, can be plotted in a ROC curve. These combinations of features may comprise a test. The ROC curve is the plot of the true positive rate (sensitivity) of a test against the false positive rate (1-specificity) of the test.

In one example embodiment an angiogenesis expression signature is directed to the 63 biomarkers detailed in Table 2 with corresponding ranks, and weights and associated bias detailed in the table or alternative rankings, and weightings and bias, depending, for example, on the disease setting. Table 2 ranks the biomarkers in order of absolute decreasing weight, in an example classifier, in the compound decision score function. The methods of the invention may rely upon measuring one or more, up to all, of the biomarkers listed in table 2. The methods of the invention may comprise measuring the expression levels of at least 2, 3, 4, 5, 6, 7, 8, 9, 10, 11, 12, 13, 14, 15, 16, 17, 18, 19, 20, 25, 30, 40, 50, 60 or each of the biomarkers from Table 2. In certain embodiments the method may comprise measuring the expression levels of 2 to 5 of the biomarkers from Table 2.

TABLE 2

63 Biomarker Signature

| Rank | Gene Symbol | Weight | Bias |
|---|---|---|---|
| 1 | IGF2 | −0.01737 | 9.8884 |
| 2 | SOX11 | −0.01457 | 4.5276 |
| 3 | INS | −0.01409 | 7.0637 |
| 4 | CXCL17 | 0.012568 | 4.8478 |
| 5 | SLC5A1 | 0.012426 | 4.8920 |
| 6 | TMEM45A | −0.0124 | 6.1307 |
| 7 | CXCR2P1 | 0.011427 | 3.1478 |
| 8 | MFAP2 | −0.01039 | 9.0516 |
| 9 | MATN3 | −0.01028 | 3.7313 |
| 10 | RTP4 | 0.010052 | 4.9852 |
| 11 | COL3A1 | −0.01002 | 8.4130 |
| 12 | CDR1 | −0.00916 | 8.1778 |
| 13 | RARRES3 | 0.009056 | 6.8964 |
| 14 | TNFSF10 | 0.008876 | 6.2325 |
| 15 | NUAK1 | −0.0087 | 6.6771 |
| 16 | SNORD114-14 | −0.00864 | 5.6385 |
| 17 | SRPX | −0.00862 | 5.0850 |
| 18 | SPARC | −0.00848 | 6.0135 |
| 19 | GJB1 | 0.008445 | 5.8142 |
| 20 | TIMP3 | −0.00823 | 6.5937 |
| 21 | ISLR | −0.0079 | 8.9876 |
| 22 | TUBA1A | −0.00754 | 9.6540 |
| 23 | DEXI | 0.007271 | 5.5913 |
| 24 | BASP1 | −0.00724 | 8.4396 |
| 25 | PXDN | −0.00724 | 7.7570 |
| 26 | GBP4 | 0.007226 | 3.1119 |
| 27 | SLC28A3 | 0.007201 | 4.2125 |
| 28 | HLA-DRA | 0.007197 | 8.3089 |
| 29 | TAP2 | 0.007189 | 4.8464 |
| 30 | ACSL5 | 0.007155 | 6.8703 |

TABLE 2-continued

| 63 Biomarker Signature | | | |
|---|---|---|---|
| Rank | Gene Symbol | Weight | Bias |
| 31 | CDH11 | −0.00708 | 4.9925 |
| 32 | PSMB9 | 0.006962 | 4.1122 |
| 33 | MMP14 | −0.00683 | 10.1689 |
| 34 | CD74 | 0.006825 | 9.2707 |
| 35 | LOXL1 | −0.00676 | 9.6429 |
| 36 | CIITA | 0.006623 | 5.5396 |
| 37 | ZNF697 | −0.00658 | 7.0319 |
| 38 | SH3RF2 | 0.006549 | 5.0029 |
| 39 | MIR198 | −0.00654 | 5.1935 |
| 40 | COL1A2 | −0.00645 | 6.0427 |
| 41 | TNFRSF14 | 0.006421 | 9.0366 |
| 42 | COL8A1 | −0.00642 | 6.4565 |
| 43 | C21orf63 | 0.006261 | 5.9811 |
| 44 | TAP1 | 0.006215 | 8.6458 |
| 45 | PDPN | −0.00612 | 5.3198 |
| 46 | RHOBTB3 | −0.00597 | 3.5609 |
| 47 | BCL11A | 0.005943 | 4.3818 |
| 48 | HLA-DOB | 0.005851 | 4.6075 |
| 49 | XAF1 | 0.005742 | 7.9229 |
| 50 | ARHGAP26 | 0.005632 | 4.3991 |
| 51 | POLD2 | −0.00558 | 9.4183 |
| 52 | DPYSL2 | −0.00533 | 8.3469 |
| 53 | COL4A1 | −0.0052 | 7.0317 |
| 54 | ID3 | −0.00516 | 7.5673 |
| 55 | CFB | 0.005077 | 5.7951 |
| 56 | NID1 | −0.00494 | 4.7186 |
| 57 | FKBP7 | −0.00489 | 2.9437 |
| 58 | TIMP2 | −0.00468 | 7.5253 |
| 59 | RCBTB1 | −0.00458 | 7.4491 |
| 60 | ANGPTL2 | −0.00448 | 5.6807 |
| 61 | ENTPD7 | −0.00442 | 7.3772 |
| 62 | SHISA4 | −0.00403 | 6.0601 |
| 63 | HINT1 | 0.003651 | 6.0724 |

In another example embodiment an angiogenesis expression signature is directed to the 63 biomarkers detailed in Table 3 with corresponding ranks detailed in the table or alternative rankings depending, for example, on the disease setting. Table 3 ranks the biomarkers in order of absolute decreasing weight, in an example classifier, in the compound decision score function. The methods of the invention may rely upon measuring one or more, up to all, of the biomarkers listed in table 3. The methods of the invention may comprise measuring the expression levels of at least 2, 3, 4, 5, 6, 7, 8, 9, 10, 11, 12, 13, 14, 15, 16, 17, 18, 19, 20, 25, 30, 40, 50, 60 or each of the biomarkers from Table 3. In certain embodiments the methods may comprise measuring the expression levels of 2 to 5 of the biomarkers from Table 3.

TABLE 3

| Gene | Total Delta HR | Rank |
|---|---|---|
| IGF2 | 0.048910407 | 1 |
| CDR1 | 0.045335288 | 2 |
| COL3A1 | 0.044869217 | 3 |
| SPARC | 0.043434096 | 4 |
| TIMP3 | 0.042053053 | 5 |
| INS | 0.04013658 | 6 |
| COL8A1 | 0.026780907 | 7 |
| NUAK1 | 0.026752491 | 8 |
| MATN3 | 0.02402318 | 9 |
| TMEM45A | 0.016999761 | 10 |
| SRPX | 0.016372168 | 11 |
| CDH11 | 0.015604812 | 12 |
| MMP14 | 0.014583388 | 13 |
| LOXL1 | 0.010315358 | 14 |
| PXDN | 0.009728534 | 15 |
| COL1A2 | 0.009267887 | 16 |
| ANGPTL2 | 0.006071504 | 17 |

TABLE 3-continued

| Gene | Total Delta HR | Rank |
|---|---|---|
| POLD2 | 0.004297935 | 18 |
| NID1 | 0.00408724 | 19 |
| ISLR | 0.003014488 | 20 |
| SNORD114-14 | 0.002992636 | 21 |
| CXCR2P1 | 0.002804432 | 22 |
| MIR198 | 0.002173041 | 23 |
| BCL11A | 0.001258286 | 24 |
| PDPN | 0.000989109 | 25 |
| TNFRSF14 | 0.000132838 | 26 |
| ENTPD7 | 6.25143E−05 | 27 |
| HINT1 | −0.000113156 | 28 |
| TAP1 | −0.000379242 | 29 |
| ID3 | −0.000452476 | 30 |
| RCBTB1 | −0.000695459 | 31 |
| SOX11 | −0.001068812 | 32 |
| SHISA4 | −0.001470801 | 33 |
| COL4A1 | −0.001714442 | 34 |
| TUBA1A | −0.001817696 | 35 |
| TIMP2 | −0.004079263 | 36 |
| FKBP7 | −0.004575097 | 37 |
| TAP2 | −0.004597761 | 38 |
| TNFSF10 | −0.005307314 | 39 |
| ZNF697 | −0.007733496 | 40 |
| CIITA | −0.008785689 | 41 |
| BASP1 | −0.009340492 | 42 |
| XAF1 | −0.009760794 | 43 |
| DEXI | −0.009798099 | 44 |
| SH3RF2 | −0.009856754 | 45 |
| HLA-DOB | −0.009987248 | 46 |
| RHOBTB3 | −0.010264542 | 47 |
| GBP4 | −0.010747831 | 48 |
| DPYSL2 | −0.012042179 | 49 |
| ARHGAP26 | −0.012380203 | 50 |
| MFAP2 | −0.013981916 | 51 |
| CD74 | −0.016415304 | 52 |
| ACSL5 | −0.016912224 | 53 |
| SLC28A3 | −0.016996213 | 54 |
| GJB1 | −0.018395345 | 55 |
| C21orf63 | −0.019853038 | 56 |
| PSMB9 | −0.020314379 | 57 |
| HLA-DRA | −0.020436677 | 58 |
| CFB | −0.022202886 | 59 |
| RARRES3 | −0.034723666 | 60 |
| CXCL17 | −0.038523986 | 61 |
| SLC5A1 | −0.042034346 | 62 |
| RTP4 | −0.045259104 | 63 |

Probesets that can be used to measure the expression of the biomarkers are shown in Table 4.

TABLE 4

| Probeset | Gene | SEQ ID No. |
|---|---|---|
| OC3P.6916.C1_s_at | ACSL5 | 489 |
| OC3P.5381.C1_s_at | ACSL5 | 490 |
| OC3P.2679.C1_s_at | ANGPTL2 | 491 |
| ADXStrongB12_at | ANGPTL2 | N/A |
| OC3P.9834.C1_s_at | ANGPTL2 | 492 |
| OCMX.9546.C1_x_at | ANGPTL2 | 493 |
| OCADA.8226_s_at | ANGPTL2 | 494 |
| OCADNP.8811_s_at | ANGPTL2 | 495 |
| OCADA.3065_s_at | ARHGAP26 | 496 |
| OCADA.1272_s_at | ARHGAP26 | 497 |
| OC3SNGnh.16379_x_at | ARHGAP26 | 498 |
| OCMX.11710.C1_at | ARHGAP26 | 499 |
| OCADA.4396_s_at | ARHGAP26 | 500 |
| OC3P.15451.C1_at | ARHGAP26 | 501 |
| OC3SNGnh.16379_at | ARHGAP26 | 502 |
| OC3SNGnh.17316_s_at | ARHGAP26 | 503 |
| OCADA.964_s_at | ARHGAP26 | 504 |
| OC3SNGnh.6403_s_at | ARHGAP26 | 505 |
| OC3P.3912.C1_s_at | ARHGAP26 | 506 |
| OC3P.2419.C1_s_at | BASP1 | 507 |
| OCRS2.9952_s_at | BASP1 | 508 |
| OCRS2.9952_x_at | BASP1 | 509 |

TABLE 4-continued

| Probeset | Gene | SEQ ID No. |
|---|---|---|
| OCRS.854_s_at | BCL11A | 510 |
| OC3P.14938.C1_s_at | BCL11A | 511 |
| OCMX.12290.C1_at | BCL11A | 512 |
| OCADA.10230_s_at | BCL11A | 513 |
| OC3SNGnh.4343_at | BCL11A | 514 |
| OC3SNGnh.16766_x_at | BCL11A | 515 |
| OCMX.1680.C1_s_at | BCL11A | 516 |
| OC3P.14938.C1-334a_s_at | BCL11A | 517 |
| OCMX.12290.C1_x_at | BCL11A | 518 |
| OCADA.2850_s_at | BCL11A | 519 |
| OCADA.1135_s_at | C21orf63 | 520 |
| OCMX.14248.C1_s_at | C21orf63 | 521 |
| OC3P.14091.C1_s_at | C21orf63 | 522 |
| OC3P.14431.C1_s_at | C21orf63 | 523 |
| OCADA.8368_x_at | CD74 | 524 |
| OC3SNGnh.19144_s_at | CD74 | 525 |
| OC3P.104.CB1_x_at | CD74 | 526 |
| OCADNP.1805_s_at | CD74 | 527 |
| OC3SNG.3064-21a_x_at | CD74 | 528 |
| OC3P.14147.C1_s_at | CDH11 | 529 |
| OCADNP.10024_s_at | CDH11 | 530 |
| OCHP.148_s_at | CDH11 | 531 |
| OCADA.6210_s_at | CDH11 | 532 |
| OC3SNGnh.5056_x_at | CDH11 | 533 |
| OC3SNGnh.4032_s_at | CDH11 | 534 |
| OCHPRC.58_s_at | CDH11 | 535 |
| OCMX.1718.C1_s_at | CDH11 | 536 |
| OCADA.8067_x_at | CDH11 | 537 |
| OCADNP.8007_s_at | CDR1 | 538 |
| OC3P.295.C1_s_at | CFB | 539 |
| ADXStrongB56_at | CFB | N/A |
| OC3P.295.C2_x_at | CFB | 540 |
| OC3SNGnh.14167_at | CFB | 541 |
| OC3SNGn.5914-165a_s_at | CFB | 542 |
| OC3SNGn.970-10a_s_at | CFB | 543 |
| OCADNP.9683_s_at | CFB | 544 |
| OC3P.295.C2_at | CFB | 545 |
| OC3SNGnh.14167_s_at | CFB | 546 |
| OCADNP.17538_s_at | CIITA | 547 |
| OC3P.805.C1_s_at | CIITA | 548 |
| OCEM.1780_s_at | CIITA | 549 |
| OC3SNGnh.16892_s_at | CIITA | 550 |
| OCADA.6540_s_at | CIITA | 551 |
| OCHP.1927_s_at | CIITA | 552 |
| OC3SNGn.354-123a_s_at | CIITA | 553 |
| OC3SNGnh.4794_at | CIITA | 554 |
| OC3SNGn.8474-50a_x_at | COL1A2 | 555 |
| OCMX.184.C11_s_at | COL1A2 | 556 |
| OC3SNG.115-2502a_at | COL1A2 | 557 |
| OC3SNG.116-9169a_s_at | COL1A2 | 558 |
| OC3P.60.CB2_x_at | COL1A2 | 559 |
| OC3P.6454.C1_s_at | COL1A2 | 560 |
| OC3SNG.115-2502a_x_at | COL1A2 | 561 |
| OCMX.184.C16_x_at | COL1A2 | 562 |
| OCHP.173_x_at | COL1A2 | 563 |
| OC3P.60.CB1_x_at | COL1A2 | 564 |
| OC3SNGn.2538-539a_x_at | COL1A2 | 565 |
| OCMX.184.C16_s_at | COL1A2 | 566 |
| OCADNP.4048_s_at | COL3A1 | 567 |
| OC3P.81.CB2_s_at | COL3A1 | 568 |
| OC3SNGnh.19127_s_at | COL3A1 | 569 |
| OC3SNGn.1211-6a_s_at | COL3A1 | 570 |
| OCADNP.11975_s_at | COL4A1 | 571 |
| OC3P.850.C1-1145a_s_at | COL4A1 | 572 |
| OCHPRC.29_s_at | COL4A1 | 573 |
| OC3SNGnh.276_x_at | COL4A1 | 574 |
| OC3SNGnh.18844_at | COL8A1 | 575 |
| OC3P.1087.C1_s_at | COL8A1 | 576 |
| OC3P.13652.C1_s_at | COL8A1 | 577 |
| OCADNP.14932_s_at | COL8A1 | 578 |
| OC3P.10562.C1_s_at | COL8A1 | 579 |
| OCHPRC.94_s_at | CXCL17 | 580 |
| OC3SNG.3604-23a_at | CXCR2P1 | 581 |
| OC3SNG.3604-23a_x_at | CXCR2P1 | 582 |
| OC3SNGnh.13095_at | DEXI | 583 |
| OC3P.7366.C1_s_at | DEXI | 584 |
| OCADA.2531_s_at | DEXI | 585 |
| OC3SNGnh.3527_at | DEXI | 586 |

TABLE 4-continued

| Probeset | Gene | SEQ ID No. |
|---|---|---|
| OC3P.10489.C1_s_at | DEXI | 587 |
| OCADNP.10600_s_at | DEXI | 588 |
| OCADA.1911_s_at | DPYSL2 | 589 |
| OC3P.7322.C1_s_at | DPYSL2 | 590 |
| OC3SNG.366-35a_s_at | ENTPD7 | 591 |
| OC3SNGnh.5644_s_at | FKBP7 | 592 |
| OC3SNGnh.17831_at | FKBP7 | 593 |
| OCADNP.7326_s_at | FKBP7 | 594 |
| OC3P.12003.C1_x_at | FKBP7 | 595 |
| OC3P.4378.C1_s_at | GBP4 | 596 |
| OC3SNGnh.5459_s_at | GBP4 | 597 |
| OCADNP.3694_s_at | GBP4 | 598 |
| OC3SNG.3671-13a_s_at | GJB1 | 599 |
| 2874688_at | HINT1 | N/A |
| 2874689_at | HINT1 | N/A |
| Adx-200093_s_at | HINT1 | 600 |
| OC3SNGnh.5235_x_at | HINT1 | 601 |
| 2874702_at | HINT1 | N/A |
| 2874727_at | HINT1 | N/A |
| 200093_s_at | HINT1 | 602 |
| 2874697_at | HINT1 | N/A |
| 2874725_at | HINT1 | N/A |
| 2874696_at | HINT1 | N/A |
| 2874737_at | HINT1 | N/A |
| 2874735_at | HINT1 | N/A |
| Adx-200093-up_s_at | HINT1 | 603 |
| OC3P.14829.C1_s_at | HLA-DOB | 604 |
| ADXBad55_at | HLA-DOB | N/A |
| OC3P.674.C1_s_at | HLA-DRA | 605 |
| OCADNP.8307_s_at | HLA-DRA | 606 |
| OC3P.2407.C1_s_at | ID3 | 607 |
| ADXGood100_at | IGF2 | N/A |
| OC3SNG.899-20a_s_at | IGF2 | 608 |
| OC3SNGn.5728-103a_x_at | IGF2 | 610 |
| OC3P.4645.C1_s_at | IGF2 | 613 |
| OC3SNGnh.19773_s_at | IGF2 | 614 |
| OCADNP.10122_s_at | IGF2 | 615 |
| OCADNP.7400_s_at | IGF2 | 616 |
| ADXGood100_at | INS | N/A |
| OCADNP.17017_s_at | INS | 609 |
| OC3SNGn.5728-103a_x_at | INS | 610 |
| OCEM.2174_s_at | INS | 611 |
| OCEM.2035_x_at | INS | 612 |
| OC3P.4645.C1_s_at | INS | 613 |
| OC3SNGnh.19773_s_at | INS | 614 |
| OCADNP.10122_s_at | INS | 615 |
| OCADNP.7400_s_at | INS | 616 |
| OCEM.2035_at | INS | 617 |
| OC3P.9976.C1_x_at | ISLR | 618 |
| OCHP.1306_s_at | LOXL1 | 619 |
| OCADA.10621_s_at | MATN3 | 620 |
| OC3P.2576.C1_x_at | MFAP2 | 621 |
| OCHP.1079_s_at | MFAP2 | 622 |
| OC3P.11139.C1_s_at | MIR198 | 623 |
| OC3P.211.C1_x_at | MIR198 | 624 |
| ADXBad7_at | MIR198 | N/A |
| OCHP.462_s_at | MIR198 | 625 |
| OC3SNGn.8954-766a_s_at | MIR198 | 626 |
| OCADNP.4997_s_at | MIR198 | 627 |
| OCHP.228_s_at | MMP14 | 628 |
| OC3P.4123.C1_x_at | MMP14 | 629 |
| OC3P.4123.C1_s_at | MMP14 | 630 |
| OCADA.1433_x_at | NID1 | 631 |
| OCADNP.7347_s_at | NID1 | 632 |
| OC3P.3404.C1_s_at | NID1 | 633 |
| OC3SNGn.3328-664a_s_at | NID1 | 634 |
| OCADNP.9225_s_at | NUAK1 | 635 |
| ADXStrongB87_at | NUAK1 | N/A |
| OC3SNGn.2676-391a_s_at | NUAK1 | 636 |
| OCHPRC.111_s_at | PDPN | 637 |
| OCADNP.10047_s_at | PDPN | 638 |
| OCHPRC.96_s_at | PDPN | 639 |
| OC3P.13523.C1_s_at | PDPN | 640 |
| OC3SNG.4571-22a_x_at | POLD2 | 641 |
| OCEM.1126_s_at | POLD2 | 642 |
| ADXGood4_at | POLD2 | N/A |
| OC3SNGn.890-5a_s_at | POLD2 | 643 |
| OC3P.14770.C1_s_at | PSMB9 | 644 |

TABLE 4-continued

| Probeset | Gene | SEQ ID No. |
|---|---|---|
| OCRS.920_s_at | PSMB9 | 645 |
| OC3P.4627.C1_s_at | PSMB9 | 646 |
| OC3SNGnh.8187_at | PSMB9 | 647 |
| OCMX.15283.C1_x_at | PSMB9 | 648 |
| OCADNP.804_s_at | PSMB9 | 649 |
| OC3SNGnh.8187_x_at | PSMB9 | 650 |
| OCMX.14440.C1_x_at | PSMB9 | 651 |
| OC3P.1307.C1_s_at | PXDN | 652 |
| OC3P.8838.C1_s_at | PXDN | 653 |
| OCHP.1891_s_at | RARRES3 | 654 |
| OC3P.8963.C1_s_at | RCBTB1 | 655 |
| OC3SNGnh.6721_x_at | RHOBTB3 | 656 |
| OC3SNGnh.6912_x_at | RHOBTB3 | 657 |
| OC3SNGnh.957_s_at | RHOBTB3 | 658 |
| OC3SNG.2402-2883a_s_at | RHOBTB3 | 659 |
| OCHPRC.1436_at | RHOBTB3 | 660 |
| OC3SNGn.5382-76a_s_at | RHOBTB3 | 661 |
| OC3SNGnh.957_x_at | RHOBTB3 | 662 |
| OC3SNGnh.957_at | RHOBTB3 | 663 |
| OC3P.12862.C1_s_at | RHOBTB3 | 664 |
| OC3SNG.2401-1265a_x_at | RHOBTB3 | 665 |
| OC3P.5737.C1_s_at | RHOBTB3 | 666 |
| OCHP.1722_s_at | RTP4 | 667 |
| OC3P.9552.C1-496a_s_at | RTP4 | 668 |
| OC3P.9552.C1_x_at | RTP4 | 669 |
| OC3P.9552.C1_at | RTP4 | 670 |
| OC3SNGnh.865_s_at | SH3RF2 | 671 |
| OC3SNGnh.16695_s_at | SH3RF2 | 672 |
| OCADNP.12161_s_at | SH3RF2 | 673 |
| OC3SNGn.439-184a_s_at | SH3RF2 | 674 |
| OCHPRC.86_s_at | SH3RF2 | 675 |
| OCADNP.2340_s_at | SHISA4 | 676 |
| OC3SNG.6118-43a_s_at | SHISA4 | 677 |
| OCADNP.8940_s_at | SLC28A3 | 678 |
| OC3SNGnh.971_s_at | SLC28A3 | 679 |
| OCADA.4025_s_at | SLC28A3 | 680 |
| OC3P.9666.C1_s_at | SLC28A3 | 681 |
| OC3P.5726.C1_s_at | SLC5A1 | 682 |
| OCADNP.7872_s_at | SLC5A1 | 683 |
| OCRS2.10331_x_at | SNORD114-14 | 684 |
| OCRS2.8538_x_at | SNORD114-14 | 685 |
| OCRS2.10331_at | SNORD114-14 | 686 |
| OC3SNGn.2110-23a_s_at | SOX11 | 687 |
| OCHP.1171_s_at | SOX11 | 688 |
| OCHP.1523_s_at | SOX11 | 689 |
| OC3SNGnh.19157_x_at | SPARC | 690 |
| OCHP.508_s_t | SPARC | 691 |
| OC3P.148.CB1-990a_s_at | SPARC | 692 |
| OCEM.2143_at | SPARC | 693 |
| OC3SNG.2614-40a_s_at | SPARC | 694 |
| OC3P.148.CB1_x_at | SPARC | 695 |
| OCEM.2143_x_at | SPARC | 696 |
| OC3SNG.1657-20a_s_at | SRPX | 697 |
| ADXGoodB4_at | TAP1 | N/A |
| OC3SNG.2665-23a_s_at | TAP1 | 698 |
| OC3P.5602.C1_s_at | TAP2 | 699 |
| OCADNP.2260_s_at | TAP2 | 700 |
| OCADNP.8242_s_at | TAP2 | 701 |
| OC3SNGnh.18127_s_at | TAP2 | 702 |
| OC3P.14195.C1_s_at | TIMP2 | 703 |
| OCHP.320_s_at | TIMP2 | 704 |
| OC3P.543.CB1_x_at | TIMP2 | 705 |
| OC3SNGnh.19238_s_at | TIMP2 | 706 |
| OC3P.543.CB1-699a_s_at | TIMP2 | 707 |
| OCADNP.14191_s_at | TIMP2 | 708 |
| OCADNP.13017_s_at | TIMP3 | 709 |
| OCADA.9324_s_at | TIMP3 | 710 |
| OCHP.1200_s_at | TIMP3 | 711 |
| ADXGood73_at | TIMP3 | N/A |
| OC3P.10470.C1_s_at | TIMP3 | 712 |
| OC3P.15327.C1_at | TIMP3 | 713 |
| OCHP.112_s_at | TIMP3 | 714 |
| OC3P.5348.C1_s_at | TMEM45A | 715 |
| OC3P.4028.C1_at | TNFRSF14 | 716 |
| OC3SNGn.2230-103a_s_at | TNFRSF14 | 717 |
| OC3P.4028.C1_x_at | TNFRSF14 | 718 |
| OC3SNG.1683-90a_s_at | TNFSF10 | 719 |
| OC3P.2087.C1_s_at | TNFSF10 | 720 |

TABLE 4-continued

| Probeset | Gene | SEQ ID No. |
|---|---|---|
| OCHP.318_x_at | TNFSF10 | 721 |
| OC3SNGn.6279-343a_s_at | TNFSF10 | 722 |
| OC3SNGn.5842-826a_x_at | TNFSF10 | 723 |
| OCADNP.9180_s_at | TNFSF10 | 724 |
| OCHP.1136_s_at | TUBA1A | 725 |
| OCADNP.7771_s_at | XAF1 | 726 |
| ADXStrongB9_at | XAF1 | N/A |
| OC3SNG.2606-619a_x_at | XAF1 | 727 |
| OC3SNGnh.10895_at | XAF1 | 728 |
| OC3P.4873.C1_s_at | XAF1 | 729 |
| OC3SNGnh.10895_x_at | XAF1 | 730 |
| OC3SNG.2605-236a_x_at | XAF1 | 731 |
| OC3SNG.5460-81a_x_at | XAF1 | 732 |
| OCADA.154_s_at | ZNF697 | 733 |
| OCADA.3112_s_at | ZNF697 | 734 |

In one example embodiment, an expression signature comprises all or a portion of the following biomarkers; IGF2, SOX11, INS, CXCL17, SLC5A1, TMEM45A, CXCR2P1, MFAP2, MATN3, RTP4, COL3A1, CDR1, RARRES3, TNFSF10, NUAK1, SNORD114-14, SRPX, SPARC, GJB1, TIMP3, ISLR, TUBA1A, DEXI, BASP1, PXDN, GBP4, SLC28A3, HLA-DRA, TAP2, ACSL5, CDH11, PSMB9, MMP14, CD74, LOXL1, CIITA, ZNF697, SH3RF2, MIR198, COL1A2, TNFRSF14, COL8A1, C21orf63, TAP1, PDPN, RHOBTB3, BCL11A, HLA-DOB, XAF1, ARHGAP26, POLD2, DPYSL2, COL4A1, ID3, CFB, NID1, FKBP7, TIMP2, RCBTB1, ANGPTL2, ENTPD7, SHISA4, and HINT1, In another example embodiment, an expression signature comprises IGF2, SOX11, INS, and CXCL17 and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59.

In another example embodiment, an expression signature comprises IGF2, INS, SPARC, TMEM45A, COL8A1 and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59.

In another example embodiment, an expression signature comprises IGF2, INS, SPARC, TMEM45A, COL8A1, COL3A1, CDR1, NUAK1, TIMP3, LOXL1 and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53.

In another example embodiment, an expression signature comprises IGF2, TIMP3, INS, CXCR2P1, NUAK1 and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59.

In another example embodiment, an expression signature comprises IGF2, TIMP3, INS, CXCR2P1, NUAK1, CDR1, MATN3, SOX11, SNORD114-14, COL3A1 and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53.

In another example embodiment, an expression signature comprises COL3A1, SPARC, CDR1, SRPX, MATN3 and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59.

In another example embodiment, an expression signature comprises COL3A1, SPARC, CDR1, SRPX, MATN3, TIMP3, CDH11, COL8A1, BCL11A, MMP14 and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53.

In another example embodiment, an expression signature comprises IGF2, CDR1, COL3A1, SPARC, TIMP3 and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59.

In another example embodiment, an expression signature comprises IGF2, CDR1, COL3A1, SPARC, TIMP3, INS, COL8A1, NUAK1, MATN3, TMEM45A and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59.

In another example embodiment, an expression signature comprises INS, SPARC, COL8A1, COL3A1, CDR1, NUAK1, TIMP3, and MMP14 and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55.

In another example embodiment, an expression signature comprises at least INS, SPARC, COL8A1, COL3A1, CDR1, NUAK1, TIMP3, and MMP14. In another example embodiment, the expression signature comprises at least IGF2, CDR1, COL3A1, SPARC, TIMP3, INS, COL8A1, NUAK1, MATN3, TMEM45A. In another example embodiment, the expression signature comprises at least IGF2, CDR1, COL3A1, SPARC, TIMP3. In another example embodiment, the expression signature comprises at least, COL3A1, SPARC, CDR1, SRPX, MATN3, TIMP3, CDH11, COL8A1, BCL11A, MMP14. In another example embodiment, the expression signature comprises at least COL3A1, SPARC, CDR1, SRPX, MATN3. In another example embodiment, the expression signature comprises at least COL3A1, SPARC, CDR1, SRPX, MATN3. In another example embodiment, the expression signature comprises at least IGF2, TIMP3, INS, CXCR2P1, NUAK1, CDR1, MATN3, SOX11, SNORD114-14, COL3A1. In another example embodiment, the expression signature comprises at least IGF2, TIMP3, INS, CXCR2P1, NUAK1. In another example embodiment, the expression signature comprises at least IGF2, INS, SPARC, TMEM45A, COL8A1, COL3A1, CDR1, NUAK1, TIMP3, LOXL1. In another example embodiment, the expression signature comprises at least IGF2, INS, SPARC, TMEM45A, COL8A1. In another example embodiment, the expression signature comprises at least IGF2, SOX11, INS, and CXCL17.

In another example embodiment, an expression signature comprises IGF2 and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises SOX11 and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises INS and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises CXCL17 and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises CDR1 and at least N additional biomarkers selected from the list of biomarkers in Table 2, and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises COL3A1 and at least N additional biomarkers selected from the list of biomarkers in Table 2, and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises SPARC and at least N additional biomarkers selected from the list of biomarkers in Table 2, and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises TIMP3 and at least N additional biomarkers selected from the list of biomarkers in Table 2, and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises COL8A1 and at least N additional biomarkers selected from the list of biomarkers in Table 2, and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises NUAK1 and at least N additional biomarkers selected from the list of biomarkers in Table 2, and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises MATN3 and at least N additional biomarkers selected from the list of biomarkers in Table 2, and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises TMEM45A and at least N additional biomarkers selected from the list of biomarkers in Table 2, and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises CXCR2P1 and at least N additional biomarkers selected from the list of biomarkers in Table 2, and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises SRPX and at least N additional biomarkers selected from the list of biomarkers in Table 2, and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises CDH11 and at least N additional biomarkers selected from the list of biomarkers in Table 2, and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises BC11A and at least N additional biomarkers selected from the list of biomarkers in Table 2, and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises LOXL1 and at least N additional biomarkers selected from the list of biomarkers in Table 2, and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an expression signature comprises MMP14 and at least N additional biomarkers selected from the list of biomarkers in Table 2, and at least N additional biomarkers selected from the list of biomarkers in Table 2, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another example embodiment, an example expression signature comprises the biomarkers and corresponding biomarker weighted values listed in Table 2. In another example embodiment, an example expression signature consists of the biomarkers and corresponding biomarker weighted values listed in Table 2. In another example embodiment, an example expression score comprises the biomarkers and rank listed in Table 3. In another example embodiment, an example expression signature consists of the biomarkers and corresponding ranks listed in Table 3.

In a further aspect, the methods of the present invention comprise conducting an assay on a biological sample from an individual to determine the expression levels of one or more biomarkers in a biomarker panel, the biomarker panel comprising all or a portion of the biomarkers listed in Table 2 or 3.

In a further aspect, the methods of the present invention comprise conducting an assay on a biological sample from an individual to determine the expression levels of one or more biomarkers in a biomarker panel, the biomarker panel comprising IGF2, SOX11, INS, and CXCL17 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59.

In a further aspect, the methods of the present invention comprise conducting an assay on a biological sample from an individual to determine the expression levels of one or more biomarkers in a biomarker panel, the biomarker panel comprising IGF2, INS, SPARC, TMEM45A, COL8A1, and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59.

In a further aspect, the methods of the present invention comprise conducting an assay on a biological sample from an individual to determine the expression levels of one or more biomarkers in a biomarker panel, the biomarker panel comprising IGF2, INS, SPARC, TMEM45A, COL8A1, COL3A1, CDR1, NUAK1, TIMP3, LOXL1 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53.

In a further aspect, the methods of the present invention comprise conducting an assay on a biological sample from an individual to determine the expression levels of one or more biomarkers in a biomarker panel, the biomarker panel comprising IGF2, TIMP3, INS, CXCR2P1, NUAK1 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59.

In a further aspect, the methods of the present invention comprise conducting an assay on a biological sample from an individual to determine the expression levels of one or more biomarkers in a biomarker panel, the biomarker panel comprising IGF2, TIMP3, INS, CXCR2P1, NUAK1, CDR1, MATN3, SOX11, SNORD114-14, COL3A1 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53.

In a further aspect, the methods of the present invention comprise conducting an assay on a biological sample from an individual to determine the expression levels of one or more biomarkers in a biomarker panel, the biomarker panel comprising COL3A1, SPARC, CDR1, SRPX, MATN3, and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59.

In a further aspect, the methods of the present invention comprise conducting an assay on a biological sample from an individual to determine the expression levels of one or more biomarkers in a biomarker panel, the biomarker panel comprising COL3A1, SPARC, CDR1, SRPX, MATN3, TIMP3, CDH11, COL8A1, BCL11A, MMP14 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53.

In a further aspect, the methods of the present invention comprise conducting an assay on a biological sample from an individual to determine the expression levels of one or more biomarkers in a biomarker panel, the biomarker panel comprising IGF2, CDR1, COL3A1, SPARC, TIMP3, and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59.

In a further aspect, the methods of the present invention comprise conducting an assay on a biological sample from an individual to determine the expression levels of one or more biomarkers in a biomarker panel, the biomarker panel comprising IGF2, CDR1, COL3A1, SPARC, TIMP3, INS, COL8A1, NUAK1, MATN3, TMEM45A and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53.

In a further aspect, the methods of the present invention comprise conducting an assay on a biological sample from an individual to determine the expression levels of one or more biomarkers in a biomarker panel, the biomarker panel comprising INS, SPARC, COL8A1, COL3A1, CDR1, NUAK1, TIMP3, and MMP14 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55.

In another example embodiment, an biomarker panel comprises at least INS, SPARC, COL8A1, COL3A1, CDR1, NUAK1, TIMP3, and MMP14. In another example embodiment, the biomarker panel comprises at least IGF2, CDR1, COL3A1, SPARC, TIMP3, INS, COL8A1, NUAK1, MATN3, TMEM45A. In another example embodiment, the biomarker panel comprises at least IGF2, CDR1, COL3A1, SPARC, TIMP3. In another example embodiment, the biomarker panel comprises at least, COL3A1, SPARC, CDR1, SRPX, MATN3, TIMP3, CDH11, COL8A1, BCL11A, MMP14. In another example embodiment, the biomarker panel comprises at least COL3A1, SPARC, CDR1, SRPX, MATN3. In another example embodiment, the biomarker panel comprises at least COL3A1, SPARC, CDR1, SRPX, MATN3. In another example embodiment, the biomarker panel comprises at least IGF2, TIMP3, INS, CXCR2P1, NUAK1, CDR1, MATN3, SOX11, SNORD114-14, COL3A1. In another example embodiment, the biomarker panel comprises at least IGF2, TIMP3, INS, CXCR2P1, NUAK1. In another example embodiment, the biomarker panel comprises at least IGF2, INS, SPARC, TMEM45A, COL8A1, COL3A1, CDR1, NUAK1, TIMP3, LOXL1. In another example embodiment, the biomarker panel comprises at least IGF2, INS, SPARC, TMEM45A, COL8A1. In another example embodiment, the biomarker panel comprises at least IGF2, SOX11, INS, and CXCL17.

In a further aspect, the methods of the present invention comprise conducting an assay on a biological sample from an individual to determine the expression levels of one or more biomarkers in a biomarker panel, the biomarker panel comprising IGF2 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising SOX11 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising INS and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising CXCL17 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising SPARC and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising TMEM45A and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising COL8A1 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising COL3A1 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising CDR1 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising NUAK1 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising TIMP3 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising LOXL1 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising CXCR2P1 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising SPARC and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising MATN3 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising SNORD114-14 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising SRPX and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising CDH11 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising BC11A and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising MMP14 and at least N additional biomarkers selected from the list of biomarkers in Table 2 or 3, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

Classifying New Test Samples Using an Expression Signature

To classify new test samples using an expression signature, such as those described above, the relative expression levels of one or more biomarkers in a cancer tissue are measured to form a test sample expression profile. In certain example embodiments, the test sample expression profile is summarized in the form of a compound decision score ("expression score") and compared to a threshold score that is mathematically derived from a training set of patient data. The score threshold is established with the purpose of maximizing the ability to separate a patient group into different groups based on characteristics such as, but not limited to, good/poor clinical prognosis. The patient training set data is preferably derived from cancer tissue samples having been characterized by prognosis, likelihood of recurrence, long term survival, clinical outcome, treatment response, diagnosis, cancer classification, or personalized genomics profile. Expression profiles, and corresponding decision scores from patient samples may be correlated with the characteristics of patient samples in the training set that are on the same side of the mathematically derived score decision threshold. In certain example embodiments, the threshold of the linear classifier scalar output is optimized to maximize the sum of sensitivity and specificity under cross-validation as observed within the training dataset.

The overall expression data for a given sample is normalized using methods known to those skilled in the art in order to correct for differing amounts of starting material, varying efficiencies of the extraction and amplification reactions, etc.

In one embodiment, the biomarker expression profile of a patient tissue sample is evaluated by a linear classifier. As used herein, a linear classifier refers to a weighted sum of the individual biomarker intensities into a compound decision score ("decision function"). The decision score is then compared to a pre-defined cut-off score threshold, corresponding to a certain set-point in terms of sensitivity and specificity which indicates if a sample is equal to or above the score threshold (decision function positive) or below (decision function negative).

Using a linear classifier on the normalized data to make a diagnostic or prognostic call (e.g. good or poor clinical prognosis) effectively means to split the data space, i.e. all possible combinations of expression values for all genes in the classifier, into two disjoint segments by means of a separating hyperplane. This split is empirically derived on a large set of training examples, for example from patients showing responsiveness or resistance to a therapeutic agent. Without loss of generality, one can assume a certain fixed set of values for all but one biomarker, which would automatically define a threshold value for this remaining biomarker where the decision would change from, for example, responsiveness or resistance to a therapeutic agent. Expression values above this dynamic threshold would then either indicate a poor clinical prognosis (for a biomarker with a negative weight) or a good clinical prognosis (for a biomarker with a positive weight). The precise value of this threshold depends on the actual measured expression profile of all other biomarkers within the classifier, but the general indication of certain biomarkers remains fixed, i.e. high values or "relative over-expression" always contributes to either a good clinical prognosis (genes with a positive weight) or a poor clinical prognosis (genes with a negative weights). Therefore, in the context of the overall gene expression classifier, relative expression can indicate if either up- or down-regulation of a certain biomarker is indicative of a good or bad clinical prognosis. In certain example embodiments, a sample expression score above the threshold expression score indicates the subject has the non-angiogenesis subtype. In certain other example embodiments, a sample expression score above a threshold score indicates the subject has a good clinical prognosis compared to a subject with a sample expression score below the threshold score. In certain other example embodiments, a sample expression score above the threshold score indicates the subject will likely experience a detrimental effect, or have a poor prognosis, if an anti-angiogenic therapeutic agent is administered.

There are a number of suitable methods for measuring expression profiles of test samples depending on the type of biomarker to be assayed. Measuring mRNA in a biological sample may be used as a surrogate for detection of the level of the corresponding protein in the biological sample. Thus, any of the biomarkers or biomarker panels described herein can also be detected by detecting the appropriate RNA. Methods of gene expression profiling include, but are not limited to, microarray, RT-PCT, qPCR, NGS, northern blots, SAGE, mass spectrometry.

mRNA expression levels are measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See Gene Expression Profiling: Methods and Protocols, Richard A. Shimkets, editor, Humana Press, 2004.

miRNA molecules are small RNAs that are non-coding but may regulate gene expression. Any of the methods suited to the measurement of mRNA expression levels can also be used for the corresponding miRNA. Recently many laboratories have investigated the use of miRNAs as biomarkers for disease. Many diseases involve widespread transcriptional regulation, and it is not surprising that miRNAs might find a role as biomarkers. The connection between miRNA concentrations and disease is often even less clear than the connections between protein levels and disease, yet the value of miRNA biomarkers might be substantial. Of course, as with any RNA expressed differentially during disease, the problems facing the development of an in vitro diagnostic product will include the requirement that the miRNAs survive in the diseased cell and are easily extracted for analysis, or that the miRNAs are released into blood or other matrices where they must survive long enough to be measured. Protein biomarkers have similar requirements, although many potential protein biomarkers are secreted intentionally at the site of pathology and function, during disease, in a paracrine fashion. Many potential protein biomarkers are designed to function outside the cells within which those proteins are synthesized.

Gene expression may also be evaluated using mass spectrometry methods. A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al., Anal. Chem. 70:647 R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an $F(ab')_2$ fragment, a single chain antibody fragment, an Fv fragment, a single chain Fv fragment, a nucleic acid, a lectin, a ligand-binding receptor, affybodies, nanobodies, ankyrins, domain antibodies, alternative antibody scaffolds (e.g. diabodies etc) imprinted polymers, avimers, peptidomimetics, peptoids, peptide nucleic acids, threose nucleic acid, a hormone receptor, a cytokine receptor, and synthetic receptors, and modifications and fragments of these.

The foregoing assays enable the detection of biomarker values that are useful in methods for determining a patient's clinical prognosis and selecting appropriate treatment regimens, where the methods comprise detecting, in a biological sample from an individual, at least N biomarker values that each correspond to a biomarker selected from the group consisting of the biomarkers provided in Tables 1 or Table 2, wherein a classification, as described in detail below, using the biomarker values indicates whether the individual has a good prognosis or a bad prognosis, or will receive a detrimental or beneficial effect if a certain therapeutic agent is administered. While some of the described predictive biomarkers are useful alone for predicting clinical prognosis, methods are also described herein for the grouping of multiple subsets of the biomarkers that are each useful as a panel of two or more biomarkers. Thus, various embodiments of the instant application provide combinations comprising N biomarkers, wherein N is at least three biomarkers. It will be appreciated that N can be selected to be any number from any of the above-described ranges, as well as similar, but higher order, ranges. In accordance with any of the methods described herein, biomarker values can be detected and classified individually or they can be detected and classified collectively, as for example in a multiplex assay format.

b) Microarray Methods

In one embodiment, the present invention makes use of "oligonucleotide arrays" (also called herein "microarrays"). Microarrays can be employed for analyzing the expression of biomarkers in a cell, and especially for measuring the expression of biomarkers of cancer tissues.

In one embodiment, biomarker arrays are produced by hybridizing detectably labeled polynucleotides representing the mRNA transcripts present in a cell (e.g., fluorescently-labeled cDNA synthesized from total cell mRNA or labeled cRNA) to a microarray. A microarray is a surface with an ordered array of binding (e.g., hybridization) sites for products of many of the genes in the genome of a cell or organism, preferably most or almost all of the genes. Microarrays can be made in a number of ways known in the art. However produced, microarrays share certain characteristics. The arrays are reproducible, allowing multiple copies of a given array to be produced and easily compared with each other. Preferably the microarrays are small, usually smaller than 5 $cm^2$, and they are made from materials that are stable under binding (e.g., nucleic acid hybridization) conditions. A given binding site or unique set of binding sites in the microarray will specifically bind the product of a single gene in the cell. In a specific embodiment, positionally addressable arrays containing affixed nucleic acids of known sequence at each location are used.

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene/biomarker. For example, when detectably labeled (e.g., with a fluorophore) cDNA or cRNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal. Nucleic acid hybridization and wash conditions are chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can be demonstrated that specific hybridization conditions result in specific hybridization by carrying out a hybridization assay including negative controls using routine experimentation.

Optimal hybridization conditions will depend on the length (e.g., oligomer vs. polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., "Current Protocols in Molecular Biology", Greene Publishing and Wiley-interscience, NY (1987), which is incorporated in its entirety for all purposes. When the cDNA microarrays are used, typical hybridization conditions are hybridization in 5×SSC plus 0.2% SDS at 65 C for 4 hours followed by washes at 25° C. in low stringency wash buffer (1×SSC plus 0.2% SDS) followed by 10 minutes at 25° C. in high stringency wash buffer (0.1SSC plus 0.2% SDS) (see Shena et al., Proc. Natl. Acad. Sci. USA, Vol. 93, p. 10614 (1996)). Useful hybridization conditions are also provided in, e.g., Tijessen, Hybridization With Nucleic Acid Probes", Elsevier Science Publishers B.V. (1993) and Kricka, "Nonisotopic DNA Probe Techniques", Academic Press, San Diego, Calif. (1992).

c) Immunoassay Methods

Immunoassay methods are based on the reaction of an antibody to its corresponding target or analyte and can detect the analyte in a sample depending on the specific assay format. To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies. Immunoassays have been designed for use with a wide range of biological sample matrices. Immunoassay formats have been designed to provide qualitative, semi-quantitative, and quantitative results.

Quantitative results may be generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte/biomarker. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Example assay formats include enzyme-linked immunosorbent assay (ELISA), radioimmunoas say, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Kits

Reagents, tools, and/or instructions for performing the methods described herein can be provided in a kit. For example, the kit can contain reagents, tools, and instructions for determining an appropriate therapy for a cancer patient. Such a kit can include reagents for collecting a tissue sample from a patient, such as by biopsy, and reagents for processing the tissue. The kit can also include one or more reagents for performing a gene or gene product expression analysis, such as reagents for performing nucleic acid amplification (e.g RT-PCR, qPCR), sequencing (e.g. next generation sequencing), northern blot, proteomic analysis, or immunohistochemistry to determine expression levels of gene or gene product markers in a sample of a patient. For example, primers for performing RT-PCR, probes for performing northern blot analyses, and/or antibodies for performing proteomic analysis such as Western blot, immunohistochemistry and ELISA analyses can be included in such kits. Appropriate buffers for the assays can also be included. Detection reagents required for any of these assays can also be included. The appropriate reagents and methods are described in further detail below. The kits may include suitable primers and/or probes to detect the expression levels of at least one (up to all) of the biomarkers of in Table 2. Where expression is determined at the protein level the kit may contain binding reagents specific for the proteins of interest. The binding reagents may comprise antibodies to include all fragments and derivatives thereof. In the context of the various embodiments of the present invention the term “antibody” includes all immunoglobulins or immunoglobulin-like molecules with specific binding affinity for the relevant protein (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, or humanized versions of non-human antibodies, or chimeric antibodies. Various techniques for antibody humanization are well established and any suitable technique may be employed. The term “antibody” also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant protein. These derivatives and fragments may include Fab fragments, F(ab') 2 fragments, Fv fragments, single chain antibodies, single domain antibodies, Fc fragments etc. The term antibody encompasses antibodies comprised of both heavy and light chains, but also heavy chain (only) antibodies (which may be derived from various species of cartilaginous fish or camelids). In specific embodiments, the antibodies may be engineered so as to be specific for more than protein, for example bi-specific to permit binding to two different target proteins as identified herein (see Tables 2).

In some embodiments, the kits may also contain the specific anti-angiogenic therapeutic agent to be administered in the event that the test predicts responsiveness. This agent may be provided in a form, such as a dosage form, that is tailored to the specific treatment. The kit may be provided with suitable instructions for administration according to an appropriate treatment regimen.

The kits featured herein can also include an instruction sheet describing how to perform the assays for measuring gene or gene product expression. The instruction sheet can also include instructions for how to determine a reference cohort, including how to determine expression levels of gene or gene product markers in the reference cohort and how to assemble the expression data to establish a reference for comparison to a test patient. The instruction sheet can also include instructions for assaying gene or gene product expression in a test patient and for comparing the expression level with the expression in the reference cohort to subsequently determine the appropriate chemotherapy for the test patient. Methods for determining the appropriate chemotherapy are described above and can be described in detail in the instruction sheet.

Informational material included in the kits can be descriptive, instructional, marketing or other material that relates to the methods described herein and/or the use of the reagents for the methods described herein. For example, the informational material of the kit can contain contact information, e.g., a physical address, email address, website, or telephone number, where a user of the kit can obtain substantive information about performing a gene expression analysis and interpreting the results, particularly as they apply to a human’s likelihood of having a positive response to a specific therapeutic agent.

The kits featured herein can also contain software necessary to infer a patient’s likelihood of having a positive response to a specific therapeutic agent from the gene product marker expression.

Therapeutic Agents

As described above, the methods described herein permit the classification of a patient as having a good or bad clinical prognosis prior to, upon or following administration of an anti-angiogeneic therapeutic agent following, or in combination with, a chemotherapeutic treatment. Some current such anti-angiogenic therapeutics used to treat cancer include, but are not limited to, the following agents; VEGF pathway-targeted therapeutic agent, including multi-targeted pathway inhibitors (VEGF/PDGF/FGF/EGFT/FLT-3/c-KIT), Angiopoietin-TIE2 pathway inhibitors, endogenous angiogenic inhibitors, immunomodulatory Agents. VEGF specific inhibitors include, but are not limited to, Bevacizumab (Avastin), Aflibercept (VEGF Trap), IMC-1121B (Ramucirumab). Multi-targeted pathway inhibitors include, but are not limited to, Imatinib (Gleevec), Sorafenib (Nexavar), Gefitinib (Iressa), Sunitinib (Sutent), Erlotinib, Tivozinib, Cediranib (Recentin), Pazopanib (Votrient), BIBF 1120 (Vargatef), Dovitinib, Semaxanib (Sugen), Axitinib (AG013736), Vandetanib (Zactima), Nilotinib (Tasigna), Dasatinib (Sprycel), Vatalanib, Motesanib, ABT-869, TKI-258. Angiopoietin-TIE2 pathway inhibitors include, but are not limited to, AMG-386, PF-4856884 CVX-060, CEP-11981, CE-245677, MEDI-3617, CVX-241, Trastuzumab (Herceptin). Endogenous angiogenic inhibitors include, but are not limited to, Thombospondin, Endostatin, Tumstatin, Canstatin, Arrestin, Angiostatin, Vasostatin, Interferon alpha. Immunomodulatory Agents include, but are not limited to, Thalidomide and Lenalidomide. In one example embodiment, the anti-angiogenic agent is bevacizumab.

The invention is further defined in the following numbered clauses:

1. A method for selecting whether to administer an anti-angiogenic therapeutic agent to subjects, comprising:

obtaining a test sample from a subject;

measuring expression levels of a biomarker panel from the test sample obtained from the subject, wherein the biomarker panel comprises one or more biomarkers selected from Table 2 or Table 3;

determining a sample expression score for the biomarker panel;

comparing the sample expression score to a threshold score; and selecting a treatment based on whether the sample expression score is above or equal to the threshold expression score, wherein if the sample expression score is above the threshold score an anti-angiogenic agent is contraindicated.

2. The method of clause 1, wherein the subject is suffering from cancer.

3. The method of clause 2, wherein the cancer is ovarian cancer.

4. The method of clause 3, wherein the ovarian cancer is high grade serous ovarian cancer.

5. The method of any one of clauses 1 to 4, wherein the subject is receiving or has received chemotherapeutic treatment.

6. The method of clause 5, wherein the chemotherapeutic treatment comprises administration of a platinum-based chemotherapeutic agent, an alkylating agent, an anti-metabolite, an anti-tumor antibiotic, a topoisomerase inhibitor, a mitotic inhibitor, or a combination thereof.

7. The method of clause 6, wherein the chemotherapeutic treatment comprises administration of a platinum based-chemotherapeutic agent, a mitotic inhibitor, or a combination thereof.

8. The method of clause 6, wherein the chemotherapeutic treatment comprises administration of carboplatin and paclitaxel.

9. The method of any one of clauses 1 to 8, wherein the anti-angiogenic therapeutic agent is a VEGF-pathway-targeted therapeutic agent, an angiopoietin-TIE2 pathway inhibitor, an endogenous angiogenic inhibitor, or an immunomodulatory agent.

10. The method of clause 9, wherein the VEGF pathway-targeted therapeutic agents include Bevacizumab (Avastin), Afibercept (VEGF Trap), IMC-1121B (Ramucirumab), Imatinib (Gleevec), Sorafenib (Nexavar), Gefitinib (Iressa), Sunitinib (Sutent), Erlotinib, Tivozinib, Cediranib (Recentin), Pazopanib (Votrient), BIBF 1120 (Vargatef), Dovitinib, Semaxanib (Sugen), Axitinib (AG013736), Vandetanib (Zactima), Nilotinib (Tasigna), Dasatinib (Sprycel), Vatalanib, Motesanib, ABT-869, TKI-258 or a combination thereof.

11. The method of clause 16, wherein the angiopoietin-TIE2 pathway inhibitor includes AMG-386, PF-4856884 CVX-060, CEP-11981, CE-245677, MEDI-3617, CVX-241, Trastuzumab (Herceptin) or a combination thereof.

12. The method of clause 9, wherein the endogenous angiogenic inhibitors include Thombospondin, Endostatin, Tumstatin, Canstatin, Arrestin, Angiostatin, Vasostatin, Interferon alpha or a combination thereof.

13. The method of clause 9, wherein the immunomodulatory agents include thalidomide and lenalidomide.

14. The method of clause 10, wherein the VEGF pathway-targeted therapeutic agent is bevacizumab.

15. The method of any one of clauses 1 to 14, wherein the biomarker panel comprises one or more of IGF2, SOX11, INS, CXCL17, SLC5A1, TMEM45A, CXCR2P1, MFAP2, MATN3, or RTP4.

16. The method of any one of clauses 1 to 14, wherein the biomarker panel comprises the biomarkers listed in Table 2.

17. The method of clause 16, wherein the expression score is calculated using a weight value and a bias value for each biomarker in the biomarker panel, and wherein the weight value and the bias value are defined for each biomarker in Table 2.

18. The method of clause 16, wherein the expression score is calculated using a weight value for each biomarker in the biomarker panel, and wherein the weight for each biomarker is ranked in decreasing absolute value as defined in Table 3.

19. The method of any one of clauses 1 to 14, wherein the biomarker panel comprises one or more of IGF2, CDR1, COL3A1, SPARC, TIMP3, INS, COL8A1, NUAK1, MATN3, TMEM45A.

20. The method of any one of clauses 1 to 14, wherein the biomarker panel comprises one or more INS, SPARC, COLA1, COL3A1, CDR1, NUAK1, TIMP3, and MMP14.

21. A method for determining clinical prognosis of subjects, comprising:

obtaining a test sample from a subject suffering from cancer;

measuring expression levels of a biomarker panel from the test sample obtained from the subject, wherein the biomarker panel comprises one or more biomarkers selected from Table 2;

determining a sample expression score for the biomarker panel;

comparing the sample expression score to a threshold score; and determining a clinical prognosis for the subject based on whether the sample expression score is above the threshold expression score, wherein if the sample expression score is above or equal to the threshold expression score the clinical prognosis is a good prognosis.

22. The method of clause 21, wherein the good prognosis indicates increased progression free survival or overall survival rates compared to samples with a sample expression score below the threshold score.

23. The method of clause 21 or clause 22, wherein the cancer is ovarian cancer.

24. The method of clause 23, wherein the ovarian cancer is high grade serous ovarian cancer.

25. The method of any one of clauses 21 to 24, wherein the chemotherapeutic treatment comprises administration of a platinum-based chemotherapeutic agent, an alkylating agent, an anti-metabolite, an anti-tumor antibiotic, a topoisomerase inhibitor, a mitotic inhibitor, or a combination thereof.

26. The method of clause 25, wherein the chemotherapeutic treatment comprises administration of a platinum-based chemotherapeutic agent, a mitotic inhibitor, or a combination thereof.

27. The method of clause 25, wherein the chemotherapeutic treatment comprises administration of paclitaxel and carboplatin.

28. The method of any one of clauses 21 to 27, wherein the biomarker panel comprises one or more of IGF2, SOX11, INS, CXCL17, SLC5A1, TMEM45A, CXCR2P1, MFAP2, MATN3, or RTP4.

29. The method any one of clauses 21 to 28, wherein the biomarker panel comprises the biomarkers listed in Table 2.

30. The method of clause 29, wherein the expression score is calculated using a weight value and a bias value for each biomarker in the biomarker panel, and wherein the weight value and bias value for each biomarker are defined in Table 2.

31. The method of clause 29, wherein the expression score is calculated using a weight value for each biomarker in the biomarker panel, and wherein the weight for each biomarker is ranked in decreasing absolute value as defined in Table 3.

32. The method of any one of clauses 21 to 28, wherein the biomarker panel comprises one or more of IGF2, CDR1, COL3A1, SPARC, TIMP3, INS, COL8A1, NUAK1, MATN3, TMEM45A.

33. The method of any one of clauses 21 to 28, wherein the biomarker panel comprises one or more INS, SPARC, COLA1, COL3A1, CDR1, NUAK1, TIMP3, and MMP14.

34. A method for selecting whether to administer Bevacizumab to a subject, comprising:

in a test sample obtained from a subject suffering from ovarian cancer, which subject is being, has been and/or will be treated using a platinum-based chemotherapeutic agent and/or a mitotic inhibitor;

measuring expression levels of one or more, up to all of the, biomarkers selected from Table 2;

determining a sample expression score for the one or more biomarkers;

comparing the sample expression score to a threshold score; and selecting a treatment based on whether the sample expression score is above the threshold expression score, wherein if the sample expression score is above or equal to the threshold score Bevacizumab is contraindicated.

35. The method of clause 34 wherein the ovarian cancer comprises serous ovarian cancer.

36. The method of clause 35 wherein the serous ovarian cancer is high grade serous ovarian cancer.

37. The method of any one of clauses 34 to 35 wherein if Bevacizumab is contraindicated the patient is treated with a platinum-based chemotherapeutic agent and/or a mitotic inhibitor.

38. The method of any one of clauses 34 to 37 wherein if the sample expression score is below the threshold score the patient is treated with a platinum-based chemotherapeutic agent and/or a mitotic inhibitor together with Bevacizumab.

39. The method of any one of clauses 34 to 38, wherein the platinum-based chemotherapeutic agent comprises carboplatin.

40. The method of any one of clauses 34 to 39, wherein the mitotic inhibitor comprises a taxane, optionally paclitaxel.

41. The method of any one of clauses 34 to 40, wherein the biomarker panel comprises one or more of IGF2, SOX11, INS, CXCL17, SLC5A1, TMEM45A, CXCR2P1, MFAP2, MATN3, or RTP4.

42. The method any one of clauses 34 to 40, wherein the biomarker panel comprises the biomarkers listed in Table 2.

43. The method of clause 42, wherein the expression score is calculated using a weight value and a bias value for each biomarker in the biomarker panel, and wherein the weight value and bias value for each biomarker are defined in Table 2.

44. The method of clause 42, wherein the expression score is calculated using a weight value for each biomarker in the biomarker panel, and wherein the weight for each biomarker is ranked in decreasing absolute value as defined in Table 3.

45. The method of any one of clauses 34 to 40, wherein the biomarker panel comprises one or more of IGF2, CDR1, COL3A1, SPARC, TIMP3, INS, COL8A1, NUAK1, MATN3, TMEM45A.

46. The method of any one of clauses 34 to 40, wherein the biomarker panel comprises one or more INS, SPARC, COLA1, COL3A1, CDR1, NUAK1, TIMP3, and MMP14.

47. A method for determining clinical prognosis of a subject, comprising:

a. in a test sample obtained from a subject suffering from ovarian cancer, which subject is being, has been and/or will be treated using a platinum-based chemotherapeutic agent and/or a mitotic inhibitor;
b. measuring expression levels of one or more, up to all of the, biomarkers selected from Table 2;
c. determining a sample expression score for the one or more biomarkers;
d. comparing the sample expression score to a threshold score; and
e. determining the clinical prognosis based on whether the sample expression score is above or equal to the threshold expression score, wherein if the sample expression score is above or equal to the threshold score the clinical prognosis is a good clinical prognosis.

48. The method of clause 47, wherein the ovarian cancer comprises serous ovarian cancer.

49. The method of clause 48, wherein the serous ovarian cancer is high grade serous ovarian cancer.

50. The method of any one of clauses 47 to 48, wherein if the patient has a good prognosis, treatment using Bevacizumab is contraindicated.

51. The method of any one of clauses 47 to 50 wherein if the sample expression score is below the threshold score the patient is treated with a platinum-based chemotherapeutic agent and/or a mitotic inhibitor together with Bevacizumab.

52. The method of any one of clauses 47 to 51, wherein the platinum-based chemotherapeutic agent comprises carboplatin.

53. The method of any one of clauses 47 to 52, wherein the mitotic inhibitor comprises a taxane, optionally paclitaxel.

54. The method of any one of clauses 47 to 53, wherein the biomarker panel comprises one or more of IGF2, SOX11, INS, CXCL17, SLC5A1, TMEM45A, CXCR2P1, MFAP2, MATN3, or RTP4.

55. The method any one of clauses 47 to 53, wherein the biomarker panel comprises the biomarkers listed in Table 2.

56. The method of clause 55, wherein the expression score is calculated using a weight value and a bias value for each biomarker in the biomarker panel, and wherein the weight value and bias value for each biomarker are defined in Table 2.

57. The method of clause 55, wherein the expression score is calculated using a weight value for each biomarker in the biomarker panel, and wherein the weight for each biomarker is ranked in decreasing absolute value as defined in Table 3.

58. The method of any one of clauses 47 to 52, wherein the biomarker panel comprises one or more of IGF2, CDR1, COL3A1, SPARC, TIMP3, INS, COL8A1, NUAK1, MATN3, TMEM45A.

59. The method of any one of clauses 47 to 52, wherein the biomarker panel comprises one or more INS, SPARC, COLA1, COL3A1, CDR1, NUAK1, TIMP3, and MMP14.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or scope of the appended claims.

EXAMPLES

Example 1: Tissue Processing, Hierarchical Clustering, Subtype Identification and Classifier Development

Tumor Material

Example expression signatures were identified from gene expression analysis of a cohort of macrodissected epithelial serous ovarian tumor FFPE tissue samples sourced from the NHS Lothian and University of Edinburgh.

TABLE 3 results of pathology review of 357 epithelial ovarian cancer samples.

| | All patients (N = 357) | | Cluster A (N = 106) | | Cluster B (N = 97) | | Cluster C (N = 79) | | Cluster D (N = 75) | | unadjusted | p-value |
|---|---|---|---|---|---|---|---|---|---|---|---|---|
| | No. | (%) | No. | (%) | No. | (%) | No. | (%) | No. | (%) | p-value | (corrected) |
| Age at diagnosis, yrs | | | | | | | | | | | | |
| Median | 60.6 | | 60.4 | | 60.6 | | 63.7 | | 57.8 | | 0.004 | 0.13 |
| Range | 23-86 | | 36-83 | | 30-86 | | 33-84 | | 23-78 | | | |
| Block age, yrs | | | | | | | | | | | | |
| Median | 8.7 | | 8.5 | | 9.0 | | 8.7 | | 8.3 | | 0.73 | 1.00 |
| Range | 2.9-24.1 | | 2.9-24.1 | | 3.0-22.2 | | 2.9-19.5 | | 2.9-19.4 | | | |
| Histology | | | | | | | | | | | | |
| High grade serous | 265 | (74) | 96 | (91) | 86 | (89) | 72 | (91) | 11 | (15) | $3.66 \times 10^{-33}$ | $1.24 \times 10^{-31}$ |
| Low grade serous | 12 | (3) | 0 | (0) | 4 | (4) | 1 | (1) | 7 | (9) | | |
| Endometrioid | 45 | (13) | 6 | (6) | 4 | (4) | 4 | (5) | 31 | (41) | | |
| Clear cell | 26 | (7) | 4 | (4) | 3 | (3) | 2 | (3) | 17 | (23) | | |
| Mucinous | 9 | (3) | 0 | (0) | 0 | (0) | 0 | (0) | 9 | (12) | | |
| Grade* | | | | | | | | | | | | |
| High | 300 | (84) | 103 | (97) | 91 | (94) | 76 | (96) | 30 | (40) | $1.21 \times 10^{-29}$ | $4.12 \times 10^{-28}$ |
| Low | 57 | (16) | 3 | (3) | 6 | (6) | 3 | (4) | 45 | (60) | | |
| FIGO stage | | | | | | | | | | | | |
| I | 46 | (13) | 6 | (6) | 1 | (1) | 7 | (9) | 32 | (43) | $2.71 \times 10^{-18}$ | $9.20 \times 10^{-17}$ |
| II | 41 | (11) | 11 | (10) | 6 | (6) | 5 | (6) | 19 | (25) | | |
| III | 206 | (58) | 67 | (63) | 72 | (74) | 51 | (65) | 16 | (21) | | |
| IV | 55 | (15) | 19 | (18) | 15 | (15) | 15 | (19) | 6 | (8) | | |
| Inadequate info | 9 | (3) | 3 | (3) | 3 | (3) | 1 | (1) | 2 | (3) | | |
| Debulking** | | | | | | | | | | | | |
| <2 cm | 166 | (46) | 41 | (39) | 34 | (35) | 34 | (43) | 57 | (76) | $1.69 \times 10^{-6}$ | $5.75 \times 10^{-5}$ |
| 2-5 cm | 68 | (19) | 22 | (21) | 20 | (21) | 21 | (27) | 5 | (7) | | |
| >5 cm | 84 | (24) | 25 | (24) | 31 | (32) | 21 | (27) | 7 | (9) | | |
| Unknown | 39 | (11) | 18 | (17) | 12 | (12) | 3 | (4) | 6 | (8) | | |
| 1$^{st}$ line chemotherapy | | | | | | | | | | | | |
| Platinum alone | 218 | (61) | 57 | (54) | 60 | (62) | 51 | (65) | 50 | (67) | 0.70 | 1.00 |
| Platinum plus taxane | 128 | (36) | 45 | (42) | 34 | (35) | 26 | (33) | 23 | (31) | | |
| Other | 11 | (3) | 4 | (4) | 3 | (3) | 2 | (3) | 2 | (3) | | |
| Relapse | | | | | | | | | | | | |
| Recurrence | 276 | (77) | 88 | (83) | 87 | (90) | 69 | (87) | 32 | (43) | $2.65 \times 10^{-14}$ | $9.02 \times 10^{-13}$ |
| Did not recur | 81 | (23) | 18 | (17) | 10 | (10) | 10 | (13) | 43 | (57) | | |

Gene Expression Profiling from FFPE

Total RNA was extracted from macrodissected FFPE tissue using the High Pure RNA Paraffin Kit (Roche Diagnostics GmbH, Mannheim, Germany). RNA was converted into complementary deoxyribonucleic acid (cDNA), which was subsequently amplified and converted into single-stranded form using the SPIA® technology of the WT-Ovation™ FFPE RNA Amplification System V2 (NuGEN Technologies Inc., San Carlos, Calif., USA). The amplified single-stranded cDNA was then fragmented and biotin labeled using the FL-Ovation™ cDNA Biotin Module V2 (NuGEN Technologies Inc.). The fragmented and labeled cDNA was then hybridized to the Almac Ovarian Cancer DSA™. Almac's Ovarian Cancer DSA™ research tool has been optimised for analysis of FFPE tissue samples, enabling the use of valuable archived tissue banks. The Almac Ovarian Cancer DSA™ research tool is an innovative microarray platform that represents the transcriptome in both normal and cancerous ovarian tissues. Consequently, the Ovarian Cancer DSA™ provides a comprehensive representation of the transcriptome within the ovarian disease and tissue setting, not available using generic microarray platforms. Arrays were scanned using the Affymentrix Genechip® Scanner 7G (Affymetrix Inc., Santa Clara, Calif.).

Data Preparation

Quality Control (QC) of profiled samples was carried out using MASS pre-processing algorithm. Different technical aspects were addressed: average noise and background homogeneity, percentage of present call (array quality), signal quality, RNA quality and hybridization quality. Distributions and Median Absolute Deviation of corresponding parameters were analyzed and used to identify possible outliers.

Almac's Ovarian Cancer DSA™ contains probes that primarily target the area within 300 nucleotides from the 3' end. Therefore standard Affymetrix RNA quality measures were adapted—for housekeeping genes intensities of 3' end probe sets with ratios of 3' end probe set intensity to the average background intensity were used in addition to usual 3'/5' ratios. Hybridization controls were checked to ensure that their intensities and present calls conform to the requirements specified by Affymetrix.

Hierarchical Clustering and Functional Analysis

Sample pre-processing was carried out using Robust Multi-array Average (RMA) [16]. The data matrix was sorted by decreasing variance, decreasing intensity and increasing correlation to cDNA yield. Following filtering of probe sets correlated with cDNA yield, incremental subsets of the data matrix were tested for cluster stability: the GAP statistic [17] was applied to calculate the number of sample and probe set clusters while the stability of cluster composition was assessed using partition comparison methods [18, 19]. The final most variable probe set list was determined based on the smallest and most stable data matrix for the selected number of sample cluster.

Following standardization of the data matrix to the median probe set expression values, agglomerative hierarchical clustering was performed using Euclidean distance and Ward's linkage method [20]. The optimal number of sample and probe set clusters was determined using the GAP statistic [17]. The significance of the distribution of clinical parameter factor levels across sample clusters was assessed using ANOVA (continuous factor) or chi-squared analysis (discrete factor) and corrected for false discovery rate (product of p-value and number of tests performed). A corrected p-value threshold of 0.05 was used as criterion for significance.

Ovarian Cancer DSA® probe sets were remapped to genes using an annotation pipeline based on Ensembl v60. Functional enrichment analysis was conducted to identify and rank biological entities which were found to be associated with the clustered gene sets using the Gene Ontology biological processes classification [21]. Entities were ranked according to a statistically derived enrichment score [22] and adjusted for multiple testing [23]. A corrected p-value of 0.05 was used as significance threshold. The identified enriched processes were summarised into an overall group function for each probe set/gene cluster.

Signature Development and Evaluation

Following subtype identification, a gene signature was developed for predicting the molecular group. To facilitate application of a signature to samples profiled on different platforms, probe sets were remapped to genes by summarizing all probe sets to their median expression and log 2 transforming the data. Signature generation was performed using the partial least squares method [24] with the selection of features/genes based on filter feature selection during 10 repeats of five-fold cross-validation.

Univariate and multivariable survival analysis was performed using the survival package [25] in R 2.15.0. Multivariable analysis corrected for the following factors: High grade serous: Debulking status, Stage, Chemotherapy and Age at diagnosis; Tothill: Grade, Stage, Neoadjuvant treatment and Residual disease. All Kaplan-Meier graphs are a univariate representation of survival data.

Results

265 HGS tumors underwent unsupervised hierarchical clustering based on 1400 most variable probe sets (corresponding to 1040 genes). Three sample clusters and four gene clusters were identified (FIG. 1). There was no significant association between HGS clusters and clinico-pathological features. Functional analysis (FIG. 1) revealed that cluster HGS3 was characterized by up regulation of genes associated with immune response and angiogenesis/vascular development (cluster referred to as Angioimmune forthwith). Cluster HGS1 was associated with upregulation of angiogenesis/vascular development (although apparently to a lesser extent than cluster HGS3) but without high expression of genes involved in immune response (cluster referred to as Angio forthwith). Cluster HGS2 was characterized by upregulation of genes involved in immune response without upregulation of genes involved in angiogenesis or vascular development (cluster referred to as Immune forthwith).

Figure 2:
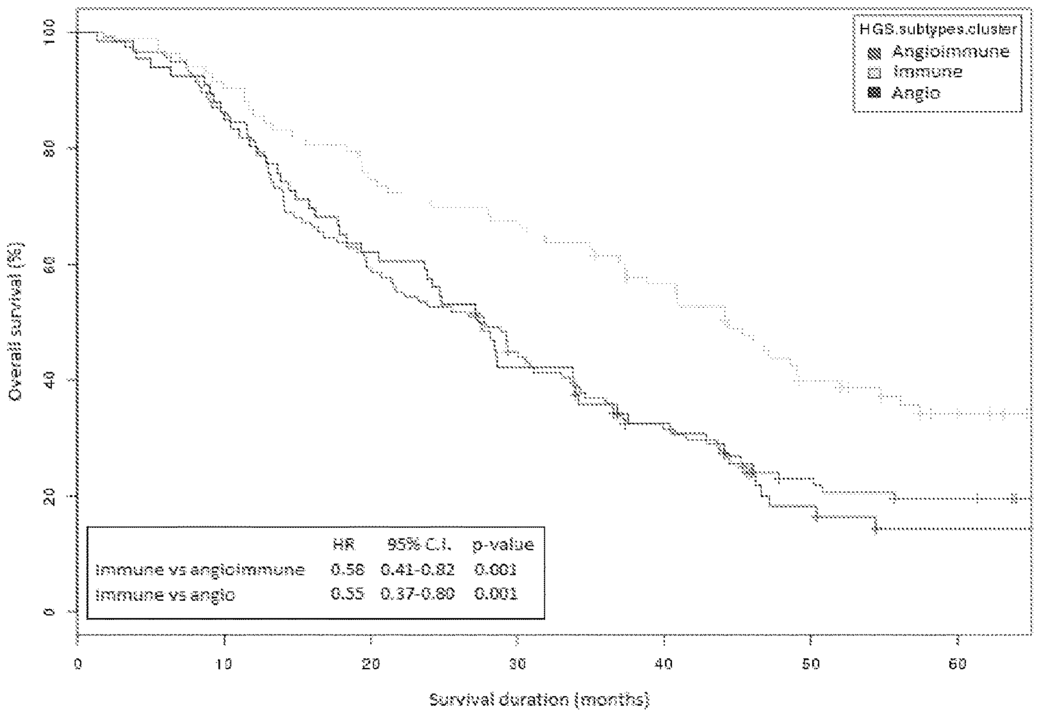
FIG. 2 provides Kaplan-Meier analysis of overall survival by cluster from unsupervised analysis of gene expression in 265 high grade serous ovarian carcinomas.

Multivariable survival analysis according to subgroup revealed that the patients in the Immune cluster had significantly prolonged OS compared to both patients in the Angioimmune (HR=0.58 [0.41-0.82], $p_{adj}$=0.001) and Angio clusters (HR=0.55 [0.37-0.80], $p_{adj}$=0.001). Kaplan-Meier curves are shown in FIG. 2 (univariable HR and p-values are shown).

Since patients in the Immune cluster had a significantly better outcome than those in the other clusters we proceeded to develop an assay to prospectively identify these patients in the clinic. In addition, given the low expression of angiogenic genes in the immune cluster, we hypothesized that this assay may identify a population that would not benefit from therapies targeting angiogenesis, although it would require additional datasets to test this theory. For the purpose of signature generation the Angio and Angioimmune clusters were grouped together and labeled as the "pro-angiogenic" group.

Figure 3:
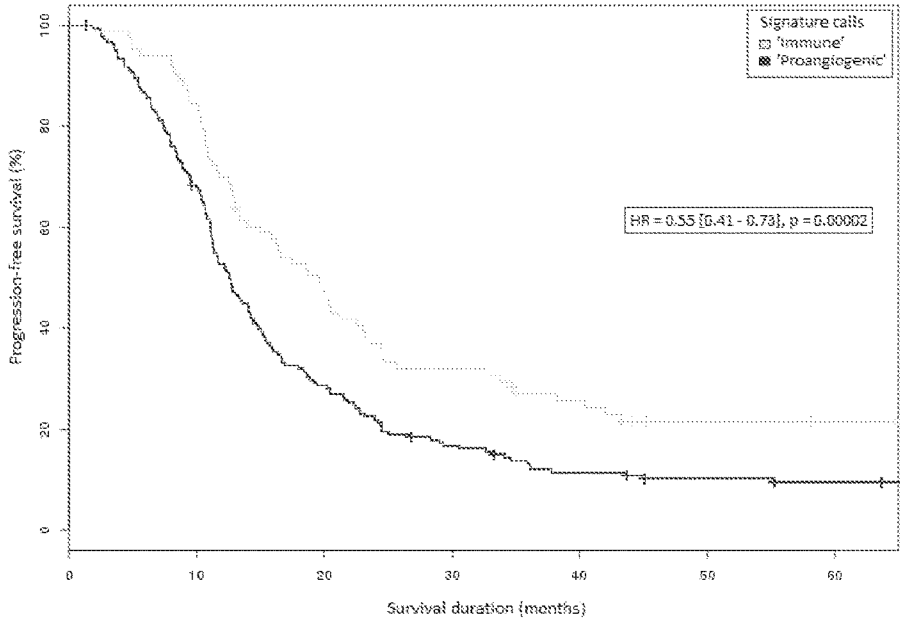
FIG. 3 provides Kaplan-Meier analysis of survival of the two classes defined by the 63-gene signature classifier in the Edinburgh (discovery) dataset. Proangiogenic group consists of Angio and Angioimmune subgroups. A. Progression-free survival. B. Overall survival.
Figure 3:
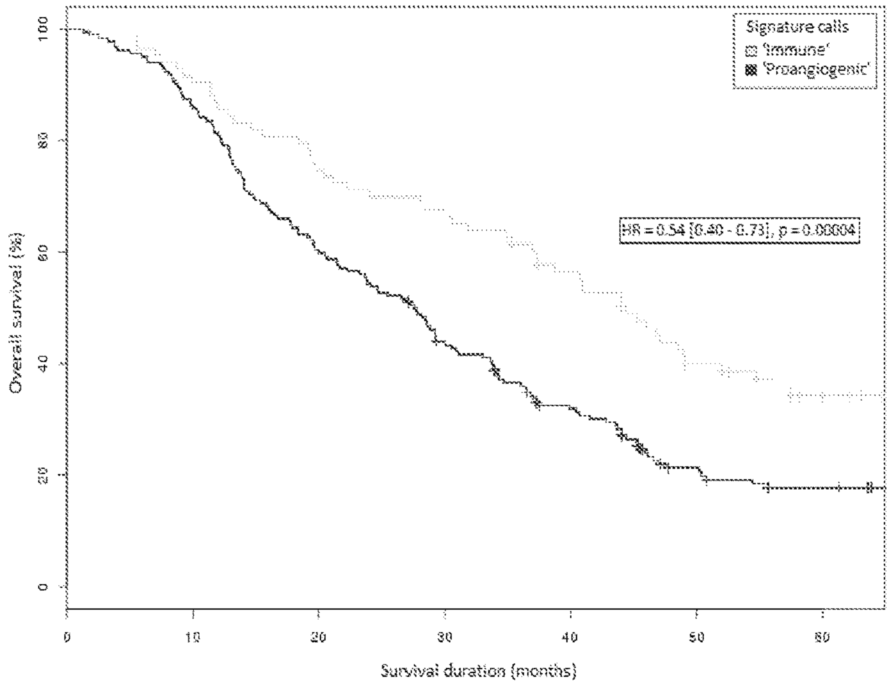

A 63-gene biomarker assay was then developed that could identify patients in the immune cluster (Table 2). Consistent with the hierarchical clustering analysis, patients classified by the assay as being in the Immune cluster had a significantly improved progression free survival (PFS) (multivariable analysis; HR=0.72 [0.52-0.99], p=0.043) and OS (multivariable analysis; HR=0.61 [0.44-0.86], p=0.004) compared to the other HGS patients. These multivariate analyses corrected for debulking status, stage, chemotherapy and age at diagnosis. Kaplan-Meier curves for PFS and OS according to signature call in the Edinburgh dataset are shown in FIGS. 3A and 3B respectively with univariate HR performance displayed on each figure.

Figure 4:
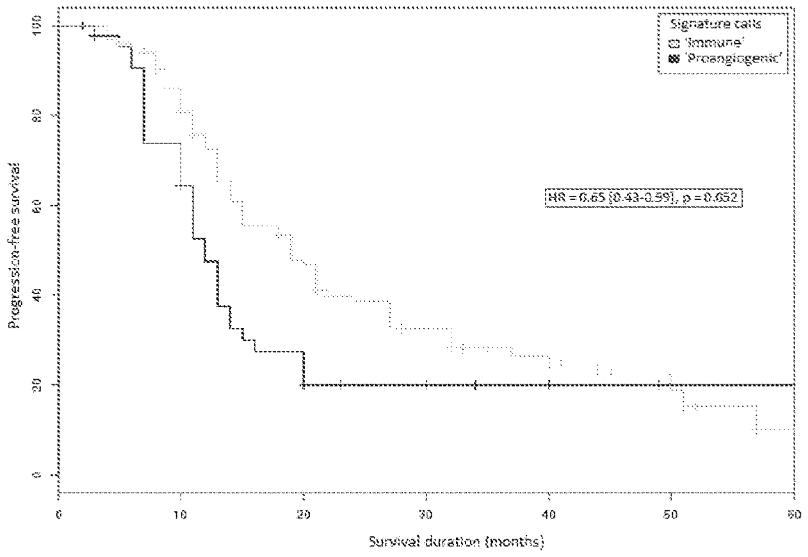
FIG. 4 provides Kaplan-Meier analysis of survival of the two classes defined by the 63-gene signature classifier in the Tothill (validation) dataset. Proangiogenic group consists of Angio and Angioimmune subgroups. A. Progression-free survival. B. Overall survival.
Figure 4:
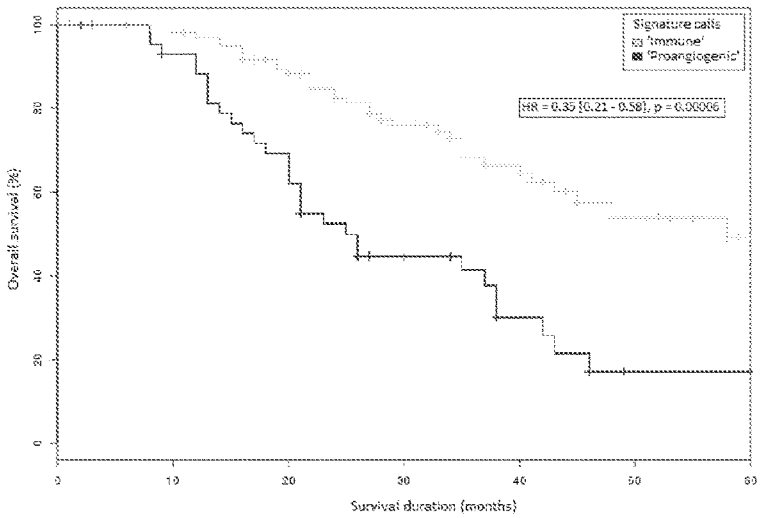
Figure 5:
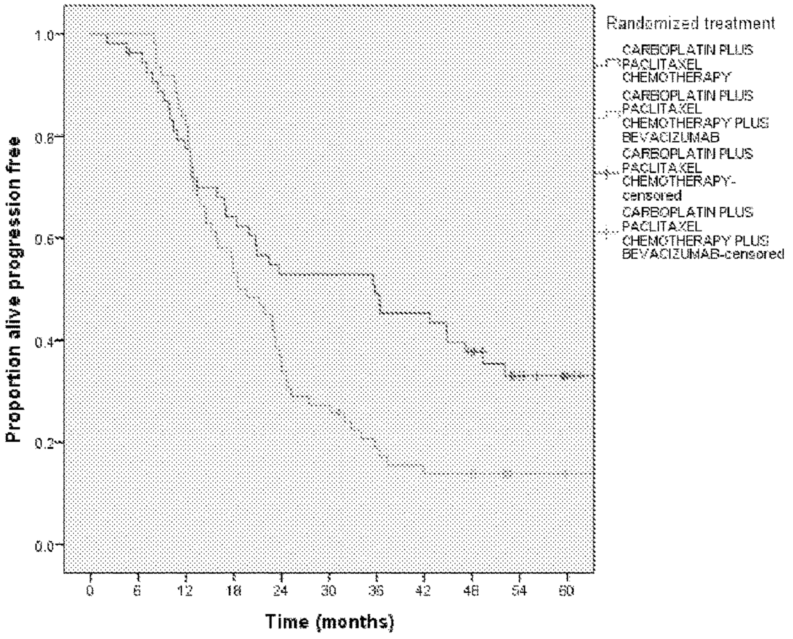
FIG. 5 provides Kaplan Meier curves for progression free survival in Immune (FIG. 5A) and Proangiogenic (FIG. 5B) subgroups of the patients in the ICON7 trail cohort. Within each figure the survival differences are displayed across the 2 randomized treatment groups: 1) Carboplatin plus paclitaxel chemotherapy and 2) Carboplatin plus paclitaxel chemotherapy plus bevacizumab.
Figure 5:
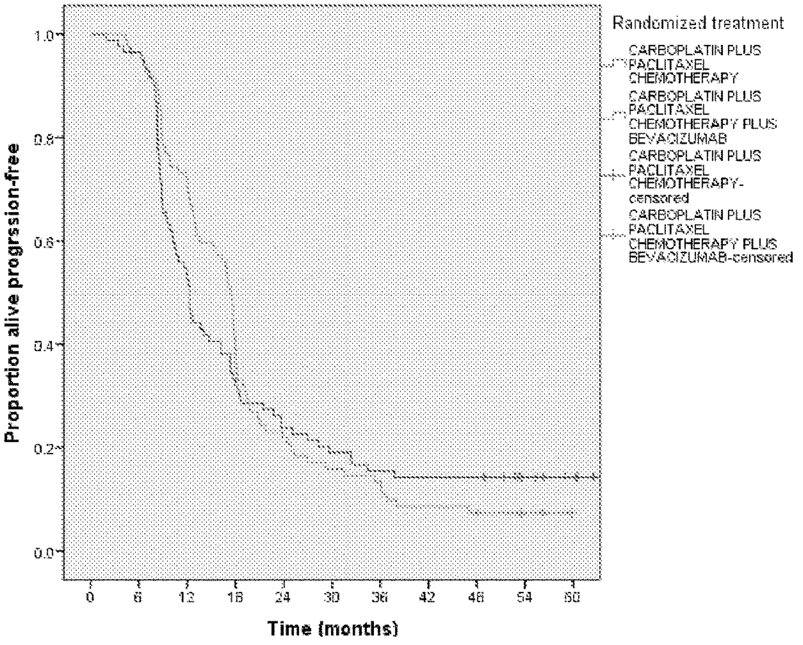
Figure 6:
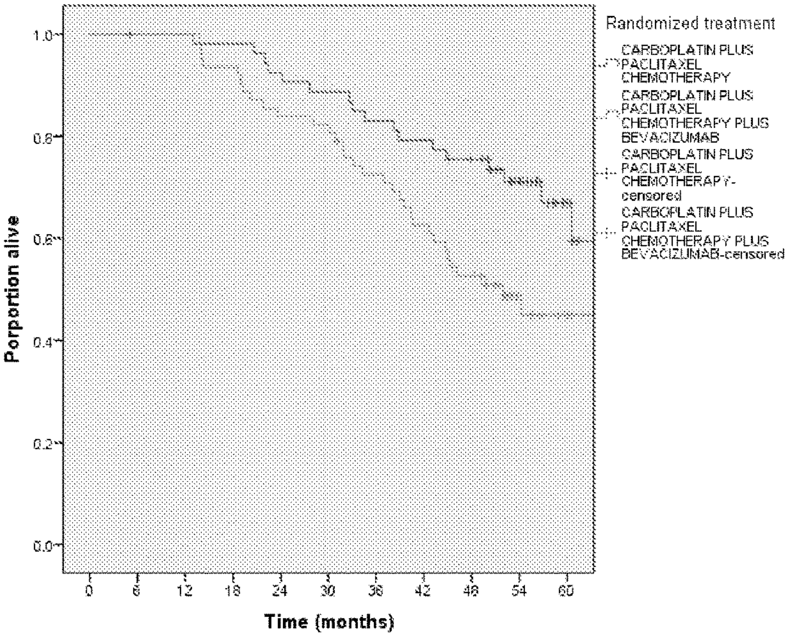
FIG. 6 provides Kaplan Meier curves for overall survival in Immune (FIG. 6A) and Proagniogenic (FIG. 6A) subgroups of patients in the ICON7 trial cohort. Within each figure the survival differences are displayed across the 2 randomized treatment groups: 1) Carboplatin plus paclitaxel chemotherapy and 2) Carboplatin plus paclitaxel chemotherapy plus bevacizumab.
Figure 6:
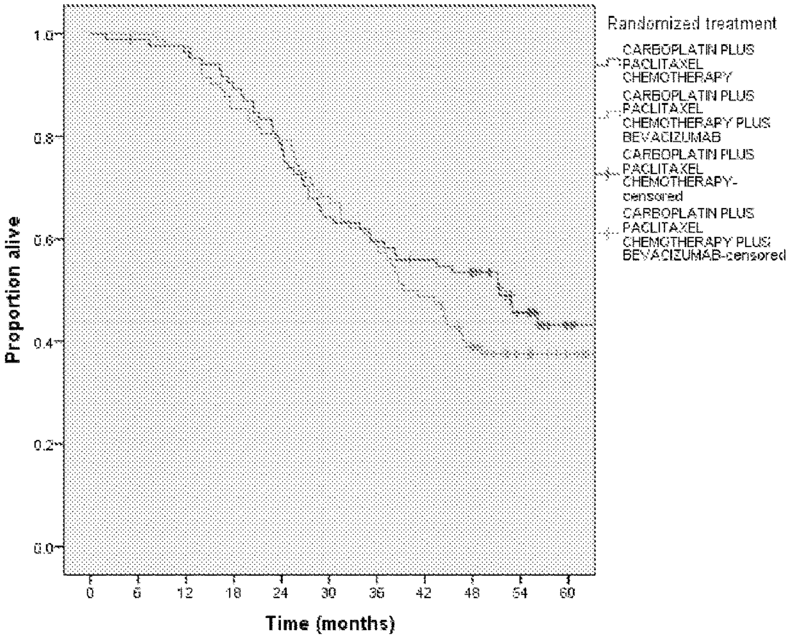

In order to independently validate our biomarker as a prognostic assay, it was applied to the HGS ovarian tumors within the dataset of Tothill et al. Clinical Cancer Research 2008: 14(16):5198-208. The patients identified as being in the Immune cluster had a significantly improved PFS (multivariable analysis; HR=0.62 [0.41-0.95], p=0.029) and OS (multivariable analysis; HR=0.32 [0.19-0.54], p=0.00001) compared to the other HGS patients. These multivariate analyses corrected for grade, stage, neoadjuvant treatment and residual disease. Kaplan-Meier curves for PFS and OS according to signature call in the Tothill dataset are shown in FIGS. 4A and 4B respectively, with univariate HR performance displayed on each figure.

Example 2: Independent Validation of the Predictive Utility of the "Immune" Signature Background The International Collaboration on Ovarian Neoplasms 7 (ICON7) trial is a Gynecologic Cancer Intergroup phase 3 trial that assessed the effects of adding bevacizumab, concurrently and as a continuation, to standard chemotherapy with carboplatin and paclitaxel in patients with primary peritoneal carcinoma, fallopian tube carcinoma, and epithelial ovarian carcinoma (Perren T J, Swart A M, Pfisterer J, Ledermann J A, Pujade-Lauraine E, Kristensen G, et al. A phase 3 trial of bevacizumab in ovarian cancer. N Engl J Med. 365(26): 2484-96, Aghajanian C, Blank S V, Goff B A, Judson P L, Teneriello M G, Husain A, et al. OCEANS: A randomized, double-blind, placebo-controlled phase III trial of chemotherapy with or without bevacizumab in patients with platinum-sensitive recurrent epithelial ovarian, primary peritoneal, or fallopian tube cancer. Journal of Clinical Oncology. 2012; 30(17): 2039-45).

Patient characteristics, progression-free survival, toxicity, and preliminary overall survival data and a summary of quality-of-life (QoL) data have been reported from ICON7. In the standard chemotherapy group, 696 (91%) of 764 women received 18 weeks of chemotherapy by protocol. In the bevacizumab group, 719 (94%) of 764 women received 18 weeks of chemotherapy and bevacizumab and 472 (62%) continued bevacizumab to protocol completion at 54 weeks. The hazard ratio for progression-free survival with standard chemotherapy and bevacizumab was 0.81 (95% CI 0.70-0.94, p=0.004). In patients at high risk of progression, defined as International Federation of Gynecology and Obstetrics (FIGO) stage IV disease or stage III disease with greater than 1.0 cm of residual disease after debulking surgery, the hazard ratio for death in the bevacizumab group was 0.64 (95% CI 0.48-0.85; p=0.002).

Methods

Access was obtained to the ICON7 trail samples via the Medical Research Council (MRC). An honest broker held the associated clinical data from the MRC. A randomization strategy for profiling the samples has been performed based on clinical factors. All reagents, arrays, and reference samples were previously tested and passed qualification criteria.

To confirm diagnosis and histological type, all samples were independently reviewed using H+E slides by two specialist gynecological pathologists and WT1 staining was used to confirm serous histology in problematic cases. Sections were taken from FFPE blocks (almost exclusively from an adnexal mass rather than peritoneal or omental disease) and macrodissected under bright field microscopy to minimize stromal contamination (<10%). The number of 10 μm sections used was dependent on the percentage of tumor in the block: two, three and four for >50%, 25-50% and <25% tumor content in the block respectively.

Total RNA was extracted from macrodissected FFPE tissue using the High Pure RNA Paraffin Kit (Roche Diagnostics GmbH, Mannheim, Germany). RNA was converted into complementary deoxyribonucleic acid (cDNA), which is subsequently amplified and converted into single-stranded form using the SPIA® technology of the WT-Ovation™ FFPE RNA Amplification System V2 (NuGEN Technologies Inc., San Carlos, Calif., USA). The amplified single-stranded cDNA is then fragemented and biotin labeled using the FL-Ovation™ cDNA Biotin Module V2 (NuGEN Technologies Inc.). The fragmented and labeled cDNA was then hybridized to the Almac Ovarian Cancer DSA, on this the signature was developed. Arrays are scanned using the Affymentrix Genechip® Scanner 7G (Affymetrix Inc., Santa Clara, Calif.).

After pathology review there were 286 patients in the sample with high grade serous ovarian cancer; 144 patients from the bevacizumab arm, and 142 from the no bevacizumab arm. It was estimated that 69% of patients would be in the pro-angiogenic patient group and that this would be the same in both study arms.

The primary study hypothesis was that within the "pro-angiogenic" subgroup there will be a marked effect of bevacizumab, corresponding to at least halving of the hazard ratio for progression-free survival compared to the immune subgroup. By contrast the expectation is that in the 'immune' subgroup bevacizumab will have at best no effect or may even be slightly disadvantageous.

Five samples failed processing QC such that there were 238 progression-free survival events (83%) in high grade serous clinical study data set. The estimated study power (using formula 6 in C Schmoor, W Sauerbrei, and M Schumacher Sample size considerations for the evaluation of prognostic factors in survival analysis Statist. Med. 2000; 19:441-452) to detect detect $\theta>2$ (corresponding to the differential effect of bevacizumab outlined in the previous paragraph) is 88% at the 10% one-sided level of statistical significance. There were 147 deaths in the data set and the power for the same analysis on survival was 75%.

Progression free survival was the primary end-point; this is the MRC calculated time provided in the data set. This is time from randomization to progression or death (from any cause) whichever occurs first. Overall survival was a secondary study end-point. This is time from randomization to death from any cause.

A stratified Cox-proportional hazards model was fitted to the progression-free survival data initially. The model had a single effect term for randomised study arm. A second stratified Cox-proportional hazards model was then fitted to the progression-free survival data. This model was also be stratified, but had separate terms for the effect of randomised study arm within each strata.

The log-likelihood of the two fitted models were compared to determine whether the effect of randomised study arm depends on pro-angiogenic status (chi-square test with degrees of freedom corresponding to number of strata-1). If the above test is statistically significant at the 5% level of statistical significance then the appropriateness of the proportional hazards assumption for the model with separate terms for randomised study arm within each strata would be assessed.

The test for proportional hazards was done via the Grambsch-Therneau test [P. Grambsch and T. Therneau (1994), Proportional hazards tests and diagnostics based on weighted residuals. *Biometrika,* 81, 515-26]. Progression-free survival times were transformed to a log scale for the test. The tests on each of the terms for study arm within each strata were assessed separately using the 5% level of statistical asignificance. If the test for proportional hazard was rejected within one or more of the strata then a restricted mean survival model would be fitted within each strata using flexible parametric survival models [P Royston, M K B Parmar The use of restricted mean survival time to estimate the treatment effect in randomized clinical trials when the proportional hazards assumption is in doubt Stat Med, 30 (2011), pp. 2409-2421]. These models would use 3 degrees of freedom to estimate the baseline distribution function and 1 degree of freedom for the time dependent treatment effect. The maximum time over which the retricted mean would be calculated in each case was 3 years.

The above analysis will be repeated for overall survival.

Results

For patients classified as in the immune subtype (39%), the addition of bevacizumab conferred a worse progression free survival (HR 1.73 (1.12-2.68)) and overall survival (HR 2.00 (1.11-3.61)) when compared to proangiogenic patients. See FIGS. 5A-B and 6A-B. Accordingly, subjects with the Immune cancer subtype exhibited a poor prognosis when bevacizumab was added to their treatment regimen compared to subjects that did not have the Immune cancer subtype.

Example 3: Independent Validation of the Prognostic Utility of Immune Signature

The primary objections of the study were: 1. predication of individual risk of tumour recurrence using the 63-gene signature on patient's gene expression data; 2. evaluation of the performance of the signature prognositic prediction with regards to patients progressive free survival (PFS) outcome as well as overall survival (OS); 3. investigation of the influence of clinical covariates on the signature prognostic performance in relation to the progressive free survival event.

This exploratory study included all the 139 patients in the control arm of the study. It was estimated that 85 (61.2%) of the patients would be categorized as pro-angiogenic (signature negative) by the gene signature. The chart and follow-up review indicated that 72 had progression-free survival events, with 46 deaths (overall survival events) occurring in the arm (information on patient numbers and percentages were provided by Jim Paul).

A retrospective power calculation using a sample size and power calculation method (Freedman, L. S. (1982). Tables of the number of patients required in clinical trials using the log-rank test. Statistics in Medicine. 1: 121-129) under a Cox proportional hazards regression showed that the above study figures will provide approximately 85% power to detect an hazard ratio (HR) of 0.5 when comparing progression free survival of 'immune only' with 'pro-angiogenic' molecular subgroups patients at 2-sided 5% level of significance.

Time to event (survival) analysis using the progression free survival as outcome was performed to evaluate the prognostic effects of the signature. The survival distributions of patient groups defined by the angiogenic status ('pro-angiogenic or signature negative' and 'immune-only or signature positive') were visualized using the Kaplan-Meier (KM) curve.

The Cox proportional hazards regression was performed to relate the patients' angiogenic status (negative or positive) to progression free survival event. In addition to the univariate (unadjusted) exploration, the multivariable (adjusted) Cox model was performed to explore the effect of the signature molecular subgroups (positive or negative) on the PFS and OS adjusting for other important clinical covariates. All estimated effects were reported with 95% confidence intervals from an analysis in which the signature and standard prognostic variables are included, regardless of their significance (P Royston, MKB Parmar The use of restricted mean survival time to estimate the treatment effect in randomized clinical trials when the proportional hazards assumption is in doubt Stat Med, 30 (2011), pp. 2409-2421). Due to size limitation only a few important covariates were considered; these included FIGO stage, tumour grade, debulking status, performance status (ECOG) and patient age.

The appropriateness of the proportional hazards assumption across the molecular subgroup was investigated before interpreting the Cox model results. In line with the previous analysis of study trial data, a restricted mean survival model was fitted for each molecular subgroup If the test for proportional hazard is rejected. The maximum time over which the retricted mean was to be calculated in 4 years.

Results

Figure 7:
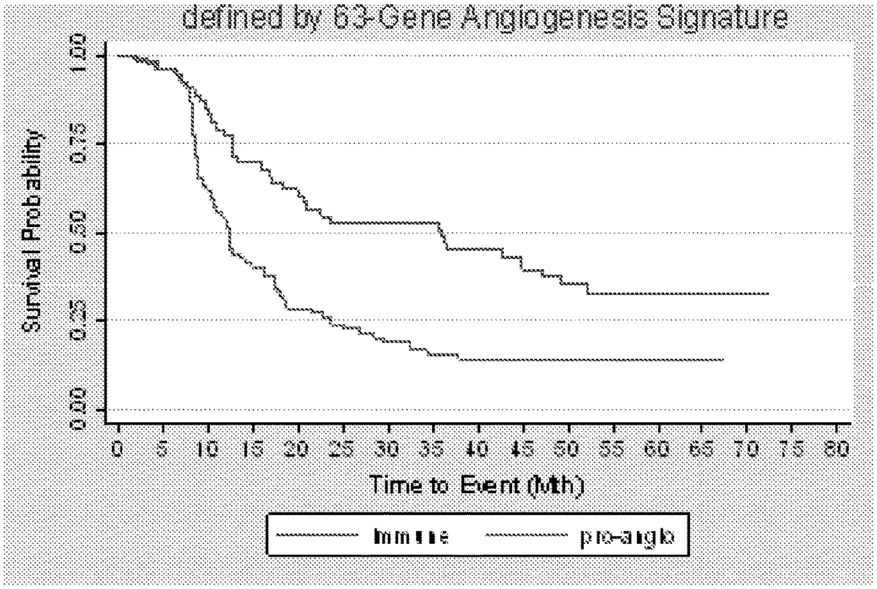
FIG. 7 provides Kaplan Meier curves for progression free survival (A) and overall survival (B) for carboplatin and paclitaxel treated ICON7 trail patients defined by the 63 gene signature.
Figure 7:
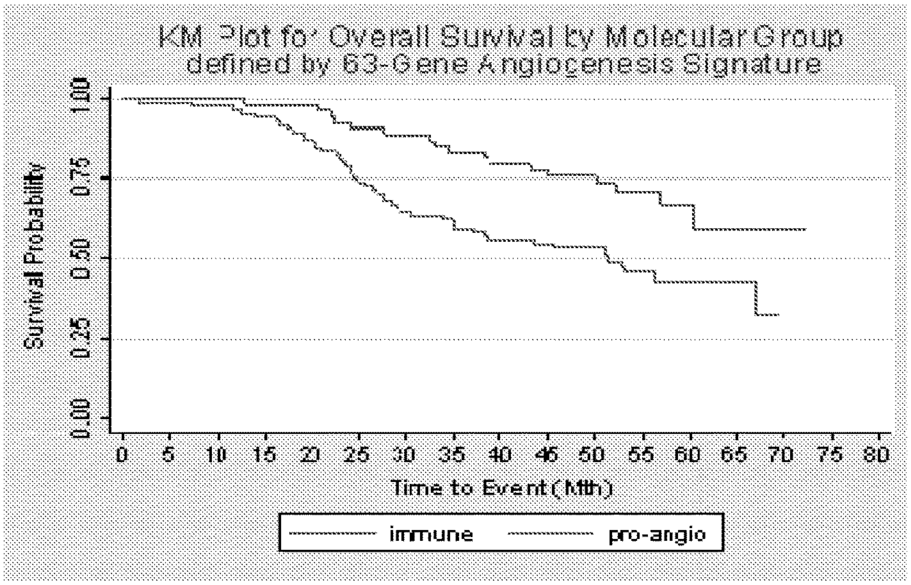

The 63-gene signature is prognostic in high grade serous (HGS) ovarian patients in the control arm (receiving carboplatin plus pacitaxel chemotherapy treatment) of ICON7 trial data. The results using Cox proportional hazards regression show that patients classified to the 'immune' molecular subgroup by the gene signature have a statistically significant improved progression free survival compared to those classified as pro-angiogenic before (Univariate HR=0.48, 95% CI=0.32, 0.72; $p<0.001$) and after (Multivariable HR=0.50; 95% CI=0.32, 0.79; p=0.003) adjusting for other clinical covariates including age, grade, ECOG, debulking status and stage see FIG. 7A Similarly, patients classified into immune molecular subgroup had a statistically significant better overall survival compared to the pro-angiogenic before (Univariate HR=0.46; 95% CI=0.26, 0.80; p=0.006) and after (Multivariable HR=0.53; 95% CI=0.29, 0.97; p=0.041) adjusting for other clinical covariates see FIG. 7B. The data show no serious departure of the proportionality assumption.

Figure 8:
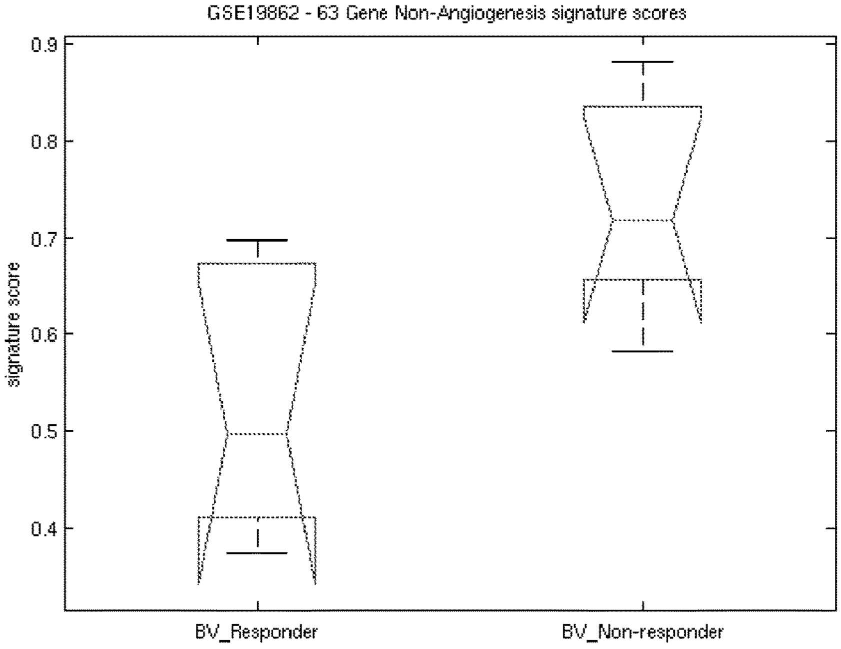
FIGS. 8A and 8B are graphs demonstrating certain classification performance benchmarks of an example non-angiogenesis signature as applied to colorectal cancer samples.
Figure 8:
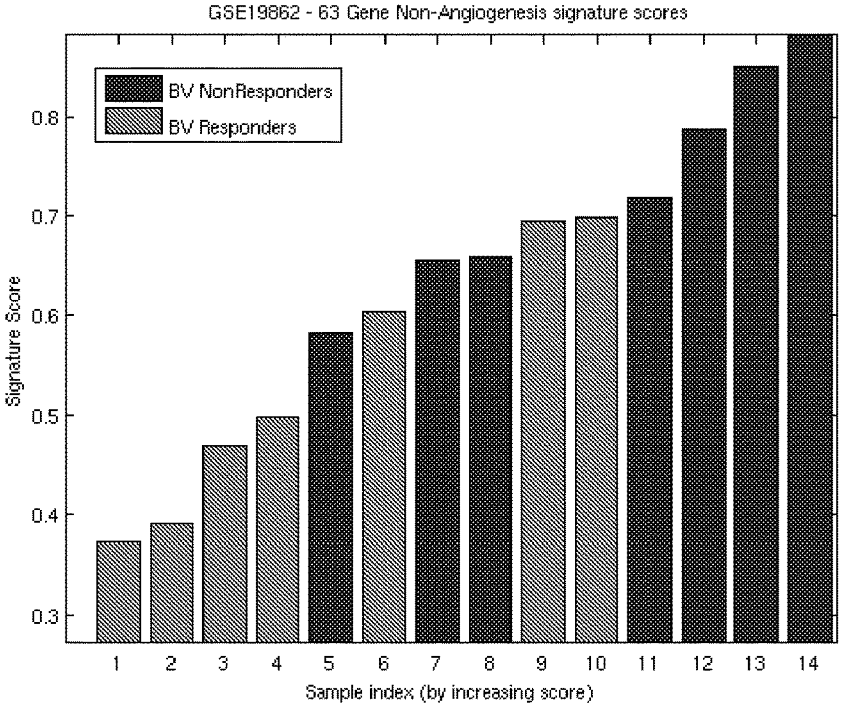

Example 4: Predictive Utility of Non-Angiogenesis Signature in Colorectal Cancer A public array data set obtained from the Gene Expression Omnibus database for a cohort of recurrent or metastatic colorectal cancer responders and non-responders to Bevacizumab on plus 2 arrays (E-GEOD-19862) was obtained and analyzed using the example 63 gene signature of Table 2. The 63 gene ovarian immune signatures predicts response to bevacizumab with an AUC: 0.86 (0.60-1.00). See FIG. 8.

Example 5: Summary of 63 Gene Signature

Samples:
- Internal training samples: This sample set comprised of 193 High Grade Serous Ovarian samples retrieved from the Edinburgh Ovarian Cancer Database
- Tothill samples: This is a publically available dataset, from which 152 High Grade Serous Ovarian samples were used for analysis
- ICON7 samples: This sample set comprises of 284 High Grade Serous samples from a phase III randomized trial of carboplatin and paclitaxel with or without bevacizumab first line cancer treatment which were accessed through the MRC (Medical Research Council).
  - ICON7 SOC (Standard of Care)—140 samples—refers to patients who did not receive the addition of bevacizumab
  - ICON7 Immune group—116 samples: this refers to the ICON7 samples predicted in the Immune group by the Immune 63 gene signature
  - ICON7 ProAngio group—168 samples: this refers to the ICON7 samples predicted in the ProAngiogenesis group by the Immune 63 gene signature Methods:

Signature Development

A balanced sample set of 193 Ovarian HGS samples were used to develop the signature using the PLS (Dejong S. Simpls—an Alternative Approach to Partial Least-Squares Regression. Chemometr Intell Lab 1993; 18:251-63) (Partial Least Squares) method during 10 repeats of 5-fold cross validation (CV). The following steps were used within signature development:
- Probesets mapped to genes and gene expression measured using the $log_2$ transformation of the median probeset expression for each gene
- Within nested CV, quantile normalization was performed following a pre-filtering to remove 75% of genes with low variance, low intensity, and high correlation to cDNA yield
- Genes/features were ranking based on correlation adjusted t-scores and feature reduction involved discarding 10% of the least important genes until 5 genes remained
- The 63 gene signature was identified as the feature set for which the hazard ratio (HR) predicting Progression free survival (PFS) under cross-validation was optimal The following datasets have been evaluated within CV to determine the performance of the 63 gene signature:
- Internal training set—193 samples
- ICON7 SOC (Standard of Care)—140 samples ICON7 Immune group—116 samples ICON7 ProAngio group—168 samples Core Gene Analysis The purpose of evaluating the core gene set of the signature is to determine a ranking for the genes based upon their impact on performance when removed from the signature. This analysis involved 1,000,000 random samplings of 10 signature genes from the original 63 signature gene set. At each iteration, 10 randomly selected signature genes were removed and the performance of the remaining 53 genes was evaluated using the PFS endpoint to determine the impact on HR performance when these 10 genes were removed in the following 3 datasets:

- Internal Validation—72 samples
- Tothill HGS (Tothill R W, Tinker A V, George J, et al. Novel molecular subtypes of serous and endometrioid ovarian cancer linked to clinical outcome. Clin Cancer Res 2008; 14:5198-208) (High Grade Serous)—152 samples
- ICON7 SOC (Standard of Care)—140 samples Within each of these 3 datasets, the signature genes were weighted based upon the change in HR performance (Delta HR) based upon their inclusion or exclusion. Genes ranked '1' have the most negative impact on performance when removed and those ranked '63' have the least impact on performance when removed.

Minimum Gene Analysis

The purpose of evaluating the minimum number of genes is to determine if significant performance can be achieved within smaller subsets of the original signature.

This analysis involved 10,000 random samplings of the 63 signature genes starting at 1 gene/feature, up to a maximum of 25 genes/features. For each randomly selected feature length, the signature was redeveloped using the PLS machine learning method under CV and model parameters derived. At each feature length, all randomly selected signatures were applied to calculate signature scores for the following 3 datasets:

- Tothill HGS (High Grade Serous)—152 samples
- ICON7 SOC (Standard of Care)—140 samples
- ICON7 Immune group—116 samples Continuous signature scores were evaluated with PFS (Progression Free Survival) to determine the HR (Hazard Ratio) effect. The HR for all random signatures at each feature length was summarized and figures generated to visualize the performance over CV.

Results

Signature Development

This section presents the results of signature development within CV.

Figure 9:
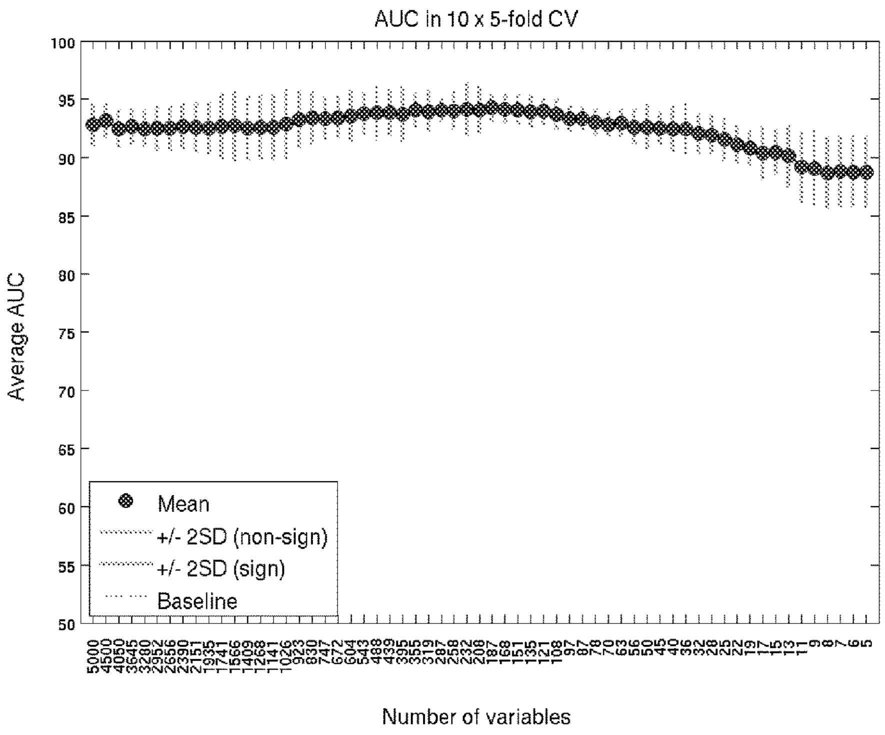
FIG. 9: Signature development: AUC of training set under CV.
Figure 10:
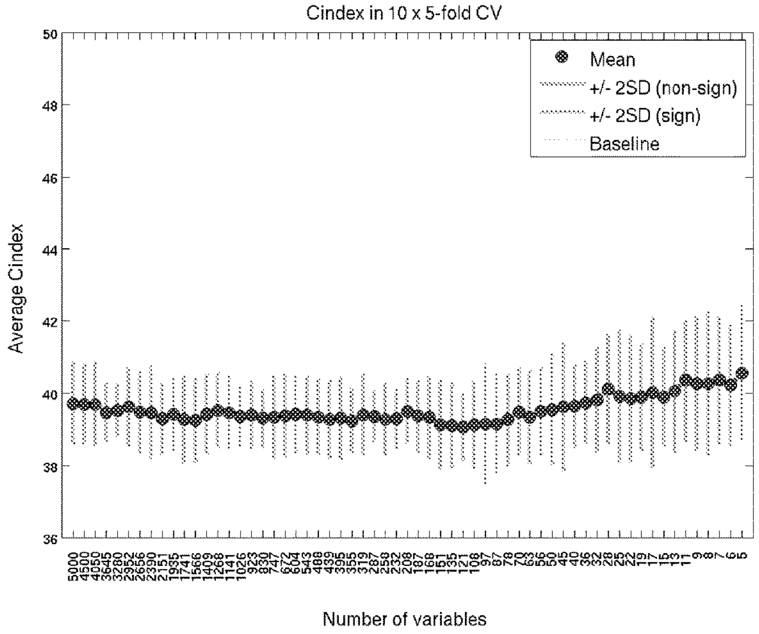
FIG. 10: Signature development: C-Index of training set under CV.
Figure 11:
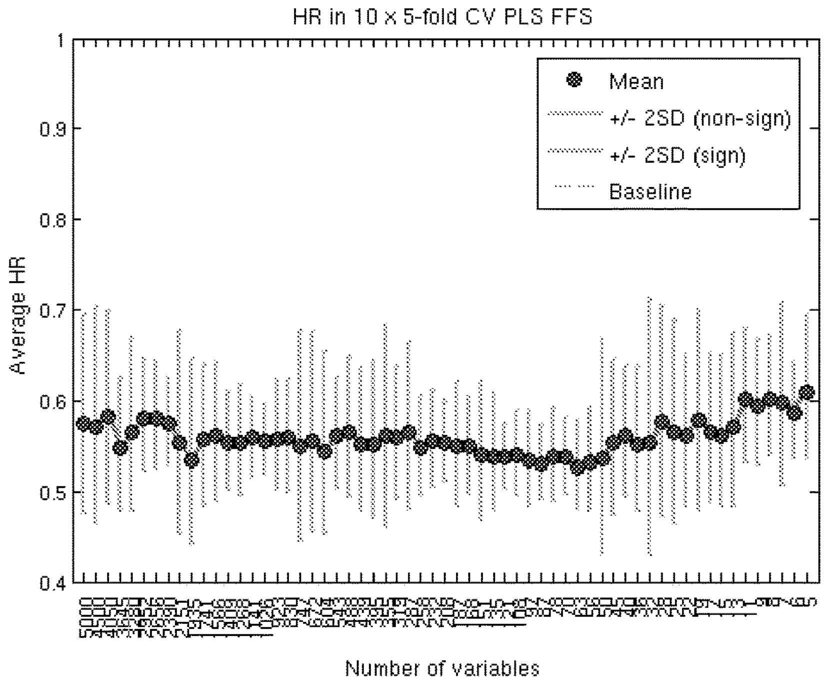
FIG. 11: Signature development: HR of training set under CV.
Figure 12:
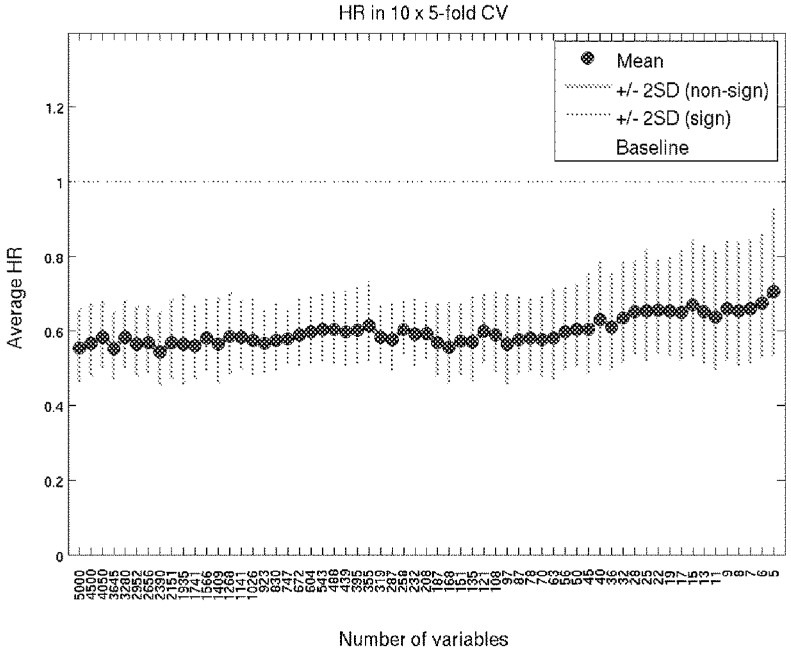
FIG. 12: Signature development: HR of ICON7 SOC samples under CV.
Figure 13:
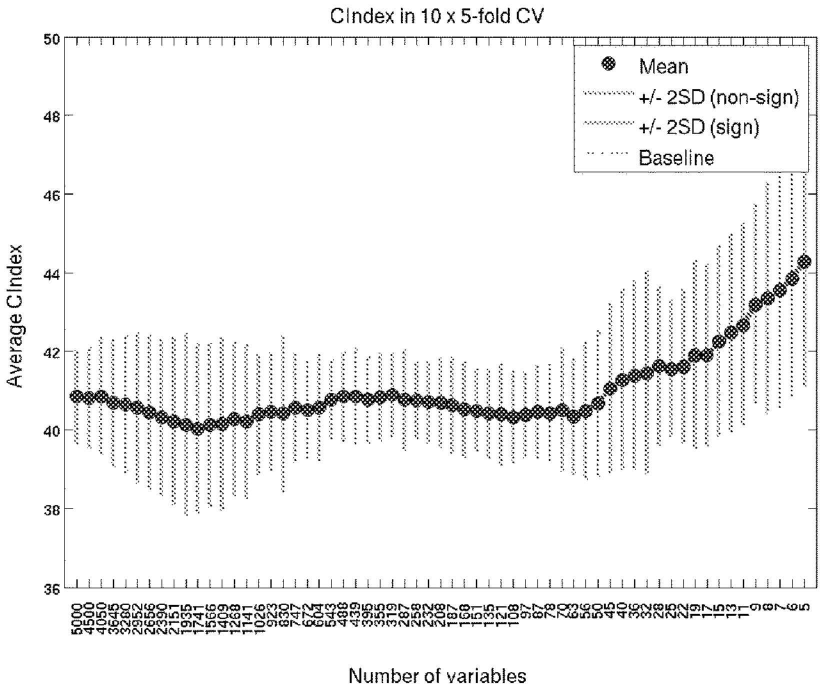
FIG. 13: Signature development: C-Index of ICON7 SOC samples under CV.
Figure 14:
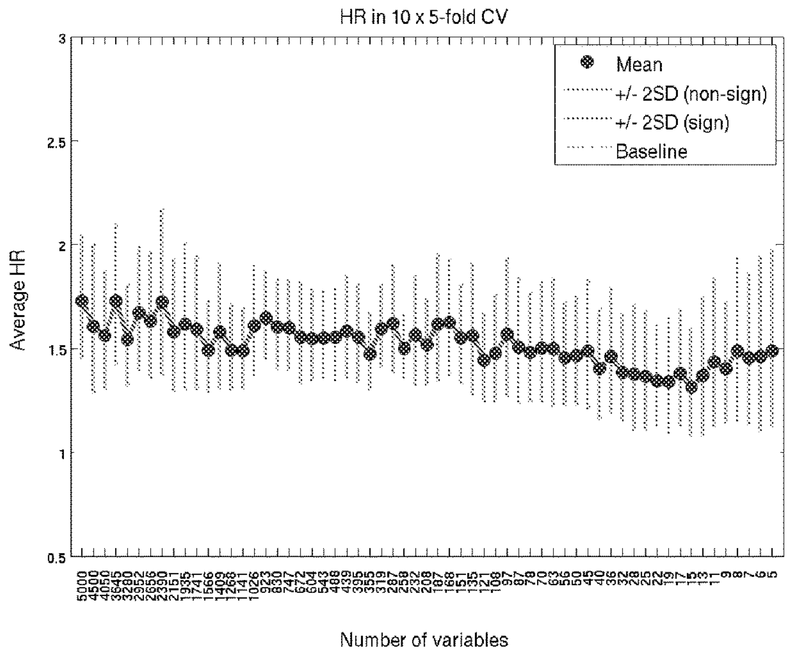
FIG. 14: Signature development: HR of ICON7 Immune samples under CV.
Figure 15:
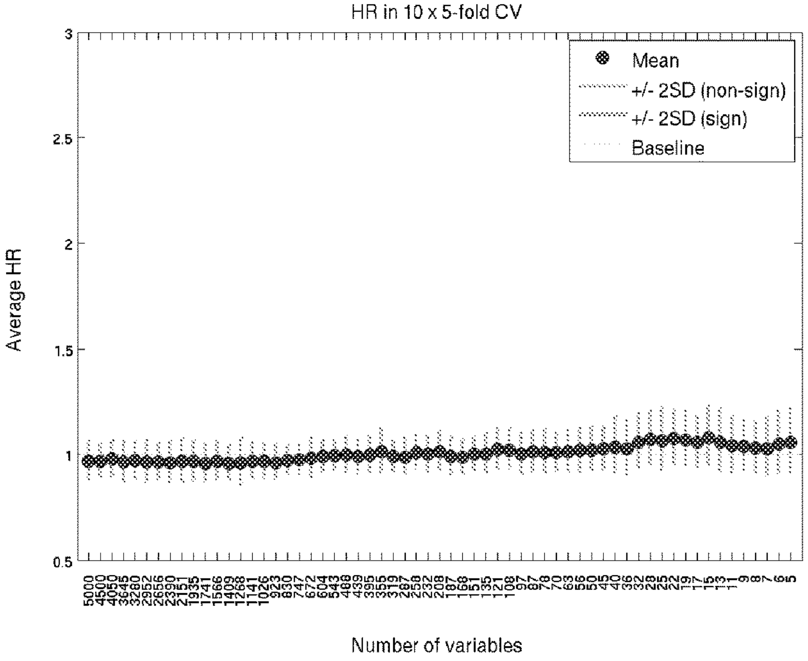
FIG. 15: Signature development: HR of ICON7 ProAngio samples under CV.

- Internal training set: FIGS. 9, 10 & 11 show the AUC (Area under the receiver operating curve), C-Index (Concordance Index) & HR of the training set, from which the 63 gene signature was identified.
- ICON7 SOC: FIGS. 12 & 13 show the HR and C-Index of the ICON7 SOC samples under CV.
- ICON7 Immune group: FIG. 14 shows the HR of the ICON7 Immune samples (as identified by the 63 gene signature) under CV.
- ICON7 ProAngio group: FIG. 15 shows the HR of the ICON7 ProAngio samples (as identified by the 63 gene signature) under CV.

Core Gene Analysis

The results for the core gene analysis of the 63 gene signature in 3 datasets is provided in this section.

Figure 16:
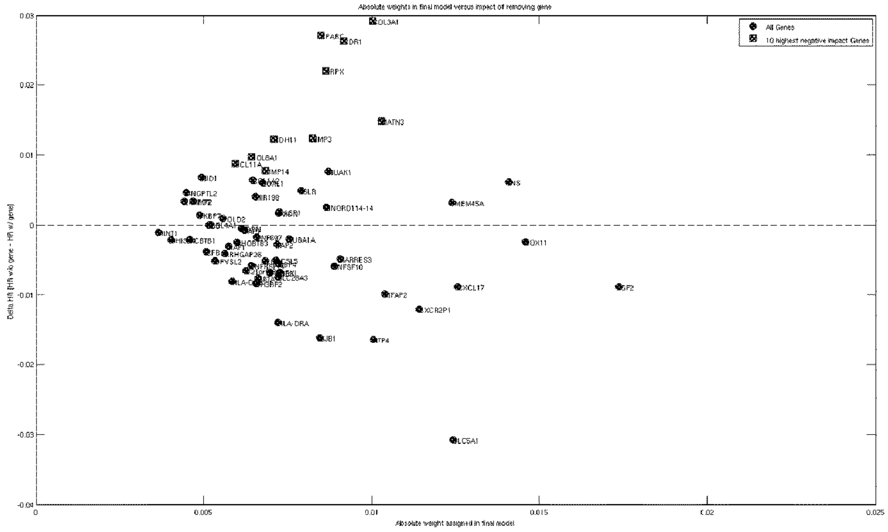
FIG. 16: Core set analysis: Immune63GeneSig_CoreGenes_InternalVal.png.
Figure 17:
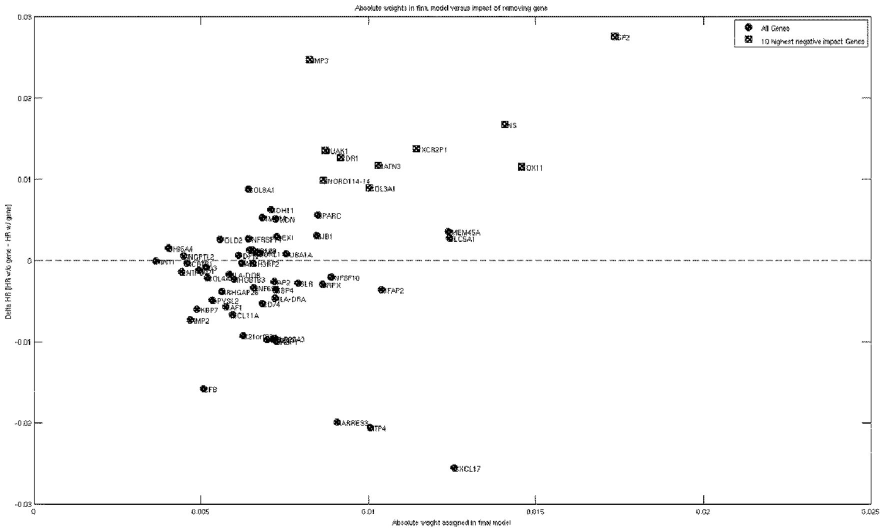
FIG. 17: Core set analysis: Immune63GeneSig_CoreGenes_Tothill.png.
Figure 18:
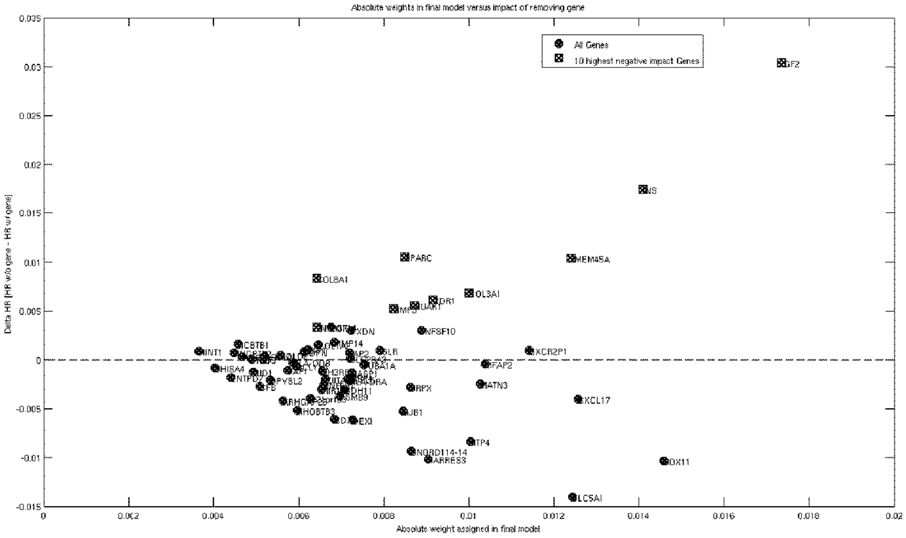
FIG. 18: Core set analysis: Immune63GeneSig_CoreGenes_ICON7_SOC.png.

- Internal Validation: Delta HR performance measured in this dataset for the 63 signature genes is shown in FIG. 16. This figure highlights the top 10 ranked genes in the signature which are the most important in retaining a good HR performance within this dataset.
- Tothill HGS: Delta HR performance measured in this dataset for the 63 signature genes is shown in FIG. 17. This figure highlights the top 10 ranked genes in the signature which are the most important in retaining a good HR performance within this dataset.
- ICON7 SOC: Delta HR performance measured in this dataset for the 63 signature genes is shown in FIG. 18. This figure highlights the top 10 ranked genes in the signature which are the most important in retaining a good HR performance within this dataset.
- Delta HR across these 3 datasets was evaluated to obtain a combined gene ranking for each of the signature genes. The ranks assigned to the signature genes based on the core set analysis have been outlined in Immune63GeneSig_CoreGenes_HR.txt.

Minimum Gene Analysis

The results for the minimum gene analysis of the 63 gene signature in 3 datasets is provided in this section.

Figure 19:
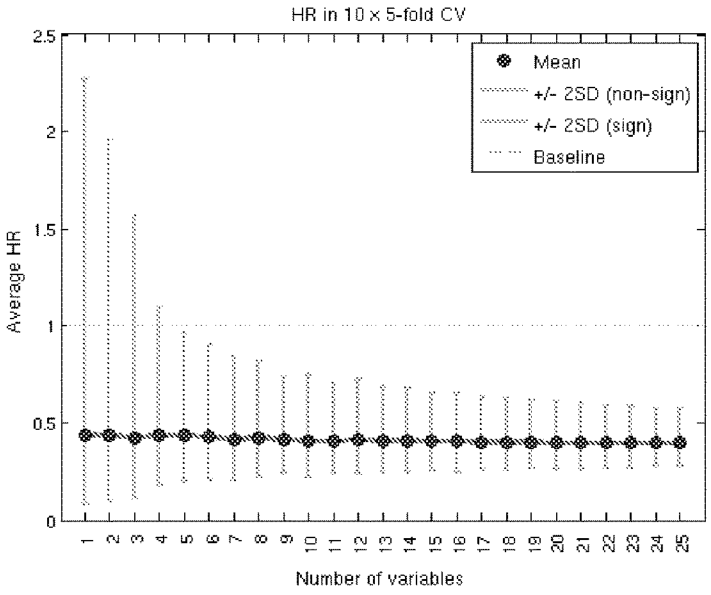
FIG. 19: Minimum gene set analysis: Immune63 GeneSig_MinGenes_Tothill.png
Figure 20:
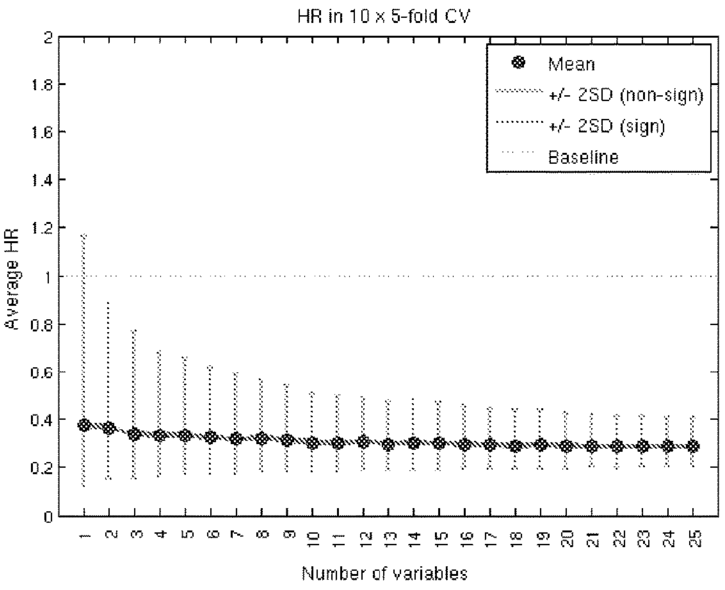
FIG. 20: ICON7 SOC: Minimum gene set analysis: Immune63GeneSig_MinGenes_ICON7_SOC.png.
Figure 21:
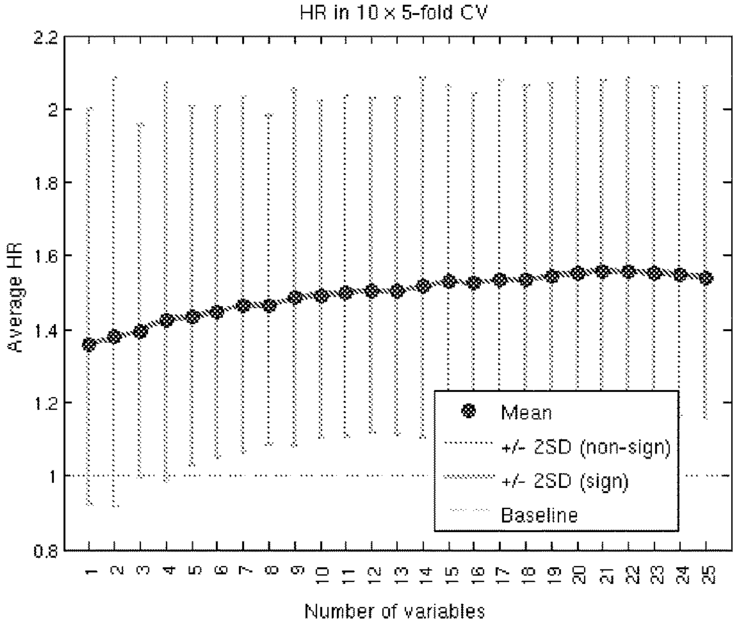
FIG. 21: ICON7 Immune: Minimum gene set analysis: Immune63GeneSig_MinGenes_ICON7_Immune.png

- Tothill HGS: The average HR performance measured in this dataset using the random sampling of the signature genes from a feature length of 1.25 is shown in FIG. 19. This figure shows that to retain a significant HR performance (i.e. HR<1) a minimum of 5 of the signature genes must be selected.
- ICON7 SOC: The average HR performance measured in this dataset using the random sampling of the signature genes from a feature length of 1.25 is shown in FIG. 20. This figure shows that to retain a significant HR performance (i.e. HR<1) a minimum of 2 of the signature genes must be selected.
- ICON7 Immune: The average HR performance measured in this dataset using the random sampling of the signature genes from a feature length of 1.25 is shown in FIG. 21. This figure shows that to retain a significant HR performance (i.e. HR<1) a minimum of 5 of the signature genes must be selected.

In summary, it is recommended that a minimum of at least 5 genes can be used and significant performance will be retained.

Example 6: Colon Cancer Samples

Samples and Methods

Samples 529 fresh-frozen (FF) primary tumour samples from patients with stage II, III or IV disease, 232 of which had progression free survival data followed up after receiving adjuvant chemotherapy, were assessed with the 63-gene signature. Microarray data from gene expression profiling on the Affymetrix U133 Plus 2.0 platform was obtained from the public domain (GEO accession number GSE40967).

Signature Score Calculation

Signature scores were calculated using the following steps:

- Robust Multi-array Analysis (RMA) background correction.
- Summarisation of probes to probesets using median expression.
- Summarisation of probesets to genes using median expression
- A quantile normalisation model is applied to the gene level matrix (or vector) on a per sample basis, which transforms the distribution of individual patient gene profiles to a similar distribution as the training data.

The signature score is calculated per sample using a weighted sum of the expression of each gene in the signature:

$$\text{Signature Score} = \sum_i w_i \times (x_i - b_i) + k$$

Where $w_i$ is a weight for each gene, $b_i$ is a gene-specific bias, $x_i$ is the observed gene expression level after pre-processing and k=0.2953 is a constant offset Statistical Analysis Cox's proportional hazard regression model is used to estimate the univariate hazard ratio (HR) effect of the 63-gene signature on progression free survival following adjuvant chemotherapy. The p-value for the HR estimate is calculated using the log-rank test.

Results

Figure 22:
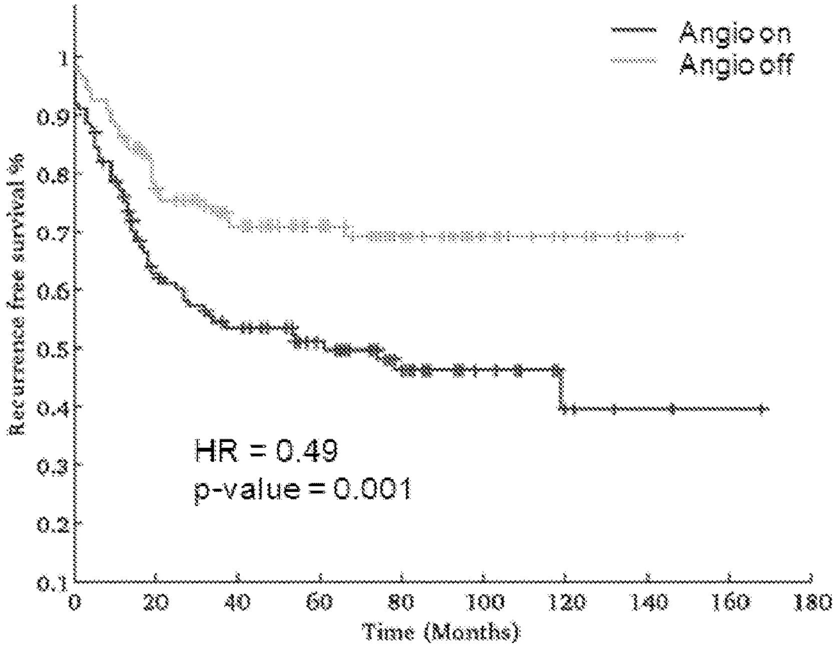
FIG. 22: Kaplan Meier to show the differences in progression free survival probability between the samples predicted as Angio-Off (inactive) versus those that are predicted as Angio-On (active) by the 63 gene signature

FIG. 22 provides the Kaplan Meier curve for the signature predictions in 232 patients that received adjuvant chemotherapy, showing that the 63 gene signature can be used to predict prognosis. The univariate HR calculated from Cox's proportional hazard regression is 0.49 with log-rank p=0.001. "Angio on" is equivalent to negative for the biomarker signature and "Angio off" is equivalent to positive for the biomarker signature.

Example 7: Prognostic Utility of Subtype in Colorectal Cancer

Samples

A public array data set was obtained from the Gene Expression Omnibus database (GSE40967) comprising a cohort of 529 patients with colorectal cancer (Marrisa et al, 2013). Samples were profiled on the Affymetrix Plus 2.0 array platform. The data comprises patients with stage II, III and IV disease, and 232 patients received adjuvant chemotherapy with follow up recurrence free survival (RFS) data.

Methods

All samples were pre-processed using RMA and semi-supervised hierarchical clustering was performed using the Entrez Gene IDs defining the "angiogenesis" gene cluster (cluster 4) in FIG. 1 to filter the data matrix. Following standardization of the filtered data matrix to the median gene expression values, agglomerative hierarchical clustering was performed using Euclidean distance and Ward's linkage method. The optimal number of sample and gene clusters was determined using the GAP statistic. As the gene list used to cluster the samples was highly enriched for the angiogenesis biology, samples clusters with up-regulation of these genes were class labelled angiogenesis active (or angio on); and those with down-regulation of these genes were class labelled angiogenesis inactive (or angio off).

The samples were further tested with the 63-gene signature and an association between the 63 gene signature score and the sample clusters (angiogenesis active or angiogenesis inactive) was evaluated using the Area Under the Receiver Operating Characteristic (ROC) Curve (AUC). The threshold for classifying patients as angiogenesis active/inactive within colorectal cancer was optimised to maximise the sensitivity+specificity with respect to predicting the subtype as defined by the hierarchical clustering analysis.

The clinical significance of the 63-gene signature predictions was evaluated using Kaplan Meier curves and Cox-proportional hazard survival analysis. The endpoint was defined as a progression free survival, and the Cox-proportional hazards modelling included an adjustment for clinical covariates: age; gender; stage; tumour location and MSI status.

Figure 23:
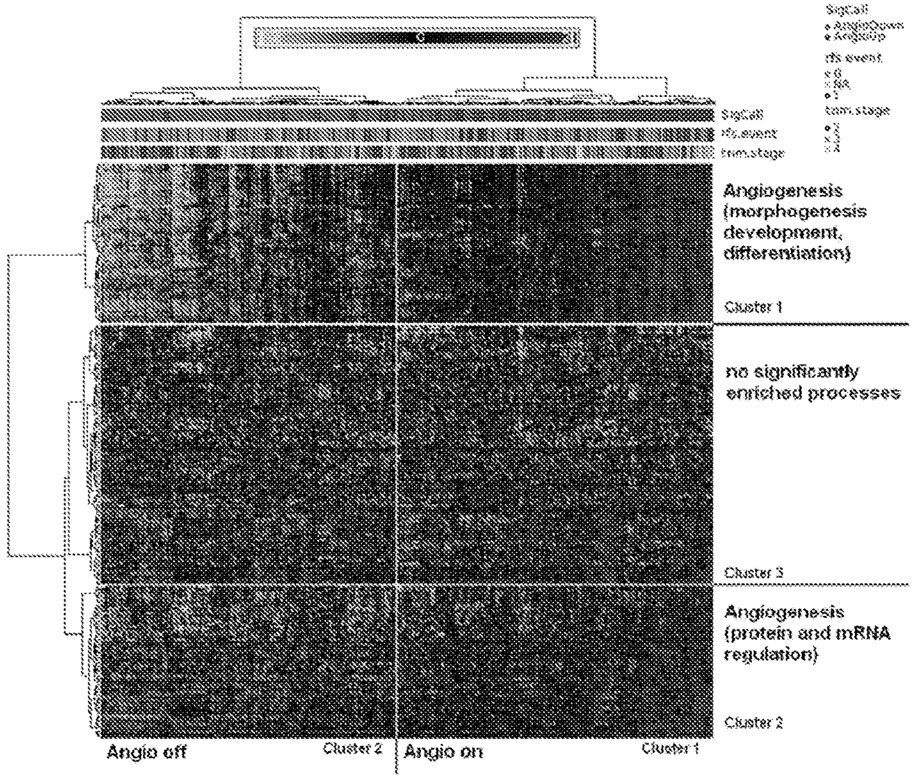
FIG. 23: Semi-supervised hierarchical clustering of the 529 CRC samples published by Marrisa et al (2013) using the angiogenesis defining gene list.

Results 520 samples underwent semi-supervised clustering based on 219 genes (the genes defining cluster 4 in FIG. 23). Two sample clusters and 3 gene clusters were identified (FIG. 23). Sample cluster 1 (273 patients) was characterised by up-regulation of expression of angiogenesis genes, therefore was labelled angiogenesis active; and sample cluster 2 (256 patients) was characterised by down-regulation of expression of angiogenesis genes, therefore was labelled angiogenesis inactive.

Figure 24:
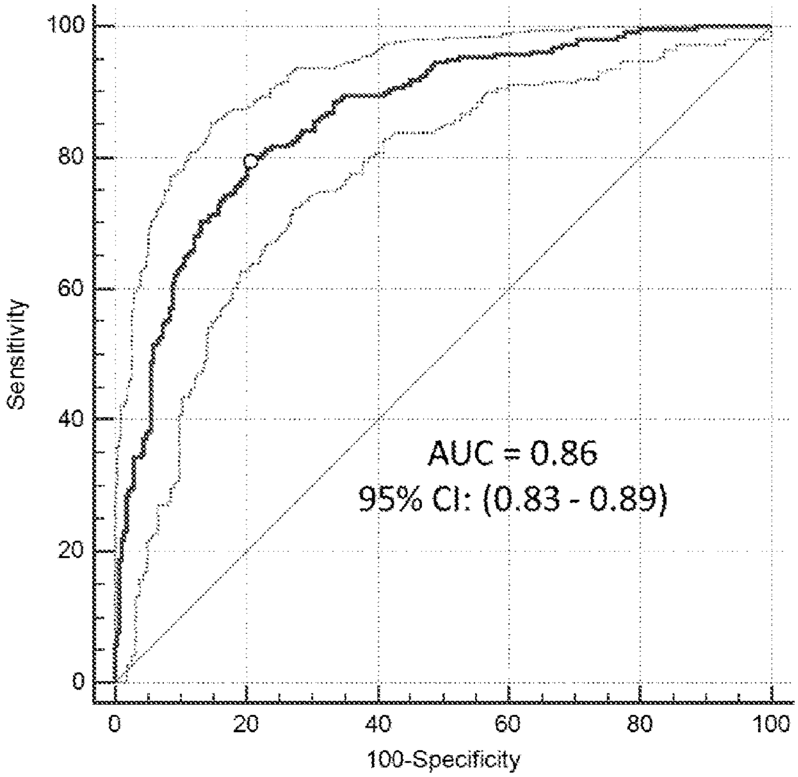
FIG. 24: ROC Curve showing the discrimination in 63 gene signature scores between the angiogenesis active subtype and angiogenesis inactive subtype in the Marissa CRC data.

The AUC calculated for the 63-gene signature with respect to predicting the two sample clusters was 0.86 [0.83-0.89], as depicted in the ROC curve in FIG. 24. The maximum sum of sensitivity and specificity for predicting the subtype was defined at a signature score threshold of 0.6604; and this is the threshold that is applied to predict patients as being in the angiogenesis active or angiogenesis inactive subtype. Patients with a signature score >0.6604 are classified as angiogenesis active and patients with a signature score ≤0.6604 are classified as angiogenesis inactive.

Cox-proportional hazard modelling of progression free survival predicted by the signature (adjusting for clinical covariates) revealed that patients in the angiogenesis inactive group had significantly improved progression free survival compared to patients in the angiogenesis active group (Table 4: HR=0.47 [0.30-0.76]). Kaplan Meier curve is shown in FIG. 22.

TABLE 4

Multivariable survival analysis results using the 232 adjuvant treated patients

| Predictive variable | HR [95% CI] |
|---|---|
| Assay Positive | 0.47 (0.30-0.76) |
| Stage (II) | 1.37 [0.74-2.55] |
| III | 3.24 [1.45-7.23] |
| IV | |
| Tumour location | 1.68 [0.99-2.85] |
| Age | 1.01 [0.99-1.03] |
| Sex | 1.23 [0.79-1.92] |
| MMR | 0.91 [0.32-2.62] |

Example 8: Independent Validation of Prognostic Utility of 63-Gene Signature

Samples

A public array data set was obtained from the Gene Expression Omnibus database (GSE14333) comprising a cohort of 290 patients with colorectal cancer (Jorissen et al, 2009). Samples were profiled on the Affymetrix Plus 2.0 platform. 87 patients received adjuvant chemotherapy with follow up recurrence free survival (RFS)

Methods

The samples were tested with the 63-gene signature classified as being angiogenesis active or angiogenesis inactive using the threshold of 0.6604 as defined in Example 5.

The clinical significance of the 63-gene signature predictions was evaluated using Kaplan Meier curves and Cox-proportional hazard survival analysis. The endpoint was defined as a progression free survival, and the Cox-proportional hazards modelling included an adjustment for all available clinical covariates: age; gender; stage and tumour location.

Figure 25:
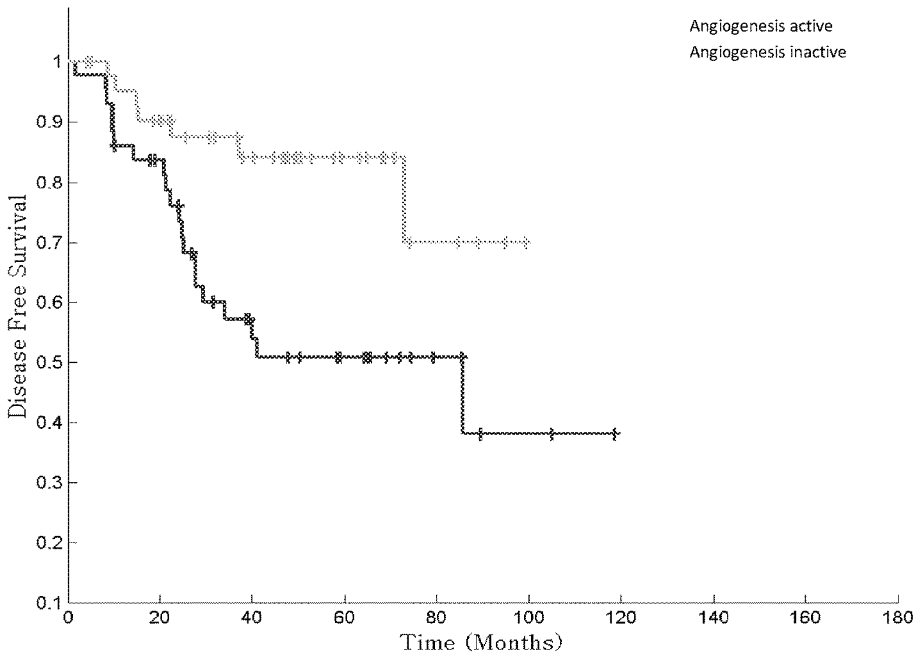
FIG. 25: Kaplan Meier Curve showing the survival differences between the angiogenesis active and angiogenesis inactive patients (treated only) as predicted by the 63 gene signature in the GSE14333 CRC data.

Results 159 patients received a signature score >0.6604 and were classified as angiogenesis active; and 131 patients received a signature score ≤0.6604 and were classified as angiogenesis inactive. Cox-proportional hazard modelling of progression free survival predicted by the signature (adjusting for clinical covariates) revealed that patients in the angiogenesis inactive group had significantly improved progression free survival compared to patients in the angiogenesis active group (Table 5: HR=0.33 [0.14-0.83]). Kaplan Meier curve is shown in FIG. 25.

TABLE 5

Multivariable survival analysis results using the 87 adjuvant treated patients

| Predictive variable | | HR [95% CI] |
|---|---|---|
| Assay Positive | | 0.33 [0.14-0.83] |
| Stage (III) | I and II | 1.03 [0.41-2.59] |
| Tumour location (Left) | Rec | 0.40 [0.08-1.95] |
| | Right | 0.50 [0.20-1.23] |
| Age | | 1.01 [0.98-1.04] |
| Sex | | 1.13 [0.47-2.68] |

REFERENCES

1. Friedman H S, Prados M D, Wen P Y, et al. Bevacizumab alone and in combination with irinotecan in recurrent glioblastoma. *J Clin Oncol;* 27:4733-40 (2009).
2. Hurwitz H, Fehrenbacher L, Novotny W, et al. Bevacizumab plus irinotecan, fluorouracil, and leucovorin for metastatic colorectal cancer. *N Engl J Med;* 350:2335-42 (2004).
3. Rini B I, Halabi S, Rosenberg J E, et al. Bevacizumab plus interferon alfa compared with interferon alfa monotherapy in patients with metastatic renal cell carcinoma: CALGB 90206. *J Clin Oncol;* 26:5422-8 (2008).
4. Sandler A, Gray R, Perry M C, et al. Paclitaxel-carboplatin alone or with bevacizumab for non-small-cell lung cancer. *N Engl J Med;* 355: 2542-50 (2006).
5. Wolmark N, Yothers G, O'Connell M J, et al. A phase III trial comparing mFOLFOX6 to mFOLFOX6 plus bevacizumab in stage II or III carcinoma of the colon: results of NSABP protocol C-08. *J Clin Oncol;* 27:LBA4 (2009).
6. Yang J C, Haworth L, Sherry R M, et al., A randomized trial of bevacizumab, an anti-vascular endothelial growth factor antibody, for metastatic renal cancer, *N Engl J Med* 349 427-434 (2003).
7. Willett C G, Boucher Y, di Tomaso E, et al., Direct evidence that the VEGF-specific antibody bevacizumab has antivascular effects in human rectal cancer, *Nat. Med.* 10, 145-147 (2004).
8. Miller K, Wang M, Gralow J, et al., Paclitaxel plus bevacizumab versus paclitaxel alone for metastatic breast cancer, *N Engl J Med* 357 2666-2676 (2007).
9. Miller K D, Chap L I, Holmes F A, et al., Randomized phase III trial of capecitabine compared with bevacizumab plus capecitabine in patients with previously treated metastatic breast cancer, *J Clin Oncol* 23 792-799 (2005).
10. O'Shaughnessy J, Miles D, Gray R J, et al., A meta-analysis of overall survival data from three randomized trials of bevacizumab (BV) and first-line chemotherapy as treatment for patients with metastatic breast cancer (MBC), *J Clin Oncol* 28 (suppl) (abstr 1005) (2010).
11. Reck M, von Pawel J, Zatloukal P, et al., Phase III trial of cisplatin plus gemcitabine with either placebo or bevacizumab as first-line therapy for nonsquamous non-small-cell lung cancer: AVAil, *J Clin Oncol* 27, 1227-1234 (2009).
12. Escudier B, Bellmunt J, Negrier S et al., Phase III trial of bevacizumab plus interferon alfa-2a in patients with metastatic renal cell carcinoma (AVOREN): final analysis of overall survival, *J Clin Oncol* 28, 2144-2150 (2010)
13. Burger R A, Sill M W, Monk B J, et al. Phase II trial of bevacizumab in persistent or recurrent epithelial ovarian cancer or primary peritoneal cancer: a Gynecologic Oncology Group Study. *J Clin Oncol;* 20; 25(33):5165-71 (2007).
14 Tothill R W et al. Novel molecular subtypes of serous and endometrioid ovarian cancer linked to clinical outcome. *Clin Cancer Res.* 14(16), 5198-208 (2008).
15. Bagri A, Berry L, Gunter B, et a. (2010) Effects of anti-VEGF treatment duration on tumor growth, tumor regrowth, and treatment efficacy. *Clin Cancer Res* 16:3887-3900.
16. Ebos J M, Lee C R, Cruz-Munoz W, et al. (2009) Accelerated metastasis after short-term treatment with a potent inhibitor of tumor angiogenesis. *Cancer Cell* 15:232-239.
17. Grepin R, Guyot M, Jacquin M, Durivault J, Chamorey E. Sudaka A, Serdjebi C, Lacarelle B. Scoazec J Y, Negrier S, Simmonet H, Pages G. Acceleration of clear cell renal cell carcinoma growth in mice following bevacizumab/Avastin treatment: the role of CXCL cytokines. Oncogene 2012 Mar. 29:31(13).
18. Ma J. Pulfer S, Li S, Chu J, Reed K, Gallo J M. Pharmacodynamic-mediated reeducation of temozolomide tumor concentrations by the angiogenesis inhibitor TNP-470. *Cancer Res.* 2001; 61:5491-5498.
19. Marissa et al. (2013) Gene Expression Classification of Colon Cancer into Molecular Subtypes: Characterization, *Validation, and Prognostic Value PLoS Med* 2013; 10(5): e1001453
20. Jorissen et al. (2009) Metastasis-associated gene expression changes predict poor outcomes in patients with Dukes stage B and C colorectal cancer. *Clin Cancer Res* 2009; 15(24):7642-51

The invention claimed is:

1. A method for diagnosing and treating a patient suffering from a subtype of cancer which is resistant to anti-angiogenic therapy, comprising:

obtaining a cancer sample from the patient;

measuring expression levels of a biomarker panel in the cancer sample, wherein the biomarker panel is a ten-biomarker panel comprising at least IGF2, TAP1, SHISA4, ENTPD7, CDR1, SPARC, INS, NUAK1, and MATN3;

determining a cancer sample expression score for the biomarker panel based on the measured expression levels;

comparing the cancer sample expression score to a threshold expression score, derived from a cohort of patients with a known status of responsiveness to an anti-angiogenic agent; and treating the patient with at least one of a platinum-based chemotherapeutic agent and a mitotic inhibitor, but not an anti-angiogenic agent if the cancer sample expression score is above or equal to the threshold expression score.

2. The method of claim 1, wherein the cancer is ovarian cancer or colorectal cancer.

3. A method for diagnosing and treating a patient suffering from a subtype of cancer which is resistant to bevacizumab, comprising:

obtaining a cancer sample from the patient;

measuring expression levels of a biomarker panel in the cancer sample, wherein the biomarker panel is a ten-biomarker panel comprising at least IGF2, TAP1, SHISA4, ENTPD7, CDR1, SPARC, INS, NUAK1, and MATN3;

determining a cancer sample expression score for the biomarker panel based on the measured expression levels;

comparing the cancer sample expression score to a threshold expression score, derived from a cohort of patients with a known status of responsiveness to an anti-angiogenic agent; and treating the patient with at least one of a platinum-based chemotherapeutic agent and a mitotic inhibitor, but not bevacizumab if the cancer sample expression score is above or equal to the threshold expression score.

4. The method of claim 3, wherein the cancer is ovarian cancer or colorectal cancer.

* * * * *

SEQUENCE LISTING

```
<160> NUMBER OF SEQ ID NOS: 734

<210> SEQ ID NO 1
<211> LENGTH: 235
<212> TYPE: DNA
<213> ORGANISM: Homo sapiens
```

-continued

<400> SEQUENCE: 1
gcagcttcct gataaagcgt gctgtgctgt gcagtaggaa cacatcctat ttattgtgat 60
gttgtggttt tattatttta aactttgttc catacacttg tataaataca tggatatttt 120
tatgtacaga agtatgtttt ttaaccagtt cacttattgt actttggcaa tttaaaagaa 180
aatcagtaaa atattttgct tgtaaaatgc ttaatatcgt gcctaggtta tgtgg 235

<210> SEQ ID NO 2
<211> LENGTH: 139
<212> TYPE: DNA
<213> ORGANISM: Homo sapiens

<400> SEQUENCE: 2
cccctccaag accctgtgtt catttggtgt tcctggaagc aggtgctaca acatgtgagg 60
cattcgggga agctgcacat gtgccacaca gtgacttggc cccagacgca tagactgagg 120
tataaagaca agtatgaat 139

<210> SEQ ID NO 3
<211> LENGTH: 172
<212> TYPE: DNA
<213> ORGANISM: Homo sapiens

<400> SEQUENCE: 3
agccaatgga aaatctgggt tcaaccagcc cctgccattt cttaagactt tttgctgcac 60
tcacaggatc ctgagctgca cttacctgtg agagtcttca aacttttaaa ccttgccagt 120
caggactttt gctattgcaa atagaaaacc caactcaacc tgcttaagca ga 172

<210> SEQ ID NO 4
<211> LENGTH: 217
<212> TYPE: DNA
<213> ORGANISM: Homo sapiens

<400> SEQUENCE: 4
ttctttgtca atctatggac atgcccatat atgaaggaga tgggtgggtc aaaaagggat 60
atcaaatgaa gtgatagggg tcacaatggg gaaattgaag tggtgcataa cattgccaaa 120
atagtgtgcc actagaaatg gtgtaaaggc tgtttttttt tttttttta aagaaaagtt 180 attaccatgt attttgtgag gcaggtttac aacacta 217

<210> SEQ ID NO 5
<211> LENGTH: 156
<212> TYPE: DNA
<213> ORGANISM: Homo sapiens

<400> SEQUENCE: 5
gcagcaacag caaatcacga ccactgatag atgtttattt ttgttggaga catgggatga 60
ttattttctg ttctatttgt gcttagtcca attccttgca catagtaggt acccaattca 120
attactattg aatgaattaa gaattggttg ccataa 156

<210> SEQ ID NO 6
<211> LENGTH: 221
<212> TYPE: DNA
<213> ORGANISM: Homo sapiens

<400> SEQUENCE: 6
taatgtcatc ctgtactcgg cacaaatcaa aggccaatac aagtctgaaa agcagaaata 60 aatattttc caggtttttg ctcgggcaca tactaactgc tttgggcatt ttaatctggt 120
ctccaaacac caaagaccca tttcgagcct gctattagcc tgctgctgac tctatcactt 180
ggagcaataa tgtggggtta tggtggtgga atcttgtata t 221

<210> SEQ ID NO 7
<211> LENGTH: 231
<212> TYPE: DNA
<213> ORGANISM: Homo sapiens

<400> SEQUENCE: 7
agctttgtgc tcagatccca ggtcccaagg agtgacaggg gcttcctccc accttctgtc 60
cttgtccagt catgtaaata atgtgctttt tctctccccg agtctttttt ttttaaacct 120
accgtggttc ctcagctaac tgcattccct acccaggcag agactgtcct atgcctcgag 180
cttccaaacg agactcagac cgcgacacag ccaccgtatt tatggaatga c 231

<210> SEQ ID NO 8
<211> LENGTH: 245
<212> TYPE: DNA
<213> ORGANISM: Homo sapiens

<400> SEQUENCE: 8
gaaatacgaa tgtagagatc cctaatcatc aaattgttga ttgaaagact gatcataaac 60
caatgctggt attgcacctt ctggaactat gggcttgaga aaacccccag gatcacttct 120
ccttggcttc cttcttttct gtgcttgcat cagtgtggac tcctagaacg tgcgacctgc 180
ctcaagaaaa tgcagttttc aaaaacagac tcagcattca gcctccaatg aataagacat 240
cttcc 245

<210> SEQ ID NO 9
<211> LENGTH: 115
<212> TYPE: DNA
<213> ORGANISM: Homo sapiens

<400> SEQUENCE: 9
tgaacaaatg gcctttatta aaaactgagt gactctatat agctgatcag ttttttcacc 60
tggaagcatt tgtttttact ttgatatgac tgtttttcgg acagtttatt tgttg 115

<210> SEQ ID NO 10
<211> LENGTH: 179
<212> TYPE: DNA
<213> ORGANISM: Homo sapiens

<400> SEQUENCE: 10
tgtggtagcc tcacttttaa tgaacaaatg gcctttatta aaaactgagt gactctatat 60
agctgatcag ttttttcacc tggaagcatt tgtttttact ttgatatgac tgtttttcgg 120
acagtttatt tgttgagagt gtgaccaaaa gttacatgtt tgcacctttt tagttgaaa 179

<210> SEQ ID NO 11
<211> LENGTH: 113
<212> TYPE: DNA
<213> ORGANISM: Homo sapiens

<400> SEQUENCE: 11
caaagtgcta ataattaact caaccaggtc tactttttaa tggctttcat aacactaact 60
cataaggtta ccgatcaatg catttcatac ggatatagac ctagggctct gga 113

<210> SEQ ID NO 12

-continued

<211> LENGTH: 92
<212> TYPE: DNA
<213> ORGANISM: Homo sapiens

<400> SEQUENCE: 12
gctgagcaaa gcagactacg agaaacacaa agtttacgcc tgcgaagtca cccatcaggg 60
cctgagctcg cccgtcacaa agagcttcaa ca 92

<210> SEQ ID NO 13
<211> LENGTH: 298
<212> TYPE: DNA
<213> ORGANISM: Homo sapiens

<400> SEQUENCE: 13
agcagactac gagaaacaca aagtttacgc ctgcgaagtc acccatcagg gcctgagctc 60
gcccgtcaca aagagcttca acaggggaga gtgttagagg gagaagtgcc cccacctgct 120
cctcagttcc agcctgaccc cctcccatcc tttggcctct gacccttttt ccacagggga 180 cctacccta ttgcggtcct ccagctcatc tttcacctca ccccctcct cctccttggc 240 tttaattatg ctaatgttgg aggagaatga ataaataaag tgaatctttg cacctgtg 298

<210> SEQ ID NO 14
<211> LENGTH: 86
<212> TYPE: DNA
<213> ORGANISM: Homo sapiens

<400> SEQUENCE: 14
actgaggggg tcctggtgtg catttgcacc ctaaagctgc ttacggtgaa aaggcaaata 60
ggtatagcta ttttgcaggc accttt 86

<210> SEQ ID NO 15
<211> LENGTH: 158
<212> TYPE: DNA
<213> ORGANISM: Homo sapiens

<400> SEQUENCE: 15
tttggtgcag tttccagggt gcagtacagc agggcctgaa tactggccct ggactccctt 60
ttccagaaca ccaggtgtgg ccacctgggg ctcaggtaca cagtggggtc tctcggaagc 120
caccgtgtgg ttctttcaca ggcacgttta ttttgctg 158

<210> SEQ ID NO 16
<211> LENGTH: 223
<212> TYPE: DNA
<213> ORGANISM: Homo sapiens

<400> SEQUENCE: 16
tggtcatgag aagaaggtaa tttccagcct tcaagaagac agacatttag aagaagagct 60
gaaatgtcag gaacaaaaag aagaacagct gcaggaaggg gtgcaccgga aggagcccca 120
gggggccacg tagcagcggc tcagtgggtg gccatcgatt tggaccgtcc cctgcccact 180
tgctccccgt gagcactgcg tacaaacatc caaaagttca aca 223

<210> SEQ ID NO 17
<211> LENGTH: 262
<212> TYPE: DNA
<213> ORGANISM: Homo sapiens

<400> SEQUENCE: 17
ccaggttagg aaaggattca gcactacagc ataccccctct acaacataca gccctgtcac 60
attgagatca taatccctcc tgtcccactc ctctctacca accccaccct actagctagg 120
tcttcagtgt tttacattga atattggtac attttaatta ttttttctca taaatgggtt 180
atttatagaa attttgttaa ctcttgagcc atatgcatgt gtagatactg gcagggctat 240
gtttgtttat gatgctctgc aa 262

<210> SEQ ID NO 18
<211> LENGTH: 245
<212> TYPE: DNA
<213> ORGANISM: Homo sapiens

<400> SEQUENCE: 18
attgtgctat aatccctatt tagttcaaaa ttaaccagaa tttttccatg tgaaatggac 60
caaactcata ttattgttat gtaaatacag agttttaatg cagtatgaca tcccacaggg 120
gaaaagaatg tctgtagtgg gtgactgtta tcaaatattt tatagaatac aatgaacggt 180
gaacagactg gtaacttgtt tgagttccca tgacagattt gagacttgtc aatagcaaat 240
cattt 245

<210> SEQ ID NO 19
<211> LENGTH: 202
<212> TYPE: DNA
<213> ORGANISM: Homo sapiens

<400> SEQUENCE: 19
taatggttaa cgaaccgggt cgacatcaca aaggagggtg gagactcttt ttactaactt 60
gaatgagaca aaagcagtgg tgtcagttta taatcctgat gcatttcagt aataatgtag 120
aaaaacatta ttttaaaaaa gttccaacac acagccatga ggagcctcag ttttgaaaga 180
ggtgcataat aaaactacta ac 202

<210> SEQ ID NO 20
<211> LENGTH: 132
<212> TYPE: DNA
<213> ORGANISM: Homo sapiens

<400> SEQUENCE: 20
acagcccacc cttgtgtcca ctgtgacccc tgttcccatg ctgacctgtg tttcctcccc 60
agtcatcttt cttgttccag agaggtgggg ctggatgtct ccatctctgt ctcaacttta 120
tgtgcactga gc 132

<210> SEQ ID NO 21
<211> LENGTH: 53
<212> TYPE: DNA
<213> ORGANISM: Homo sapiens

<400> SEQUENCE: 21
aagcaagata tcaatgtagc agaattgcac ttgtgcctca cgaacataca taa 53

<210> SEQ ID NO 22
<211> LENGTH: 151
<212> TYPE: DNA
<213> ORGANISM: Homo sapiens

<400> SEQUENCE: 22
ttggaatgtt gtagttacct actgagtagg cggcgatttt tgtatgttat gaacatgcag 60
ttcattattt tgtggttcta ttttactttg tacttgtgtt tgcttaaaca aagtgactgt 120
ttggcttata aacacattga atgcgcttta t 151

<210> SEQ ID NO 23
<211> LENGTH: 205
<212> TYPE: DNA
<213> ORGANISM: Homo sapiens

<400> SEQUENCE: 23
aatcccaatt ttcaggagtg gtggtgtcaa taaacgctct gtggccagtg taaaagaaaa 60
tccctcgcag ttgtggacat ttctgttcct gtccagatac catttttcct agtatttctt 120
tgttatgtcc cagaactgat gttttttttt taaggtactg aaaagaaatg aagttgatgt 180
atgtcccaag ttttgatgaa actgt 205

<210> SEQ ID NO 24
<211> LENGTH: 269
<212> TYPE: DNA
<213> ORGANISM: Homo sapiens

<400> SEQUENCE: 24
gcctggcctg attcagggcc ttgtggcccc cagcttctgt ttcaagctgg gcagacccca 60
ggatcccttc cctccctaag gactcagctg aggggcccct ctgcccccctt ctacctccac 120 ctcagcaccc tcccccagct tgatgtttgg gtctccccag caccctcctc cctggccggt 180
gcaaagtaca gggaggtaaa gcaggaccct tgcagacatg ttgcccagca cacagtaggc 240
cctcaataaa agccatttgc actttaaat 269

<210> SEQ ID NO 25
<211> LENGTH: 169
<212> TYPE: DNA
<213> ORGANISM: Homo sapiens

<400> SEQUENCE: 25
gagaagtcac tcacactggc cacaaggacg ctggctactg tctattaaaa ttttgatgtt 60
tctgtgaaat tctcagagtg tttaattgta ctcaatggta tcattacaat tttctgtaag 120
agaaaatatt acttatttat cctagtattc ctaacctgtc agaataata 169

<210> SEQ ID NO 26
<211> LENGTH: 234
<212> TYPE: DNA
<213> ORGANISM: Homo sapiens

<400> SEQUENCE: 26
ctgtggcatg ctcagaggtt cctgctggat tccagctgga gcggtgtgat acccttcttt 60
ttcagctgtt cgtgccttcc tttcttgtat ccaccaaagt ggagacaaat acatgatttc 120
aaagatacac agtacctact taattccagc tgatgggaga ccaaagaatt tgcaagtgga 180
tggtttggta tcactgtaaa taaaaagagg gcctgggaat tcttgcgatt ccat 234

<210> SEQ ID NO 27
<211> LENGTH: 232
<212> TYPE: DNA
<213> ORGANISM: Homo sapiens

<400> SEQUENCE: 27
tgaaccaaaa tagagtcagc tgacccagca tcagccacac tttgggttgg aaaatgtttg 60
cctgttggaa ttaatttaag cttaagtata tatcaacatt attttattgt gcaattaaaa 120
caatacaaat tcatggtttt ttaaagttaa aaattttaac cactgtaaca acagtttttg 180
tgttattttc tgtattaaac atcttgttgc acgcatttga ggtcatcagg gt 232

<210> SEQ ID NO 28
<211> LENGTH: 147
<212> TYPE: DNA
<213> ORGANISM: Homo sapiens

<400> SEQUENCE: 28
atgttcatag gttctcaacc ctcacccccc accacgggag actagagctg caggatccca 60
ggggaggggt ctctcctccc accccaaggc atcaagccct tctccctgca ctcaataaac 120
cctcaatata tattctcatt gtcaatc 147

<210> SEQ ID NO 29
<211> LENGTH: 149
<212> TYPE: DNA
<213> ORGANISM: Homo sapiens

<400> SEQUENCE: 29
aatgttcata ggttctaaac cctcaccccc cccacgggag actagagctg caggatccca 60
ggggaggggt ctctcctccc accccaaggc atcaagccct tctccctgca ctcaataaac 120
cctcaataaa tattctcatt gtcaatcag 149

<210> SEQ ID NO 30
<211> LENGTH: 152
<212> TYPE: DNA
<213> ORGANISM: Homo sapiens

<400> SEQUENCE: 30
aatgttcata ggttctaaac cctcaccccc cccacgggag actagagctg caggatccca 60
ggggaggggt ctctcctccc accccaaggc atcaagccct tctccctgca ctcaataaac 120
cctcaataaa tattctcatt gtcaatcagc aa 152

<210> SEQ ID NO 31
<211> LENGTH: 150
<212> TYPE: DNA
<213> ORGANISM: Homo sapiens

<400> SEQUENCE: 31
aatgttcata ggttctcaac cctcaccccc caccacggga gactagagct gcaggatccc 60
aggggagggg tctctcctcc caccccaagg catcaagccc ttctccctgc actcaataaa 120
ccctcaataa atattctcat tgtcaatcag 150

<210> SEQ ID NO 32
<211> LENGTH: 151
<212> TYPE: DNA
<213> ORGANISM: Homo sapiens

<400> SEQUENCE: 32
atgttcatag gttctcaacc ctcacccccc ccacgggaga ctagagctgc aggatcccag 60
gggaggggtc tctcctccca ccccaaggca tcaagccctt ctccctgcac tcaataaacc 120
ctcaataaat attctcattg tcaatcagca a 151

<210> SEQ ID NO 33
<211> LENGTH: 254
<212> TYPE: DNA
<213> ORGANISM: Homo sapiens

<400> SEQUENCE: 33
gcagctattt gagcctgacg cctgagcagt ggaagtccca cagaagctac agctgccagg 60
tcacgcatga agggagcacc gtggagaaga cagtggcccc tacagaatgt tcataggttc 120
taaaccctca cccccccac gggagactag agctgcagga tcccagggga ggggtctctc 180
ctcccacccc aaggcatcaa gcccttctcc ctgcactcaa taaaccctca ataaatattc 240
tcattgtcaa tcag 254

<210> SEQ ID NO 34
<211> LENGTH: 239
<212> TYPE: DNA
<213> ORGANISM: Homo sapiens

<400> SEQUENCE: 34
aagaacaact cctcaccagt tcatcctgag gctgggagga ccgggatgct ggattctgtt 60
ttccgaagtc actgcagcgg atgatggaac tgaatcgata cggtgttttc tgtccctcct 120
actttccttc acaccagaca gcccctcatg tctccaggac aggacaggac tacagacaac 180
tctttcttta aataaattaa gtctttacaa taaaaacaca actgcaaagt accttcata 239

<210> SEQ ID NO 35
<211> LENGTH: 270
<212> TYPE: DNA
<213> ORGANISM: Homo sapiens

<400> SEQUENCE: 35
gaaagagcat cgttccaatg cttgttcact gttcctctgt catactgtat ctggaatgct 60
ttgtaatact tgcatgcttc ttagaccaga acatgtaggt ccccttgtgt ctcaatactt 120
tttttttctt aattgcattt gttggctcta ttttaatttt tttcttttaa aataaacagc 180
tgggaccatc ccaaaagaca agccatgcat acaactttgg tcatgtatct ctgcaaagca 240
tcaaattaaa tgcacgcttt tgtcatgtca 270

<210> SEQ ID NO 36
<211> LENGTH: 97
<212> TYPE: DNA
<213> ORGANISM: Homo sapiens

<400> SEQUENCE: 36
ttctccccaa ccacttagta gcaacgctac cccagggggt aatgactgca cactgggctt 60
cttttcagaa tgaccctaac gagacacatt tgcccaa 97

<210> SEQ ID NO 37
<211> LENGTH: 213
<212> TYPE: DNA
<213> ORGANISM: Homo sapiens

<400> SEQUENCE: 37
tgtgttgggg tagactgctc ctgcagagtt tggaagaagt caccagcaaa gccggcctaa 60
ccaagaaaag tcaaggccct tcatgacctt gctgggcaca gaaaacaccc tcgtggagta 120
cactaatttg aactggactg gtctcagtgt gagcacttgg cacactttac taaacacata 180
tacaacccca ccgtgagtca actttaaagt aaa 213

<210> SEQ ID NO 38
<211> LENGTH: 151
<212> TYPE: DNA
<213> ORGANISM: Homo sapiens

<400> SEQUENCE: 38
tgtaatgcta aaactgaaat ggtccgtgtt tgcattgtta aaaatgatgt gtgaaataga 60
atgagtgcta tggtgttgaa aactgcagtg tccgttatga gtgccaaaaa tttgtcttga 120
aggcagctac actttgaagt ggtctttgaa t 151

<210> SEQ ID NO 39
<211> LENGTH: 116
<212> TYPE: DNA
<213> ORGANISM: Homo sapiens

<400> SEQUENCE: 39
ctgggccttg gtccccagaa gatggcggct agggcctcgc cgccaggaca gagaagggac 60
ggggtggctg ggcagtcagg gaaggagggt cgcccggatc cgacattttg gagaga 116

<210> SEQ ID NO 40
<211> LENGTH: 220
<212> TYPE: DNA
<213> ORGANISM: Homo sapiens

<400> SEQUENCE: 40
gaacaggaac gccttctcaa ggagggattc gagaatgaga gcaagagact tcaaaaagac 60
atatgggata tccagatgag aagcaaatca ttggagccaa tatgtaacat actttaaaag 120
tccaaggagc aaaatttgcc tgtccagctc cctctcccca agaaacaaca tgaatgagca 180
acttcagagt gtcaaacaac tgccattaaa cttaactcaa 220

<210> SEQ ID NO 41
<211> LENGTH: 232
<212> TYPE: DNA
<213> ORGANISM: Homo sapiens

<400> SEQUENCE: 41
tttgttagta catttcagtg tagtcattca tttctagctg tacataggat gaaggagaga 60
tcagatacat gaacatgttt tacatgggtt gctgtattta gaattataaa catttttcat 120
tattggaaag tgtaacgggg accttttgca tacctgttta gaaccaaaac caccatgaca 180
cagtttttat agtgtctgta tatttgtgat gcaatggtct tgtaaaggtt tt 232

<210> SEQ ID NO 42
<211> LENGTH: 53
<212> TYPE: DNA
<213> ORGANISM: Homo sapiens

<400> SEQUENCE: 42
gaccaggaat tcggcttcga cgttggccct gtctgcttcc tgtaaactcc ctc 53

<210> SEQ ID NO 43
<211> LENGTH: 132
<212> TYPE: DNA
<213> ORGANISM: Homo sapiens

<400> SEQUENCE: 43
aaaagttcac agtcaaatgg ggaggggtat ttttcatgca ggagacccca ggccctggag 60
gctgcaacat acctcaatcc tgtcccaggc cggatcctcc tgaagccctt ttcgcagcac 120
tgctatcctc ca 132

<210> SEQ ID NO 44

<211> LENGTH: 287
<212> TYPE: DNA
<213> ORGANISM: Homo sapiens

<400> SEQUENCE: 44
agtgagactg actgcaagcc ccaccctcct tgagactgga gctggcgtct gcatacgaga 60
gacttggttg aacttggttg gtccttgtct gcaccctcga caagaccaca ctttgggact 120
tgggagctgg ggctgaagtt gctctgtacc catgaactcc cagtttgcga attatagaga 180
caatctattt tgttacttgc acttgttatt cgaaccactg agagcgagat gggaagcata 240
gatatctata tttttatttt tactatgagg gccttgtaat aaatttc 287

<210> SEQ ID NO 45
<211> LENGTH: 157
<212> TYPE: DNA
<213> ORGANISM: Homo sapiens

<400> SEQUENCE: 45
tatgaattcc attcaaatcg ttcctttttg ttaacaaggg gcatggggag gggtgggggt 60
gggggggcag aggcgtctga ccccaggaac ctgcagggcg gggctgggtc ggtgcccttt 120
aaggacaatt ttgaccttgt tcaacctttc cacaaag 157

<210> SEQ ID NO 46
<211> LENGTH: 212
<212> TYPE: DNA
<213> ORGANISM: Homo sapiens

<400> SEQUENCE: 46
gatgcatgag gctctgcaca accactacac gcagaagagc ctctccctgt ctccgggtaa 60
atgagtgcga cggccggcaa gcccccgctc cccaggctct cggggtcgcg cgaggatgct 120
tggcacgtac cccgtgtaca tacttcccgg gcgcccagca tggaaataaa gcacccagcg 180
ctgccctggg cccctgcgca actttcttgt ac 212

<210> SEQ ID NO 47
<211> LENGTH: 262
<212> TYPE: DNA
<213> ORGANISM: Homo sapiens

<400> SEQUENCE: 47
gtcctctcta tcctggatga gctcatgaac atttctcttg tgttcctgac tccttcccaa 60
tgaacacctt tctgccaccc caagctttgc tctcctcctc tgtgagctct gggcttccca 120
gtttgtttac ccgggaaagt acgtctagat tgtgtggttt gcctcattgt gctatttgcc 180
cactttcctt ccctgaagaa atatctgtga accttctttc tgttcagtcc taaaattcga 240
aataaagtga gactatggtt ca 262

<210> SEQ ID NO 48
<211> LENGTH: 135
<212> TYPE: DNA
<213> ORGANISM: Homo sapiens

<400> SEQUENCE: 48
gggcccagct cagaaccggg cagacacccc cttcaaatgt cttcgcacgt aggttttgca 60
cagtgtttat ttgctggtgt ctcagggatt tgacagtttc cttaatattc ccacacatgg 120
ccgagaaaaa taaat 135

-continued

<210> SEQ ID NO 49
<211> LENGTH: 235
<212> TYPE: DNA
<213> ORGANISM: Homo sapiens

<400> SEQUENCE: 49
ttctacacta gtgccatggg aaccaggtct gaaaaagtag agagaagtga aagtagagtc 60
tgggaagtag ctgcctataa ctgagactag acggaaaagg aatactcgtg tattttaaga 120
tatgaatgtg actcaagact cgaggccgat acgaggctgt gattctgcct ttggatggat 180
gttgctgtac acagatgcta cagacttgta ctaacacacc gtaatttggc atttg 235

<210> SEQ ID NO 50
<211> LENGTH: 236
<212> TYPE: DNA
<213> ORGANISM: Homo sapiens

<400> SEQUENCE: 50
attggagtgg atgggttctg ccttaaattg ggaggactcc aagccgggaa ggaaaattcc 60
cttttccaac ctgtatcaat ttttacaact tttttcctga aagcagttta gtccatactt 120
tgcactgaca tactttttcc ttctgtgcta aggtaaggta tccaccctcg atgcaatcca 180
ccttgtgttt tcttagggtg gaatgtgatg ttcagcagca aacttgcaac agactg 236

<210> SEQ ID NO 51
<211> LENGTH: 243
<212> TYPE: DNA
<213> ORGANISM: Homo sapiens

<400> SEQUENCE: 51
gggatctcct tttgtgaaaa ccagtttgat gtgctaaaag taaaaagtct attttccagt 60
gtggtcttgt tcagaagcag ccagatttcc aatgttgttt ttcccctcca ctcagaaacc 120
cctgcccttt cccttcagaa aacgatggca ggcattcctt tgagtttaca agcagagact 180
cactccaacc caaactagct gggagttcag aaccatggtg gaataaagaa atgtgcatct 240
ggt 243

<210> SEQ ID NO 52
<211> LENGTH: 221
<212> TYPE: DNA
<213> ORGANISM: Homo sapiens

<400> SEQUENCE: 52
cctgtaagac aataggccat gttaattaaa ctgaagaagg atatatttgg ctgggtgttt 60
tcaaatgtca gcttaaaatt ggtaattgaa tggaagcaaa attataagaa gaggaaatta 120
aagtcttcca ttgcatgtat tgtaaacaga aggagatggg tgattccttc aattcaaaag 180
ctctctttgg aatgaacaat gtgggcgttt gtaaattctg g 221

<210> SEQ ID NO 53
<211> LENGTH: 225
<212> TYPE: DNA
<213> ORGANISM: Homo sapiens

<400> SEQUENCE: 53
gagtaccgcg cagacattaa aagtcatgta aaagaacatt tgactgaaag aaaaatgctc 60
cttgaatatt aaaaggttgt aaaaatagtg catgttatgt gatttcaatt ttgtttttta 120
aaatatgggt gtatgcttgt atacgtagag cagataaaaa agacggaagg catactaaaa 180

-continued aatgttgagt ggttatcttt gtatggtgga acaaagtcac tgtaa 225

<210> SEQ ID NO 54
<211> LENGTH: 182
<212> TYPE: DNA
<213> ORGANISM: Homo sapiens

<400> SEQUENCE: 54
atgctgagtg acactcttgt gtatatttcc aaatttttgt acagtcgctg cacatatttg 60
aaatcatata ttaagacttt ccaaagatga ggtccctggt tttcatggc aacttgatca 120 gtaaggattt cacctctgtt tgtaactaaa accatttact atatgttaga catgacattc 180
tt 182

<210> SEQ ID NO 55
<211> LENGTH: 157
<212> TYPE: DNA
<213> ORGANISM: Homo sapiens

<400> SEQUENCE: 55
tgtgttttca gagctaggta cagaggaatg tttgctacct ttagcggtga aaaaagaaag 60
agagtcaaga attttgttgg attgtgtttg tgtgtgcata tatttgatat catcattata 120
tttgtaatct ttggacttgt aatcatagcc tgtttat 157

<210> SEQ ID NO 56
<211> LENGTH: 249
<212> TYPE: DNA
<213> ORGANISM: Homo sapiens

<400> SEQUENCE: 56
tctccagagg gcacttcggc tgcctttgct tcctttcatt cgaggcccgg ctcttgctga 60
cagaataggt tccgttttgg gcggtggttc tcgagcctgc cattcaaaac caaagcaaat 120
tggagcattt ctcacaacat ggtattgaag ttcctttttg ttctcaaaag ttgtgaccgt 180
gttaaattgt actcccttag tcctgtaagg tatgttaagt gaatcgcagt tacgctgtac 240
ttttattaa 249

<210> SEQ ID NO 57
<211> LENGTH: 73
<212> TYPE: DNA
<213> ORGANISM: Homo sapiens

<400> SEQUENCE: 57
tctgtaattc attgagcagt tagctcattt gagataaagt caaatgccaa acactagctc 60
tgtattaatc ccc 73

<210> SEQ ID NO 58
<211> LENGTH: 123
<212> TYPE: DNA
<213> ORGANISM: Homo sapiens

<400> SEQUENCE: 58
atggtataat ggttgactgg gtttctctgt atagtactgg catggtacgg agatgtttca 60
cgaagtttgt tcatcagact cctgtgcaac tttcccaatg tggcctaaaa atgcaacttc 120
ttt 123

<210> SEQ ID NO 59
<211> LENGTH: 292

<212> TYPE: DNA
<213> ORGANISM: Homo sapiens

<400> SEQUENCE: 59
acagtgttgt atgaggtttg aggattttga tccaagctgg tcccactcag tccatagcag 60
agaatgaaag ggcccagaga gggtggtgac ctctgcctga agtcacacag tgagtcgagg 120
acagggaggt gaccccaggt ttctatgtgt agggcgggag gatgttttgg gacacagttc 180
aattctcatt tgtcacacac tttggctatt agagatcaac cccttcgctc ctgtgtcttg 240
caatggcagc cttggcaaac gctaaatgaa aatcgtgaca acacttgtgt ta 292

<210> SEQ ID NO 60
<211> LENGTH: 223
<212> TYPE: DNA
<213> ORGANISM: Homo sapiens

<400> SEQUENCE: 60
tcatgttaaa gagccgtgtc tcccgccagc actcctcacc ccggtatgaa tgtgtttcct 60
ccacattgta tatccttcca ccctctggct gcctagatca gtaaataaaa ttgatgtaat 120
ataatttata agtaacactg ttgaaaccct gatcccagtg gaggctgtaa cccacctgcc 180
cccgcaccac ccccctgacc cctgttaccg catttgtgtg tat 223

<210> SEQ ID NO 61
<211> LENGTH: 275
<212> TYPE: DNA
<213> ORGANISM: Homo sapiens

<400> SEQUENCE: 61
gttatggtgc taatgtactt tcacttttaa actctagatc agaattgttg acttgcattc 60
agaacataaa tgcacaaaat ctgtacatgt ctcccatcag aaagattcat tggcatgcca 120
caggggattt tcctccttca tcctgtaaag gtcaacaata aaaaccaaat tatggggctg 180
cttttgtcac actagcatag agaatgtgtt gaaatttaac tttgtaagct tgtatgtggt 240
tgttgatctt ttttttcctt acagacaccc ataat 275

<210> SEQ ID NO 62
<211> LENGTH: 296
<212> TYPE: DNA
<213> ORGANISM: Homo sapiens

<400> SEQUENCE: 62
tgaggatgtc accaattaac cagaaatcca gttattttcc gccctcaaaa tgacagccat 60
ggccggccgg gtgcttttgg gggctcgtcg gggggacagc tccactttga ctggcacagt 120
ctttgcatgg agacttgagg agggagggct tgaggttggt gaggttaggt gcgtgtttcc 180
tgtgcaagtc aggacatcag tttgattaaa ggtggtgcca atttatttac atttaaactt 240
gtcagggtat aaaatgacat cccattaatt atattgttaa tcaatcacgt gtatag 296

<210> SEQ ID NO 63
<211> LENGTH: 108
<212> TYPE: DNA
<213> ORGANISM: Homo sapiens

<400> SEQUENCE: 63
acatgcagta ctgtataccc cccatccctc cctcggtcca ctgaacttca gagcagttcc 60
cattcctgcc ccgcccatct ttttgtgtct cgctgtgata gatcaata 108

<210> SEQ ID NO 64
<211> LENGTH: 243
<212> TYPE: DNA
<213> ORGANISM: Homo sapiens

<400> SEQUENCE: 64
acaaaagagc cagagttctg gacccatgtt tggagcattt gtagccttat ttttttgcgt 60
gtgaatcttt taccctgaaa aaaagccata atgaattaag ccagactgac cacttgcttg 120
gagtgtgtgc ttgaaaaaac cagagcaata ctgttgggta ttgtatcagg cttcagtaca 180
aactggtaac accaatgtgg atcctgacag ctttcagttt tagcaaaaat acacgtgaaa 240
tct 243

<210> SEQ ID NO 65
<211> LENGTH: 52
<212> TYPE: DNA
<213> ORGANISM: Homo sapiens

<400> SEQUENCE: 65
agtgcaacgt attcaagtcc tcaatatcct gatcataata ccatgctata gg 52

<210> SEQ ID NO 66
<211> LENGTH: 286
<212> TYPE: DNA
<213> ORGANISM: Homo sapiens

<400> SEQUENCE: 66
actttgccgg cgagcacacc gcctacccgc acggctgggt ggagacggcg gtcaagttgg 60
cgctgcgcgc cgccatcaag atcaacagcc ggaaggggcc tgcatcggac acggccagcc 120
ccgaggggca cgcatttgac atggaggggc aggggcatgt gcatggggtg gccagcagcc 180
cctcgcatga cctggcaaag gaagaaggca gccaccctcc agtccaaggc cagttatctt 240
tccaaaacac gacccacacg aggacctcgc attaaagtat tttcgg 286

<210> SEQ ID NO 67
<211> LENGTH: 168
<212> TYPE: DNA
<213> ORGANISM: Homo sapiens

<400> SEQUENCE: 67
catttcatgt ttggcgggca tgtgagtgca caagatggaa agagcgattg gagcatcctg 60
gtataattac ccccattgtg cttttaatgg aaatttcaaa ggacgggagt attttgttgg 120
ttggtgtcca ggtttgtggc actgttccaa gaggccttac acacacac 168

<210> SEQ ID NO 68
<211> LENGTH: 150
<212> TYPE: DNA
<213> ORGANISM: Homo sapiens

<400> SEQUENCE: 68
aatgttcata ggttctcaac cctcaccccc caccacggga gactagagct gcaggatccc 60
aggggagggg tctctcctcc caccccaagg catcaagccc ttctccctgc actcaataaa 120
ccctcaataa atattctcat tgtcaatcaa 150

<210> SEQ ID NO 69
<211> LENGTH: 64
<212> TYPE: DNA
<213> ORGANISM: Homo sapiens

<400> SEQUENCE: 69
atgttcatag gttctcaacc ctcacccccc accacgggag actagagctc aggatcccag 60
ggga 64

<210> SEQ ID NO 70
<211> LENGTH: 167
<212> TYPE: DNA
<213> ORGANISM: Homo sapiens

<400> SEQUENCE: 70
tctgagcggg tcatggggca acacggttag cggggagagc acggggtagc cggagaaggg 60
cctctggagc aggtctggag gggccatggg gcagtcctgg gtgtggggac acagtcgggt 120
tgacccaggg ctgtctccct ccagagcctc cctccggaca atgagtc 167

<210> SEQ ID NO 71
<211> LENGTH: 129
<212> TYPE: DNA
<213> ORGANISM: Homo sapiens

<400> SEQUENCE: 71
aatgcatatg gaggtaggct gaaaagaatg taatttttat tttctgaaat acagatttga 60
gctatcagac caacaaacct tccccctgaa aagtgagcag caacgtaaaa acgtatgtga 120
agcctctct 129

<210> SEQ ID NO 72
<211> LENGTH: 150
<212> TYPE: DNA
<213> ORGANISM: Homo sapiens

<400> SEQUENCE: 72
aatgttcata ggttctcatc cctcaccccc caccacggga gactagagct gcaggatccc 60
aggggagggg tctctcctcc caccccaagg catcaagccc ttctccctgc actcaataaa 120
ccctcaataa atattctcat tgtcaatcaa 150

<210> SEQ ID NO 73
<211> LENGTH: 83
<212> TYPE: DNA
<213> ORGANISM: Homo sapiens

<400> SEQUENCE: 73
ttccaccatc aaatgctgta gaatgcttgg cactccctaa ccaaatgctg tctccataat 60
gccactggtg ttaagatata ttt 83

<210> SEQ ID NO 74
<211> LENGTH: 121
<212> TYPE: DNA
<213> ORGANISM: Homo sapiens

<400> SEQUENCE: 74
atataccata ggctaaaact aaggctttca ctctagaatg caaagctgtt ttgcagctgt 60
tttcccttaa agatgtcctg ttgctttagt gatatttaga cccctctcag ttaagaaatg 120
c 121

<210> SEQ ID NO 75
<211> LENGTH: 285
<212> TYPE: DNA

<213> ORGANISM: Homo sapiens

<400> SEQUENCE: 75
caagacctag gctcatggac gagatgggaa ggcacaggga gaagggataa ccctacaccc 60
agaccccagg ctggacatgc tgactgtcct ctcccctcca gcctttggcc ttggcttttc 120
tagcctattt acctgcaggc tgagccactc tcttcccttt ccccagcatc actccccaag 180
gaagagccaa tgttttccac ccataatcct ttctgccgac ccctagttcc ctctgctcag 240
ccaagcttgt tatcagcttt cagggccatg gttcacatta gaata 285

<210> SEQ ID NO 76
<211> LENGTH: 105
<212> TYPE: DNA
<213> ORGANISM: Homo sapiens

<400> SEQUENCE: 76
gtatttattg agtcacggat tattgtgcat caagcaattg ttaatatgac ctggtcctat 60
ggggtagaac ttaggaaaaa taaagttggt tcttattcaa tattt 105

<210> SEQ ID NO 77
<211> LENGTH: 248
<212> TYPE: DNA
<213> ORGANISM: Homo sapiens

<400> SEQUENCE: 77
atgccctgag gccagttggc gaggggtggc tcctgagggt ttttataccc tttgtttgct 60
aatgtttaat tttgcatcat aatttctaca ttgtccctga gtgtcagaac tataatttat 120
tccatttctc tctgtgtctg tgccaagaaa cgcaggctct gggcctgccc cttgcccagg 180
aggccttgcc agcctgtgtg cttgtgggaa caccttgtac ctgagcttac aggtaccaat 240
aaagaggc 248

<210> SEQ ID NO 78
<211> LENGTH: 55
<212> TYPE: DNA
<213> ORGANISM: Homo sapiens

<400> SEQUENCE: 78
atactggaaa cctaactgca atgtggatgt tttacccaca tgacttatta tgcat 55

<210> SEQ ID NO 79
<211> LENGTH: 237
<212> TYPE: DNA
<213> ORGANISM: Homo sapiens

<400> SEQUENCE: 79
agaagaccca cgtgctaggg gatgaggggc ttcctgggtc ctgttcccta ccccatttgt 60
ggtcacagcc atgaagtcac cgggatgaac ctatccttcc agtggctcgc tccctgtagc 120
tctgcctccc tctccatatc tccttcccct acacctccct ccccacacct ccctactccc 180
ctgggcatct tctggcttga ctggatggaa ggagacttag gaacctacca gttggcc 237

<210> SEQ ID NO 80
<211> LENGTH: 151
<212> TYPE: DNA
<213> ORGANISM: Homo sapiens

<400> SEQUENCE: 80
gcagaaatat gtaaccttag actcagccag tttcctctgc agctgctaaa actacatgtg 60
gccagctcca ttcttccaca ctgcgtacta catttcctgc ctttttcttt cagtgttttt 120
ctaagactaa ataaatagca aactttcacc t 151

<210> SEQ ID NO 81
<211> LENGTH: 286
<212> TYPE: DNA
<213> ORGANISM: Homo sapiens

<400> SEQUENCE: 81
taaagacgca tgttatggtg ctaatgtact ttcactttta aactctagat cagaattgtt 60
gacttgcatt cagaacataa atgcacaaaa tctgtacatg tctcccatca gaaagattca 120
ttggcatgcc acaggggatt ctcctccttc atcctgtaaa ggtcaacaat aaaaaccaaa 180
ttatggggct gcttttgtca cactagcata gagaatgtgt tgaaatttaa ctttgtaagc 240
ttgtatgtgg ttgttgatct ttttttcct tacagacacc cataat 286

<210> SEQ ID NO 82
<211> LENGTH: 189
<212> TYPE: DNA
<213> ORGANISM: Homo sapiens

<400> SEQUENCE: 82
ttaccctcca aaagcaagta gccaaagccg ttgccaaacc ccacccataa atcaatgggc 60
cctttattta tgacgacttt atttattcta atatgatttt atagtattta tatatattgg 120
gtcgtctgct tcccttgtat ttttcttcct ttttttgtaa tattgaaaac gacgatataa 180
ttattataa 189

<210> SEQ ID NO 83
<211> LENGTH: 211
<212> TYPE: DNA
<213> ORGANISM: Homo sapiens

<400> SEQUENCE: 83
gtcaggtctt ggtaggtgcc tgcatctgtc tgccttctgg ctgacaatcc tggaaatctg 60
ttctccagaa tccaggccaa aaagttcaca gtcaaatggg gaggggtatt cttcatgcag 120
gagaccccag gccctggagg ctgcaacata cctcaatcct gtcccaggcc ggatcctcct 180
gaagcccttt tcgcagcact gctatcctcc a 211

<210> SEQ ID NO 84
<211> LENGTH: 211
<212> TYPE: DNA
<213> ORGANISM: Homo sapiens

<400> SEQUENCE: 84
gaaaaaactt tctctttgcc atttcttctt cttctttttt aactgaaagc tgaatccttc 60
catttcttct gcacatctac ttgcttaaat tgtgggcaaa agagaaaaag aaggattgat 120
cagagcattg tgcaatacag tttcattaac tccttccccc gctcccccaa aaatttgaat 180 tttttttca acactcttac acctgttatg g 211

<210> SEQ ID NO 85
<211> LENGTH: 89
<212> TYPE: DNA
<213> ORGANISM: Homo sapiens

<400> SEQUENCE: 85
tgactgaatt gctgaccctt caagctctgt ccttatccat tacctcaaag cagtcattcc 60
ttagtaaagt ttccaacaaa tagaaatta 89

<210> SEQ ID NO 86
<211> LENGTH: 162
<212> TYPE: DNA
<213> ORGANISM: Homo sapiens

<400> SEQUENCE: 86
gcattctcaa gaggtcgtgc caatcagcca ctgaaaggaa aggcatcact atggactttc 60
tctattttaa aatggtaaca atcagaggaa ctataagaac acctttagaa ataaaaatac 120
tgggatcaaa ctggcctgca aaaccatagt cagttaattc tt 162

<210> SEQ ID NO 87
<211> LENGTH: 86
<212> TYPE: DNA
<213> ORGANISM: Homo sapiens

<400> SEQUENCE: 87
atcatttcat agtcatttat gtttcatcgg tcctcatgtg tactagtgcg ttattttact 60
tatactcccg gatatcatat tattta 86

<210> SEQ ID NO 88
<211> LENGTH: 146
<212> TYPE: DNA
<213> ORGANISM: Homo sapiens

<400> SEQUENCE: 88
atgttcatag gttctcaacc ctcaccccca ccacgggaga ctagagctgc aggatcccag 60
gggaggggtc tctcctccca ccccaaggca tcaagccctt ctccctgcac tcaataaacc 120
ctcaataaat attctcattg tcaagg 146

<210> SEQ ID NO 89
<211> LENGTH: 186
<212> TYPE: DNA
<213> ORGANISM: Homo sapiens

<400> SEQUENCE: 89
gctgagcaaa gcagactacg agaaacacaa agtctacgcc tgcgaagtca cccatcaggg 60
cctgagctcg cccgtcacaa agagcttcaa caggggagag tgttagaggg agaagtgccc 120
ccacctgctc ctcagttcca gcctgacccc ctcccatcct ttggcctctg accctttttc 180
cacagg 186

<210> SEQ ID NO 90
<211> LENGTH: 41
<212> TYPE: DNA
<213> ORGANISM: Homo sapiens

<400> SEQUENCE: 90
tacaagacca cgcctcccgt gctggactcc gacggctcct t 41

<210> SEQ ID NO 91
<211> LENGTH: 211
<212> TYPE: DNA
<213> ORGANISM: Homo sapiens

<400> SEQUENCE: 91
gaaaaaactt tctctttgcc atttcttctt cttctttttt aactgaaagc tgaatccttc 60
catttcttct gcacatctac ttgcttaaat tgtgggcaaa agagaaaaag aaggattgat 120
cagagcattg tgcaatacag tttcattaac tccttccctc gctcccccaa aaatttgaat 180
ttttttttca acactcttac acctgttatg g 211

<210> SEQ ID NO 92
<211> LENGTH: 105
<212> TYPE: DNA
<213> ORGANISM: Homo sapiens

<400> SEQUENCE: 92
ggacctgaag ggtgacatcc caggaggggc ctctgaaatt tcccacaccc cagcgcctgt 60
gctgaggact ccctccatgt ggccccaggt gccaccaata aaaat 105

<210> SEQ ID NO 93
<211> LENGTH: 100
<212> TYPE: DNA
<213> ORGANISM: Homo sapiens

<400> SEQUENCE: 93
tgcccccctt aaggctagag gtgagcatgt ccctcacaat tgcacatgtc aagccatcag 60
caaggcgcat cacacaaaag gcaccaagac gtgaaacttt 100

<210> SEQ ID NO 94
<211> LENGTH: 115
<212> TYPE: DNA
<213> ORGANISM: Homo sapiens

<400> SEQUENCE: 94
gcatgctcag tcttttcctc ttatctacaa tacaaagggt ttgtctgaaa agtctggttt 60
tttttctttt tacaaatgta ccttagctgc atcaacagga gtaagatgta gaaaa 115

<210> SEQ ID NO 95
<211> LENGTH: 74
<212> TYPE: DNA
<213> ORGANISM: Homo sapiens

<400> SEQUENCE: 95
cgatatgact tccatgtaaa cgttcatcca ctctgcctgc ttacaccctg ccctcatgct 60
aatgtaataa actc 74

<210> SEQ ID NO 96
<211> LENGTH: 164
<212> TYPE: DNA
<213> ORGANISM: Homo sapiens

<400> SEQUENCE: 96
gtgtggatgc taaggtgttt gttttgtttt gtatttttat gtagcgcgtg ggtattgtgc 60
ctagaaatga agtcattatt agggatttaa atatgcaact catggagtgg atgagaccag 120
ctagaaagat aatagagtgt gaagaggaga tcggaaattc aata 164

<210> SEQ ID NO 97
<211> LENGTH: 211
<212> TYPE: DNA
<213> ORGANISM: Homo sapiens

<400> SEQUENCE: 97
gtttgtgtgg gaactttgca agtcagtttc cctgtatgaa gtgatggaga gagtgattaa 60
gatactgagc tttctctgtg ttcttgccgt taaccattgc cggtttgtgg gagattaaga 120
agtcgatgcg ttttatggag aattaattta ttttgatata gacagatgga cgggtcatga 180
aaatttgttg acatacttta ctaaactgct a 211

<210> SEQ ID NO 98
<211> LENGTH: 127
<212> TYPE: DNA
<213> ORGANISM: Homo sapiens

<400> SEQUENCE: 98 tttttagtt gccaacagtt gtatttttgc tgattattta tgaccttaaa taatatattt 60 tttttttaa gaagacattt tgttacataa ggaaaacttt tttattcaat ggaataaatt 120
atggcat 127

<210> SEQ ID NO 99
<211> LENGTH: 251
<212> TYPE: DNA
<213> ORGANISM: Homo sapiens

<400> SEQUENCE: 99
gaacaggagc aactactaaa agagggattt caaaaagaaa gcagaataat gaaaaatgag 60
atacaggatc tccagacgaa aatgagacga cgaaaggcat gtaccataag ctaaagacca 120
gagccttcct gtcaccccta accaaggcat aattgaaaca attttagaat ttggaacaag 180
cgtcactaca tttgataata attagatctt gcatcataac accaaaagtt tataaaggca 240
tgtggtacaa t 251

<210> SEQ ID NO 100
<211> LENGTH: 163
<212> TYPE: DNA
<213> ORGANISM: Homo sapiens

<400> SEQUENCE: 100
ctttcattgg aagttcatca ctgttaggcg ttatcttgag tattataaca aagcaaatcc 60
acaagtattc aatataagat taggaaaaaa attcctgcga tactttgttg tcaaacactt 120
gccactgata gacgttattt tagcttttaa ggcctgtcac att 163

<210> SEQ ID NO 101
<211> LENGTH: 258
<212> TYPE: DNA
<213> ORGANISM: Homo sapiens
<220> FEATURE:
<221> NAME/KEY: misc_feature
<222> LOCATION: (61)..(61)
<223> OTHER INFORMATION: n is a, c, g, or t

<400> SEQUENCE: 101
atggagtata agctgtttgt agtcaggcct ggagtaatga gggtacctaa atactgaagg 60
natttttatg cagattgact gaaacctgaa tcaaattgga aggagagggc tgaattttga 120
tagactggaa gtattagaga attttctata ctttgactca aggaatggtc aacttttagg 180
aaaagcaact atattatgtc tgttaagatc atagaatctt aacctgaaag ggaccttgga 240
gactatttag tacaactc 258

<210> SEQ ID NO 102
<211> LENGTH: 193
<212> TYPE: DNA
<213> ORGANISM: Homo sapiens
<220> FEATURE:
<221> NAME/KEY: misc_feature
<222> LOCATION: (120)..(125)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t

<400> SEQUENCE: 102
gaagaaagct aactcagtac actaagagtg atttacatgc ctgcaaataa tttgtgtctg 60
gggtcttgac cctccccaaa tgccttgtta tttatatctc tgcttttaga taacagatgn 120
nnnnntntct atgggcttgt accggcagag gcaacagcag gtccttaaga ctccccaggt 180
gccatgatga aaa 193

<210> SEQ ID NO 103
<211> LENGTH: 173
<212> TYPE: DNA
<213> ORGANISM: Homo sapiens

<400> SEQUENCE: 103
gtaccatctt acatgcttaa ataactccac atttatttgt gtttattact ctgtgttata 60
aatatacatt tgttggtctc tctcttggat tattttgttt ctttgtcctg taactaccac 120
tgaaagggtg caatacagct ttcttgaaat gtgtattgaa cggatgaatg tat 173

<210> SEQ ID NO 104
<211> LENGTH: 217
<212> TYPE: DNA
<213> ORGANISM: Homo sapiens

<400> SEQUENCE: 104
gttcccagtg acacttcaga gagctggtag ttagtagcat gttgagccag gcctgggtct 60
gtgtctcttt tctctttctc cttagtcttc tcatagcatt aactaatcta ttgggttcat 120
tattggaatt aacctggtgc tggatatttt caaattgtat ctagtgcagc tgattttaac 180
aataactact gtgttcctgg caatagtgtg ttctgat 217

<210> SEQ ID NO 105
<211> LENGTH: 233
<212> TYPE: DNA
<213> ORGANISM: Homo sapiens
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t

<400> SEQUENCE: 105
tggagtaaca cccagatctc tgcagcagtt aagcntgggg gcctagaact agnctagagn 60
tagaagaagg gacaaatgca atccgacctt tggatctaca cattcctctt gcttcaatgg 120
gtgtcattta agaattagag gaaaatatta ggagatggag aactagagtt gaggaaacca 180
aaagaagagg agtcacagaa aaccagctct ctctgtgcaa ggcatcttga aag 233

<210> SEQ ID NO 106

<211> LENGTH: 178
<212> TYPE: DNA
<213> ORGANISM: Homo sapiens

<400> SEQUENCE: 106
ctttggatag aggtgaagaa cttggacatg gctgtttcag gcagctgaag tcaaagggaa 60
tagtaattgg ggaaggggaa gtgggcagaa aggattgttg gccaatatac cttccactcc 120
agtagagagg gaggacttgg ctctgagaac ctccatctga cctaagagga accctcct 178

<210> SEQ ID NO 107
<211> LENGTH: 163
<212> TYPE: DNA
<213> ORGANISM: Homo sapiens

<400> SEQUENCE: 107
ctgcaaaagc cgagatgggt tccatgcagt tctccagtgg gacatcagtg cttatccgaa 60
tgtcatcaat ggcaatctct ccggaacgtc ctttccctat cactccctcg aacacaatct 120
ggtactccat gtcgtagctg ggcaggatga tccgcccgtg ctt 163

<210> SEQ ID NO 108
<211> LENGTH: 267
<212> TYPE: DNA
<213> ORGANISM: Homo sapiens

<400> SEQUENCE: 108
ttgctttgta tgcactttgt ttttttcttt gggtcttgtt ttttttttcc acttagaaat 60
tgcatttcct gacagaagga ctcaggttgt ctgaagtcac tgcacagtgc atctcagccc 120
acatagtgat ggttcccctg ttcactctac ttagcatgtc cctaccgagt ctcttctcca 180
ctggatggag gaaaaccaag ccgtggcttc ccgctcagcc ctccctgccc ctcccttcaa 240
ccattcccca tgggaaatgt caacaag 267

<210> SEQ ID NO 109
<211> LENGTH: 146
<212> TYPE: DNA
<213> ORGANISM: Homo sapiens

<400> SEQUENCE: 109
gctttgatat ttcaatgtta gcctcaattt ctgaacacca taggtagaat gtaaagcttg 60
tctgatcgtt caaagcatga aatggatact tatatggaaa ttctgctcag atagaatgac 120
agtccgtcaa aacagattgt ttgcaa 146

<210> SEQ ID NO 110
<211> LENGTH: 174
<212> TYPE: DNA
<213> ORGANISM: Homo sapiens

<400> SEQUENCE: 110
gatcagcaaa caggaatacg atgaagccgg gccttccatt gtccaccgca aatgcttcta 60
aaacactttc ctgctcctct ctgtctctag cacacaactg tgaatgtcct gtggaattat 120
gccttcagtt cttttccaaa tcattcctag ccaaagctct gactcgttac ctat 174

<210> SEQ ID NO 111
<211> LENGTH: 165
<212> TYPE: DNA
<213> ORGANISM: Homo sapiens

<400> SEQUENCE: 111

```
ctcagggagc gaacgtggat gaaaaccaca gggattccgg acgccagacc ccattttata     60

cttcactttt ctctacagtg ttgttttgtt gttgttggtt tttatttttt atactttggc    120

cataccacag agctagattg cccaggtctg ggctgaataa aacaa                    165


<210> SEQ ID NO 112
<211> LENGTH: 257
<212> TYPE: DNA
<213> ORGANISM: Homo sapiens

<400> SEQUENCE: 112

ttgttactgc tgattcttgt aaatcttttt gcttctactt tcatcttaaa ctaatacgtg     60

ccagatataa ctgtcttgtt tcagtgagag acgccctatt tctatgtcat ttttaatgta    120

tctatttgta caattttaaa gttcttattt tagtatacgt ataaatatca gtattctgac    180

atgtaagaaa atgttacggc atcacactta tattttatga acattgtact gttgctttaa    240

tatgagcttc aatataa                                                   257


<210> SEQ ID NO 113
<211> LENGTH: 191
<212> TYPE: DNA
<213> ORGANISM: Homo sapiens

<400> SEQUENCE: 113

taggtggtag atattgaggc caagaatatt gcaaaataca tgaagcttca tgcacttaaa     60

gaagtatttt tagaataaga atttgcatac ttacctagtg aaacttttct agaattattt    120

ttcactctaa gtcatgtatg tttctctttg attatttgca tgttatgttt aataagctac    180

tagcaaaata a                                                         191


<210> SEQ ID NO 114
<211> LENGTH: 116
<212> TYPE: DNA
<213> ORGANISM: Homo sapiens

<400> SEQUENCE: 114

tgctgtgaaa gaggctggct acacaatcga atggtttgag gtgatctcgc aaagttattc     60

ttccaccatg gccaacaacg aaggactttt ctccctggtg gcgaggaagc tgagca        116


<210> SEQ ID NO 115
<211> LENGTH: 227
<212> TYPE: DNA
<213> ORGANISM: Homo sapiens

<400> SEQUENCE: 115

tatttgaact atatgttgaa gacatctacc agtttctcca aatgcctttt ttaaaactca     60

tcacagaaga ttggtgaaaa tgctgagtat gacacttttc ttcttgcatg catgtcagct    120

acataaacag ttttgtacaa tgaaaattac taatttgttt gacattccat gttaaactac    180

ggtcatgttc agcttcattg catgtaatgt agacctagtc catcaga                  227


<210> SEQ ID NO 116
<211> LENGTH: 293
<212> TYPE: DNA
<213> ORGANISM: Homo sapiens

<400> SEQUENCE: 116

ttgcttttca ttcagatgta tacataaact tatttaaaat gtcatttaag tgaaccattc     60
```

-continued caaggcataa taaaacccga ggtagcaaat gaaaattaaa gcatttattt tggtagttct 120
tcaataatga tgcgagaaac tgaattccat ccagtagaag catctccttt tgggtaatct 180
gaacaagtgc caacccagat agcaacatcc actaatccag caccaattcc ttcacaaagt 240
ccttccacag aagaagtgcg atgaatatta attgttgaat tcatttcagg gct 293

<210> SEQ ID NO 117
<211> LENGTH: 37
<212> TYPE: DNA
<213> ORGANISM: Homo sapiens

<400> SEQUENCE: 117
gatgcttaac aaaggttacc ataagccaca aattcat 37

<210> SEQ ID NO 118
<211> LENGTH: 179
<212> TYPE: DNA
<213> ORGANISM: Homo sapiens

<400> SEQUENCE: 118
agaggttata ggtcactcct ggggcctctt gggtccccca cgtgacagtg cctgggaatg 60
tattattctg cagcatgacc tgtgaccagc actgtctcag tttcactttc acatagatgt 120
ccctttcttg gccagttatc ccttcctttt agcctagttc atccaatcct cactgggtg 179

<210> SEQ ID NO 119
<211> LENGTH: 220
<212> TYPE: DNA
<213> ORGANISM: Homo sapiens

<400> SEQUENCE: 119
ctgtatcact gccttcgttt atattttttt aactgtgata atccccacag gcacattaac 60
tgttgcactt ttgaatgtcc aaaatttata ttttagaaat aataaaaaga aagatactta 120
catgttccca aaacaatggt gtggtgaatg tgtgagaaaa actaacttga tagggtctac 180
caatacaaaa tgtattacga atgcccctgt tcatgttttt 220

<210> SEQ ID NO 120
<211> LENGTH: 237
<212> TYPE: DNA
<213> ORGANISM: Homo sapiens

<400> SEQUENCE: 120
acaaaagctc ccctgatcca actagcacac tgtcaaatac agtgtcatat gagaggtcca 60
cagacggtag tttccaagac cgtttcaggg aattcgagga ttccacctta aaacctaaca 120
gaaaaaaacc cactgaaaat attatcatag acctggacaa agaggacaag gatttaatat 180
tgacaattac agagagtacc atccttgaaa ttctacctga gctgacatcg gataaaa 237

<210> SEQ ID NO 121
<211> LENGTH: 197
<212> TYPE: DNA
<213> ORGANISM: Homo sapiens

<400> SEQUENCE: 121
agtgctaagg agtatagcag atgacttata tgtgtgttgg ctgggagaat atcatcttaa 60
agtgagagtg atgttgtgga gacagttgaa atgtcagtgc tagagcctct gtggtgtgaa 120
tgggcacgtt aggttgttgc attagaaagt gactgtttct gacagaaatt tgtagctttg 180
tgcaaactca cccacca 197

<210> SEQ ID NO 122
<211> LENGTH: 131
<212> TYPE: DNA
<213> ORGANISM: Homo sapiens

<400> SEQUENCE: 122
ctacttcccc gaaccggtga cggtgtcgtg gaactcaggc gccctgacca gcggcgtgca 60
caccttcccg gctgtcctac agtcctcagg actctactcc ctcagcagcg tggtgaccgt 120
gccctccagc a 131

<210> SEQ ID NO 123
<211> LENGTH: 95
<212> TYPE: DNA
<213> ORGANISM: Homo sapiens

<400> SEQUENCE: 123
ccagacctac acctgcaacg tagatcacaa gcccagcaac accaaagtgg acaagacagt 60
tgagcgcaaa tgttgtgtcg agtgcccacc gtgcc 95

<210> SEQ ID NO 124
<211> LENGTH: 131
<212> TYPE: DNA
<213> ORGANISM: Homo sapiens

<400> SEQUENCE: 124
gtaatttgtg attgtcgagg aagaggtgtg gctgttggtg tgatagtaat actgctggtg 60
actttattgg ttgttttgtt tagtgccccg ttaattaagc cttgagttcg gttatcctgc 120
agtggtgctg a 131

<210> SEQ ID NO 125
<211> LENGTH: 38
<212> TYPE: DNA
<213> ORGANISM: Homo sapiens

<400> SEQUENCE: 125
tttcccccac tgtctggaca ctggtgaatg acattaga 38

<210> SEQ ID NO 126
<211> LENGTH: 173
<212> TYPE: DNA
<213> ORGANISM: Homo sapiens

<400> SEQUENCE: 126
gaaggagaac gaatccagtg gaaagaaagc tggtgaggga aaagatgccc tgcagaaaag 60 tccccttcc cccactgtct ggacactggt gaatgacatt agaagagacc caccccattc 120
aagtcccctc actggctcct tttctcccca ctacaccact tccaaaatct gaa 173

<210> SEQ ID NO 127
<211> LENGTH: 145
<212> TYPE: DNA
<213> ORGANISM: Homo sapiens

<400> SEQUENCE: 127
gataccgact gaccgtgggc cttacccgaa gaggacagcc catgcagtac aatgtgggtc 60
cctctgtctt caagtaccca ctgaggaatc tgcagcctgc atctgagtac accgtattcc 120
tcgtggccat aaagggcaac caaga 145

<210> SEQ ID NO 128
<211> LENGTH: 111
<212> TYPE: DNA
<213> ORGANISM: Homo sapiens

<400> SEQUENCE: 128
ttaagacatt ggagtgattt ctggaaatgt tttctttaag aaggctcacg tgatgtttgt 60
gtttacttgt ggttgcccta tcctatgctg cataaatcct tgaaaggaaa g 111

<210> SEQ ID NO 129
<211> LENGTH: 137
<212> TYPE: DNA
<213> ORGANISM: Homo sapiens

<400> SEQUENCE: 129
ttaagacatt ggagtgattt ctggaaatgt tttctttaag aaggctcacg tgatgtttgt 60
gtttacttgt ggttgcccta tcctatgctg cataaatcct tgaaaggaaa ggttttagtt 120
agttgctttc tttcttc 137

<210> SEQ ID NO 130
<211> LENGTH: 156
<212> TYPE: DNA
<213> ORGANISM: Homo sapiens

<400> SEQUENCE: 130
ctgagtaaat gggactgctg tcgttggatg gcactgcgca gctcaggggt gggctctggg 60
aggcggaggc ggaggaggcc gctggagatg gtgctgagga cgaggaggcc ggtgggttgg 120
tcatgctcac taggccactg accaagctga agaggg 156

<210> SEQ ID NO 131
<211> LENGTH: 163
<212> TYPE: DNA
<213> ORGANISM: Homo sapiens

<400> SEQUENCE: 131
agaattaact gactatggtt ttgcaggcca gtttgatccc agtattttta tttctaaagg 60
ggttcttata gttcctctga ttgttaccat tttaaaatag agaaagtcca tagtgatgcc 120
tttcctttca gtggctgatt ggcacgacct cttgagaatg cat 163

<210> SEQ ID NO 132
<211> LENGTH: 269
<212> TYPE: DNA
<213> ORGANISM: Homo sapiens

<400> SEQUENCE: 132
atttgcattt taccatgggt cctcaataaa taaatagaat gttgtttttt gtattttaag 60
tttttttttg tttttcccct cagaggaagg atgaaaaaaa gaattaactg actatggttt 120
tgcaggccag tttgatccca gtatttttat ttctaaaggg gttcttatag ttcctctgat 180
tgttaccatt ttaaaataga gaaagtccat agtgatgcct ttcctttcag tggctgattg 240
gcacgacctc ttgagaatgc atgcatgaa 269

<210> SEQ ID NO 133
<211> LENGTH: 105
<212> TYPE: DNA
<213> ORGANISM: Homo sapiens

<400> SEQUENCE: 133
atttccatca catatgtgcc aagacttgtg ttctgtatcc aggagtgtgt tagatactaa 60
catagtgttt catttacatg tgtgtgaaac ctgggtgaag agcca 105

<210> SEQ ID NO 134
<211> LENGTH: 174
<212> TYPE: DNA
<213> ORGANISM: Homo sapiens

<400> SEQUENCE: 134
ccatcagttt ttccaatgtg aatggactgg ttcatatcac accatattta gagatacaag 60
gtgattataa ctaacgtgtc tacaagacat actgggtcaa acaatgtgat caatccaaag 120
ggtatctttt taaaaagaat ttaagtactc agctgcaaag ataagttcac taat 174

<210> SEQ ID NO 135
<211> LENGTH: 218
<212> TYPE: DNA
<213> ORGANISM: Homo sapiens

<400> SEQUENCE: 135
gtacatggtc tggagtaacc tttatatgaa gtggctgccc aggtgtgtgg cttaggacta 60
gatctccagg ttgcacaaag ttggcattgg gtttagtttg catttttcca ttctgaagat 120
ggccctcctt ggatttcatc caggaaatcc atagctttct gttaacagga catggagtag 180
actggctgca tttgaaggac agcacagatc cctcatca 218

<210> SEQ ID NO 136
<211> LENGTH: 103
<212> TYPE: DNA
<213> ORGANISM: Homo sapiens

<400> SEQUENCE: 136
aaaccttgtt ttattcagcc cagacctggg agatctagct ctgtggtatg gccaaagtat 60
aaaaaataaa aaccaacaac aacaaaacaa cactgtagag aaa 103

<210> SEQ ID NO 137
<211> LENGTH: 194
<212> TYPE: DNA
<213> ORGANISM: Homo sapiens

<400> SEQUENCE: 137
tcaaactcag gtatgtgaca ctctacagtt caatgctagc acacctgtgt gaggcttaac 60
aacatgagga actgatagcc agtgatacac aaatccagca cttcctctcc atttactctg 120
tcaggctgta tatggggagc aacacatatg gctttgtggc agccagaaag tgaaggtctt 180
tttaggaggt gaca 194

<210> SEQ ID NO 138
<211> LENGTH: 268
<212> TYPE: DNA
<213> ORGANISM: Homo sapiens

<400> SEQUENCE: 138
gtaaagcttt ggcacataca gtataaaaaa taatcaccca ccataattat accaaattcc 60
tcttatcaac tgcatactaa gtgttttcaa tacaattttt tccgtataaa aatactggga 120
aaaattgata aataacaggt aagagaaaga tatttctagg caattactag gatcatttgg 180
aaaaagtgag tactgtggat atttaaaata tcacagtaac aagatcatgc ttgttcctac 240
agtattgcgg gccagacact taagtgaa 268

<210> SEQ ID NO 139
<211> LENGTH: 37
<212> TYPE: DNA
<213> ORGANISM: Homo sapiens

<400> SEQUENCE: 139
tgggctggag ccgcacacgc tctcctccca tgttaaa 37

<210> SEQ ID NO 140
<211> LENGTH: 158
<212> TYPE: DNA
<213> ORGANISM: Homo sapiens

<400> SEQUENCE: 140
ttttcgtagt ccaaaggctt tattgttctg ctgaaatgct tacaaatact gaaaaccccc 60
agcctgggcc caggcaacca agggctcaat gctgggaagg agagcagggg aggtgggctt 120
agtgttaagg cgtgaagggc gaggccagac agctggag 158

<210> SEQ ID NO 141
<211> LENGTH: 182
<212> TYPE: DNA
<213> ORGANISM: Homo sapiens

<400> SEQUENCE: 141
tgagtaggtg agtttattgg gacttacaca caggtcaatc ctgggcggcg acaagacagc 60
tctagagatc tgagcttcct cccaatgcta aactgctttc atgctaattt tctgactgtt 120
tacttaccgg gtaagagcga tgggactgtt ttcattggtt ggttctcaca tactctctgg 180
ga 182

<210> SEQ ID NO 142
<211> LENGTH: 94
<212> TYPE: DNA
<213> ORGANISM: Homo sapiens

<400> SEQUENCE: 142
gcctcccatt caagtgaagt tataatttac actgagggtt tcaaaattcg actagaagtg 60
gagatatatt atttatttat gcactgtact gtat 94

<210> SEQ ID NO 143
<211> LENGTH: 165
<212> TYPE: DNA
<213> ORGANISM: Homo sapiens

<400> SEQUENCE: 143
tttcctgccc caaggcagat ccacatcacc gaagctccct agaggggcaa aagatggagt 60
gagccacagg aagtttgggg cgtggtgagt tggaatgata cgtccatttc tctatgaaat 120
atttgctact agactgttca tttctctctg acatgtttgt tgaat 165

<210> SEQ ID NO 144
<211> LENGTH: 227
<212> TYPE: DNA
<213> ORGANISM: Homo sapiens

<400> SEQUENCE: 144
agcccaactt cttacccgaa agcatcactg ccttggcccc tccctcccgg ctgcccccat 60
cacctctact gtctcctccc tgggctaagc aggggagaag cgggctgggg gtagcctgga 120
tgtgggccaa gtccactgtc ctccttggcg gcaaaagccc attgaagaag aaccagccca 180
gcctgccccc tatcttgtcc tggaatattt ttggggttgg aactcaa 227

<210> SEQ ID NO 145
<211> LENGTH: 57
<212> TYPE: DNA
<213> ORGANISM: Homo sapiens

<400> SEQUENCE: 145
tattgaggac ccatggtaaa atgcaaatag atccggtgtc taaatgcatt catattt 57

<210> SEQ ID NO 146
<211> LENGTH: 135
<212> TYPE: DNA
<213> ORGANISM: Homo sapiens

<400> SEQUENCE: 146
tacccgggaa agtacgtcta gattgtgtgg tttgcctcat tgtgctattt gcccactttc 60
cttccctgaa gaaatatctg tgaaccttct ttctgttcag tcctaaaatt cgaaataaag 120
tgagactatg gttca 135

<210> SEQ ID NO 147
<211> LENGTH: 174
<212> TYPE: DNA
<213> ORGANISM: Homo sapiens

<400> SEQUENCE: 147
ttgcatggag acttgaggag ggagggcttg aggttggtga ggttaggtgc gtgtttcctg 60
tgcaagtcag gacatcagtc tgattaaagg tggtgccaat ttatttacat ttaaacttgt 120
cagggtataa aatgacatcc cattaattat attgttaatc aatcacgtgt atag 174

<210> SEQ ID NO 148
<211> LENGTH: 132
<212> TYPE: DNA
<213> ORGANISM: Homo sapiens

<400> SEQUENCE: 148
acagcccacc cttgtgtcca ctgtgacccc tgttcccatg ctgacctgtg tttcctcccc 60
agtcatcttt cttgttccag agaggtgggg ctggatgtct ccatctctgt ctcaacttta 120
cgtgcactga gc 132

<210> SEQ ID NO 149
<211> LENGTH: 173
<212> TYPE: DNA
<213> ORGANISM: Homo sapiens

<400> SEQUENCE: 149
aaatgctcct tgaatattaa aaggttgtaa aaatagtgca tgttatgtga tttcaatttt 60
gttttttaaa atatgggtgt atgcttgtat acgtagagca gataaaaaag acggaaggca 120
tactaaaaaa tgttgagtgg ttatctttgt atggtggaac aaagtcactg taa 173

<210> SEQ ID NO 150
<211> LENGTH: 247
<212> TYPE: DNA
<213> ORGANISM: Homo sapiens

<400> SEQUENCE: 150
ggcaggcttc tctgtagaac cccaggggct tcggcccaga ccacagcgtc ttgccctgag 60
cctagagcag ggagtcccga acttctgcat tcacagacca cctccacaat tgttataacc 120
aaaggcctcc tgttctgtta tttcacttaa atcaacatgc tattttgttt tcactcactt 180
ctgactttag cctcgtgctg agccgtgtat ccatgcagtc atgttcacgt gctagttacg 240
tttttct 247

<210> SEQ ID NO 151
<211> LENGTH: 112
<212> TYPE: DNA
<213> ORGANISM: Homo sapiens

<400> SEQUENCE: 151
attttagtat ggtgtctgtt tatgtaactc tgacttgctg gaaaagttga aactccaaat 60
aatctgaaac tagaaaagaa atagcacata attactacct tccccttggc gg 112

<210> SEQ ID NO 152
<211> LENGTH: 278
<212> TYPE: DNA
<213> ORGANISM: Homo sapiens

<400> SEQUENCE: 152
aaatggcttc cgatttccag cttgggcctg gggattggag atgtccccac tgagagtagg 60
gcacaagtga ggaaatggtt tggagaggaa gatgataagt tacatcatgg atgtgctgag 120
tctgagttgc ctatgggact tggaatgggg ggtggcaaaa ggtgtgtgat cttgagcaag 180
atattcaact cttctgggcc ttggtcttct catttgtaaa acggtgataa gaatattact 240
tcccatttgt gttgctgtga atattaaatg cgctacca 278

<210> SEQ ID NO 153
<211> LENGTH: 137
<212> TYPE: DNA
<213> ORGANISM: Homo sapiens

<400> SEQUENCE: 153
gtgggcagca cttagattcg gagccatgga tagtccggag tccaaggtct ctgggtgagc 60
agacagtcgg ccaaaggcca gcctggagtc aaagagacca gacccctgct tagattgcca 120
tactcgcacc attccaa 137

<210> SEQ ID NO 154
<211> LENGTH: 252
<212> TYPE: DNA
<213> ORGANISM: Homo sapiens

<400> SEQUENCE: 154
agttcggcaa aggtgtccta gaaatggcca gagtttttga cagacagagt gtagtctcct 60
tattagaaga aaggaaaaaa aagcagaggc caaagaagtt ttgtgtttgc tgatgagagc 120
cccactcatt tgcgaaacgc acgtaaaaca aagtgaaccg tgactgttaa actagggatg 180
ggaaattttg catcttgggg ggctgtacat ttatttattt agttgaagat tcactgatcc 240
cactttgaaa ta 252

<210> SEQ ID NO 155
<211> LENGTH: 106
<212> TYPE: DNA
<213> ORGANISM: Homo sapiens

<400> SEQUENCE: 155
gtgcatgtgt gtgctgtgtc tttgtgtgtg tgctgtgtgc tagtgtgtgt gctgtgtgtg 60
catgtgtgtg cgtgtgctgt gcgtttgtgt gctgtgtgct cgtgtg 106

<210> SEQ ID NO 156
<211> LENGTH: 294
<212> TYPE: DNA
<213> ORGANISM: Homo sapiens

<400> SEQUENCE: 156
tgggaagcgg cgagatcctc gggctggggg tgcccacgtt tgctacctcc ccctgtgaaa 60
tcgctggtgc tcacaattgt ctttcacagt gtatgtgatt tttttaagga aaaaaaaaaa 120
atccctattt aagattttga aggtgctacc attattttgc cacagacttt gaagaaactt 180
ttggatgtgg ggcatcatcc gcatctttct ctctcctcca aatgacaaag tttggggaat 240
ttttgaattt tcctagcatc gcccttgtgc tcatcaggta atctgctaag gagg 294

<210> SEQ ID NO 157
<211> LENGTH: 238
<212> TYPE: DNA
<213> ORGANISM: Homo sapiens

<400> SEQUENCE: 157
acccatcctg ttcgtgaata ggtctcaggg gttgggggag ggactgccag atttggacac 60
tatatttttt tttaaattca acttgaagat gtgtatttcc cctgaccttc aaaaaatgtt 120
ccaaggtaag cctcgtaaag gtcatcccac catcaccaaa gcctccgttt ttaacaacct 180
ccaacacgat ccatttagag gccaaatgtc attctgcagg tgccttcccg atggatta 238

<210> SEQ ID NO 158
<211> LENGTH: 258
<212> TYPE: DNA
<213> ORGANISM: Homo sapiens

<400> SEQUENCE: 158
cattctttcc tccacaggat tgctttgtcc atctcctgct ttcatttcaa gtgcataaac 60
aaaacctcaa agggcctggg aaggtgaggc aggccagagt ctgtgttctg tgttgagtgt 120
caagctattt gttaagaagg tttgcaacag gcctttggtg tgggctttgc cagagactgt 180
tttgaacact ttgcttgaga tccgtgccct gtaaaatgga tatgatgttt tactgatgtc 240
tgtaatacat ttgtaaac 258

<210> SEQ ID NO 159
<211> LENGTH: 85
<212> TYPE: DNA
<213> ORGANISM: Homo sapiens

<400> SEQUENCE: 159
ttaagcgcat tagaaaacaa ttgtttgtaa tggaatcaaa gtgtttccct ggacagtttg 60
atgtgcttat ggttgagatt tataa 85

<210> SEQ ID NO 160
<211> LENGTH: 299
<212> TYPE: DNA
<213> ORGANISM: Homo sapiens
<220> FEATURE:
<221> NAME/KEY: misc_feature
<222> LOCATION: (127)..(127)
<223> OTHER INFORMATION: n is a, c, g, or t
<220> FEATURE:

<221> NAME/KEY: misc_feature
<222> LOCATION: (194)..(194)
<223> OTHER INFORMATION: n is a, c, g, or t

<400> SEQUENCE: 160
atttgcaaca gcctagtgga tttggtaggg tcctgaatca tctctataag gcaaacaagg 60
aaattgtaac acaaagaaat aaacatattg aatataattg ctattctgta agacatacag 120
tctgtgnaag atgtatctta tttacagaga catttttgaa aattaaaata ttaaatactt 180
tttgttatat aganacaatg atctggaagt ataaaaagaa aaatattatc ttgttgatgt 240
aaatatgata tccttatata tattagaatc caataagata tcatgggcgc aatattagc 299

<210> SEQ ID NO 161
<211> LENGTH: 229
<212> TYPE: DNA
<213> ORGANISM: Homo sapiens

<400> SEQUENCE: 161
gatggctggg agataagtcc ttgaatggag gaaccaagag gtgagttaga ggcataaact 60
aaggaatttc agttagtagg gtttaggagt gacagtctag aatgagtgga gactaggaga 120
ttcatcttga tgcaagcata cttagatcca tgttactcag gatagcatag gtgagagagg 180
agctggtaga attttaatgt catacctggg tagtacaact ggttattat 229

<210> SEQ ID NO 162
<211> LENGTH: 213
<212> TYPE: DNA
<213> ORGANISM: Homo sapiens

<400> SEQUENCE: 162
tattttccgg ttgaccccag aattcattag attttttaa aaaacaattt caaaatagtt 60
gctgttttaa attagttgca tccagttcat atcaatgttt gcatgctttt tagtctttgt 120
tatttattga aaacctttgg tacctaaact taagtttgat tgtttcagtg tgtacttggt 180
aaatatgtca gtggcctttt aactaaacat caa 213

<210> SEQ ID NO 163
<211> LENGTH: 174
<212> TYPE: DNA
<213> ORGANISM: Homo sapiens

<400> SEQUENCE: 163
caccccagga ctttatcaac ttgttcaagt tctgaatccc agcacatgac aacacttcag 60
aagggtcccc ctgctgactg gagagctggg aatatggcat ttggacactt catttgtaaa 120
tagtgtacat tttaaacatt ggctcgaaac ttcagagata agtcatggag agga 174

<210> SEQ ID NO 164
<211> LENGTH: 32
<212> TYPE: DNA
<213> ORGANISM: Homo sapiens

<400> SEQUENCE: 164
atggacaatt ctgtacccca ataatcagaa ca 32

<210> SEQ ID NO 165
<211> LENGTH: 166
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n is a, c, g, or t

<400> SEQUENCE: 165
agagaggttt gtcccatata tcttgttcca gcagccatat atcttgtggt ctacagcctg 60
aagcatgatt tcccttgaag tcttggggtt gtttaaagga nagtcccttc aatataaaac 120
ctctgaaata ttagtgagaa tggctcacta atgtgaacaa tgttta 166

<210> SEQ ID NO 166
<211> LENGTH: 213
<212> TYPE: DNA
<213> ORGANISM: Homo sapiens

<400> SEQUENCE: 166
tacaaagaat atttgggccc agtgctacag aaaaacatga actacatctt atcgtcacaa 60
aatagccatt ataaaatgaa ttttgcagcc tctgtttttt tgaactttga aataaaatgt 120
tcagacaaat attcaacttt ttaaaaacct ccattcattg atagcctgag aaatgtacaa 180
tgaacatgtt taggcagact gctagtattt tgc 213

<210> SEQ ID NO 167
<211> LENGTH: 225
<212> TYPE: DNA
<213> ORGANISM: Homo sapiens

<400> SEQUENCE: 167
cctccaccaa tcatactttg acatttatct atttccttct ccacttatgg atgtaattgg 60
cttgctatag aaactacagt tcagatgctt tgaatgtatg aactacaatg aacaataaag 120
tcctcttctt ttgaagcata ttttggcttc agctttaaga taatcttatg acaagaaggg 180
tcacactgat tcacttaata aattccattc ttacctaaca caagg 225

<210> SEQ ID NO 168
<211> LENGTH: 259
<212> TYPE: DNA
<213> ORGANISM: Homo sapiens

<400> SEQUENCE: 168
gctggtgtgt ggatcggatg ggcaagtccc tgccagggtc tccagatggc aatggaagct 60
cctcctgccc cactgggagt agcggctaaa gctgggggat agaggggctg cagggccact 120
ggaaggaaca tggagctgtc atcactcaac aaaaaaccga ggccctcaat ccaccttcag 180
gccccgcccc atgggcccct caccgctggt tggaaagagt gttggtgttg gctggggtgt 240
caataaagct gtgcttggg 259

<210> SEQ ID NO 169
<211> LENGTH: 217
<212> TYPE: DNA
<213> ORGANISM: Homo sapiens

<400> SEQUENCE: 169
gaccccagtg gaaaacaaag ccaaacaaaa ctgaaccaca aaaaaaaggc tggtgttcac 60
caaaaccaaa cttgttcatt tagataattt gaaaaagttc catagaaaag gcgtgcagta 120
ctaagggaac aatccatgtg attaatgttt tcattatgtt catgtaagaa gccccttatt 180
tttagccata attttgcata ctgaaaatcc aataatc 217

<210> SEQ ID NO 170

<211> LENGTH: 243
<212> TYPE: DNA
<213> ORGANISM: Homo sapiens

<400> SEQUENCE: 170
gagtaaaaag aaccctttgc tgagtaacca agcctttaat tttgtgtttt tatgaaagga 60
attaaaatac ccacgataaa tatttaccac aacctgtgtc agataaatgg gaaattaaac 120
acagattgta caatgtgagc ttgggagtta atggcccaga ttttactgtt aggcagtaag 180
agttggagta ggtagtcttg ttatcatgag aagaaccttg aacagataca actaatttac 240
ata 243

<210> SEQ ID NO 171
<211> LENGTH: 172
<212> TYPE: DNA
<213> ORGANISM: Homo sapiens

<400> SEQUENCE: 171
aacacccata atcaatcaca gagataacca ctgttcataa ttccttccag tcttcttact 60
tggcacatat acatttgtct ttctttatat atgacatatg gatattttac aaagttagga 120
tcctactcta tgcactgctt ggtgatcgga tctattcaat gtacaaaata tt 172

<210> SEQ ID NO 172
<211> LENGTH: 100
<212> TYPE: DNA
<213> ORGANISM: Homo sapiens

<400> SEQUENCE: 172
ttttctaacc ttgattgacc atgggcaaat gaaactgcag aaagtgaaac tgcggatagg 60
ggggatgact gtattcaata gattccgaca ttatgtctgc 100

<210> SEQ ID NO 173
<211> LENGTH: 32
<212> TYPE: DNA
<213> ORGANISM: Homo sapiens

<400> SEQUENCE: 173
ttataatgag tgcgatatat gttgtcgagg ct 32

<210> SEQ ID NO 174
<211> LENGTH: 210
<212> TYPE: DNA
<213> ORGANISM: Homo sapiens

<400> SEQUENCE: 174
gttttgatgc tgtgtgcttt tggctgggcc tcgggctcca ggccctggga ccccttgcca 60
gggagacccc cgaacctttg tgccaggaca cctcctggtc ccctgcacct ttcctgttcg 120
gtttagaccc ccaaactgga gggggcatgg agaaccgtag agcgcaggaa cgggtgggta 180
attttagaga caaaagccaa ttaaagtcca 210

<210> SEQ ID NO 175
<211> LENGTH: 115
<212> TYPE: DNA
<213> ORGANISM: Homo sapiens

<400> SEQUENCE: 175
ttcattgagg ttcgtgtgtg ctgtgttcgc gtgtgtgtgc tgtgtgtgca tgtgtgtgct 60
gtgtcttagt gtgtgtgctg tgtgctagtg tgtgtgctgt ggggtaccga gctcg 115

<210> SEQ ID NO 176
<211> LENGTH: 241
<212> TYPE: DNA
<213> ORGANISM: Homo sapiens

<400> SEQUENCE: 176
ttcatcatat ccaagttcac tctgtcttcc tgagcagtgg aagatcatat tgctgtaact 60
tcttttaagt agttgatgtg gaaaacattt taaagtgaat ttgtcaaaat gctggttttg 120
tgttttatcc aacttttgtg catatatata aagtatgtca tggcatggtt tgcttaggag 180
ttcagagttc cttcatcatc gaaatagtga ttaagtgatc ccagaacaag gaatactaga 240
g 241

<210> SEQ ID NO 177
<211> LENGTH: 148
<212> TYPE: DNA
<213> ORGANISM: Homo sapiens
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (91)..(93)
<223> OTHER INFORMATION: n is a, c, g, or t

<400> SEQUENCE: 177
gtcattgata cctgtagtaa gttgacaatg tggtgaaatt tcaaaattat atgtaacttc 60
tactagtttt actttctccc ccaagtctnt nnnaactcat gatttttaca cacacaatcc 120
agaacttatt atatagcctc taagtctt 148

<210> SEQ ID NO 178
<211> LENGTH: 198
<212> TYPE: DNA
<213> ORGANISM: Homo sapiens

<400> SEQUENCE: 178
gattttcttt tgacacagct ccaaggccac cagctatgca aggccacaag ttatgcacta 60
tatgattaac tgcttttgtt ttacttttgt aagtccactt ataaaaaccc tgctctgtct 120
ttgtttaatg ctcagctttt tggatttgaa tccactcagc cggtgcacac cttaaaataa 180
acatcctcct gtactctc 198

<210> SEQ ID NO 179
<211> LENGTH: 269
<212> TYPE: DNA
<213> ORGANISM: Homo sapiens

<400> SEQUENCE: 179
agacctagaa ggttgtagat gggaaatcag gaatgatttg aactgataaa gatttcagac 60
tcataagaac acattttata aatgttaaac acaaaaacta catgactgaa gatagaagag 120
aatgcgatgg attttattac acatggtgga agagagaaga ggcgtgtagg tttgcaaaca 180
aagttaagaa ataggaaact gaatttttca ttgtacagaa aatgtatctc ttggggaggg 240
cctgtgtacc cccattctct gattataaa 269

<210> SEQ ID NO 180
<211> LENGTH: 243
<212> TYPE: DNA

<213> ORGANISM: Homo sapiens

<400> SEQUENCE: 180 ggatttttc ccctgtagta gtgaggtaac atgcttgaat gtcactgtga tatttatttc 60
ctctttgttc agttgttttt gaattcctgt taagtacatg ttttaatact ttgagcgatt 120
taagatactt ttctttttgc ccatcatttt ccccaaggaa tgtaattcac ataaatccaa 180
agctcatttt tttttttatt gtacacaagt agtataatgt ttgcttttcc caataaacct 240
caa 243

<210> SEQ ID NO 181
<211> LENGTH: 178
<212> TYPE: DNA
<213> ORGANISM: Homo sapiens
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t

<400> SEQUENCE: 181
gagacaagga cagacaaatt ttctggctgt ccccatttct cctgggggag gggtttgggg 60
ctggtttgac tttaattggt gggngggtng tttctgccgc tctgtttgct gcagtccccg 120
tgncctgctt ggggactgag aaatttgagc caggtatcca gagccacagc ccatcttg 178

<210> SEQ ID NO 182
<211> LENGTH: 238
<212> TYPE: DNA
<213> ORGANISM: Homo sapiens

<400> SEQUENCE: 182
agttggtgcc ctgattccat ttttctcaag ttgtagaaga aacaaactaa tttacggtag 60
gagaaattca aattcagatt ctccccatcc ccaccagtta cctttggttg gtggagaggg 120
ggagaattgg caggaaaggg gcacaaagaa actttttggg gtgatggaaa tattttgtac 180
cttgctttag atgttggtca gatggaatat acgtttgtgg aaacctgcca aactgtac 238

<210> SEQ ID NO 183
<211> LENGTH: 155
<212> TYPE: DNA
<213> ORGANISM: Homo sapiens

<400> SEQUENCE: 183
aaacattacc gggcatggta gcttgcacct gcagtcccag ctacttggga gactgaggtg 60
agaggatcac ctgagtgtag gaggtgaaag cctcaccgaa ctatgactga accactgcac 120
tccagcgtgg gcacttggca ccagagcaag attct 155

<210> SEQ ID NO 184
<211> LENGTH: 47
<212> TYPE: DNA
<213> ORGANISM: Homo sapiens

<400> SEQUENCE: 184
gggatgcata aagtatgagt gccttttagg atgggaattg agatgta 47

<210> SEQ ID NO 185
<211> LENGTH: 235
<212> TYPE: DNA
<213> ORGANISM: Homo sapiens
<220> FEATURE:
<221> NAME/KEY: misc_feature
<222> LOCATION: (157)..(157)
<223> OTHER INFORMATION: n is a, c, g, or t

<400> SEQUENCE: 185
aggatttccc aaaccagccg aggccccagc acccgccgtc tccccagaag ccccctcctc 60
cttcccccat gggtcatatg ttgaaagtct attttaaaaa ctatgttcct tgccgtagat 120
tgcagagcta atttatcacg tttctctcct gtgaganccc cccttttata tgatatatcc 180
agaggaagtt ttgtaatata aaacaggacg cccacactga tggttttgca ctggt 235

<210> SEQ ID NO 186
<211> LENGTH: 38
<212> TYPE: DNA
<213> ORGANISM: Homo sapiens

<400> SEQUENCE: 186
tttggatttg aatccactca gccggtgcac accttaaa 38

<210> SEQ ID NO 187
<211> LENGTH: 265
<212> TYPE: DNA
<213> ORGANISM: Homo sapiens

<400> SEQUENCE: 187
tgttttagaa ccagccgtat tttacatgaa gctgtataat taattgtcat tatttttgtt 60
agcaaagatt aaatgtgtca ttggaagcca tcccttttt tacatttcat acaacagaaa 120
ccagaaaagc aatactgttt ccattttaag gatatgatta atattattaa tataataatg 180
atgatgatga tgatgaaaac taaggatttt tcaagagatc tttctttcca aaacattttt 240
ggacagtacc tgattgtatt ttttt 265

<210> SEQ ID NO 188
<211> LENGTH: 56
<212> TYPE: DNA
<213> ORGANISM: Homo sapiens

<400> SEQUENCE: 188
cacaatctga gcacgctacc aaatctcaaa atatcctaag actaacaaag gcagct 56

<210> SEQ ID NO 189
<211> LENGTH: 289
<212> TYPE: DNA
<213> ORGANISM: Homo sapiens

<400> SEQUENCE: 189
tcccaagtag tgctgactga ctctcctggt gacaggggtt tgtgtccgag cccctgcggt 60
caaggagtgt ggagcaaaac gtgggtacta gggtgggagg cggggaaagg ccacagcaca 120
ctggcgctcc agcaaagcca aatcatgtct cctctggcca ctgcggtcct ctccttggta 180
catgtcatcc cccagaggag tatccaaagc tattccacta tgcactcatc aaccctggct 240
tgtcagcctt ggggaaggtc actttattca taaaaatgcc tctttgagt 289

<210> SEQ ID NO 190

<211> LENGTH: 212
<212> TYPE: DNA
<213> ORGANISM: Homo sapiens

<400> SEQUENCE: 190
cctgagtcct gggatcagac acccccttcac gtgtatcccc acacaaatgc aagctcacca 60
aggtcccctt tcagtcccct tccctacacc ctgaccggcc actgccgcac acccacccag 120
agcacgccac ccgccatggg agtgtgctca ggagtcgcgg gcagcgtgga catctgtccc 180
agagggggca gaatctccaa tagaggactg ag 212

<210> SEQ ID NO 191
<211> LENGTH: 294
<212> TYPE: DNA
<213> ORGANISM: Homo sapiens

<400> SEQUENCE: 191
cagggttcct ttgcctgcta acaagcccac gtggaccagt ttgaatgtct ttcctttaca 60
cctatgtttt taagtagtca aacttcaaga aacaatttaa acaagttttt gttgcatatg 120
tgtttgtgaa cttgtatttg tatttagtag gcttctatat tgcatttaac ttgtttttgt 180
aactcctgat ttttcctttt cggatactat tgatgaataa agaaattaaa gtgatagttt 240
tattggtttc ctttccccca attaaggcca aataaagtcg tgagaacatt accc 294

<210> SEQ ID NO 192
<211> LENGTH: 52
<212> TYPE: DNA
<213> ORGANISM: Homo sapiens

<400> SEQUENCE: 192
gaggccggtg ccagtgcagg tccttggtgt gctgtgtgcc ggtcccctgg gc 52

<210> SEQ ID NO 193
<211> LENGTH: 297
<212> TYPE: DNA
<213> ORGANISM: Homo sapiens

<400> SEQUENCE: 193
atggtaatgt aggatccttt cacagagtgc caggctaaag agctgaactt tgtggtggaa 60
gagacagacc ccctatgtgc tctgtagaca cctgtgatga agtagaactc atgaggatat 120
gaagagaaac atttgtaatt tgagtgatta aactaggaac gaaagaggag gggagaaata 180
ggaagagaga atcaccggcc ctgttgactg atttgagctg ggaatgaaga agaaaaccct 240
gcaggtgtgg gcaccaatgt ttgaaacccc cacagtgtga gtctcaactc tgtgtga 297

<210> SEQ ID NO 194
<211> LENGTH: 223
<212> TYPE: DNA
<213> ORGANISM: Homo sapiens

<400> SEQUENCE: 194
ccatgtcagc ctggatagag gtatatgacg tgtgccaaga atttatccca gactcccctg 60
tgtgacagct tcataataaa gttacttaac tgtgcctctt cctccttcct ctccccacac 120
aggatggatg ggcatctttc tccttgacca ccctactctc ccttcctccc ctgatcacct 180
cccctccctg ctctcccctg gtgatggact tctaacatga gat 223

<210> SEQ ID NO 195
<211> LENGTH: 238

<212> TYPE: DNA
<213> ORGANISM: Homo sapiens

<400> SEQUENCE: 195
actggtatat tattgcttca tgttttgtac catcataaga ttttgtgcag atttttttta 60
cagaaattat tattttttat gacaatatga cacttgtaaa ttgttgtttc aaaatgaaca 120
gcgaagcctt aactttaaat gacatttgta ttttcagaca ctgagtagca taaaaaccac 180
atagaactga actgtaactt aaattccaaa ctatgactac tacattccaa agaaacag 238

<210> SEQ ID NO 196
<211> LENGTH: 129
<212> TYPE: DNA
<213> ORGANISM: Homo sapiens

<400> SEQUENCE: 196
cgtccccaac atgcatctca ctctgggtgt cttggtcttt tattttttgt aagtgtcatt 60
tgtataactc taaacgccca tgatagtagc ttcaaactgg aaatagcgaa ataaaataac 120
tcagtctgc 129

<210> SEQ ID NO 197
<211> LENGTH: 277
<212> TYPE: DNA
<213> ORGANISM: Homo sapiens

<400> SEQUENCE: 197
tggaggattc aagatgagca ggtatgtttt ctgctttcaa taactcattt tctgctgcag 60
agatagcctt gtaagcaagc aaaggaaaac tttgacattt ctctgcaaag ataatgcatt 120
acatataagg gtgtgtctgg gagggtacca ggtgcctgtc agcaaaagtt gcaaaaacag 180
cttgataagg gtattaagtg ggcctgttgg gaaaggcagg agtgtcaaat gtcggacaga 240
actccagaca gagaaatcca gatatccagt aggttag 277

<210> SEQ ID NO 198
<211> LENGTH: 231
<212> TYPE: DNA
<213> ORGANISM: Homo sapiens
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (169)..(170)
<223> OTHER INFORMATION: n is a, c, g, or t
<220> FEATURE:
<221> NAME/KEY: misc_feature
<222> LOCATION: (172)..(176)
<223> OTHER INFORMATION: n is a, c, g, or t
<220> FEATURE:
<221> NAME/KEY: misc_feature
<222> LOCATION: (178)..(180)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:

<221> NAME/KEY: misc_feature
<222> LOCATION: (186)..(187)
<223> OTHER INFORMATION: n is a, c, g, or t

<400> SEQUENCE: 198
gaatggcaaa acacaaatgg caacataaat gtccatttga cttacctaac ttcacaactt 60
tcaagttgag gatgtcattt attcttgaat tntgtttttt tactnagatg ctttcaatta 120
atagccctat atttttgtgc aggcgaactg tataacaggn ataaaaaann annnnnannn 180
antgannagg aggagaaatt ctcacagaac accatatgag ctttagacca a 231

<210> SEQ ID NO 199
<211> LENGTH: 262
<212> TYPE: DNA
<213> ORGANISM: Homo sapiens

<400> SEQUENCE: 199
gaggtgtgat tttaaggcat tgttatattt ttttttattt gtgagtgttt taaaattttg 60
tatttctttt aaacttttta ttttagaaaa atttccaaca tatatagaag tagactattg 120
taaggaaccc ttatgtaccc tccaccagct tcaacaacta tcaacaaaag tttgatcttg 180
ttttaaccac attcctttcc aatttttgtg tttacccccca gattattttg aagcaaattc 240
ctgacctcat aacattttca aa 262

<210> SEQ ID NO 200
<211> LENGTH: 187
<212> TYPE: DNA
<213> ORGANISM: Homo sapiens

<400> SEQUENCE: 200
ttcagtttgt cctcataggg aatcaagtat tttagctagg tgatgtcttg caagtacgtt 60
ccactttgtt acaatctact atctgtatat actatttgta tcttaattct tttatgagat 120
gttctgtaac atttttctca ctttgacaaa tgtttttaga ctgtacagtc aagatctggc 180
gcttggg 187

<210> SEQ ID NO 201
<211> LENGTH: 180
<212> TYPE: DNA
<213> ORGANISM: Homo sapiens

<400> SEQUENCE: 201
acagtgattc cccacgtgtg ttcatctgca cccaccgagc caggcagagg ccagccctcc 60
gtggtgcaca cagcacgcgc ctcagtccat cccattttag tctttaaacc ctcaggaagt 120
cacagtctcc ggacaccaca ccacatgagc ccaacaggtc cacgatggat ccaccagtcc 180

<210> SEQ ID NO 202
<211> LENGTH: 55
<212> TYPE: DNA
<213> ORGANISM: Homo sapiens

<400> SEQUENCE: 202
cagatcgaca cgcagctagc ctcctgcatt gtatggttat aaatagcacc ctagt 55

<210> SEQ ID NO 203
<211> LENGTH: 207
<212> TYPE: DNA
<213> ORGANISM: Homo sapiens

<400> SEQUENCE: 203
aagtgttcta caaaagaatc cctgtggtta gcttactctt aggttagatc ttctaataag 60
gctgaaattc aaaatcaaaa ccttagtgtg tccgagtcca gcctgggttc cagcattctg 120
ttcaggccac ttctgaacgg ccgaaggtgc cccattccag acctgcccat ttgatggaca 180
gagcagacag cccggaacag attcaag 207

<210> SEQ ID NO 204
<211> LENGTH: 241
<212> TYPE: DNA
<213> ORGANISM: Homo sapiens
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t

<400> SEQUENCE: 204
taagaattta tgaaactggg caagttattt cctgggactc aatggtaaag acacagcagt 60
aatccaaatt ttccatcttt gaaattttcc atncttncag tcaatattag taatacctgg 120
gtcaaagggg agagttaggc ataccaatta atgatcatca gaaatgacat agtcctacaa 180
aagcaaagaa aatttagaga cactttctta aaaatacgac tcttggtact gttgaagaaa 240
a 241

<210> SEQ ID NO 205
<211> LENGTH: 261
<212> TYPE: DNA
<213> ORGANISM: Homo sapiens

<400> SEQUENCE: 205
agccgctgcc aagtctgtat gagaagaaca taatgaagcc tgactcagct aatgtcacaa 60
catggtgcta cttcttcttc tttttgttaa cagcaacgaa ccctagaaat atatcctgtg 120
tacctcactg tccaatatga aaaccgtaaa gtgccttata ggaatttgcg taactaacac 180
accctgcttc attgacctct acttgctgaa ggagaaaaag acagcgataa gctttcaata 240
gtggcatacc aaatggcact t 261

<210> SEQ ID NO 206
<211> LENGTH: 274
<212> TYPE: DNA
<213> ORGANISM: Homo sapiens

<400> SEQUENCE: 206
ggttgagttt gtccattgct agggagagac ttccagtaat aaaatttact attctagatg 60
cttctactgt tatgttttat ctgcccattt atctttctta gttaccagga gaaatgtgtg 120
acacctatat tataatgaaa acaatcttat tacttatagt ttatctatat taaacaaatt 180
taattgcatt ttaaagcatt ctttgatatt gttgcttttg caataaatat ggataatctt 240
ggttataagg gagttaaaac aatgctgtaa taaa 274

<210> SEQ ID NO 207
<211> LENGTH: 179
<212> TYPE: DNA
<213> ORGANISM: Homo sapiens

<400> SEQUENCE: 207

-continued

```
tcatggaatg ctacatgctt tctgtttttt tcattttgga tttctccaaa actaactgaa     60

tttaagcttc aggtcccttt gtatgcagta gaaaggaatt attaaaaaca ccaccaaaga    120

aaataaatat atcctacttg aaatttactt tatggactta cccactgcta gaataaatg     179


<210> SEQ ID NO 208
<211> LENGTH: 249
<212> TYPE: DNA
<213> ORGANISM: Homo sapiens

<400> SEQUENCE: 208

cggttgttaa aactggttta gcacaattta tattttccct ctcttgcctt ttttatttgc     60

aataaaaggt attgagccat tttttaaatg acatttttga taaattatgt ttgtactagt    120

tgatgaagga gttttttta acctgtttat ataattttgc agcagaagcc aaatttttg     180

tatattaaag caccaaattc atgtacagca tgcatcacgg atcaatagac tgtacttatt    240

ttccaataa                                                            249


<210> SEQ ID NO 209
<211> LENGTH: 64
<212> TYPE: DNA
<213> ORGANISM: Homo sapiens

<400> SEQUENCE: 209

ccatgaagga gcaagttttg tatttgtgac ctcagctttg ggaataaagg atcttttgaa     60

ggcc                                                                  64


<210> SEQ ID NO 210
<211> LENGTH: 57
<212> TYPE: DNA
<213> ORGANISM: Homo sapiens

<400> SEQUENCE: 210

atgaggcaga atctggttgg gtatgtttct tatatatgtt tgaagcagat ggctgac        57


<210> SEQ ID NO 211
<211> LENGTH: 141
<212> TYPE: DNA
<213> ORGANISM: Homo sapiens

<400> SEQUENCE: 211

atttttgcct ttccgtttct gtctatgatg taggcttctg aggagaacca agaagcttgg     60

ctttagtggt agaatgacag aacttaggga tcccttgcag gctagaacaa agttctgacc    120

cttagaccaa atctttatgt t                                              141


<210> SEQ ID NO 212
<211> LENGTH: 108
<212> TYPE: DNA
<213> ORGANISM: Homo sapiens

<400> SEQUENCE: 212

gaggaggtgg gcctcgttag actgctcaga ttactggaac ctcgttatca catcccattc     60

tacaagtttt tcactgaatg tttcctgaca tctataaatg agggtgcc                 108


<210> SEQ ID NO 213
<211> LENGTH: 158
<212> TYPE: DNA
<213> ORGANISM: Homo sapiens

<400> SEQUENCE: 213
```

gttcaaatga tctacactta cattttgcaa atcttttttt ttaaattttt taaattttat 60 atttttttc cagccaactc aaggccaaaa aaaatttctt aatatagtta ttatgcgagg 120
ggaggggaag caaaggagca caggtagtcc acagaata 158

<210> SEQ ID NO 214
<211> LENGTH: 157
<212> TYPE: DNA
<213> ORGANISM: Homo sapiens

<400> SEQUENCE: 214
aggtggtttt gataacacac ttataaggct ttctgtaaaa ggtactatag aagggcgaag 60
aatcgttcaa ctgtcaatca gcctcttgat tctttgtaaa ttgccagggt gggtgggtac 120
atatctcttc ttgattctgc atttcatact taactat 157

<210> SEQ ID NO 215
<211> LENGTH: 273
<212> TYPE: DNA
<213> ORGANISM: Homo sapiens

<400> SEQUENCE: 215
gactgagtga gtaactgcaa gctacagggg gcagcttacg tatggcacac agggtggggc 60
tagcttggtt tcataggctc tctgtggatt ggatgattta aataattttg gtgggccctg 120
gggtttaggg actgtcccta gttgtttggt gctaggtccc agggcagatt agggcagatg 180
tgagtgtgag agcatgataa ggaaagtctt caaggtgtgg aattactcaa ctgctggaga 240
aagggaattt atcagccttt agccagggcc tca 273

<210> SEQ ID NO 216
<211> LENGTH: 257
<212> TYPE: DNA
<213> ORGANISM: Homo sapiens

<400> SEQUENCE: 216
gaaagcctga gtttgcaacc agttgtaggg tttttgttgt gtttttttt tttttttgaa 60 ataaaactat aatataaatt ctcctattaa ataaaattat tttaagtttt agtgtcaaaa 120
gtgagatgct gagagtaggt gataatgtat attttacaga gtgggggttg gcaggatggt 180
gacattgaac atgattgctc tctgtctctt ttttcagctt atgggtattt atcttctatt 240
agtatttgta tcttcag 257

<210> SEQ ID NO 217
<211> LENGTH: 268
<212> TYPE: DNA
<213> ORGANISM: Homo sapiens

<400> SEQUENCE: 217
atgagtcaaa atccgctctc catgcttact cttgacaccc cattgaagcc actcattgtg 60
tgtgcgtctg ggtgtgaagt ccagctccgt gtggtcctgt gcttgtactg ccctgctttg 120
cagttccttt gcacttactc atcgagtgct gttttgaaat gctgacatta tataaacgta 180
aaagaaaatg taaaaaaaaa aaacccacac acaaacaaac ccatacgatc tgtatttgta 240
tatacacgtg tccgtacaag tataacta 268

<210> SEQ ID NO 218
<211> LENGTH: 290
<212> TYPE: DNA

<213> ORGANISM: Homo sapiens

<400> SEQUENCE: 218
gaccaaatgg attagactgt aaactgcaaa gtgctgtccg cacatgaggt catctgatta 60
ctgtcctcag atctcttttg tagaggattt caatgtattt ctttatcatt tgagtgtgtg 120
tgtgatggac gaatatgtgt gtgagtttga gaagcatatc gttcgtgtcc agttactttg 180
caaatttgtg gacatttgtg attggacaga ggggtttgtg ctgtggccta acacttgcca 240
agtgaggtgt aggttatgcc tatatgcaaa ttaaacttca cctttcttga 290

<210> SEQ ID NO 219
<211> LENGTH: 205
<212> TYPE: DNA
<213> ORGANISM: Homo sapiens

<400> SEQUENCE: 219
cctttctaag gatgagggaa tccacaacag actttctcta gaaaacacta atgatggaca 60
actttttggt gtcatcaatg agttggctac taccttgatg taaaaatttg taaggaaaat 120
tttcaccatt tcgagtgtca agtgtatttt taactgtctg gtttgtactt ttatgacttt 180
tgtactacca aagcggagtt aaaaa 205

<210> SEQ ID NO 220
<211> LENGTH: 278
<212> TYPE: DNA
<213> ORGANISM: Homo sapiens

<400> SEQUENCE: 220
ctatcaggta ctgtgctcat ctgaacaaca aacctcaaca acacgcaatt tatccatgta 60
attaacctgc acatgtaccc ccgaaaccta aaataaaagt tcaaaaaaaa cctgtggtat 120
ttaaataggt attgtgtcta aaaatgcatg ctatctaaaa atgtagtttt attgcactgt 180
ataagaatac gagaggttta aaatagacac tctaaaagtt ataagcccta atttacatat 240
attctctagc ctttctccac cttctatcta ccaaaaaa 278

<210> SEQ ID NO 221
<211> LENGTH: 41
<212> TYPE: DNA
<213> ORGANISM: Homo sapiens

<400> SEQUENCE: 221
tcctcatggt ggcagcgctc atagcgaaag cctactgtaa t 41

<210> SEQ ID NO 222
<211> LENGTH: 133
<212> TYPE: DNA
<213> ORGANISM: Homo sapiens

<400> SEQUENCE: 222
aatgcagaat attcctctga acacttccct catacatcat tcaatattat aaattaaaca 60
caaagagcct ctccacttag atttttatca tgcatcctac attgtaatgt ctttactctt 120
ccatagaaaa ggt 133

<210> SEQ ID NO 223
<211> LENGTH: 74
<212> TYPE: DNA
<213> ORGANISM: Homo sapiens

<400> SEQUENCE: 223
ggtgcaatta ttatactgcg aaaatgaaaa tattgcatac taaacagtac ctagggtatg 60
atctcaatgt aaaa 74

<210> SEQ ID NO 224
<211> LENGTH: 172
<212> TYPE: DNA
<213> ORGANISM: Homo sapiens

<400> SEQUENCE: 224
aactgtgacc gtttctgtgt gaagattttt agctgtattt gtggtctctg tatttatatt 60
tatgtttagc accgtcagtg ttcctatcca atttcaaaaa aggaaaaaaa agagggaaaa 120
ttacaaaaag agagaaaaaa agtgaatgac gtttgtttag ccagtaggag aa 172

<210> SEQ ID NO 225
<211> LENGTH: 258
<212> TYPE: DNA
<213> ORGANISM: Homo sapiens

<400> SEQUENCE: 225
actcaaggct gtgaacaaac atacgctgct ttattctttc caatttttct cttgttttct 60
agaactctta tccatatgtt tttaaaataa gtacctaaaa gtggtttgat agtgtcctaa 120
acgacttttt taacttccta aatggaaaga gcataacaat gtagttgatt ggtaagattt 180
acagggattt ggtttctgag tttgaggcac attcccagtg aataagctga gtcccatacc 240
acactcaaaa ggttttaa 258

<210> SEQ ID NO 226
<211> LENGTH: 103
<212> TYPE: DNA
<213> ORGANISM: Homo sapiens

<400> SEQUENCE: 226
attaaagtac tcaagttagt tgttttgcag agatgttgcc ttcagatgtt aatcaggtct 60
ctcaagtttc atggagtcta tgctgatcct ttaattgaca aat 103

<210> SEQ ID NO 227
<211> LENGTH: 258
<212> TYPE: DNA
<213> ORGANISM: Homo sapiens

<400> SEQUENCE: 227
ggatgaagtg gcacacactc taactgaaag cagagtatta aagaacacta gacatccctt 60
tttaacatcc ttgaaatatt ccttccagac aaaagaccgt ttgtgttttg tgatggaata 120
tgttaatggg ggcgagctgt ttttccattt gtcgagagag cgggtgttct ctgaggaccg 180
cacacgtttc tatggtgcag aaattgtctc tgccttggac tatctacatt ccggaaagat 240
tgtgtaccgt gatctcaa 258

<210> SEQ ID NO 228
<211> LENGTH: 252
<212> TYPE: DNA
<213> ORGANISM: Homo sapiens

<400> SEQUENCE: 228
ggttctgtaa ggtctttatt tcccataagt aaatattgcc atgggagggg ggtggaggtg 60
gcaaggaagg ggtgaagtgc tagtatgcaa gtgggcagca attatttttg tgttaatcag 120
cagtacaatt tgatcgttgg catggttaaa aaatggaata taagattagc tgttttgtat 180
tttgatgacc aattacgctg tattttaaca cgatgtatgt ctgtttttgt ggtgctctag 240
tggtaaataa at 252

<210> SEQ ID NO 229
<211> LENGTH: 210
<212> TYPE: DNA
<213> ORGANISM: Homo sapiens

<400> SEQUENCE: 229
tttcaagatc ttttgctcac aattcactgc aactgagggg atgtgaatat cattatgcaa 60
taaattaaga gccacagttg gctgaggtga tatgaaagcc aacctgccta aggggggtat 120
gaaagatgtg tatctttcca aacttttaaa acaacgtaag tctgagataa gaacatattt 180
gatggcactg tttggaaaga ggtgtcctta 210

<210> SEQ ID NO 230
<211> LENGTH: 258
<212> TYPE: DNA
<213> ORGANISM: Homo sapiens

<400> SEQUENCE: 230
ctcaccagga ctcgtctctc cattcccgtc agagtttgct ttgatttccc tttcctttcc 60
ttctcgggga ccagttctta cttcctttta tttttagctt tgcactccat gtggtttcag 120
ggttcagttt gatccatcaa aaggttcttt ttttataatc ccttttgaaa atgataatca 180
aaggaagaga tgtggtgttt ggtcatgtgg aaaactcaat gtataattta gacgtctgtc 240
aaaaatccga caaataaa 258

<210> SEQ ID NO 231
<211> LENGTH: 218
<212> TYPE: DNA
<213> ORGANISM: Homo sapiens

<400> SEQUENCE: 231
gtttcaattg attcacaact ttaaaaaata tccacagagg cgtaagagga gatattgtat 60
tgcacccacg aaccagtttt atgctgttta agaaagggac attcaagaaa caaaaaggga 120
gctttgggaa atttgaacaa taaataatag tagaataaaa aattcagaga aagtttggat 180
gataaatttg agccaatctc ccagtaagca gagcaaaa 218

<210> SEQ ID NO 232
<211> LENGTH: 267
<212> TYPE: DNA
<213> ORGANISM: Homo sapiens

<400> SEQUENCE: 232
atgactgtgc tagagccacc ctctcacttt agcctcctga gtagctggga ctacaggtgc 60
ttcccactgt gcctggccaa ttaacaattt catttttatt tttagtagag atgagatctc 120
actatgttgc ccaggctggt cctgaactcc tgagctcaag agatcctccc accttggcct 180
cccaaagtac tgggattaca aacaagagcc actgtgcctg accaggctct aagattgcta 240
atctggctat agaaggacta atgttag 267

<210> SEQ ID NO 233
<211> LENGTH: 230
<212> TYPE: DNA
<213> ORGANISM: Homo sapiens

<400> SEQUENCE: 233
aagccgaggg gcccgagact ctgcagcggg gccagaaaga gaagagtggg ggaggaggcc 60
gggagtggtg catggaccag ggggtagagg gaggtgggtg tggacctggg gtcgggcgcc 120
agtcagcttg cagcctatga aggacggaag ggagggctac agagataggg gaagagtggg 180
gctgaggata gccagagcgg cttggcacac agttttaggg taaaagcatc 230

<210> SEQ ID NO 234
<211> LENGTH: 196
<212> TYPE: DNA
<213> ORGANISM: Homo sapiens

<400> SEQUENCE: 234
tttatttata ccaagcctcc tcctgaaatt tctcttcctt tctttctacc tacccaagac 60
ataccacgtg cttcaataac cagtcccttc ctcctacaaa cactacaacc tggaaagcac 120
tcttgctttt ctgaagtcct ctatacttag tgtaactctt ctgtgatgaa gattaaagtg 180
tattatggca actctc 196

<210> SEQ ID NO 235
<211> LENGTH: 267
<212> TYPE: DNA
<213> ORGANISM: Homo sapiens

<400> SEQUENCE: 235
aggcattata tatactacac agagtacaat taaaccataa ttgggaatta tattttgttt 60
ttttcttccc aggcaataca cctctgaaca tgtgtgtgat aaatgggttt gctaatgtgc 120
tgttttaaag tataaagcat aatatgtttt ggttaacaca atgtactttt tgaactataa 180
atctttattt taatatggaa atgtttggaa caggagatgc aagccactaa cagagaactt 240
taataattct accctgtatt ttataaa 267

<210> SEQ ID NO 236
<211> LENGTH: 280
<212> TYPE: DNA
<213> ORGANISM: Homo sapiens

<400> SEQUENCE: 236
acccacactt aaactaaagg ctaagaatat aggcttgatg ggaaattgaa ggtaggctga 60
gtattgggaa tccaaattga attttgattc tccttggcag tgaactactt tgaagaagtg 120
gtcaatgggt tgttgctgcc atgagcatgt acaacctttg gagctagaag ctcctcagga 180
aagccagttc tccaagtttt taacctgtgg cactgaaagg aatgttgagt tacctcttca 240
tgttttagac agcaaaccct atccattaaa gtacttgtta 280

<210> SEQ ID NO 237
<211> LENGTH: 72
<212> TYPE: DNA
<213> ORGANISM: Homo sapiens

<400> SEQUENCE: 237
acatgagtat ggaatggtgt tttattatga ctttagtttg cattttcctc aattctcgtt 60
aaatccttca tt 72

<210> SEQ ID NO 238
<211> LENGTH: 260
<212> TYPE: DNA

<213> ORGANISM: Homo sapiens

<400> SEQUENCE: 238
gagtaggttc ggtctgaaag gtgtggcctt tatatttgat ccacacacgt tggtctttta 60
accgtgctga gcagaaaaca aaacaggtta agaagagccg ggtggcagct gacagaggaa 120
gccgctcaaa taccttcaca ataaatagtg gcaatatata tatagtttaa gaaggctctc 180
catttggcat cgtttaattt atatgttatg ttctaagcac agctctcttc tcctattttc 240
atcctgcaag caactcaaaa 260

<210> SEQ ID NO 239
<211> LENGTH: 222
<212> TYPE: DNA
<213> ORGANISM: Homo sapiens

<400> SEQUENCE: 239
atgattatag aaggctgtct tagtgcaaaa aacatactta catttcagac atatccaaag 60
ggaatactca catttttgtta agaagttgaa ctatgactgg agtaaaccat gtattccctt 120
atcttttact ttttttctgt gacatttatg tctcatgtaa tttgcattac tctggtggat 180
tgttctagta ctgtattggg cttcttcgtt aatagattat tt 222

<210> SEQ ID NO 240
<211> LENGTH: 216
<212> TYPE: DNA
<213> ORGANISM: Homo sapiens

<400> SEQUENCE: 240
gcaatatatt tgtgattccc catgtaattc ttcaatgtta aacagtgcag tcctctttcg 60
aaagctaaga tgaccatgcg ccctttcctc tgtacatata cccttaagaa cgccccctcc 120
acacactgcc ccccagtata tgccgcattg tactgctgtg ttatatgcta tgtacatgtc 180
agaaaccatt agcattgcat gcaggtttca tattct 216

<210> SEQ ID NO 241
<211> LENGTH: 35
<212> TYPE: DNA
<213> ORGANISM: Homo sapiens

<400> SEQUENCE: 241
ttggatagca gctatcttgt tggatgtgag gtgga 35

<210> SEQ ID NO 242
<211> LENGTH: 258
<212> TYPE: DNA
<213> ORGANISM: Homo sapiens

<400> SEQUENCE: 242
atgaaaggtg gaagttctac ctagatttga atgagtgttt ttttaaggga atgagaatgt 60
catggtgcta aacctgacaa ataagagatc attgaaatgc tgaaaatttt aacagttttt 120
ttaaaagtat tgagggggca aaaattacca attatggtat acaaaaataa gcctataaat 180
gtgtttcaca ttgctaactt gagtttcagt tgattcagtt tgtaataact agtaatgagc 240
ttctgtttac aataaaaa 258

<210> SEQ ID NO 243
<211> LENGTH: 275
<212> TYPE: DNA
<213> ORGANISM: Homo sapiens
<220> FEATURE:
<221> NAME/KEY: misc_feature
<222> LOCATION: (195)..(195)
<223> OTHER INFORMATION: n is a, c, g, or t

<400> SEQUENCE: 243
ccacagtgtt cccactaatg ctatttttta attttttaat ttagtttgtc ataatttggt 60
ttcatcaact cctttgtttt ttccttcttt tttttttttt gagatgaggt ctcactatct 120
tgcccagact ggtttcgaat tgccctccag caattctccc acctcagcct tcagagtagc 180
tggcattgtg ggtangcacc actgtgccca gctcctgttt tataataaat aagccagagc 240
tctatctcca aatggtgcaa atcatcaatg ctatt 275

<210> SEQ ID NO 244
<211> LENGTH: 281
<212> TYPE: DNA
<213> ORGANISM: Homo sapiens

<400> SEQUENCE: 244
gggcccctgg tatttatagg gtccaagagg aggcacctgc ttttcaactg caccctcagt 60
gctgcctctt cacggcccct aaacgtttcc ctttgaggtt gtgatgctgg gaatcacaga 120
cttcactctc tgcctgcacc cttccccgag gtctcatctt ttctgggtcc cacatctttg 180
taataatgtg aaaaagcaca atttgtctga tcacccccca ggtggttccc caccttatta 240
tcactacctg atccgagtta ctgcaataag tacggtgtcg c 281

<210> SEQ ID NO 245
<211> LENGTH: 274
<212> TYPE: DNA
<213> ORGANISM: Homo sapiens

<400> SEQUENCE: 245
tgctcagtgt catgctgtgt gtgcatgtgt gtgctgtgtg ttttgtgtgt gtgctgtgtt 60
catgtgtgct gtgcatgcgt gtgtgctgtg tgtgcctgtg tgtgcggtgt gctgtgtcct 120
tgtgtgtgct gtgtgtgcgt gtgctgtgtg catgtgtgtg ctgtgttatg tcgtgtgtgc 180
agtgtgtgct gtgtccgatg tgtgctgtgt acacatgaga gagcagagtg tacatgtgtg 240
tgctgagtct atcagaagat gtgtgtagct gcgg 274

<210> SEQ ID NO 246
<211> LENGTH: 89
<212> TYPE: DNA
<213> ORGANISM: Homo sapiens

<400> SEQUENCE: 246
tgtgcccagc ctaagccatt tcttaaaata aaaatgctaa aggactagta agtaaaaata 60
aaacttccta tgggatttcc cagtggaaa 89

<210> SEQ ID NO 247
<211> LENGTH: 72
<212> TYPE: DNA
<213> ORGANISM: Homo sapiens

<400> SEQUENCE: 247
gggagattgg tggcccttgc caggaagtgt cttaacactt tgtggatact gctgcctgtt 60
gtctttaaaa gc 72

<210> SEQ ID NO 248

<211> LENGTH: 177
<212> TYPE: DNA
<213> ORGANISM: Homo sapiens

<400> SEQUENCE: 248
gataacagtc ttgcatgttt atcatgttac aatttaatat tccatcctgc ccaacccttc 60
ctttcccatc ctcaaaaaag ggccatttta tgatgcattg cacaccctct ggggaaattg 120
atctttaaat tttgagacag tataaggaaa atctggttgg tgtcttacaa gtgagct 177

<210> SEQ ID NO 249
<211> LENGTH: 117
<212> TYPE: DNA
<213> ORGANISM: Homo sapiens

<400> SEQUENCE: 249
ttaaacagtc tagagtgaag ggaatgtttt aaaatccaga ggcgatcaag tgaagccaac 60
ctttggaggc ccgtagaagt catttggagg aatttggact tcgtgcagta ggaaaga 117

<210> SEQ ID NO 250
<211> LENGTH: 164
<212> TYPE: DNA
<213> ORGANISM: Homo sapiens

<400> SEQUENCE: 250
caggggggcc tgagagtaac agtgaggatt atccaggtgc cctgagtgta acagtgagga 60
ttatccaggg gggccctgag tgtaacagcg aggattatcc agggggccct gagtgcaaca 120
gtgaggatta tccagggggg cctgagtgta acagtgagga ttat 164

<210> SEQ ID NO 251
<211> LENGTH: 259
<212> TYPE: DNA
<213> ORGANISM: Homo sapiens
<220> FEATURE:
<221> NAME/KEY: misc_feature
<222> LOCATION: (139)..(139)
<223> OTHER INFORMATION: n is a, c, g, or t

<400> SEQUENCE: 251
caaaaatgag tcacaactct tgattccatc cacctccaaa atccaggtat tttccttaat 60
tctcattctt tcacaactcc acatatatcc atatcctcat tatctcagga caacgtgacc 120
atttcttgcc acttcccanc acttccatgc ctaccaaaga agcctatctt ctctcaccag 180
gaccactgaa aaagtcttgc aactgatttc ccttgtcctc ttcttgcctc tctacagtca 240
attctctata caacagtca 259

<210> SEQ ID NO 252
<211> LENGTH: 104
<212> TYPE: DNA
<213> ORGANISM: Homo sapiens

<400> SEQUENCE: 252
tgctgcggtc gcctctctca ggctcccccg ctcccccggg cctccgcttc tcagccgggt 60
gctgtgcgtt tgagtgtgtg ctgctgctcg ctgtgtgtgc tgtg 104

<210> SEQ ID NO 253
<211> LENGTH: 147
<212> TYPE: DNA
<213> ORGANISM: Homo sapiens

<400> SEQUENCE: 253
tatatacatg gtgctcaata gcaacatctt agcagatgaa gcagtttatg attccactcc 60
ctcctgtatg acaggtagcc actatactga atcaaggtgc tgaactcaaa tcacaaaatt 120
ctggcttacc gatacaacaa ccaatac 147

<210> SEQ ID NO 254
<211> LENGTH: 208
<212> TYPE: DNA
<213> ORGANISM: Homo sapiens

<400> SEQUENCE: 254
ctctgagttt tatatgctgg aatccaatgc agagttggtt tgggactgtg atcaagacac 60
cttttattaa taaagaagag acacaggtgt agatatgtat atacaaaaag atgtacggtc 120
tggccaaacc accttcccag cctttatgca aaaaaagggg agaatcaaag ctttcatttc 180
agaaatgttg cgtggaaaag tatctgta 208

<210> SEQ ID NO 255
<211> LENGTH: 139
<212> TYPE: DNA
<213> ORGANISM: Homo sapiens

<400> SEQUENCE: 255
aaaaagagag aatatgtcct gtgttagctt gcttaggaaa taaagagaga gagagagagg 60
gagggaggga aagagagaaa gagagagaga gaaagagagt gagagaaaga gagagcaaga 120
gagcaagagt aagaaagaa 139

<210> SEQ ID NO 256
<211> LENGTH: 243
<212> TYPE: DNA
<213> ORGANISM: Homo sapiens

<400> SEQUENCE: 256
ggcagtagat agtcaaagtc aaatcatttc taatgtttta aaaatgtgct ggtcattttc 60
tttgaaattg acttaactat tttcctttga agagtctgta gcacagaaac agtaaaaaat 120
ttaacttcat gacctaatgt aaaaaagagt gtttgaaggt ttacacaggt ccaggccttg 180
ctttgttacc attctgatgt tggactaatt gactaatcac ctacttatca gacaggaaac 240
ttg 243

<210> SEQ ID NO 257
<211> LENGTH: 298
<212> TYPE: DNA
<213> ORGANISM: Homo sapiens

<400> SEQUENCE: 257
agaggcccat gccaacagtc taatctaaga gattagtctt tcaaactcac catccagttg 60
cctgttacag aataactctt cttaactaaa aacctagtca aacaaggaag ctgtaggtga 120
ggagatctgt ataatattct aatttaagta agtttgagtt tagtcactgc aaatttgact 180
gtgactttaa tctaaattac tatgtaaaca aaaagtagat agtttcactt tttaaaaaat 240
ccattactgt tttgcatttc aaaagttgga ttaaagggtt gtaactgact acagcatg 298

<210> SEQ ID NO 258
<211> LENGTH: 193
<212> TYPE: DNA
<213> ORGANISM: Homo sapiens

<400> SEQUENCE: 258
agagggaact gtgcagtccc caggccgccc cggctccggg ctagaggcaa taaataaacc 60
cgatcctgcc gggcacagcc gcgcccgcgc ctccggcgcc gtccccgggc tgacggggga 120
gggagcggag aagcgagcgc agattctgcg tataaatcag ctctggagca gacacagccc 180
ggctgtgaaa agc 193

<210> SEQ ID NO 259
<211> LENGTH: 275
<212> TYPE: DNA
<213> ORGANISM: Homo sapiens

<400> SEQUENCE: 259
gtaggtttgg gagtataacg gtcacccagg gagggggtga agacggagaa gacttacata 60
gcacggtcag gttagggctg gacagatgag gaagagctag caaagggggc ttgaggagca 120
gtggccacta agacaggagt gtgacatttt agaagccaaa agaagaccat gtaattcaag 180
ggagaggtat gatttgctgg gtcagatcta aaaataaatc acacgttttt ttaaactgta 240
gtaattaacc actgaaaact tatgagtgat ccaat 275

<210> SEQ ID NO 260
<211> LENGTH: 143
<212> TYPE: DNA
<213> ORGANISM: Homo sapiens

<400> SEQUENCE: 260
gtgtgagcca ctgctggcta atttttgtat tttcagtaga gacggggctt caccatattg 60
gccaggctgg tcttgaactc cttccctcgc tcccccaaaa atttgaattt ttttttcaac 120
acttttacac ctgttatgga aaa 143

<210> SEQ ID NO 261
<211> LENGTH: 263
<212> TYPE: DNA
<213> ORGANISM: Homo sapiens

<400> SEQUENCE: 261
gagatcactt ggtaactggt ttcatgtgta tccaaaaatc agcatttgga tttaagcttt 60
ctgaatttgg tagtttaaga aacagattta gtttttcagt ggttttaact catgtgaaat 120
aatgattttc caccagcttt gatgcaaaga gatataattt taatgaacga tttatccagc 180
agtttgttcc aggggttgcc tctccttatt tacggggatt actttgtaca tgcagataag 240
ttttcgcaaa cctatttcca ttt 263

<210> SEQ ID NO 262
<211> LENGTH: 300
<212> TYPE: DNA
<213> ORGANISM: Homo sapiens

<400> SEQUENCE: 262
gatgataatc tttactggtg aaaaggatgg aaaaataaat caacaaatgc aaccagtttg 60
tgagaaaaaa aaaaaaaagc cgaaaaaaaa aaaaaaaaca cctgaatgcg gaagagctcg 120
gctcccgttt agcattttgt acttaaggaa ataaaaaacc aacaaaggat ctcacatttt 180
cttaaaaagt gaagattgct gtatactatt tattcaactt ataatttatg ttactccttg 240
atctttgtct tttgtcatga caaagcattt atttaataaa gttatgcatt cagttcccaa 300

<210> SEQ ID NO 263
<211> LENGTH: 238
<212> TYPE: DNA
<213> ORGANISM: Homo sapiens

<400> SEQUENCE: 263
agaattccag ataaacacac agcctttccc ataccttttt ttttcttact ataaaatatt 60
ataagatcca ttgatgtcca aataatacca ccgagcatct cttcacctct cctcctcttg 120
gtccacttgc taatgcccag ttttcttctc catttccact ttttcttagg ctccctattt 180
actattcatt ttgacttcct tctgttttat ttttttccct ttagcattgc atgtgaat 238

<210> SEQ ID NO 264
<211> LENGTH: 101
<212> TYPE: DNA
<213> ORGANISM: Homo sapiens

<400> SEQUENCE: 264
tgagtgtgct gtgctcgcgt gtgtgctgtg ttcatgcgtg tgctgtgtgt tgtgtgtgtg 60
tagctgcggg gatgcataaa gtatgagtgc tttttaggat g 101

<210> SEQ ID NO 265
<211> LENGTH: 34
<212> TYPE: DNA
<213> ORGANISM: Homo sapiens

<400> SEQUENCE: 265
tttatgaaca gcagactcta tgtaaaggca tttt 34

<210> SEQ ID NO 266
<211> LENGTH: 168
<212> TYPE: DNA
<213> ORGANISM: Homo sapiens

<400> SEQUENCE: 266
aggagggaaa ataatagccc agtgagagct gaatgaaaag ggactgaatt taaatatttg 60
taagaacttt gtgatgatga gtaattgtca gacgtgggat agataactga gaggctcaga 120
atctttacca aggatatttt ttaggataag gtagctgcct gttcatga 168

<210> SEQ ID NO 267
<211> LENGTH: 150
<212> TYPE: DNA
<213> ORGANISM: Homo sapiens

<400> SEQUENCE: 267
agggacccag taagaccaaa ggaggggagg acagagcatg aaaaccaaaa tccatgcaaa 60
tgaaatgtaa ttggcacgac cctcaccccc aaatcttaca tctcaattcc catcctaaaa 120
agcactcata ctttatgcat ccccgcagct 150

<210> SEQ ID NO 268
<211> LENGTH: 124
<212> TYPE: DNA
<213> ORGANISM: Homo sapiens

<400> SEQUENCE: 268
ggctcaggtc ctccctacaa gacctaccac tcacccatgc ctatgccact ccatctggac 60
atttaatgaa actgagagac agaggcttgt ttgctttgcc ctcttttcct ggtcaccccc 120
actc 124

<210> SEQ ID NO 269
<211> LENGTH: 93
<212> TYPE: DNA
<213> ORGANISM: Homo sapiens

<400> SEQUENCE: 269
tggagaagca ctggtgtctg cagcacccct cagttcctgt gcctcagccc acaggccact 60
gtgataatgg tctgtttagc acttctgtat tta 93

<210> SEQ ID NO 270
<211> LENGTH: 76
<212> TYPE: DNA
<213> ORGANISM: Homo sapiens

<400> SEQUENCE: 270
ggaggatgcg ctgtggggtt gtttttgcca taagcgaact ttgtgcctgt cctagaagtg 60
aaaattgttc agtcca 76

<210> SEQ ID NO 271
<211> LENGTH: 220
<212> TYPE: DNA
<213> ORGANISM: Homo sapiens

<400> SEQUENCE: 271
tctggtagat aaagccctag accttgtcca cactctcacc cccatcccca actttccctg 60
gaccggtgcc gcccccactt gatgcttgct caaggccggg gactggagcg ggctacttgt 120
atatttcgtt gtcagtctgc agaatgtgtt tgatttttat ttttccctcc ttctctgaca 180
tgtgtcaagg aataaagact ggatacaggt ccattacgtc 220

<210> SEQ ID NO 272
<211> LENGTH: 98
<212> TYPE: DNA
<213> ORGANISM: Homo sapiens

<400> SEQUENCE: 272
tggatcgatg atgagtcccc ccaaaaaaac attccttgga aaagctgaac aaaatgagtg 60
aaaactcata ccgtcgttct cagcggaact gaggtcca 98

<210> SEQ ID NO 273
<211> LENGTH: 97
<212> TYPE: DNA
<213> ORGANISM: Homo sapiens

<400> SEQUENCE: 273
ggccaaaaag tctacattgc gtgtgtggat ggatgaatga gcagtgggag tgcagcgcca 60
ggtgacaaga tgttgtgagg ggttttgagt catccag 97

<210> SEQ ID NO 274
<211> LENGTH: 87
<212> TYPE: DNA
<213> ORGANISM: Homo sapiens

<400> SEQUENCE: 274
gccctgcgcc ggcaaccacc tagtggccca gggaaggccg ataatttaaa cagtctccca 60
ccacctaccc caagagatac tggttgt 87

<210> SEQ ID NO 275
<211> LENGTH: 36

<212> TYPE: DNA
<213> ORGANISM: Homo sapiens

<400> SEQUENCE: 275
aaaaaagttc aactagtatg aaagggttat aaagta 36

<210> SEQ ID NO 276
<211> LENGTH: 116
<212> TYPE: DNA
<213> ORGANISM: Homo sapiens

<400> SEQUENCE: 276
gtgagtaaat aatgttctag tgcaacagga caaactactc tctccacagg aaacccaacc 60
acaacaggat caatagaaag aaaagagaaa acgttagccc ccaactacaa ataaat 116

<210> SEQ ID NO 277
<211> LENGTH: 264
<212> TYPE: DNA
<213> ORGANISM: Homo sapiens

<400> SEQUENCE: 277
tttcttcttt atgtccaatt ttgtgggtgg gaggaggatt tagtctcttc ctgatttcga 60
agagctcatt tactatttcg ggaaataaga tttggattgt caaccattat agctattttt 120
tacacacttt tcaactttgt ttttgttata agaatgtgta tgattgttac atgtccaagt 180
ataaccatgt tcgcttttat ggcttttgag tttcatgtca tttttggaaa gatatatata 240
ttgagtccat aaaacccttc acct 264

<210> SEQ ID NO 278
<211> LENGTH: 119
<212> TYPE: DNA
<213> ORGANISM: Homo sapiens

<400> SEQUENCE: 278
actttaataa aggttatcca taccaataaa aagtgtacaa cacagcattt tctgttaaat 60
tattattggt tttcagttgt aatttggtat tttttctggc atgcgtttat taatttatt 119

<210> SEQ ID NO 279
<211> LENGTH: 279
<212> TYPE: DNA
<213> ORGANISM: Homo sapiens

<400> SEQUENCE: 279
gtaggtttgg gagtataacg gtcacccagg gagggggtga agacggagaa gacttacata 60
gcacggtcag gttagggctg gacagatgag gaagagctag caaagggggc ttgaggagca 120
gtggccacta agacaggagt gtgacatttt agaagccaaa agaagaccat gtaattcaag 180
ggagaggtat gatttgctgg gtcagatcta aaaataaatc acacgttttt ttaaactgta 240
gtaattaacc actgaaaact tatgagtgat ccaatatta 279

<210> SEQ ID NO 280
<211> LENGTH: 130
<212> TYPE: DNA
<213> ORGANISM: Homo sapiens

<400> SEQUENCE: 280
gggacaaggt cccttggtgc tgatggcctg aaggggcctg agctgtgggc agatgcagtt 60
ttctgtgggc ttggggaacc tctcacgttg ctgtgtcctg gtgagcagcc cgaccaataa 120
acctgctttt 130

<210> SEQ ID NO 281
<211> LENGTH: 262
<212> TYPE: DNA
<213> ORGANISM: Homo sapiens

<400> SEQUENCE: 281
tttcactctt gctgtctgct cctctcacat catccttgcc tctgtctgtt taatcctcct 60
gtccttcatt ttcctttttt gcctctgcat tcagcatttc tacttccaat ctccctcctc 120
tgctctttct tatttcctct gatctgcaga cttgcttctg tcccctcctt ctgttcccct 180
cctggatgtg tctttggcca acctttcctt ctctgagact tcgtgttctt gttggtagat 240
gggggctgat acttctgggt ct 262

<210> SEQ ID NO 282
<211> LENGTH: 140
<212> TYPE: DNA
<213> ORGANISM: Homo sapiens

<400> SEQUENCE: 282
ttattattat gaaccttcag cctactttct tgagtgccgt aaaagtgctt gtaaattttt 60
ttttttttta agaagaaaga aaaaaatggt gtttgacgtt gatggaaatt caaaaatata 120
tatggaactg aaacattaac 140

<210> SEQ ID NO 283
<211> LENGTH: 143
<212> TYPE: DNA
<213> ORGANISM: Homo sapiens

<400> SEQUENCE: 283
cttgttcttt tgaagcttgt gctgaggttt tagcttttct atgttttata tgccgctgct 60
ttgaaagaga acctagattc tatagttgta ttattgttgt ttcatacttt aaatttatat 120
ggctgtggaa aaacgaatta aaa 143

<210> SEQ ID NO 284
<211> LENGTH: 151
<212> TYPE: DNA
<213> ORGANISM: Homo sapiens

<400> SEQUENCE: 284
gtgtgtcaag gatttgacaa actgccattt ttctccagaa gtcaagcccc taagtgattg 60
tctagaggca agaatttttt gatatgttgt ctcaacaatg cttctcactt cgtcttcagg 120
tgccccaacc cgcaagtaca catactatgt a 151

<210> SEQ ID NO 285
<211> LENGTH: 150
<212> TYPE: DNA
<213> ORGANISM: Homo sapiens

<400> SEQUENCE: 285
aatgttcata ggttctcaac cctcaccccc caccacggga gactagagct gcaggatccc 60
aggggagggg tctctcctcc caccccaagg catcaagccc ttctccctgc actcaataaa 120
ccctcaataa atattctcat tgtcaatcaa 150

<210> SEQ ID NO 286
<211> LENGTH: 115

<212> TYPE: DNA
<213> ORGANISM: Homo sapiens

<400> SEQUENCE: 286
gatgggaatt gagatgtaag atttgggggt gagggtcgtg ccaattacat ttcatttgca 60
tggattttgg ttttcatgct ctgtcctccc ctcctttggt cttactgggt ccctc 115

<210> SEQ ID NO 287
<211> LENGTH: 223
<212> TYPE: DNA
<213> ORGANISM: Homo sapiens

<400> SEQUENCE: 287
tacattgtaa gagcaacatc ctacgttaat aaatgttcta gcccggtgct tcgcgaacat 60
ttatgtgcat acaaatcacc tgggatcttg ttagaaggca gtaggtctgg ggtggggcct 120
gagattctgc atttctaacc aggtcctggg agatgctgat gctatcgagc cacaaccaca 180
ctttgagtag caagcctctg gcctatcctt attgtttgtt ata 223

<210> SEQ ID NO 288
<211> LENGTH: 272
<212> TYPE: DNA
<213> ORGANISM: Homo sapiens

<400> SEQUENCE: 288
tttcactctt gctgtctgct cctctcacat catccttgcc tctgtctgtt taatcctcct 60
gtccttcatt ttcctttttt gcctctgcat tcagcatttc tacttccaat ctccctcctc 120
tgctctttct tatttcctct gatctgcaga cttgcttctg tcccctcctt ctgttcccct 180
cctggatgtg tctttggcca acctttcctt ctctgagact tcgtgttctt gttggtagat 240
gggggctgat acttctgggt cttgggcatg tc 272

<210> SEQ ID NO 289
<211> LENGTH: 221
<212> TYPE: DNA
<213> ORGANISM: Homo sapiens

<400> SEQUENCE: 289
ttgctggggc ttgtcctaga ggctccagct ttggcacagt ggttcctggc tgctgccatg 60
tttcagatga ggagggagag aaggaggccg ccagactcga gaggtgggag gaactccttg 120
cacacaccct gagcttttgc cacttttatc atttttgagc aactcccttt cagctaaaag 180
gccacccctt tatcgcattg ctgtccttgg gtagaatata a 221

<210> SEQ ID NO 290
<211> LENGTH: 183
<212> TYPE: DNA
<213> ORGANISM: Homo sapiens

<400> SEQUENCE: 290
acaaaactct ccaataatga ctctgctcag ctcaggggca gcaggagtgg agtgtcgggg 60
gcccttggtg ctgagtgaag ataaattaaa aatcccaaca agccagtgac attatgtaca 120
ggaggaaagg ggtggggctt ccaggacaga ggccgagggt ggcagggcag gacttggagt 180
ggc 183

<210> SEQ ID NO 291
<211> LENGTH: 237
<212> TYPE: DNA

<213> ORGANISM: Homo sapiens

<400> SEQUENCE: 291
cagacacatg agcaggactt tggggagtgt gttttatatc tgtcagatgc ctagaacagc 60
acctgaaata tgggactcaa tcattttagt ccccttcttt ctataagtgt gtgtgtgcgg 120
atatgtgtgc tagatgttct tgctgtgtta ggaggtgata aacatttgtc catgttatat 180
aggtggaaag ggtcagacta ctaaattgtg aagacatcat ctgtctgcat ttattga 237

<210> SEQ ID NO 292
<211> LENGTH: 189
<212> TYPE: DNA
<213> ORGANISM: Homo sapiens

<400> SEQUENCE: 292
tcaagttaat ggcagctaaa acgctcccag tccatttatt ggccacatga ggtggtcgtc 60
aagaaacaag ttagaaggtt atgacaggaa gtagtataat aaatgcccgg cagtacgagg 120
ggttcaacag aagtgaacaa ggcacaagaa agaggtctgt gttcaggaaa caggccagtc 180
cccacatgg 189

<210> SEQ ID NO 293
<211> LENGTH: 246
<212> TYPE: DNA
<213> ORGANISM: Homo sapiens

<400> SEQUENCE: 293
tgaactaaaa ctatgagcct tattcaatat ctataattct atgatttttt taaattatgg 60
gaaattaatg aaagatgttt acatgaataa tgtttgccct tactgtgtta tgaatgagtt 120
ttttgtagtg tgtctgggtg catgatgcaa gagagtagga aaaatgtttt tgaaacaaaa 180
cttgacaaat atttgtaatg aaagtaaatt taaagattgc tataattgcg ctatagaaac 240
aatgca 246

<210> SEQ ID NO 294
<211> LENGTH: 65
<212> TYPE: DNA
<213> ORGANISM: Homo sapiens

<400> SEQUENCE: 294
ttaacagtac atttgtgtgg ctctcaaaca tccctttgga agggattgtg tgtactatgt 60
aatat 65

<210> SEQ ID NO 295
<211> LENGTH: 120
<212> TYPE: DNA
<213> ORGANISM: Homo sapiens

<400> SEQUENCE: 295
tacaatgatg gttgagtgaa aatacagaag gggggtttga gtattcagat ttcataaaac 60
acttccttgg aatatagctg cattaacttg gaaagaagcc tgttgggcca gaagacagaa 120

<210> SEQ ID NO 296
<211> LENGTH: 156
<212> TYPE: DNA
<213> ORGANISM: Homo sapiens

<400> SEQUENCE: 296
aactgatggg aaaggaccaa ttatttatag tttcccaaca aaagttttaa gattttttac 60

-continued ctttgcatca gtgcattttt atttatatca aaaggtgcta aaatgattca atttgcattt 120
tttgatcctg tagtgcctct atagaagtac ccacag 156

<210> SEQ ID NO 297
<211> LENGTH: 169
<212> TYPE: DNA
<213> ORGANISM: Homo sapiens

<400> SEQUENCE: 297
tgttaaactt tggaacacct accaaaaaat aagtttgata acatttaaaa gatgggcgtt 60
tcccccaatg aaatacacaa gtaaacattc caacattgtc tttaggagtg atttgcacct 120
tgcaaaaatg gtcctggagt tggtagattg ctgttgatct tttatcaat 169

<210> SEQ ID NO 298
<211> LENGTH: 87
<212> TYPE: DNA
<213> ORGANISM: Homo sapiens

<400> SEQUENCE: 298
aaatgacttt caactaacct tgtgaatctt ttgcagtgta ctgtgtgcaa taccaagggc 60
atagctccct gtaatttggg aaataca 87

<210> SEQ ID NO 299
<211> LENGTH: 96
<212> TYPE: DNA
<213> ORGANISM: Homo sapiens

<400> SEQUENCE: 299
catatatttt ttgctacttt tgctgtttta ttttttttaaa ttatgttcta aacctatttt 60
cagtttaggt ccctcaataa aaattgctgc tgcttc 96

<210> SEQ ID NO 300
<211> LENGTH: 269
<212> TYPE: DNA
<213> ORGANISM: Homo sapiens

<400> SEQUENCE: 300
tgctggcact gatattatcc atcatctctt tttggacact tctgtaaatg tgattggatt 60
gtttgaaaga agatttaaag tttcaaagtt ttttgttctg tttttgcttt gcatttggag 120
aaaatattga aagcagggta tgttgtttca ttcaccttga aaaaaccatg agtaaatggg 180
gatatagaat ctctgaatag ctcgctaaaa gattcaagca agggacatga attttgttcc 240
atctatcaat aatatccaga agaacaact 269

<210> SEQ ID NO 301
<211> LENGTH: 188
<212> TYPE: DNA
<213> ORGANISM: Homo sapiens

<400> SEQUENCE: 301
tctgtgtgtg tcctagcatg gagagttcct tccttttccc ttcagttagg ttgacccttt 60
ccatttgttt agtatccgtg cacatgtcgt actagacccc aatcaagttg cttatttaaa 120
attctttcag ctgtttccct attatttcct tactttgctg aacatgtccg ctgttttacc 180
tcactgct 188

<210> SEQ ID NO 302

<211> LENGTH: 246
<212> TYPE: DNA
<213> ORGANISM: Homo sapiens

<400> SEQUENCE: 302
ggagccaaca attcgagtgc aaacatgatg gctcagaccc ttctctgccc tttactagcc 60
ttcatgatct gtcgggtctc agcagctcag gccacaggag gaggtgggtc tcctgactgg 120
cctgtgcatt ctcccaaaca agatgtttaa gactcttctt tatctcgtca caaacgcaca 180
ggacacacac gcacacacat gcacacacag tttacaaacg cacggtacac acacgcatga 240
cacatg 246

<210> SEQ ID NO 303
<211> LENGTH: 217
<212> TYPE: DNA
<213> ORGANISM: Homo sapiens

<400> SEQUENCE: 303
agcgaaggga aggttgcggg agaaagagcg ggggccgggg ccagacgcca agaggggcgc 60
ggggagcaca gagaagcgga gggaagggcg ccacgtcgag gggccggggg aggcggtgac 120
tggggggcgg agtggaggct gcacccggac cgcgggcgcc cagctcggtt tgggccgacg 180
gagccctctg ccgtcgcgag cccgggcctc gggaggg 217

<210> SEQ ID NO 304
<211> LENGTH: 172
<212> TYPE: DNA
<213> ORGANISM: Homo sapiens

<400> SEQUENCE: 304
tgcagtgcta gtcccggcat cctgatggct ccgacaggcc tgctccagag cacggctgac 60
catttttgct ccgggatctc agctcccgtt ccccaagcac actcctagct gctccagtct 120
cagcctgggc agcttccccc tgccttttgc acgtttgcat ccccagcatt tc 172

<210> SEQ ID NO 305
<211> LENGTH: 188
<212> TYPE: DNA
<213> ORGANISM: Homo sapiens

<400> SEQUENCE: 305
tattcctggt agaggaattt ctgtatttga aaattctcca gaaggaataa tataaactgt 60
ggactttggg tgataatgat atgtaggttc gtcagttgtt aacaaatgta tccctctgtt 120
gggggctatt gataatgggg aaggctgtgc atgtgtggga gtaggaggtg tatgggacat 180
ctctgtac 188

<210> SEQ ID NO 306
<211> LENGTH: 242
<212> TYPE: DNA
<213> ORGANISM: Homo sapiens

<400> SEQUENCE: 306
aaagagtcaa ctttccggcg gcgggggaga aatgataaaa gagagagagg agggcagatc 60
accacctaga agcacatcct ttgttcgcag aggggggaga aaaagtcgga gagaaagaat 120
gaaagagggg aaaaaaggca gttcggcacc cggagaaagg aggcaattcg gggagaggag 180
gaggagaaga agaaaacaca cacgcgcgca cgcacacaca caccgcggag agaaaagaac 240
ag 242

<210> SEQ ID NO 307
<211> LENGTH: 33
<212> TYPE: DNA
<213> ORGANISM: Homo sapiens

<400> SEQUENCE: 307
gtgagcccat atcgtactgc tgcagtccag cct 33

<210> SEQ ID NO 308
<211> LENGTH: 83
<212> TYPE: DNA
<213> ORGANISM: Homo sapiens

<400> SEQUENCE: 308
taaccttagg aaaccagaat agcgtttggc agacacgacg ttttcagttt acctttgaca 60
cctgccccac tccattttgc ttt 83

<210> SEQ ID NO 309
<211> LENGTH: 201
<212> TYPE: DNA
<213> ORGANISM: Homo sapiens

<400> SEQUENCE: 309
ccggacagtg gccttctcca ctcccctctg acttctccaa gggggctcag tggccagtgc 60
cccccaggag gctccaccct caactcaacc caagcaacag ggacagatga aaaacaaaat 120
ccaatcaggg cgataaatgg cggggggcag gacgtggtgg tctccaggct ggcttcgtgc 180
gttcttgctt ttgtcactgc c 201

<210> SEQ ID NO 310
<211> LENGTH: 275
<212> TYPE: DNA
<213> ORGANISM: Homo sapiens

<400> SEQUENCE: 310
acacaataca atcaggagtt ttcaaatttt tgattcagta tttgaatttc ttcttcataa 60
atgtagttgg aatttatcct agtatttttc tttacctgaa ggagggccat ttatttttaa 120
tttcactaca tttttctttg catgattatt aaaataaaaa ctgcctctgt tgtgtttctc 180
actggaggct ggaatgaatg atcactagaa cacaaaagag tgaatgatga cacttgaagt 240
caaagcagtt gtactgatca ccagaaccaa taaag 275

<210> SEQ ID NO 311
<211> LENGTH: 220
<212> TYPE: DNA
<213> ORGANISM: Homo sapiens

<400> SEQUENCE: 311
ctaattgatt agaactgagt cttttatatc aagctaatat ctagctttta tatcaagcta 60
atatcttgac ttctcagcat catagaaggg ggtactgatt tcctaaagtc tttcttgaat 120
ttctattatg caaaattgcc ctgaggccgg gtgtggtggc tcacacctgt aatcccagca 180
ctttgggagg ctgaggtggg aagatccctt actgccagga 220

<210> SEQ ID NO 312
<211> LENGTH: 187
<212> TYPE: DNA
<213> ORGANISM: Homo sapiens

<400> SEQUENCE: 312
ttctttatag tgttatgctt attttcaatt tttttttcc tgattctgtc tggtacttag 60
aattgtagtg tcttcatcat caattaaaga aaactgtcta aatgaattca tggatgtaaa 120
tattagtggt ccttaatgtc tttgattgct ggacatgaaa caaactgcca attaaatttt 180
gcggaga 187

<210> SEQ ID NO 313
<211> LENGTH: 176
<212> TYPE: DNA
<213> ORGANISM: Homo sapiens

<400> SEQUENCE: 313
tcctgcaggc atccgtgggg gaaaaaaaat ctctcagaac cctcaactat tctgttccac 60
acccaatgct gctccaccct cccccagaca cagcccaagt ccctccgcgg ctggagcgaa 120
gccttctgca gcaggaactc tggacccctg ggcctcatca cagcaatatt taacaa 176

<210> SEQ ID NO 314
<211> LENGTH: 266
<212> TYPE: DNA
<213> ORGANISM: Homo sapiens

<400> SEQUENCE: 314
aaatgtttga cattcattat cagaatgagg gaaaatttaa acaattccgt tttttctttt 60
gctagtaggc atattatgct aataaaatta ctaaattaaa agtgtgtcaa ggatttgaca 120
aactgccatt tttctccaga agtcaagccc ctaagtgatt gtctagaggc aagaattttt 180
tgatatgttg tctcaacaat gcttctcact tcgtcttcag gtgccccaac ccgcaagtac 240
acatactatg tactcacttg aaaatg 266

<210> SEQ ID NO 315
<211> LENGTH: 286
<212> TYPE: DNA
<213> ORGANISM: Homo sapiens

<400> SEQUENCE: 315
aactgggggc tctgtggggg ctctgtatat agctatgaag aaaacacaaa gtgtataaat 60
ctgagtatat atttacatgt ctttttaaaa gggtcgttac cagagattta cccatcgggt 120
aagatgctcc tggtggctgg gaggcatcag ttgctatata ttaaaaacaa aaaagaaaaa 180
aaaggaaaat gtttttaaaa aggtcatata ttttttgcta cttttgctgt tttatttttt 240
taaattatgt tctaaaccta ttttcagttt aggtccctca ataaaa 286

<210> SEQ ID NO 316
<211> LENGTH: 278
<212> TYPE: DNA
<213> ORGANISM: Homo sapiens
<220> FEATURE:
<221> NAME/KEY: misc_feature
<222> LOCATION: (214)..(214)
<223> OTHER INFORMATION: n is a, c, g, or t

<400> SEQUENCE: 316
gctggtctcg ggcaacaagc agcctcctag gagcagaagg tgatggaggg ccacgggggc 60
agggaggagc agatggccat gtggctcagc ccctgcctgg gaaagcgagt ccacagttca 120
ctaacaaaca caataccatc cacaaacaag tagccacaaa gaccacagtt agcaaacaca 180
cacagtcaca cacacacaca cacacacaca catnacggga ggtgggcagg accgcagtct 240
gcagtgggga ggcaagtgtt agttgcatca tcaggtgg 278

<210> SEQ ID NO 317
<211> LENGTH: 122
<212> TYPE: DNA
<213> ORGANISM: Homo sapiens

<400> SEQUENCE: 317
aggtggtgtt ggcagaggct atcgggctgg acaaggacaa acccaaccgt gtgaccaaag 60
tggctgtgaa gatgttgaag tcggacgcaa cagagaaaga cttgtcagac ctgatctcag 120
aa 122

<210> SEQ ID NO 318
<211> LENGTH: 161
<212> TYPE: DNA
<213> ORGANISM: Homo sapiens

<400> SEQUENCE: 318
aatgaaattg ttaattggcc aggcacagtg ggaagcacct gtagtcccag ctactcagga 60
ggctaaagtg agagggtggc tctagcacag tcatcaaggc tgcaggaggc tatgatggag 120
ccactgcact ccagcctaga tgacaaggtg agacgctgtc t 161

<210> SEQ ID NO 319
<211> LENGTH: 162
<212> TYPE: DNA
<213> ORGANISM: Homo sapiens

<400> SEQUENCE: 319
tgtttttgac atcagctgta atcattcctg tgctgtgttt tttattaccc ttggtaggta 60
ttagacttgc cctttttttaa aaaaaggttt ttgcatcgtg gaagcatttg acccagagtg 120
gaacgcgtgg cctatgcagg tggattcctt caggtctttc ct 162

<210> SEQ ID NO 320
<211> LENGTH: 114
<212> TYPE: DNA
<213> ORGANISM: Homo sapiens

<400> SEQUENCE: 320
ttttttagtt gccaacagtt tatgtttgct gattatttat gacctgaaat tatatatttt 60 ttttttttaag aagacatttt gttacataag gatgactttt ttatacaaag gaaa 114

<210> SEQ ID NO 321
<211> LENGTH: 223
<212> TYPE: DNA
<213> ORGANISM: Homo sapiens

<400> SEQUENCE: 321
gcatttgaat tgactaggct tttcctatat aaaaaactca aaacttgtta actctgtact 60
ttaataaaat ttaaaattaa aactgtgttg tttttttctc ttctgctaga tacatatata 120
attaaagtac tcaagttagt tgttttgcag agatgttgcc ttcagatgtt aatcaggtct 180
ctcaagtttc atggagtcta tgctgatcct ttaattgaca aat 223

<210> SEQ ID NO 322
<211> LENGTH: 289
<212> TYPE: DNA
<213> ORGANISM: Homo sapiens

<400> SEQUENCE: 322
tatacagaat agtcactggt cttgggctaa atggtgactt caagtgtagt ggctgcatag 60
tcaaaaatga attagatgag tacaaaagtg acgaaatgaa agaatgtcaa gaatggacca 120
caaagacagt gttttatgac ctaaagatta agatttatcc atttgtgtac aattgtggac 180
tatataaaat aaaacaagac tttgacctca gtggataaga agtatttgga tgtactaatc 240
aatatttttg gtctgggtca gtggtgggtt catctgtgtt tgttgtatt 289

<210> SEQ ID NO 323
<211> LENGTH: 246
<212> TYPE: DNA
<213> ORGANISM: Homo sapiens

<400> SEQUENCE: 323
tccaacaaca gtgctgactg tccggataag agctggcaag tgcccttagg atgccgcatg 60
ggaaaaatcg gttatcataa tttcaaagta taaatatatt tattatgtag cgctgcggtt 120
aagaaggaag agtgaggggt ctgtccatgg ggtggcagtg atttcccacc cgcctttctt 180
gaatggcttc gtgttattca gccgtgccct ggcaggaatg gaactccatc agggaacagg 240
gcagct 246

<210> SEQ ID NO 324
<211> LENGTH: 156
<212> TYPE: DNA
<213> ORGANISM: Homo sapiens

<400> SEQUENCE: 324
aatatacctg atgcgctgta gaatgaaaat gtaaaagata acctgtatgt gttccgagct 60
ttaatttttt gtttacaaat tgaacagtgt tacatgggct gtccagtcct gattatagag 120
aggaagaaat ggtaacagta tggcagataa gaatta 156

<210> SEQ ID NO 325
<211> LENGTH: 298
<212> TYPE: DNA
<213> ORGANISM: Homo sapiens

<400> SEQUENCE: 325
agcaggagta agtttctcat cccatgggcg accagggcca tctcctccca ccagtggccc 60
ccactcacag ggagctggca atgccctacc tgcctgttct ccagatggag aaacaggctc 120
tgagatttca caggtcttgc ccaaagtcat tgattttgat gattaaaaag aataaacaca 180
gtgtttcctg agtagcagtg attgttatgc cttgctattt taataaagat tctattttcg 240
tataacattg tcaagtggaa acatgctgaa atctattaaa ccatctttgt ttgtggaa 298

<210> SEQ ID NO 326
<211> LENGTH: 98
<212> TYPE: DNA
<213> ORGANISM: Homo sapiens

<400> SEQUENCE: 326
aaagagtcaa ctttccggcg gcgggggaga aatgataaaa gagagagagg agggcagatc 60
accacctaga agcacatcct ttgttcgcag aggggga 98

<210> SEQ ID NO 327
<211> LENGTH: 103
<212> TYPE: DNA
<213> ORGANISM: Homo sapiens

<400> SEQUENCE: 327
gtttgtcttg cgcagtgctt actccagctg tggcatgcag gtgtcagcaa gtatgatcag 60
caatgaggcg gtggtcaata tcctgtcgag ctcatcacca cag 103

<210> SEQ ID NO 328
<211> LENGTH: 191
<212> TYPE: DNA
<213> ORGANISM: Homo sapiens

<400> SEQUENCE: 328
aatctctttt tttctggagg ctggcacctg attttgtatc cccctgtagc agcattactg 60
aaatacatag gcttatatac aatgcttctt tcctgtatat tctcttgtct ggctgcaccc 120
ctttttcccg cccccagatt gataagtaat gaaagtgcac tgcagtgagg gtcaaaggag 180
agtcaacata t 191

<210> SEQ ID NO 329
<211> LENGTH: 220
<212> TYPE: DNA
<213> ORGANISM: Homo sapiens

<400> SEQUENCE: 329
tgcccccagt atgtttagga cgcgagcccc agaaggattt gggagtaaac ttaacattca 60
ctgtgttttt gctttgcatc cgccatttgt gtgtgttttt ggactgtggg ctgtgtgtac 120
cttggttggt gactcagtga gaagaagcag gaatgccaaa gatactatga atgttttgag 180
ttttgttgct gttgttgttg agaggttgtt tcactggtat 220

<210> SEQ ID NO 330
<211> LENGTH: 258
<212> TYPE: DNA
<213> ORGANISM: Homo sapiens

<400> SEQUENCE: 330
gatcgtctgg taactttcta actttaaata atatgtttga gcaataattt cttgacttac 60
tgactttaca acatctttaa taattcccca ttacaaaaga taaggattta acttacacta 120
tcgccacttt cctttgtcca tctctctcca aatgtctgat agttacatca ctttttaata 180
catctattgg tttgatttta tagctttgaa caatacacta atcctctagt tcttgttcca 240
ttaactgaag atcttttc 258

<210> SEQ ID NO 331
<211> LENGTH: 233
<212> TYPE: DNA
<213> ORGANISM: Homo sapiens

<400> SEQUENCE: 331
gaaacacaag agacttaaag gacaggagga ggagatggcc ataggagagg agggttcctc 60
ttaggtcaga tggaggttct cagagccaag tcctccctct ctactggagt ggaaggtcta 120
ttggccaaca atcctttctg cccacttccc cttccccaat tactattccc tttgacttca 180
gctgcctgaa acagccatgt ccaagttctt cacctctatc caaagaactt gat 233

<210> SEQ ID NO 332
<211> LENGTH: 96
<212> TYPE: DNA
<213> ORGANISM: Homo sapiens -continued

<400> SEQUENCE: 332
ggatcgatga tgagtccccc ataaaaacat tccttggaaa agctgaacaa aatgagtgag 60
aactcatacc gtcgttctca tcggaactga ggtcca 96

<210> SEQ ID NO 333
<211> LENGTH: 181
<212> TYPE: DNA
<213> ORGANISM: Homo sapiens

<400> SEQUENCE: 333
tggtgacaga gtttgggacc gaggtggagc ccgagtttgg gaccaaggtg gagcccgagt 60
ttgagaccca gttggagcct gagtttgaga cccagctgga acccgagttt gaggaagagg 120
aggaggagga gaaagaggag gagatagcca ctggccaggc attccccttc acaacagtag 180
a 181

<210> SEQ ID NO 334
<211> LENGTH: 135
<212> TYPE: DNA
<213> ORGANISM: Homo sapiens

<400> SEQUENCE: 334
gatatcagat cagttgagac taacagttga aagcagtaaa catattacgg acatattatt 60
gataaaagac atttatgaag aggataaact gtgaaggtgt acagacacta aaccatagtt 120
gctaaacaca tacaa 135

<210> SEQ ID NO 335
<211> LENGTH: 80
<212> TYPE: DNA
<213> ORGANISM: Homo sapiens

<400> SEQUENCE: 335
agagccagga cagtgaggtc aactttgaca attccatcca cccagaagtc ttggagctgc 60
tgcttgacta tgcgtactcc 80

<210> SEQ ID NO 336
<211> LENGTH: 96
<212> TYPE: DNA
<213> ORGANISM: Homo sapiens

<400> SEQUENCE: 336
ggatcgatga tgagtccccc ataaaaacat tccttggaaa agctgaacaa aatgagtgag 60
aactcatacc gtcgttctca tcagaactga ggtcca 96

<210> SEQ ID NO 337
<211> LENGTH: 290
<212> TYPE: DNA
<213> ORGANISM: Homo sapiens

<400> SEQUENCE: 337
ttgacagtct gccttactat gaaattctag gtacaaaaat tttccttaag ctctgaagat 60
gttgatccat tgacttctgg cattcagtgt tgctgatgac aaatctgtta gcagtctatt 120
tctcatccat ttttgtgttg agctaatcgt gatgacctca tttgttttct ccctggccac 180
tttaatatct tccttctatc cttaatattc caaaatttta caatattgtg tctagatgta 240
gattgtattg ggccctctca atctggagac ttagcttgct ctgttcttca 290

-continued

<210> SEQ ID NO 338
<211> LENGTH: 197
<212> TYPE: DNA
<213> ORGANISM: Homo sapiens

<400> SEQUENCE: 338
atgtcaagaa aatgacggtc acagaccagg tgaactgccc caagctctcg taaccaggtt 60
ctacagggag gctgcaccca ctccatgtta cttctgcttc gctttcccct accccacccc 120
ccccccataa agacaaacca atcaaccacg acaaaggaag ttgacctgaa catgtaacca 180
tgccctaccc tgttacc 197

<210> SEQ ID NO 339
<211> LENGTH: 113
<212> TYPE: DNA
<213> ORGANISM: Homo sapiens

<400> SEQUENCE: 339
tgtcactggt gaaagacgac ttggtgccca atttttaata aacacaatgc tattagcgtc 60
actccaattt agtgtctgat tgttaaatgt taatgtactg cactctacag ttt 113

<210> SEQ ID NO 340
<211> LENGTH: 183
<212> TYPE: DNA
<213> ORGANISM: Homo sapiens

<400> SEQUENCE: 340
ggattataat atcctcactg gccacaatct gtaaaagtcg atactggcac ttttttttgcc 60 ccctcaaagg aaatatgcta atagacagcc cctttgcaaa tataattcct ccttcccaac 120
ccttcaaatt gctaaggccc cactggtcag caccttccct ttcgagtcca ggactactgt 180
tct 183

<210> SEQ ID NO 341
<211> LENGTH: 275
<212> TYPE: DNA
<213> ORGANISM: Homo sapiens

<400> SEQUENCE: 341
agcattaata atttccatgc atgtgtcttt ttccagtagg tatggttgaa tttatgtaaa 60
tttattgcta atcccatccc ttacgattta gagtataagc tgcgcaaggg cagaagtttt 120
tatttggttt gttcatggat gtattttaag agctgagaac agggcctgga cacaataagc 180
attcaataaa tatttactga atgaatgaac tcctacctat attcctattt ataatttggc 240
tccactttat cctactttag ctcccattca attca 275

<210> SEQ ID NO 342
<211> LENGTH: 123
<212> TYPE: DNA
<213> ORGANISM: Homo sapiens

<400> SEQUENCE: 342
catttaaata agaggagatc cacaaagagc aacagagata agagaagaaa ggaaataatc 60
aataaaataa ttcaagaaaa tccaaggaca tgagttttca gattgtaaga gactacttga 120
gtg 123

<210> SEQ ID NO 343
<211> LENGTH: 99
<212> TYPE: DNA

<213> ORGANISM: Homo sapiens

<400> SEQUENCE: 343
aattcatatc ccctgttcgt ctcatgcgcg tcctccgtcc ccaatctaaa aagcaattga 60
aaaggtctat gcaataaagg cagtcgcttc attcctctc 99

<210> SEQ ID NO 344
<211> LENGTH: 97
<212> TYPE: DNA
<213> ORGANISM: Homo sapiens

<400> SEQUENCE: 344
tggatcgatg atgagtcctc caaaaaaaca ttccttggaa aagctgaaca aaatgagtga 60
gaactcatac cgtcgttctc atcggaactg aggtcca 97

<210> SEQ ID NO 345
<211> LENGTH: 119
<212> TYPE: DNA
<213> ORGANISM: Homo sapiens

<400> SEQUENCE: 345
attttctatc tgtggttgga ttcagaccac atgaacactg agggctgact gtagttttga 60
atgtctgtta ctgaggaggc accagcataa agtattttat cacttcagac gctgacaat 119

<210> SEQ ID NO 346
<211> LENGTH: 121
<212> TYPE: DNA
<213> ORGANISM: Homo sapiens

<400> SEQUENCE: 346
ttatatttat gtttagcacc gtcagtgttc ctatccaatt tcaaaaaagg aaaaaaaaga 60
gggaaaatta caaaaagaga gaaaaaaagt gaatgacgtt tgtttagcca gtaggagaaa 120
a 121

<210> SEQ ID NO 347
<211> LENGTH: 168
<212> TYPE: DNA
<213> ORGANISM: Homo sapiens

<400> SEQUENCE: 347
gtttgagcta tcgaagagta agtaaccaga aatttgagaa cagcctgggc agcatagtga 60
gaccccatct ttacaaaaac ttcacagatt agccaggtat ggtggcattt tcctgtagtc 120
ccagctactc agaatgctga ggcaggagag tggcttgtga ccaagagt 168

<210> SEQ ID NO 348
<211> LENGTH: 47
<212> TYPE: DNA
<213> ORGANISM: Homo sapiens

<400> SEQUENCE: 348
aggataaact tgtgtggtgt agagaagtta aaatcctcac gttgtac 47

<210> SEQ ID NO 349
<211> LENGTH: 286
<212> TYPE: DNA
<213> ORGANISM: Homo sapiens

<400> SEQUENCE: 349
acttcaggga agtttcataa aaggaagaat tttaactcag cgtagaaaga tgggtaaatt 60
ttcctcatgt gaaggtgtac tgcctggggt gctgcaggct ggagatgagt attaaaatag 120
gaggagagtg agtgaaagca caggaggagg aagggtcagg caagtttggt gaacacagca 180
actggctata gaacaggagc agtgggagaa agtccagaaa ggtctgctga gcttcagttg 240
tacaaagctg tggagtttgg cctttggtca tggctagatt aggtct 286

<210> SEQ ID NO 350
<211> LENGTH: 94
<212> TYPE: DNA
<213> ORGANISM: Homo sapiens

<400> SEQUENCE: 350
tggatcgatg atgacctcaa tacatgcatt ccttggaaag ctgaacaaaa tgagtgaaaa 60
ctctataccg tcgtcctcgt caaactgagg tcca 94

<210> SEQ ID NO 351
<211> LENGTH: 174
<212> TYPE: DNA
<213> ORGANISM: Homo sapiens

<400> SEQUENCE: 351
gtttgaggta tttaactgac acctaagtgg atctgttgag gaaacagttg gatatacaaa 60
tttagtgttt aaggcagact tccaggcttg aaggaaaaat ttggaagtca tcacgacata 120
tatgtggtat ttaaaattgt gaggttcaag gaccaagccc cataccattt agag 174

<210> SEQ ID NO 352
<211> LENGTH: 255
<212> TYPE: DNA
<213> ORGANISM: Homo sapiens

<400> SEQUENCE: 352
tggagatagc tcttaaagat ataaatgttt atggctgaaa tgttatggca tcttggattt 60
gctttaaaat aacccagctt gctgcaggag gtgggtattg tgtgtgtggg aaggtgggga 120
ggctgcggga ggaagagatg acccaagatt aggcagatgt tgttaactgt ggaagcaggg 180
tggtgagtgg gggctcatga cattatgctc tctactttgt gtacgtgtga acatttccgt 240
aataaaagat gcctt 255

<210> SEQ ID NO 353
<211> LENGTH: 137
<212> TYPE: DNA
<213> ORGANISM: Homo sapiens

<400> SEQUENCE: 353 ggatttttc ccctgtagta gtgaggtaac atgcttgaat gtcactgtga tatttatttc 60
ctctttgttc agttgttttt gaattcctgt taagtacatg ttttaatact ttgagcgatt 120
taagatactt ttcttttt 137

<210> SEQ ID NO 354
<211> LENGTH: 33
<212> TYPE: DNA
<213> ORGANISM: Homo sapiens

<400> SEQUENCE: 354
aaacgatgat aatctttact ggtgaaaagg atg 33

<210> SEQ ID NO 355

<211> LENGTH: 195
<212> TYPE: DNA
<213> ORGANISM: Homo sapiens

<400> SEQUENCE: 355
tatgagttat tcaaggagga gactttttaa agacagcaac gcaattcttg taacttgtgt 60
aaatagcccc atctttcaga gtgataccat ttctacattt gataatgcct gtattcctgt 120
aggatgtata tagtttaggg gatttttttt ttgtttggtt ttgtttttta gaagtcaata 180
tgtctggttt tattt 195

<210> SEQ ID NO 356
<211> LENGTH: 255
<212> TYPE: DNA
<213> ORGANISM: Homo sapiens

<400> SEQUENCE: 356
attattttga tagcagatgt gctatttatt tatttaatat gtataaggag cctaaacaat 60
agaaagctgt agagattggg tttcattgtt aattggtttg ggagcctcct atgtgtgact 120
tatgacttct ctgtgttctg tgtatttgtt tgaattaatg acctgggata taaagctatg 180
ctagctttca aacaggagat gcctttcaga aatttgtata ttttgcagtt gccagaccaa 240
taaaatacct ggttg 255

<210> SEQ ID NO 357
<211> LENGTH: 217
<212> TYPE: DNA
<213> ORGANISM: Homo sapiens

<400> SEQUENCE: 357
gtgtgttaaa atgagggtct cactgcttta ggattgaagt ggctggaaag agtgatgcct 60
ggggaaggag atggagttat gagggtactg tggctggtac tttctgtact aaacatttcc 120
tttttctatt ttaccactaa ttttgtttta aactgtgagc cgtccaagtc agaagaagac 180
agcaaaaaaa gcaacttttc caacatacaa tttactt 217

<210> SEQ ID NO 358
<211> LENGTH: 92
<212> TYPE: DNA
<213> ORGANISM: Homo sapiens

<400> SEQUENCE: 358
cctgcctggg aaagcgagtc cacagttcac taacaaacac aataccatcc acaaacaagt 60
agccacaaag accacagtta gcaaacacac ac 92

<210> SEQ ID NO 359
<211> LENGTH: 251
<212> TYPE: DNA
<213> ORGANISM: Homo sapiens

<400> SEQUENCE: 359
atataattgg acaaacgctg gcaaaaagaa aaaaatggta agcaaaaaac ccaagataaa 60
gtttcgagga catcaggcct tttgaaatac aatgtcaaat gacacattgt acggtttcaa 120
aaaatccgct agacatgtca taagttttaa ctgtaatgcc caggaaagga tatcttaaaa 180
tattctaaac ttgtgtaaca aaggaataat taactgtaat agtttttcaa taaatcgagt 240
tgggtgtttc c 251

<210> SEQ ID NO 360
<211> LENGTH: 261
<212> TYPE: DNA
<213> ORGANISM: Homo sapiens

<400> SEQUENCE: 360
gaatggttac tgtttatact gtggtatgtt tttgattaca gcagataatg ctttcttttc 60
cagtcgtctt tgagaataaa ggaaaaaaaa tcttcagatg caatggtttt gtgtagcatc 120
ttgtctatca tgttttgtaa atactggaga agctttgacc aatttgactt agagatggaa 180
tgtaactttg cttacaaaaa ttgctattaa actcctgctt aaggtgttct aattttctgt 240
gagcacacta aaagcgaaaa a 261

<210> SEQ ID NO 361
<211> LENGTH: 175
<212> TYPE: DNA
<213> ORGANISM: Homo sapiens

<400> SEQUENCE: 361
tatttcttgc tattgtgata tgacaagaga cttaacttat cttgctctgt tttcccctgt 60
acacgctgta tataggggtc aatgtgatgc tgctggagac gagaataaac tggactagaa 120
tagtgcattg tatttagtct gtattgatca tggatgccct ccttaatagc catat 175

<210> SEQ ID NO 362
<211> LENGTH: 251
<212> TYPE: DNA
<213> ORGANISM: Homo sapiens

<400> SEQUENCE: 362
gaaccgcaga ttatggttaa tccaattctg tgcacctgag gtccataaat aaaagaataa 60
gtattgaaat gaaagaatga cagaaagaat gaatggacac atgaacgact gaattagaaa 120
tggaaatgcc tggcacagcc aggaaggagc tgcccatggg attgtcattc atttcactct 180
gggcacctga ggtccataag cgtgaaaaga ggcaggaaga gaagtgtcag ggagtcaaag 240
atagagctaa g 251

<210> SEQ ID NO 363
<211> LENGTH: 237
<212> TYPE: DNA
<213> ORGANISM: Homo sapiens

<400> SEQUENCE: 363
ttattttatt tcgctatttc cagtttgaag ctactatcat gggcgtttag agttatacaa 60
atgacactta caaaaaataa aagaccaaga cacccagagt gagatgcatg ttggggacgg 120
gggaggctgg cagcaggggg gccccggcgg ctcaccccag ggctcccgga gggggctgtt 180
tccatccacc acccaaaaaa acaccacaag ggtcagtcct agcccacccg acagctt 237

<210> SEQ ID NO 364
<211> LENGTH: 133
<212> TYPE: DNA
<213> ORGANISM: Homo sapiens

<400> SEQUENCE: 364
gtatggatgg gtatgttgag actcaattac ttttttatta gcttccccgt ttggaagatc 60
ccaaacacca aagatggaag gtgaaaataa agactgcgtg accgggaaga aagtttgaat 120
tactaatagt ggg 133

<210> SEQ ID NO 365
<211> LENGTH: 263
<212> TYPE: DNA
<213> ORGANISM: Homo sapiens

<400> SEQUENCE: 365
aatcaaccaa tgcaaccagt ttgtgagaaa aaaaaaaaaa agccgaaaaa aaaaaaaaaa 60
aacacctgaa tgcggaagag ctcggctccc gtttagcatt ttgtacttaa ggaaataaaa 120
aaccaacaaa ggatttcaca ttttttaaa aagtgaagat tgctgtatac tatttattca 180
acttataatt tatgttactc cttgatcttt gtcttttgtc atgacaaagc atttatttaa 240
taaagttatg cattcagcaa ctt 263

<210> SEQ ID NO 366
<211> LENGTH: 48
<212> TYPE: DNA
<213> ORGANISM: Homo sapiens

<400> SEQUENCE: 366
taggttgtca acaggtacta tttgtcacat aactaacttt cgaggcac 48

<210> SEQ ID NO 367
<211> LENGTH: 161
<212> TYPE: DNA
<213> ORGANISM: Homo sapiens

<400> SEQUENCE: 367
attagtgaac ttatctttgc agctgagtac ttaaattctt tttaaaaaga taccctttgg 60
attgatcaca ttgtttgacc cagtatgttt tgtagacacg ttagttataa tcaccttgta 120
tctctaaata tggtgtgata tgaaccagtc cattcacatt g 161

<210> SEQ ID NO 368
<211> LENGTH: 286
<212> TYPE: DNA
<213> ORGANISM: Homo sapiens

<400> SEQUENCE: 368
gtcttcacca actaagaaag ctctgttatt ctggcctggg tgcttgctcc agactcagga 60
acatctggtc aacacaagca tcactgggct ggggaattgt gtgtgtgctg catcatctcc 120
gactctcttg tagttccttc cttccctccc tcactcttac atgcagacac agacagacac 180
agtctggttg ggacatgcag tggcagctcc tggtgtataa catctttcac acaccttgag 240
tctatctgct tgctgccttt gactgatcct gaaatggttg gccttt 286

<210> SEQ ID NO 369
<211> LENGTH: 208
<212> TYPE: DNA
<213> ORGANISM: Homo sapiens

<400> SEQUENCE: 369
gaggccccag aggacttatc tcagctgtac atgctctgcc tgtggagaca tggcttttct 60
ttgtgctgtg gcagactggg gctttggaag tggtgtatgt ttaacttacc tgagagtgag 120
agatgtgtag gaagaatagc tggaagaaag tgaaagatga gtgccagtac ttttggcctg 180
ttatccagta gagagaaagt gacagtga 208

<210> SEQ ID NO 370
<211> LENGTH: 201

<212> TYPE: DNA
<213> ORGANISM: Homo sapiens

<400> SEQUENCE: 370
aactctgtaa ggaggaccat gtcagactat tgtaagctaa gcattaggac tgatacaaat 60
aatatatgct cctggcatag aaaaataaac cacagagaac gagttcaaag aatagcaaag 120
aaagaaagag gacccagtgg gcgaaagatg agagtgtact tttaccaaaa gttatctaag 180
cctgagcact tgaagtctgc a 201

<210> SEQ ID NO 371
<211> LENGTH: 119
<212> TYPE: DNA
<213> ORGANISM: Homo sapiens
<220> FEATURE:
<221> NAME/KEY: misc_feature
<222> LOCATION: (91)..(91)
<223> OTHER INFORMATION: n is a, c, g, or t

<400> SEQUENCE: 371
aaaatagaga gacatacctg gctccaaaac aaggctgtat cttctgccac tgtaataaaa 60
tagatgcaat tgaggttcat aaataaaaga ntaaatactt aaacgtgaaa ggtgactaa 119

<210> SEQ ID NO 372
<211> LENGTH: 36
<212> TYPE: DNA
<213> ORGANISM: Homo sapiens

<400> SEQUENCE: 372
ataatgaaag ttagtaacgt ccattattta ataaag 36

<210> SEQ ID NO 373
<211> LENGTH: 91
<212> TYPE: DNA
<213> ORGANISM: Homo sapiens

<400> SEQUENCE: 373
tgtacagggt cattttgaca gtaactggta tattcctttg cattttatgt tgcattgcca 60
atttttagtg tatccagttt gaaagtataa t 91

<210> SEQ ID NO 374
<211> LENGTH: 178
<212> TYPE: DNA
<213> ORGANISM: Homo sapiens

<400> SEQUENCE: 374
tactgatctt tatattacag attttttttt cttttaggat tagttcagct tgccccccct 60
ttccatttcc accatttata gtgagcctct ccataattag tgccaaccat tagtttcgtt 120
catattttta caccaggagt caacaaactg tggccattgg ccaaatatgg cctcccaa 178

<210> SEQ ID NO 375
<211> LENGTH: 242
<212> TYPE: DNA
<213> ORGANISM: Homo sapiens

<400> SEQUENCE: 375
aggaagtacc cgctccataa gacccttaca tttggacagt caaggtgcac aattgtatgt 60
gaccacaacc atgcaccttg gacataaatg tgtgtaactg cacatggccc atcccatctg 120
aataaggtcc tactctcaga ccccttttgc agtacagtag gtgtgctgat aaccaaggcc 180
cctcttcctg gcctgttaac gtatgtgatt atatttgtct gggttccagt gtataagaca 240
tg 242

<210> SEQ ID NO 376
<211> LENGTH: 199
<212> TYPE: DNA
<213> ORGANISM: Homo sapiens

<400> SEQUENCE: 376
gggagtcaat gaatagtacc taaaatggaa accaaacaaa acaacttcag gaagtaacaa 60
gggcttgctt agagacatga cggtaaaccc tgaaccatca gctaaaagag gtagatagca 120
gtggttgccc ctggggagag gtaaatgtga tggagaggga acaactgtgt acaaacatgt 180
gactttacgt tttgatcaa 199

<210> SEQ ID NO 377
<211> LENGTH: 127
<212> TYPE: DNA
<213> ORGANISM: Homo sapiens

<400> SEQUENCE: 377
aagagttaaa cagtctagag tgaagggaat gttttaaaat ccagaggcga tcaagtgaag 60
ccaacctttg gaggcccgta gaagtcattt ggaggaattt ggacttcgtg cagtaggaaa 120
gagggaa 127

<210> SEQ ID NO 378
<211> LENGTH: 46
<212> TYPE: DNA
<213> ORGANISM: Homo sapiens

<400> SEQUENCE: 378
gacaggggtt ctaattactg tctgtgagag ttactacttt gtaact 46

<210> SEQ ID NO 379
<211> LENGTH: 115
<212> TYPE: DNA
<213> ORGANISM: Homo sapiens

<400> SEQUENCE: 379
taatattttt tgctgcctag gcaaatggct tttgtgaaaa cacttgtatg aaaagcaata 60
caccatttgt ttttacttac caatcactat cattaggttt tgatgcaaat gggaa 115

<210> SEQ ID NO 380
<211> LENGTH: 138
<212> TYPE: DNA
<213> ORGANISM: Homo sapiens

<400> SEQUENCE: 380
ttcccaagcc catgagtcct tgaaaatatt ttttatatat acagtaactt tatgtgtaaa 60
tacataagcg gcgtaagttt aaaggatgtt ggtgttccac gtgttttatt cctgtatgtt 120
gtccaattgt tgacagtt 138

<210> SEQ ID NO 381
<211> LENGTH: 269
<212> TYPE: DNA
<213> ORGANISM: Homo sapiens

<400> SEQUENCE: 381
cttaggatat gaaatcttca gaggatggta gaagagaaag gtaaatgcca taagaaagta 60
gagtacttgt ggtcattgaa accatggaat ttactcaggg atagtgtata tagtgagaaa 120
tcaggtaact aagatttgag cctaaacgta atctgtaaaa ggggagctca aaggaaaagg 180
gaatgggagg accggatttt gtaaggatag tagggcaaat gttaagagag agaatgagag 240
agttgagtat ggcaaagagt gactcaatt 269

<210> SEQ ID NO 382
<211> LENGTH: 282
<212> TYPE: DNA
<213> ORGANISM: Homo sapiens

<400> SEQUENCE: 382
tcacctcctg ctggctaccg gggcaggcat gcacccggtg ccagccccgc tctgggcacc 60
acctgccttc cagcccctcc aggacccggt ccccctgctg cccctcactt caggaggggc 120
ctggagcagg gtgaggctgg actttggggg gctgtgaggg aaatatactg gggtccccag 180
attttgcttt aagggggcca gaccctttgc caggctggat tgtacgggcc ccaccttcgc 240
tgtgttcttg ctgcaaagtc tggtcaataa atcactgcac tg 282

<210> SEQ ID NO 383
<211> LENGTH: 131
<212> TYPE: DNA
<213> ORGANISM: Homo sapiens

<400> SEQUENCE: 383
atacctgtta aatagatcaa ttttgattgc ctactatgtg aactcactgt taaaggcact 60
gaaaatttat catatttcat ttagccacag ccaaaaataa cgcaatacct atgttagcat 120
tttgtgaact c 131

<210> SEQ ID NO 384
<211> LENGTH: 183
<212> TYPE: DNA
<213> ORGANISM: Homo sapiens

<400> SEQUENCE: 384
tcacctgagg cgttcaaaag atataaccaa ataaacaagt catccacaat caaaatacaa 60
cattcaatac ttccaggtgt gtcagacttg ggatgggacg ctgatataat agggtagaaa 120
gaagtaacac gaagaagtgg tggaaatgta aaatccaagt catatggcag tgatcaatta 180
tta 183

<210> SEQ ID NO 385
<211> LENGTH: 263
<212> TYPE: DNA
<213> ORGANISM: Homo sapiens

<400> SEQUENCE: 385
ttgttggtag agacggtgat tcactatgtt ggccaggcta gtcacgaact cctgacctcg 60
tgatccgccc acctcggcct cccaaagtgc tgggattaca ggtgtgagcc accgtgcccg 120
gcctcttttt atttattcct aaaatattac cttgaggcca aattctgcgc ttaaggagaa 180
tgtgcaccaa gtgctggggt gggggctggt tataaacgag gccacaaatc atgcttgtta 240
ataaattgtg tggttcaaat ctg 263

<210> SEQ ID NO 386
<211> LENGTH: 140
<212> TYPE: DNA

<213> ORGANISM: Homo sapiens
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t

<400> SEQUENCE: 386
cacagccaaa acctctacat ccctacattc acacacttcc tccacacacc atcctgaagt 60
caccccaact nctaccacca anatcaccac caancccacc agtataggaa gcagcacacc 120
catggcccac actacctcag 140

<210> SEQ ID NO 387
<211> LENGTH: 134
<212> TYPE: DNA
<213> ORGANISM: Homo sapiens

<400> SEQUENCE: 387
cagaggagct ttattagagg gacagggtga aacatattta caccggccga gcagggacct 60
taagaagcag gcgtgggagc agggtcccag ctcagacgag ttccaccttg gcattggggt 120
acaccgccac cacg 134

<210> SEQ ID NO 388
<211> LENGTH: 207
<212> TYPE: DNA
<213> ORGANISM: Homo sapiens

<400> SEQUENCE: 388
gagtatgagt atgcctgagt gtgaatgtgt atgagtgtga atgagtgtgt gcacatgagt 60
gcacgggtgt cagcatgtgt atataagtgt gggcatgtgt atgtgattgt gtgagtgtgg 120
gcaggtgagt gtgttgggga tgtgggttag ggtggggagt ggtgctttct ctagtgtgtc 180
ctccggaaca tcttgcctac ctagcaa 207

<210> SEQ ID NO 389
<211> LENGTH: 113
<212> TYPE: DNA
<213> ORGANISM: Homo sapiens

<400> SEQUENCE: 389
gaaaactgtt agatgcacac tgttgatttt catggtggat tcaagaactc cctagtgagg 60
agctgaactt gctcaatcta aggctgattg tcgtgttcct ctttaaattg ttt 113

<210> SEQ ID NO 390
<211> LENGTH: 66
<212> TYPE: DNA
<213> ORGANISM: Homo sapiens

<400> SEQUENCE: 390
gtttttatta aaacacaaac gcacacacac acaaaattag ccaggcatgg tggtccatcc 60
ctgtaa 66

<210> SEQ ID NO 391
<211> LENGTH: 66

<212> TYPE: DNA
<213> ORGANISM: Homo sapiens

<400> SEQUENCE: 391
gtcaccccag agtcattgtc acctcagagt cattgtcact ccagagtcat tgtcacctca 60
gagtca 66

<210> SEQ ID NO 392
<211> LENGTH: 128
<212> TYPE: DNA
<213> ORGANISM: Homo sapiens

<400> SEQUENCE: 392
caggctgggc cgtgagcagg tgggccgttg agttacctct gtgctggatc ccgtgccccc 60
acttgcctac cctctgtcct gccttgttat tgtaagtgcc ttcaatactt tgcattttgg 120
gataataa 128

<210> SEQ ID NO 393
<211> LENGTH: 49
<212> TYPE: DNA
<213> ORGANISM: Homo sapiens

<400> SEQUENCE: 393
tgattactag tgtaaactgg ttattgagat agattatgac attggtgga 49

<210> SEQ ID NO 394
<211> LENGTH: 209
<212> TYPE: DNA
<213> ORGANISM: Homo sapiens

<400> SEQUENCE: 394
cagagtcatt cattgtcacc ccagagtcat tgtcacccga gtcattgtca gctcagagtc 60
attgtcaccc cagagtcatt gtcaccccag agtcattgtc accccattgt caccccagag 120
tcattgtcac ctcagagtca ttgtcactcc agagtcattg tcacctcaga gtcaatgtca 180
ccccagagtc atcgtcaccc cagagacat 209

<210> SEQ ID NO 395
<211> LENGTH: 237
<212> TYPE: DNA
<213> ORGANISM: Homo sapiens

<400> SEQUENCE: 395
aataaatgcc tcaggcgtgc tttttgattc atttgataaa caaagcatct tttatgtgga 60
atataccatt ttgggtcctg aggataagag agatgagggc attagatcac tgacagctga 120
agatagaaga acatctttgg tttgattgtt taaataatat ttcaatgcct attctttgca 180
aggtactatg tttcgtaaat taaataggtc tggcccagaa gacccactca attgcct 237

<210> SEQ ID NO 396
<211> LENGTH: 62
<212> TYPE: DNA
<213> ORGANISM: Homo sapiens

<400> SEQUENCE: 396
tatgtaatta taagatgaag cgtagtgaat tgtacagctg ttgtaataat gacctatttc 60
ta 62

<210> SEQ ID NO 397

<211> LENGTH: 277
<212> TYPE: DNA
<213> ORGANISM: Homo sapiens

<400> SEQUENCE: 397 taccccttt tatatctaat gtagaaaaag cgaaattgaa tctggaaagc aaactgttgt 60
atatagttgc ggtaacaatc atgaagagag agccgggctg tcccctcagt aattcatttt 120
aaataacaaa ttatttaaaa ataaaattca tgccagagcc agctgaagag gccttccttc 180
atcaccactg aggccacccc caatctgggc cctctgtcca tctggcatgt ctcctcccag 240
caagattcat ctgttcaatg ccatttgcgt ttcaata 277

<210> SEQ ID NO 398
<211> LENGTH: 203
<212> TYPE: DNA
<213> ORGANISM: Homo sapiens

<400> SEQUENCE: 398
ttttcccaac tctatagcta gatttaaaag tcccagtaaa attttgtaaa caaaatcata 60
taagaaaagg caaggctggc tcttccctat ggtcctttag tggagctata tttgcataga 120
tcctagacaa atgatgcaaa acaaattccc tccaatttcc actagcaatc tccctaattc 180
gctcaaccct tacataagca tca 203

<210> SEQ ID NO 399
<211> LENGTH: 75
<212> TYPE: DNA
<213> ORGANISM: Homo sapiens

<400> SEQUENCE: 399
agaacctgag tataaattta ctttctcaaa ttcttgccat gagaggttga tgagttaatt 60
aaaggagaag attcc 75

<210> SEQ ID NO 400
<211> LENGTH: 248
<212> TYPE: DNA
<213> ORGANISM: Homo sapiens

<400> SEQUENCE: 400
aaaaactcaa cctatctggt gttttatttt aatggataaa aatgtaattt ttttaaggta 60
gcaacttatt tccaaattaa tatagatgaa aaatagatac caattagact aaattgaaag 120
ctttttgttc tatatttgca tagcctttga aatatttctt agtgcctagg aggtctgggg 180
attcctcttt cgtggtggtc actaacctta cttgatgcag ataaaatcac ttgtcaatgc 240
aaaatgtg 248

<210> SEQ ID NO 401
<211> LENGTH: 174
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t

<400> SEQUENCE: 401
acgagccctc tcacagtgga atggagngca cggtctgaat ctgcacagag caagatgctg 60
agtggagtcg ggggcttngt gctgggcctg ctcttncttg gggccgggct gttcatctac 120
ttnaggaatc agaaaggaca ctctggactt cagccaacag gattcctgaa ctga 174

<210> SEQ ID NO 402
<211> LENGTH: 251
<212> TYPE: DNA
<213> ORGANISM: Homo sapiens

<400> SEQUENCE: 402
agagagtgga catttgtcgg gaaactccta acatatgccc ccattctgga gagaacacag 60
agtacgacac aatccctcac actaatagaa caatcctaaa ggaagatcca gcaaatacgg 120
tttactccac tgtggaaata ccgaaaaaga tggaaaatcc ccactcactg ctcacgatgc 180
cagacacacc aaggctattt gcctatgaga atgttatcta gacagcagtg cactgcccct 240
aagtctctgc t 251

<210> SEQ ID NO 403
<211> LENGTH: 88
<212> TYPE: DNA
<213> ORGANISM: Homo sapiens

<400> SEQUENCE: 403
gccctcatgg ttggcatcac atatgcctgc atgccattaa caccagctgg ccctacccct 60
ataatgatcc tgtgtcctaa attaatat 88

<210> SEQ ID NO 404
<211> LENGTH: 284
<212> TYPE: DNA
<213> ORGANISM: Homo sapiens

<400> SEQUENCE: 404
aactgaaatg tcaacctgtg gactgtggca ttcctgaatc cattgagaat ggtaaagttg 60
aagacccaga gagcactttg tttggttctg tcatccgcta cacttgtgag gagccatatt 120
actacatgga aaatggagga ggtggggagt atcactgtgc tggtaacggg agctgggtga 180
atgaggtgct gggcccggag ctgccgaaat gtgttccagt ctgtggagtc cccagagaac 240
cctttgaaga aaaacagagg ataattggag gatccgatgc agat 284

<210> SEQ ID NO 405
<211> LENGTH: 214
<212> TYPE: DNA
<213> ORGANISM: Homo sapiens

<400> SEQUENCE: 405
gacttattcc cgctgactga gtttttgagg ggctaccagg aaagcgcctc caaccctagc 60
aaaagtgcaa gatggggagt gagaggctgg gaatggaggg gcagagccag gaagatcccc 120
cagaaaagaa agctacagaa gaaactgggg ctcctccagg gtggcagcaa caataaatag 180
acacgcacgg cagccacagc ttgggtgtgt gttc 214

<210> SEQ ID NO 406

<211> LENGTH: 72
<212> TYPE: DNA
<213> ORGANISM: Homo sapiens

<400> SEQUENCE: 406
gaatggcagt accagaaggc attggttaag tgtcccagga accacacaag cagtgactcc 60
taaagaagtt ca 72

<210> SEQ ID NO 407
<211> LENGTH: 180
<212> TYPE: DNA
<213> ORGANISM: Homo sapiens

<400> SEQUENCE: 407
gcttccttaa aggtcagaac atcaggccaa agtacaacgt ttaatttcag aacttgcctt 60
ccaatttacg cattttcaat ttgctctccc catttgttga gtcagaagaa gcagcattgc 120
ccagaaacag gtattacgta acatgcacat actttaaaaa gtactcatcc cttgttttct 180

<210> SEQ ID NO 408
<211> LENGTH: 173
<212> TYPE: DNA
<213> ORGANISM: Homo sapiens

<400> SEQUENCE: 408
gctgagtatg ttaagctctt tatgactgtt tttgtagtgg tatagagtac tgcagaatac 60
agtaagctgc tttattgtag catttcttga tgttgcttag tcacttattt cataaacaac 120
ttaatgtttt gaataatttc ttactaaaca ttttgttatt gggcaagtga ttg 173

<210> SEQ ID NO 409
<211> LENGTH: 243
<212> TYPE: DNA
<213> ORGANISM: Homo sapiens

<400> SEQUENCE: 409
aaaacttggc actttttcgt gtggatcttg ccacatttct gatcagaggt gtacactaac 60
atttcccccg agctcttggc ctttgcattt atttatacag tgccttgctc ggcgcccacc 120
accccctcaa gccccagcag ccctcaacag gcccagggag ggaagtgtga gcgccttggt 180
atgacttaaa attggaaatg tcatctaacc attaagtcat gtgtgaacac ataaggacgt 240
gtg 243

<210> SEQ ID NO 410
<211> LENGTH: 201
<212> TYPE: DNA
<213> ORGANISM: Homo sapiens

<400> SEQUENCE: 410
ccctgctgcc tctgatcgta ggaattgagg agtgtcccgc cttgtggctg agaactggac 60
agtggcaggg gctggagatg ggtgtgtgtg tgtgtgtgtg tgtgtgtgtg tgtgtgcgcg 120
cgcgccagtg caagaccgag attgagggaa agcatgtctg ctgggtgtga ccatgtttcc 180
tctcaataaa gttcccctgt g 201

<210> SEQ ID NO 411
<211> LENGTH: 174
<212> TYPE: DNA
<213> ORGANISM: Homo sapiens

<400> SEQUENCE: 411
tgggcgtccg ggcccccaat attcacgcac tcgcaccacg cactcatatt ccctcacccc 60
accatcacgg ccccaaagaa ggtcttccct ctcgcgaagt ccaccatatc ggggtgactg 120
atgttggacg tacaccctct cgcccctccg gagctgcacc aggccgccga accc 174

<210> SEQ ID NO 412
<211> LENGTH: 259
<212> TYPE: DNA
<213> ORGANISM: Homo sapiens

<400> SEQUENCE: 412
ctacaacagg caggtactgc tgccaggggg ctttgaacta gtgcctgcta cccaggacac 60
ccgggccatg cccctggctg ggcagcctgg cacaagtgaa gaagaaggca gtgggaaaac 120
tgggtttatt tcaaggcagc agcctgagcc caggagcaga ggacccagtt gttataaggc 180
gctgggagag gatgggcagc tcccactgcc ccagagcgga gctcgaagca cccaggttgc 240
ccacggaaaa tccaataaa 259

<210> SEQ ID NO 413
<211> LENGTH: 60
<212> TYPE: DNA
<213> ORGANISM: Homo sapiens

<400> SEQUENCE: 413
tttctggggt ctttgagctc caaaaaataa acacttcctt tgagggagag ccccccccca 60

<210> SEQ ID NO 414
<211> LENGTH: 159
<212> TYPE: DNA
<213> ORGANISM: Homo sapiens

<400> SEQUENCE: 414
gagcttcctt cttcgttctt ggcaccatct tatgaaaagg gtccagatta agatttttga 60
ctgagtcatt ctaaagtaag ttgcaagacc catgatacta gaccactaaa tacttcatca 120
cacacctcct aagaataaga accaacatta tcacaccaa 159

<210> SEQ ID NO 415
<211> LENGTH: 278
<212> TYPE: DNA
<213> ORGANISM: Homo sapiens

<400> SEQUENCE: 415
ggaagccatt atcctaaatg aactcactca gaaacagaaa accaaatacc acatgttctc 60
acttataagt agaagctaaa cattgagtac acatggatac aaagaaggga accgcagaca 120
ctggggccta cctgaggtcg gagcatggaa ggagggtgag gatcaaaaaa ctacctatct 180
ggtactatgc tttttatctg gatgatgaaa taatctgtac aacaaaccct ggtgacatgc 240
aatttaccta tatagcaagc ctacacatgt gcccctga 278

<210> SEQ ID NO 416
<211> LENGTH: 241
<212> TYPE: DNA
<213> ORGANISM: Homo sapiens

<400> SEQUENCE: 416
ttcccatctc gtccatgagc ctaggtcttg gagccttgtg ttggaggctg ctgtgatgtc 60
aggaacgggg atctttctag cttttggcca cttcctggga cctcacgccc ctgttgacag 120
atggagattg ggcagcaggg ccttgctgca ttgttatctg ctgttccgac ttggtttgtc 180
ttgtccaagg gtgacgaaag agccaggcac cagggtctca tgggatgagg tccaactttt 240
t 241

<210> SEQ ID NO 417
<211> LENGTH: 283
<212> TYPE: DNA
<213> ORGANISM: Homo sapiens

<400> SEQUENCE: 417
gtgagaggta acactctaaa tagcccattt catgctcaag acatccaagt caaagaaacc 60
caatagcaca ggtgagtccc ctctgttccc ccccaacacc ccactcacat cagggcccct 120
gccctggagt gtcaccttta ttagctgtga gagacacccc agagccctgg gcactgtcag 180
tgattggggt agaacaaaaa caggacctgg tcagagccca cagatgtggc tagaggaact 240
gtggggtggt gagctccctc ataggctcct gaccacaata tcc 283

<210> SEQ ID NO 418
<211> LENGTH: 186
<212> TYPE: DNA
<213> ORGANISM: Homo sapiens

<400> SEQUENCE: 418
gagacttgta tgaaagatgg ctgtgcctct gcctgtctcc cccaccgggc tgggagctct 60
gcagagcagg aaacatgact cgtatatgtc tcaggtccct gcagggccaa gcacctagcc 120
tcgctcttgg caggtactca gcgaatgaat gctgtatatg ttgggtgcaa agttccctac 180
ttcctg 186

<210> SEQ ID NO 419
<211> LENGTH: 267
<212> TYPE: DNA
<213> ORGANISM: Homo sapiens

<400> SEQUENCE: 419
gcatttcaaa gtgacttcta tgaagctttt tttttaatgt gaaattttca gaatgttgtt 60
tttttcatgt agatactcca ggaagagtta agcactgctt tcagttttaa tatccacctt 120
gaggggtcgc tgcttgaggg ctcttatccc aggggacttt ttaattcgga tgttacttaa 180
tgtggcttct ctaatgtagt ttctttgatt accgactaca caattatgta ccatcacagt 240
attagtggaa aagtaccatg tgattta 267

<210> SEQ ID NO 420
<211> LENGTH: 45
<212> TYPE: DNA
<213> ORGANISM: Homo sapiens

<400> SEQUENCE: 420
tgcttataca cttacacttt atgcacaaaa tgtagggtta taata 45

<210> SEQ ID NO 421
<211> LENGTH: 241
<212> TYPE: DNA
<213> ORGANISM: Homo sapiens

<400> SEQUENCE: 421
aactggaccc tgtcgttctc catcttctca gtcagttgtt tcaagtgttc ctgataactc 60
ctctccttct gttccatcat ctgctcattc tttctttgca tttcctgcaa catttttgct 120
gaagcctgtg cagactcagc tttcacaagt tccacttcaa tctccttttc tttttctgtg 180
agagtctggt ctgtctggag aattgcatca gtcatagact ccttggattt caagtatgtc 240
t 241

<210> SEQ ID NO 422
<211> LENGTH: 159
<212> TYPE: DNA
<213> ORGANISM: Homo sapiens

<400> SEQUENCE: 422
gagcttcctt cttcgttctt ggcaccatct tatgaaaagg gtccagatta agatttttga 60
ctgagtcatt ctaaagtaag ttgcaagacc catgatacta gaccactaaa tacttcatca 120
cacacctcct aagaataaga accaacatta tcacaccaa 159

<210> SEQ ID NO 423
<211> LENGTH: 107
<212> TYPE: DNA
<213> ORGANISM: Homo sapiens

<400> SEQUENCE: 423
tactcccgag gctctgtaca ttgctgccac atactcctgc cagcttgggg gagtgttcct 60
tcaccctcac agtatttatt atcctgcacc acctcactgt tccccat 107

<210> SEQ ID NO 424
<211> LENGTH: 273
<212> TYPE: DNA
<213> ORGANISM: Homo sapiens

<400> SEQUENCE: 424
tagaagatga cctcgttccg gagctgggta tttcaaattt gctttcatcc agccactgcc 60
caaagccatt ttcctgccta ctggatgctt acagtgactg tggatacggg ggttcccttt 120
ccccattcag tgacatgtcc tctttgcttg gtgtaaacca ttcttgggag gacacttttg 180
ccaatgaact ctttccccag ctgattagtg tctaaggaat gatccaatac tgttgccctt 240
ttccttgact attacactgc ctggaggata gca 273

<210> SEQ ID NO 425
<211> LENGTH: 228
<212> TYPE: DNA
<213> ORGANISM: Homo sapiens

<400> SEQUENCE: 425
atgtaggaga acgtgcccta ttcacacttt gggaagacgc taatttgtga cattttttt 60 tcaagcctgc catcaaggac attttttaag acccaactgg catgagttgg ggtaatttcc 120
tattattttc attttggaca acttttttaa cttatattct ttatagagga ttccccaaaa 180
tgtgctcctc atttttggcc tctcatgttc caaacctcat tgaataaa 228

<210> SEQ ID NO 426
<211> LENGTH: 286
<212> TYPE: DNA
<213> ORGANISM: Homo sapiens

<400> SEQUENCE: 426
gctgtgttgg ccctcacttg ggattctcag cagttacatg aaagttgtgc tgataatctc 60
ttctcttgta ccaattttag tcaggcagaa aatggtaaac atgagggtgc tcttgtgact 120
taatttttgt tcaagggact aaattgctta tgtttattcc ctgtcagcgg agtggagaat 180
gtcattcatc aataaaccaa agccaatagc tggagaattg agatctggtt gaaagtggtt 240
tatggtttac atgctgtact atcctgagga attgcgagat attgct 286

<210> SEQ ID NO 427
<211> LENGTH: 266
<212> TYPE: DNA
<213> ORGANISM: Homo sapiens
<220> FEATURE:
<221> NAME/KEY: misc_feature
<222> LOCATION: (214)..(214)
<223> OTHER INFORMATION: n is a, c, g, or t

<400> SEQUENCE: 427
ccctgcgcct atcaggtcgt gagtccaggg gtctacaagt cccgggcccc ccagttcacg 60
attctggcgc ggacttcgct cccccaagac aacactcgga agccagggcc cgcggcctac 120
aacgtggatc agcaccggaa gccccgcggc tggagtttcg ggatccggca ctcggactac 180
ctggccccgc tggtgaccga cgcggacaac tganccgcca ggcgggagcg gccccacacg 240
tgtttgctta aagtctgcga gtccgc 266

<210> SEQ ID NO 428
<211> LENGTH: 270
<212> TYPE: DNA
<213> ORGANISM: Homo sapiens

<400> SEQUENCE: 428
ccagggctga gagacacgtg aaggaagatg atgggaggaa aagcccagga gaagtcccac 60
cagggaccag cccagcctgc atacttgcca cttggccacc aggactcctt gttctgctct 120
ggcaagagac tactctgcct gaacactgct tctcctggac cctggaagca gggactggtt 180
gagggagtgg ggaggtggta agaacacctg acaacttctg aatattggac attttaaaca 240
cttacaaata aatccaagac tgtcatattt 270

<210> SEQ ID NO 429
<211> LENGTH: 227
<212> TYPE: DNA
<213> ORGANISM: Homo sapiens

<400> SEQUENCE: 429
gaagatgaag ccccatgctc agtcccctcc catcccccac gcagctccac cccagtccca 60
agccaccagc tgtttgctcc tggtgggagg tggcctcctc agcccctcct ttctgacctt 120
taacctcact ctcaccttgc accgtgcacc aacccttcac ccctcctgga aagcaggcct 180
gatggcttcc cactggcctc caccacctga ccagagtgtt ctcttca 227

<210> SEQ ID NO 430
<211> LENGTH: 279
<212> TYPE: DNA
<213> ORGANISM: Homo sapiens

<400> SEQUENCE: 430
gcatttgctg tgtttcgtta gcatctggct ccaggacaga ccttcaactt ccaaattgga 60
tactgctgcc aagaagttgc tctgaagtca gtttctatca ttttgctctt tgattcaaag 120
cactgtttct ctcactgggc ctccaaccat gttccctttt ttttagcacc acaaataatc 180
aaaacccaac atgactgttt gttttccttt aaaaatatgc accaaatcat ctctcatcac 240
ttttctttga gggttttagt agacagtagg agttaataa 279

<210> SEQ ID NO 431
<211> LENGTH: 123
<212> TYPE: DNA
<213> ORGANISM: Homo sapiens
<220> FEATURE:
<221> NAME/KEY: misc_feature
<222> LOCATION: (52)..(52)
<223> OTHER INFORMATION: n is a, c, g, or t

<400> SEQUENCE: 431
gcggactcgc agactttaag caaacacgtg tggggccgct cccgcctggg tngcagttgt 60
ccgcgtcggt caccagcggg gccaggtagt ccgagtgccg gatcccgaaa ctccagccgc 120
ggg 123

<210> SEQ ID NO 432
<211> LENGTH: 82
<212> TYPE: DNA
<213> ORGANISM: Homo sapiens

<400> SEQUENCE: 432
gtgctcagta gtcagactgg atagtccgtt tttgcttatc cgttagccgt ggggatttag 60
caggaagctg tgagagcagt tt 82

<210> SEQ ID NO 433
<211> LENGTH: 151
<212> TYPE: DNA
<213> ORGANISM: Homo sapiens

<400> SEQUENCE: 433
acacagaaga gtgacatgtt tacaaacctc aagccagcct tgctcctggc tggggcctgt 60
tgaagatgct tgtattttac ttttccattg taattgctat cgccatcaca gctgaacttg 120
ttgagatccc cgtgttactg cctatcagca t 151

<210> SEQ ID NO 434
<211> LENGTH: 82
<212> TYPE: DNA
<213> ORGANISM: Homo sapiens

<400> SEQUENCE: 434
tttaaaatac tcagaggaca ggatcactgt ggaatcgaat cagaagtggt ggctggaatt 60
ccacgcaccg atcagtactg gg 82

<210> SEQ ID NO 435
<211> LENGTH: 109
<212> TYPE: DNA
<213> ORGANISM: Homo sapiens

<400> SEQUENCE: 435
aagagaagac tcacagtatc aggtctactg aaggagatac ggtgattcct gttcttggct 60
ttgtagattc atctggtata aacagcactc ctgagttatg accttttga 109

<210> SEQ ID NO 436
<211> LENGTH: 118
<212> TYPE: DNA
<213> ORGANISM: Homo sapiens

<400> SEQUENCE: 436
tttgaagatt agaaatttag ccgtaggtaa agaatacaaa ggaaaaataa ttttaaaatc 60
atcaaccaga tcaacaaaat atatgttaat gccgagactt tgaattagag tgcgaatt 118

<210> SEQ ID NO 437
<211> LENGTH: 242
<212> TYPE: DNA
<213> ORGANISM: Homo sapiens

<400> SEQUENCE: 437
catcttctag cagatctttt tcagttaaga ttacttgttc ttccatgtat tcatatttag 60
ccagctcctt gatcagccgc agtatgtcac tgcagtcggc ggcagtggct gggcggatca 120
cgaatttagc cattttcgtc ttttgctttt cttccctttg cggaccaggc ccctgtactt 180
gaacagtagg aggaggtggt tcctcattcg tctcccggga gcgtcctctt ctcagtcagg 240
ct 242

<210> SEQ ID NO 438
<211> LENGTH: 34
<212> TYPE: DNA
<213> ORGANISM: Homo sapiens

<400> SEQUENCE: 438
gaaatcattg tgggattgct agctttccct ctta 34

<210> SEQ ID NO 439
<211> LENGTH: 272
<212> TYPE: DNA
<213> ORGANISM: Homo sapiens

<400> SEQUENCE: 439
caacctctta caacccaggc attcctttct atcgataatt actctttcaa ccaattgcca 60
atcagaaaat tgttatatct acctataatc tagaagcccc cacatcaagt tgttttgcct 120
ttctggacag gaccaatgta tatcttaaat gtatttgatt gatctctcat gtctccctaa 180
aatgtataaa accacgctgt tccccgacca cctggagcac atgttctcag ggtctcctga 240
gggctgtgtc acaggccatg ttcacttaca tt 272

<210> SEQ ID NO 440
<211> LENGTH: 189
<212> TYPE: DNA
<213> ORGANISM: Homo sapiens

<400> SEQUENCE: 440
ccctgcagag aatcacgtcc tggaactgca tgttcttgcg actcttggga cttcatttta 60
acttctcgct gccccagcca tgttttcaac catggcatcc ctcccccaat tagttccctg 120
tcatcctcgt caaccttctc tgtaagtgcc tggtaagctt gcccttgctt aagaactcaa 180
aacatagct 189

<210> SEQ ID NO 441
<211> LENGTH: 163
<212> TYPE: DNA
<213> ORGANISM: Homo sapiens

<400> SEQUENCE: 441
tgagcagact gcaccccaag ctcccgactc caggtcccct gatcttgggg cctgtttccc 60
atgggattca agagggacag ccccagcttt gtgtgtgttt aagcttagga atcgccttta 120
tggaaagggc tatgtgggag agtcagctat cttgtctggt ttt 163

<210> SEQ ID NO 442
<211> LENGTH: 296
<212> TYPE: DNA
<213> ORGANISM: Homo sapiens
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t

<400> SEQUENCE: 442
atgggtgtag atcaaggcag gagcaggaac caaaaagaaa ggcataaaca taagaaaaaa 60
aatggaaggg gtggnaaaca gagtacaata acatgagtaa tttgatgggg gctattatga 120
actgagaaat gaactttgaa aagtatcttg gggccaaatc atgtagactc ttgagtgatg 180
tgttaaggaa tgctatgagt gctgagaggg catcagaagt ccttgagagc ctccagagaa 240
aggctcttaa aaatgcagcg cnatctccag tgacagaaga tactgctaga aatctg 296

<210> SEQ ID NO 443
<211> LENGTH: 246
<212> TYPE: DNA
<213> ORGANISM: Homo sapiens

<400> SEQUENCE: 443
tgtacagatt caagcaatgg atgcaaggaa catgctgtat gtaatagaag aaagaagtcc 60
acgttttcgg cagaagtagt gagtcagtgt ggaagagagg tgagggtgtg ctttactttt 120
tgataaagag aaagatgttt actcataaac ccttcaaaag gtattaacaa atgtttacca 180
aacctattgc tttattttaa aaacataatt tgtgttttct atttgtaaga tctgacattt 240
cgaggc 246

<210> SEQ ID NO 444
<211> LENGTH: 121
<212> TYPE: DNA
<213> ORGANISM: Homo sapiens

<400> SEQUENCE: 444
ggcagcgacc cggaaacagc gtatcactga gaccgagtcg ccttatcagg agctccaggg 60
tcagaggtcg gatgtctaca gcgacctcaa cacacagagg ccgtattaca aatgagcccg 120
a 121

<210> SEQ ID NO 445
<211> LENGTH: 262
<212> TYPE: DNA
<213> ORGANISM: Homo sapiens

<400> SEQUENCE: 445
tggtgaccag ttctcggttt catagttttt actatcagtt tgcctttggg attctttgaa 60
agctcttgag gctttttccg cagcttctag gagatgtgtt aggtcattaa cagtaatgct 120
cctacagttt ttgttcccat ccaaccacca tttgatttca cttttgtaga cttgacctag 180
tgtatctgaa atataggaat ttttaggtgc tttcattttg gcctgacgtg cccagtccag 240
agctgtgtta aagtccttct ct 262

<210> SEQ ID NO 446
<211> LENGTH: 226
<212> TYPE: DNA

<213> ORGANISM: Homo sapiens

<400> SEQUENCE: 446
gtcattcaca actgatttca agagtcacct tcaccaggaa gtcttccttg accaccatca 60
ttcctgcctg attagagggc ttcctcatgg taatatgtgt tctcaagttt tcagtgtcaa 120
ggaatgccat cccagaagct cattttcaga tgcacaacag ccagaacagt ctcaagcagc 180
attctagagc ttggaattta agaactacgc attgcctata aagtga 226

<210> SEQ ID NO 447
<211> LENGTH: 272
<212> TYPE: DNA
<213> ORGANISM: Homo sapiens

<400> SEQUENCE: 447
agagctcttg agtgggctag tgactccccc tgcagcctgg tggagatggt gtgaggagcg 60
aagagccctc tgctctagga tttgggttga aaaacagaga gagaagtggg gagttgccac 120
aggagctaac acgctgggag gcagttgggg gcgggtgaac tttgtgtagc cgaggccgca 180
ccctccctca ttccaggctc attcattttc atgctccatt gccagactct tgctgggagc 240
ccgtccagaa tgtcctccca ataaaactcc at 272

<210> SEQ ID NO 448
<211> LENGTH: 151
<212> TYPE: DNA
<213> ORGANISM: Homo sapiens

<400> SEQUENCE: 448
tagggattaa cttcctgtat gctgcaactc atgaacttgg ccattctttg ggtatgggac 60
attcctctga tcctaatgca gtgatgtatc caacctatgg aaatggagat ccccaaaatt 120
ttaaactttc ccaggatgat attaaaggca t 151

<210> SEQ ID NO 449
<211> LENGTH: 243
<212> TYPE: DNA
<213> ORGANISM: Homo sapiens

<400> SEQUENCE: 449
tcccctgctt gaacactgaa gggcaggtgg tgggccatgg ccatggtccc cagctgagga 60
gcaggtgtcc ctgagaaccc aaacttccca gagagtatgt gagaaccaac caatgaaaac 120
agtcccatcg ctcttacccg gtaagtaaac agtcagaaaa ttagcatgaa agcagtttag 180
cattgggagg aagctcagat ctctagagct gtcttgtcgc cgcccaggat tgacctgtgt 240
gta 243

<210> SEQ ID NO 450
<211> LENGTH: 82
<212> TYPE: DNA
<213> ORGANISM: Homo sapiens

<400> SEQUENCE: 450
cagatgttgg tatctgcagg gatcctggaa ccaaacccct gcagatacta agggctgacg 60
atctaggtaa gactggattt aa 82

<210> SEQ ID NO 451
<211> LENGTH: 236
<212> TYPE: DNA
<213> ORGANISM: Homo sapiens

<400> SEQUENCE: 451
actctcaggc tgcgtccagc gacagtgccc agggctctga tgtgtctctc acagcttgaa 60
aagcctgaga cagctgtctt gtgagggact gagatgcagg atttcttcac gcctcccctt 120
tgtgacttca agagcctctg gcatctcttt ctgcaaaggc acctgaatgt gtctgcgtcc 180
ctgttagcat aatgtgagga ggtggagaga cagcccaccc ttgtgtccac tgtgac 236

<210> SEQ ID NO 452
<211> LENGTH: 119
<212> TYPE: DNA
<213> ORGANISM: Homo sapiens

<400> SEQUENCE: 452
gccagagaga ccaagtgtta tgtaagaagt agtgtcggct gtgtagaacc actgactaca 60
caggccgaag ttactgagaa cttggacaga aaaaatagcc agcaagtgtt caaactact 119

<210> SEQ ID NO 453
<211> LENGTH: 264
<212> TYPE: DNA
<213> ORGANISM: Homo sapiens

<400> SEQUENCE: 453
gccaacagca tcttttccgg gttcctgctc tttccagata tggaggcctg acctgtgggc 60
tgcttcacat ccaccccggc tccccctgcc agcaacgctc actctacccc caacaccacc 120
ccttgcccag ccaatgcaca cagtagggct tggtgaatgc tgctgagtga atgagtaaat 180
aaacttttca aggccaaggg acagtggttt aattcaactc tgtgtcccag cacctggcac 240
accagaagtg ccatgctcag aaat 264

<210> SEQ ID NO 454
<211> LENGTH: 273
<212> TYPE: DNA
<213> ORGANISM: Homo sapiens

<400> SEQUENCE: 454
ttcaaactca atgatgctac catgcctctc caacattttc aacccccctga cattatcttg 60 gatcctatgg tttctccatc caattctttg aatttcccag tctcccctat gtaaaactta 120
gcaacttggg ggacctcatt cctgggacta tgctgtaacc aaattattgt ccaaggctat 180
atttttggga tgaatataat ttgaggaagg gagttaaaga ccctcctggg gctctcagtg 240
tgccatagag gacagcaact ggtgattgtt tca 273

<210> SEQ ID NO 455
<211> LENGTH: 275
<212> TYPE: DNA
<213> ORGANISM: Homo sapiens

<400> SEQUENCE: 455
acttacatac tagcttccaa ggacaggtgg aggtagggcc agcctggcgg gagtggagaa 60
gcccagtctg tcctatgtaa gggacaaagc caggtttaat ggtactgggt agggggcact 120
gccaagacaa taagctaggc tactgggtcc agctactact ttggtgggat tcaggtgagt 180
ctccatgcac ttcacatgtt acccagtgtt cttgttactt ccaaggagaa ccaagaatgg 240
ctctgtcaca ctcgaagcca ggtttgatca ataaa 275

<210> SEQ ID NO 456

<211> LENGTH: 261
<212> TYPE: DNA
<213> ORGANISM: Homo sapiens

<400> SEQUENCE: 456
tcactcccac ctgttactgc tgggagtcaa gtcagctagg aaggaagcag gacatttttt 60
caaacagcaa gtggggccca tggaactgaa tctttactcc ttggtgcacc gcttttgtcg 120
tgcgttgcct tgctccgttt ttcccaaaaa gcactggctt catcaaggcc accgacgatt 180
tcctgagtgc actgggaaat ttgggtatag gtcaggcttg gcagccttga tcccaggaga 240
gtactaatgg taacaagtca a 261

<210> SEQ ID NO 457
<211> LENGTH: 241
<212> TYPE: DNA
<213> ORGANISM: Homo sapiens

<400> SEQUENCE: 457
ttgttcccga ctagctgcct tgcacattat tttcattttc ctggaatttg atacagagag 60
caatttatag ccaattgata gcttatgctg tttcaatgta aattcgtggt aaataactta 120
ggaactgcct tttctttttc tttgaaaacc tacttataac tgttgctaat aagaatgtgt 180
attgttcagg acaacttgtc tccatacagt tgggttgtaa ccctcatgct tggcccaaat 240
a 241

<210> SEQ ID NO 458
<211> LENGTH: 107
<212> TYPE: DNA
<213> ORGANISM: Homo sapiens

<400> SEQUENCE: 458
taaatataat atcgacacag tgctttccgt ggcactgcat acaatctgag gcctcctctc 60
tcagttttta tatagatggc gagaacctaa gtttcagttg attttac 107

<210> SEQ ID NO 459
<211> LENGTH: 252
<212> TYPE: DNA
<213> ORGANISM: Homo sapiens
<220> FEATURE:
<221> NAME/KEY: misc_feature
<222> LOCATION: (180)..(182)
<223> OTHER INFORMATION: n is a, c, g, or t

<400> SEQUENCE: 459
gtggagcagt tggactgctc tctctgctct caggatgata ctgtgagaac aatttaaata 60
tgctaagcac atgtcaggaa acagttttgt ggtctttgga cactcgctgt agccattccg 120
ttccatttca ggtgatttta ttcatttcat ttgtagaata aaataaatcc atttcacacn 180
nncacacaca cacacacaca cacacacaca caccctctat acaccactaa agcctcccat 240
taaacccata ga 252

<210> SEQ ID NO 460
<211> LENGTH: 96
<212> TYPE: DNA
<213> ORGANISM: Homo sapiens

<400> SEQUENCE: 460
tcgacacagt gctttccgtg gcactgcata caatctgagg cctcctctct cagtttttat 60
atagatggcg agaacctaag tttcagttga ttttac 96

<210> SEQ ID NO 461
<211> LENGTH: 181
<212> TYPE: DNA
<213> ORGANISM: Homo sapiens
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (78)..(79)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t

<400> SEQUENCE: 461
gccagagaag cgattagaaa cccctgaggg ccgattactg acnncataaa tcatgagttt 60
gggggctttg cctgggtnnt gttggtacca ggagacatng ttataaccan caacgtcact 120
gctggttcca gtgcaggaga tggtgatcga ctgtccagga gacccagaca cggaggcagg 180
c 181

<210> SEQ ID NO 462
<211> LENGTH: 115
<212> TYPE: DNA
<213> ORGANISM: Homo sapiens

<400> SEQUENCE: 462
aggagctgag gtgctacccg gagccccatt cacccccacc tgcccacttg ggaatctgag 60
gcagaggagg gtgaggcctg tgtgccaacc ttgttcacat accaccttcg tcccc 115

<210> SEQ ID NO 463
<211> LENGTH: 53
<212> TYPE: DNA
<213> ORGANISM: Homo sapiens

<400> SEQUENCE: 463
aagcaagata tcaatgtagc agaattgcac ttgtgcctca cgaacataca taa 53

<210> SEQ ID NO 464
<211> LENGTH: 155
<212> TYPE: DNA
<213> ORGANISM: Homo sapiens

<400> SEQUENCE: 464
gttgttgatc atggatcata ctccccttgt ttctttgggt gagaagggat cgcagtttgg 60
aaactccggc ggctgcgtgc ggggtttcag tcccagctgt aggcttgtaa atacccgccc 120
cgccaaaccg catagagaac gtggcagcaa gctga 155

<210> SEQ ID NO 465
<211> LENGTH: 190
<212> TYPE: DNA
<213> ORGANISM: Homo sapiens

<400> SEQUENCE: 465
cacagggaaa tcagggttac aaatcttctt gatccacttc tctcaggatc ccctctcttc 60
ctacccttcc tcaccacttc cctcagtccc aactcctttt ccctatttcc ttctcctcct 120
gtctttaaag cctgcctctt ccaggaagac ccccctattg ctgctggggc tccccatttg 180
cttactttgc 190

<210> SEQ ID NO 466
<211> LENGTH: 63
<212> TYPE: DNA
<213> ORGANISM: Homo sapiens

<400> SEQUENCE: 466
attagaacct tagtataaat ttactttctc aaattcttgc catgagaggt tgatgagtta 60
att 63

<210> SEQ ID NO 467
<211> LENGTH: 281
<212> TYPE: DNA
<213> ORGANISM: Homo sapiens

<400> SEQUENCE: 467
ggagacagat ggagggtacc ctatttacaa ctgagtcagc caagccactg atgggaatat 60
acagatttag gtgctaaacc atttattttc cacggatgag tcacaatttg aagaatcaaa 120
cttccatcct gaaaatttat atgtttcaaa accacttgcc atcctgttag attgccagtt 180
cctgggacca ggcctcagac tgtgaagtat atatcctcca gcattcagtc caggggggagc 240 cacggaaacc atgtttttgc ttaagccatt aaagtcagag a 281

<210> SEQ ID NO 468
<211> LENGTH: 239
<212> TYPE: DNA
<213> ORGANISM: Homo sapiens

<400> SEQUENCE: 468
agatgcgctc gagacccacg ggccttccac ctccctcagc ttcctgcatg gacccacctt 60
actggccagt ctgcatcctt gcctagacca ttctcccctc cagggagccc accctgaccc 120
acccccactg cacccccctcc ccatgggttc tctccttcct ctgaacttct ttaggagtca 180
ctgcttgtgt ggttcctggg acacttaacc aatgccttct ggtactgcca ttcttttt 239

<210> SEQ ID NO 469
<211> LENGTH: 196
<212> TYPE: DNA
<213> ORGANISM: Homo sapiens

<400> SEQUENCE: 469
gcctttaaga taccttgatg aagacctgga ctattgaatg gagcagaaat tcacctctct 60
cactgactat tacagttgca tttttatgga gttcttcttc tcctaggatt cctaagactg 120
ctgctgaatt tataaaaatt aagtttgtga atgtgactac ttagtggtgt atatgagact 180
ttcaagggaa ttaaat 196

<210> SEQ ID NO 470
<211> LENGTH: 38
<212> TYPE: DNA
<213> ORGANISM: Homo sapiens

<400> SEQUENCE: 470
agtctgccta tgatctttga atgagctttt taaggaag 38

<210> SEQ ID NO 471
<211> LENGTH: 110
<212> TYPE: DNA
<213> ORGANISM: Homo sapiens

<400> SEQUENCE: 471
tttaacttga gggtgtagag gtcctccacg cttgtttgcc tgaaagtaat ataatgatgc 60
tgtctgaaca ggttttactg cttgctttcc aagtaaaggt taattatgat 110

<210> SEQ ID NO 472
<211> LENGTH: 173
<212> TYPE: DNA
<213> ORGANISM: Homo sapiens

<400> SEQUENCE: 472
tattttccct ctttcgaaca aagacattgg tttgcccaag gactacaaat aaaccaacgg 60
gaaaaaagaa aggttccagt tttgtctgaa aattctgatt aagcctctgg gccctacagc 120
ctggagaacc tggagaatcc tacacccaca gaacccggct ttgtccccaa aga 173

<210> SEQ ID NO 473
<211> LENGTH: 82
<212> TYPE: DNA
<213> ORGANISM: Homo sapiens

<400> SEQUENCE: 473
gttatttaag atggctatcc agataatcct gaacactgtg tatttatttt atttagacta 60
ccagcaaaga ttaaagcatg aa 82

<210> SEQ ID NO 474
<211> LENGTH: 266
<212> TYPE: DNA
<213> ORGANISM: Homo sapiens

<400> SEQUENCE: 474
gcttggggaa caatgatggt gcacaaaggc ttagatttgc cttgtctcaa aataaggaat 60
tttgtagtgg ttttcaaaaa taattcaaca aagaaacaat acaaaaagtg ggtagaatta 120
cctatcacat ttcccaatct tgactattca gaatgctgtt tatttagtga tgaggattag 180
cacttgattg aagattcttt taaaatacta tcagttaaac atttaatatg attatgatta 240
atgtattcat tatgctacag aactga 266

<210> SEQ ID NO 475
<211> LENGTH: 115
<212> TYPE: DNA
<213> ORGANISM: Homo sapiens

<400> SEQUENCE: 475
cagaaagcca agtggactca acggagaggc cagcaagttt caggaaatgg tgcatttggt 60
gaacaaggag tcgtcagaaa ctccagacca gtttatgaca gctgatgaga caagg 115

<210> SEQ ID NO 476
<211> LENGTH: 262
<212> TYPE: DNA
<213> ORGANISM: Homo sapiens

<400> SEQUENCE: 476
gttcacccgg tgaactattt atgagttctt ttggtgtgaa gaaagggctc atgttgcatt 60
tccagccatt gctacaaaga acctttattt gttcagtaac ggtagaaaat ccttcccgat 120
taaaaacttc agacttgctg aatatcctgc aatgtcaaga tgaccgatgt tgagttgggt 180
ggatttgcta acgagtcaga tttgaacatg aggctattgg aacccaatag gcgtcattga 240
tggcggcaag ccatagcttt ca 262

<210> SEQ ID NO 477
<211> LENGTH: 94
<212> TYPE: DNA
<213> ORGANISM: Homo sapiens

<400> SEQUENCE: 477
ggggagccag gcttccctca cgcagcctgt ggtggatgtg ggaaggagat caacttctcc 60
tcactctggg acagacgatg tatggaaact aaaa 94

<210> SEQ ID NO 478
<211> LENGTH: 114
<212> TYPE: DNA
<213> ORGANISM: Homo sapiens

<400> SEQUENCE: 478
ctgcacagct cagcacaaca ttccaagctc aaaatagaag ccttctcagt gagctccagc 60
acgcccagag gactgttaat aacgatgatc catgtgtttt actctaaagt gcta 114

<210> SEQ ID NO 479
<211> LENGTH: 37
<212> TYPE: DNA
<213> ORGANISM: Homo sapiens

<400> SEQUENCE: 479
cagggactgg ctatcccaag acctggcaga tgtggct 37

<210> SEQ ID NO 480
<211> LENGTH: 74
<212> TYPE: DNA
<213> ORGANISM: Homo sapiens

<400> SEQUENCE: 480
gtgaaaggga agtagaaccg aaacaagatt agtcctgagt taacaatggc tgcaagctgg 60
atacatggaa ttca 74

<210> SEQ ID NO 481
<211> LENGTH: 201
<212> TYPE: DNA
<213> ORGANISM: Homo sapiens

<400> SEQUENCE: 481
tggtgaatgc gtgctgccca ggaccagtga agacagacat ggatgggaaa gacagcatca 60
ggactgtgga ggagggggct gagacccctg tctacttggc cctcttgcct ccagatgcca 120
ctgagccaca aggccagttg gtccatgaca aagttgtgca aaactggtaa acgtctgctt 180
cggagcttgc tgcttaataa a 201

<210> SEQ ID NO 482
<211> LENGTH: 217
<212> TYPE: DNA
<213> ORGANISM: Homo sapiens

<400> SEQUENCE: 482
atgctgtggt tggatcaagg actcattcct gccttggaga aaatacttca accagagcag 60
ggagcctggg ggtgtcgggg caggaggctg gggatggggg tgggatatga gggtggcatg 120
cagctgaggg cagggccagg gctggtgtcc ctaaggttgt acagactctt gtgaatattt 180
gtattttcca gatggaataa aaaggcccgt gtaatta 217

<210> SEQ ID NO 483
<211> LENGTH: 33
<212> TYPE: DNA
<213> ORGANISM: Homo sapiens

<400> SEQUENCE: 483
ttctgtgcct cagccgttct tgacatcaag aat 33

<210> SEQ ID NO 484
<211> LENGTH: 222
<212> TYPE: DNA
<213> ORGANISM: Homo sapiens

<400> SEQUENCE: 484
gacacagtcg ggttgaccca gggctgtctc cctccagagc ctccctccgg acaatgagtc 60
ccccctcttg tctcccaccc tgagattggg catggggtgc ggtgtggggg gcatgtgctg 120
cctgttgtta tgggtttttt ttgcgggggg ggttgctttt ttctggggtc tttgagctcc 180
aaaaaataaa cacttccttt gagggagagc acaccttccc aa 222

<210> SEQ ID NO 485
<211> LENGTH: 278
<212> TYPE: DNA
<213> ORGANISM: Homo sapiens

<400> SEQUENCE: 485
tgagaggcaa gagttgttcc tgcccttccc tttgtgactt gaagaaccct gactttgttt 60
ctgcaaaggc acctgcatgt gtctgtgttc gtgtaggcat aatgtgagga ggtgggggaga 120 gcaccccacc cccatgtcca ccatgaccct cttcccacgc tgacctgtgc tccctctcca 180
atcatctttc ctgttccaga gaggtggggc tgaggtgtct ccatctctgt ctcaacttca 240
tggtgcactg agctgtaact tcttccttcc ctattaaa 278

<210> SEQ ID NO 486
<211> LENGTH: 199
<212> TYPE: DNA
<213> ORGANISM: Homo sapiens
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t

<400> SEQUENCE: 486
aagggagccg ggaggatggg ctgcagctgt ggaggagggt ttcagaggag agaggtcgga 60
gagcagaggc ctgagaagcc agaggcaggt ggagagaggg tggaaagtga gcntnagcgg 120
gncttgggct ggagccgcac acgctctcct cccatgttaa atagcacctt tagaaaaatt 180
cacaagtccc catccacat 199

<210> SEQ ID NO 487

<211> LENGTH: 168
<212> TYPE: DNA
<213> ORGANISM: Homo sapiens

<400> SEQUENCE: 487
aagaaaagga gaagcactac aagcttttga aaaatggaaa gagaaaaaga tggaatatct 60
taaagagaaa aatagaaagg agagagaata tgaaagagca aagaaacaga aagaggagga 120
aactgttgcc gagaaaaaga aagataattt aactgctgtt gagaaatg 168

<210> SEQ ID NO 488
<211> LENGTH: 66
<212> TYPE: DNA
<213> ORGANISM: Homo sapiens

<400> SEQUENCE: 488
ggagaaccac cccaccccca atgtccacca tgaccctctt cccaacgctg aacctgtgct 60
ccctcc 66

<210> SEQ ID NO 489
<211> LENGTH: 185
<212> TYPE: DNA
<213> ORGANISM: Homo sapiens

<400> SEQUENCE: 489
ttgacaggtg ggcccagtga acttttccag taaatgaagc aagcactgaa taaaaacctc 60
ctgaactggg aacaaagatc tacaggcaag caagatgccc acacaacagg cttattttct 120
gtgaaggaac caactgatct cccccaccct tggattagag ttcctgctct accttaccca 180
cagat 185

<210> SEQ ID NO 490
<211> LENGTH: 160
<212> TYPE: DNA
<213> ORGANISM: Homo sapiens

<400> SEQUENCE: 490
gaaaatgggc tcttgacacc aacattgaaa gcaaagcgag gagagctttc caaatacttt 60
cggacccaaa ttgacagcct gtatgagcac atccaggatt aggataaggt acttaagtac 120
ctgccggccc actgtgcact gcttgtgaga aaatggatta 160

<210> SEQ ID NO 491
<211> LENGTH: 239
<212> TYPE: DNA
<213> ORGANISM: Homo sapiens

<400> SEQUENCE: 491
aagaacaact cctcaccagt tcatcctgag gctgggagga ccgggatgct ggattctgtt 60
ttccgaagtc actgcagcgg atgatggaac tgaatcgata cggtgttttc tgtccctcct 120
actttccttc acaccagaca gcccctcatg tctccaggac aggacaggac tacagacaac 180
tctttcttta aataaattaa gtctttacaa taaaaacaca actgcaaagt accttcata 239

<210> SEQ ID NO 492
<211> LENGTH: 244
<212> TYPE: DNA
<213> ORGANISM: Homo sapiens

<400> SEQUENCE: 492
cactcccggg actattgcca agaaggggca agggatgagt caagaaggtg agacccttcc 60

-continued cggtgggcac gtgggccagg ctgtgtgaga tgttggatgt ttggtactgt ccatgtctgg 120
gtgtgtgcct attacctcag catttctcac aaagtgtacc atgtagcatg ttttgtgtat 180
ataaaaggga gggttttttt aaaaatatat tcccagatta tccttgtaat gacacgaatc 240
tgca 244

<210> SEQ ID NO 493
<211> LENGTH: 192
<212> TYPE: DNA
<213> ORGANISM: Homo sapiens

<400> SEQUENCE: 493
agatcatccg ccagcgggaa caacgcgttg gagctctccc agctggagta acagatcctg 60
gaaccaacag ccgacatgtt gcaccttgcc cgcaagtaca aggaccctgg agcacaagtc 120
cccgcccctg ggcccattgg cccccaaccc aatcaaaaat ctttccccca ccttgaggaa 180
gcactgccca aa 192

<210> SEQ ID NO 494
<211> LENGTH: 214
<212> TYPE: DNA
<213> ORGANISM: Homo sapiens

<400> SEQUENCE: 494
ggatcttgat gcctgaaaat cccaagattg gtacttggca aactgaaaga aatctagaaa 60
accctagaga tcaggcatct gtggccagct aactggtcat acaaatggat tgttgtggtg 120
aacttgtata gtattaatcc tgagatgctg tccccctcca cccccacccc cacaaaaaaa 180
ataaataaag tagtattaag ttagcctcat acaa 214

<210> SEQ ID NO 495
<211> LENGTH: 164
<212> TYPE: DNA
<213> ORGANISM: Homo sapiens

<400> SEQUENCE: 495
ccatggcaat gcgggtgact cctttacatg gcacaacggc aagcagttca ccaccctgga 60
cagagatcat gatgtctaca caggaaactg tgcccactac cagaagggag gctggtggta 120
taacgcctgt gcccactcca acctcaacgg ggtctggtac cgcg 164

<210> SEQ ID NO 496
<211> LENGTH: 249
<212> TYPE: DNA
<213> ORGANISM: Homo sapiens
<220> FEATURE:
<221> NAME/KEY: misc_feature
<222> LOCATION: (128)..(128)
<223> OTHER INFORMATION: n is a, c, g, or t

<400> SEQUENCE: 496
attgactatt gactcgtgca tagaatccaa tgctgtaatt agaaagtaat ctgtgactag 60
aatagacctt tgtccctgtt agtagccctg ttgccatgtt caggctttta aaaaatgctt 120
ttgtgtcncc aaatatatct ataaagaaaa caaaatttct gttcagaggc ctctgaaact 180
tggctttctt acatgtggtt ggtttatgtg acaatcccta tgaaatgagt ggacgtatga 240
tttttgaat 249

<210> SEQ ID NO 497

<211> LENGTH: 270
<212> TYPE: DNA
<213> ORGANISM: Homo sapiens

<400> SEQUENCE: 497
ctctcttcct tcctgctatt gactactgtg cagactcagc tggattttag ataatcttta 60
taatatcaca atggtttcca tggagatgga tcatgatgtc acaaaagtag atatatattc 120
tttggatact gaaaaatcaa agggcaatag agggaggaag agaagaattt tcaaactggt 180
atatagagga gggggaaatc tagagaacag gaaagaaaac taagaaaggg tgtgagtgaa 240
acagagaaat ggctattcaa aggctattca 270

<210> SEQ ID NO 498
<211> LENGTH: 256
<212> TYPE: DNA
<213> ORGANISM: Homo sapiens

<400> SEQUENCE: 498
tgtggaccag aaacaggcca ctctccctgc tgcaggtgtt gcttagcaat caaaaagcaa 60
atcctctttc taactgggct gtgccacagt taaagtttca taaacctaac catgctctgc 120
ccacctttag aggaggaagt taaactcagc cctaaaaaaa ttatagaaaa gtacacatct 180
gctaataaaa ttggttgata tggtatttca ataaaggctc agtttaaaaa ccagcgctta 240
aggcagtata atctct 256

<210> SEQ ID NO 499
<211> LENGTH: 229
<212> TYPE: DNA
<213> ORGANISM: Homo sapiens

<400> SEQUENCE: 499
ataggggcct caattcagcc cttgacagtg tggttcagga atgcagttcc aaaatacact 60
catgttacct aagccttgag ttcctcaggt gggcctctga gggccagcag ggaagacaag 120
gtcagccagc tttaggcttg ggtgtggact tggtggccac cattactagt ttaataagat 180
cttactggtg gcttaggcaa gttggctgtt cctcaggagg ttattggca 229

<210> SEQ ID NO 500
<211> LENGTH: 210
<212> TYPE: DNA
<213> ORGANISM: Homo sapiens

<400> SEQUENCE: 500
cctcacattg aggaacactg cttatcaaga gtttcaggag accccaacgt tgagaattca 60
gttctgagcc atcccaactt cttaggattg ttgtgcggtg gttaaaactt tcttgttaag 120
agtttttgag atctttggac gaaaggtttc tggataaatt tatatcacaa attagtaagg 180
gtttcatagt aaggtggctt tcttttccct 210

<210> SEQ ID NO 501
<211> LENGTH: 289
<212> TYPE: DNA
<213> ORGANISM: Homo sapiens

<400> SEQUENCE: 501
aacagtcatt ctgtcgttat ccacccaatt ttcaaaatca agccccatgt aaatagtcat 60
ttccataaat cctgtcaaga aaattaattt ttagggtaca gtcattggtt ttattgtagt 120
cctcctaatc ctgtgtgaca tagatccttt ggaaagttgg tgctaccagt tgggaagtgc 180
cccagcaggc cccgtggttg tctggctttg ttgactgtct gaatgcaaca cgttgacaat 240
gggttagctg ctttggtttt agggttattc tccttatgcc tcatgcaaa 289

<210> SEQ ID NO 502
<211> LENGTH: 198
<212> TYPE: DNA
<213> ORGANISM: Homo sapiens

<400> SEQUENCE: 502
aaatcctctt tctaactggg ctgtgccaca gttaaagttt cataaaccta accatgctct 60
gcccaccttt agaggaggaa gttaaactca gccctaaaaa aattatagaa aagtacacat 120
ctgctaataa aattggttga tatggtattt caataaaggc tcagtttaaa aaccagcgct 180
taaggcagta taatctct 198

<210> SEQ ID NO 503
<211> LENGTH: 172
<212> TYPE: DNA
<213> ORGANISM: Homo sapiens

<400> SEQUENCE: 503
gttaacttac ttaaagtcat gtcgcaagaa agatcaaacc catgaatgct tagtagctaa 60
ggctagtgtt caaaagcact ttaaaagaca ttttgtccac attttggaaa agaaaatatt 120
tgcatgttta attcataatt taggctatct ttgagtatac tgtaaagtgc tg 172

<210> SEQ ID NO 504
<211> LENGTH: 220
<212> TYPE: DNA
<213> ORGANISM: Homo sapiens

<400> SEQUENCE: 504
aaggataaac aaggcctgcg tccagacaga gttgtttctc tgaaacattg ctggcttctt 60
ctgagtttga ttcagctgtt ctctgatgaa attcagggaa aacttgcctt cagagatatc 120
tctcaaattt tactaatctt cagctttagt tggtcaacat tcattccaca aatatcaatt 180
gaactcctac tgtgggcctg gtggtggtct gagtgctgaa 220

<210> SEQ ID NO 505
<211> LENGTH: 205
<212> TYPE: DNA
<213> ORGANISM: Homo sapiens

<400> SEQUENCE: 505
aacaaagtta tgttctagta tggttttaaa agtcttccct tttggttatt tggaaaatag 60
tgcaaacgtg cggtctagtg gttatggcca aaggcagagc aaagggagtg cggccttagc 120
cagccccagc cagctgccat tgctcccacg ctctgtgtgg tcttgaccca atgcccagaa 180
aagcaaggtt ccccactttc tacct 205

<210> SEQ ID NO 506
<211> LENGTH: 177
<212> TYPE: DNA
<213> ORGANISM: Homo sapiens

<400> SEQUENCE: 506
aattcacttg gcctgcaaac aacagagtta tccgtatttt ccacatgtga atgtcattgc 60
aagggtgact ctagacaaac tacaaaccga tggaccgtca agctccccag gagccccttg 120

-continued gatggcagcg ttgcttcaga gtgtttcctg tttctggaat tccttgttag ggaactt 177

<210> SEQ ID NO 507
<211> LENGTH: 168
<212> TYPE: DNA
<213> ORGANISM: Homo sapiens

<400> SEQUENCE: 507
cagctttcag acagagccca cttagcttgt ccacatggat ttcaatgcca atcctccatt 60
tttcctctcc agatattttt gggagtgaca aacattcttt catcctactt agcctaccta 120
gatttttcat gacgagttaa tgcatgtccg tggttgggtg cacctgta 168

<210> SEQ ID NO 508
<211> LENGTH: 42
<212> TYPE: DNA
<213> ORGANISM: Homo sapiens

<400> SEQUENCE: 508
tcatgacgag ttaatgcatg tccgtggttg ggtgcacctg ta 42

<210> SEQ ID NO 509
<211> LENGTH: 250
<212> TYPE: DNA
<213> ORGANISM: Homo sapiens

<400> SEQUENCE: 509
gatttctcat gacgagttaa tgcatgtccg tggttgggtg cacctgtagt tctgtttatt 60
ggtcagtgga aatgaaaaaa aaaaaaaaaa aaagtctgcg ttcattgcag ttccagtttc 120
tcttccattc tgtgtcacag acaccaacac accactcatt ggaaaatgga aaaaaaaaac 180
aaaaaaaaaa caaaaaaatg tacaatggat gcattgaaat tatatgtaat tgtataaatg 240
gtgcaacagt 250

<210> SEQ ID NO 510
<211> LENGTH: 225
<212> TYPE: DNA
<213> ORGANISM: Homo sapiens

<400> SEQUENCE: 510
ttctttctgg cccagttaat ttgcacagaa cttttctcag tttggtattt tttactgctt 60
ggagatccag aagagaatta gaaacaacat agcaaattaa aataggtttg tcaataatag 120
agctcagaca cctgtgtgct gtagattcac atacaggccg tgaacctaag tggggaaaat 180
cctacctatc caccttctgg ctagattacc tagcttagtg aaaag 225

<210> SEQ ID NO 511
<211> LENGTH: 210
<212> TYPE: DNA
<213> ORGANISM: Homo sapiens

<400> SEQUENCE: 511
cctacagaca cccatcgggt gggtaggagg aacagatttg agaaatgggc aggagatgta 60
ggaggggaac taggttaccg cttatcagat ggcataaatt ttcaaggaga atcaaaatgc 120
aaaacttggg aataaatcat agcaatatca taattaatgt agtagtaata ttgctgttta 180
ttaatgctga agtgtggttt tcctaactgt 210

<210> SEQ ID NO 512
<211> LENGTH: 197

<212> TYPE: DNA
<213> ORGANISM: Homo sapiens

<400> SEQUENCE: 512
gggatgtacc tgaaacctag tgagagtcat cctgactctg gggaagagcc gttcaaagat 60
gagaaagata aagtaatttg ccaccccaa cccctcacag gctagactat ccatggattt 120
cagtggggtg gtgagtcctc atgatccctg aacctctcct caaatggtga ctgttctggg 180
ggtcctttct ctgcctt 197

<210> SEQ ID NO 513
<211> LENGTH: 261
<212> TYPE: DNA
<213> ORGANISM: Homo sapiens

<400> SEQUENCE: 513
tcttttccat acactgtgtg ctatttgtgt taacatggaa gaggattcat tgtttttatt 60
tttatttttt taattttttc ttttttatta agctagcatc tgccccagtt ggtgttcaaa 120
tagcacttga ctctgcctgt gatatctgta tcttttctct aatcagagat acagaggttg 180
agtataaaat aaacctgctc agataggaca attaagtgca ctgtacaatt ttcccagttt 240
acaggtctat acttaaggga a 261

<210> SEQ ID NO 514
<211> LENGTH: 253
<212> TYPE: DNA
<213> ORGANISM: Homo sapiens

<400> SEQUENCE: 514
gggcattcaa agttatcctt tggataatga tgatttaaaa ctttctttta ttatcccatg 60
tgctcagagt aaggggcaaa tgaatcagtt gtgaaatatg tgttccttgt aggacacagg 120
cactcttgag atctatagct tcaataaaaa ggtaatttat ttaaattact gcctctttaa 180
tttataatgt tttggggatt tttaataggc atgctctgta agggcactgg taatcagctg 240
tttctgattt tac 253

<210> SEQ ID NO 515
<211> LENGTH: 38
<212> TYPE: DNA
<213> ORGANISM: Homo sapiens

<400> SEQUENCE: 515
tgctgtaatt aagaaagcag tgtaaggctg ggcgcagt 38

<210> SEQ ID NO 516
<211> LENGTH: 219
<212> TYPE: DNA
<213> ORGANISM: Homo sapiens

<400> SEQUENCE: 516
atgtctcgcc gcaagcaagg caaaccccaa cacttaagca aacgggaatt ctcgcccgag 60
cctcttgaag ccattcttac agatgatgaa ccagaccacg gcccgttggg agctccagaa 120
ggggatcatg acctcctcac ctgtgggcag tgccagatga acttcccata gggggacatt 180
cttattttta tcgagcacaa acggaaacaa tgcaatggc 219

<210> SEQ ID NO 517
<211> LENGTH: 253
<212> TYPE: DNA

<213> ORGANISM: Homo sapiens

<400> SEQUENCE: 517
agcctaggcc tgcagcgcca ttttatttat attttttaat aaaaagtaaa aacaaaaaaa 60
cagacccaca ttggaacagt gaatcagtcc catagagagg gcccgtggac catcgctgtc 120
atgagtgatg ccctggccct tttgaaacca gccaacctaa ttacctgtat tgtggaaatg 180
cgcatgagtc cccaacccct tgtttctata cattctatgt tgtcttttaa aaagtgtgct 240
taacattgac aca 253

<210> SEQ ID NO 518
<211> LENGTH: 298
<212> TYPE: DNA
<213> ORGANISM: Homo sapiens

<400> SEQUENCE: 518
tttagcatct tggagccgtg tcagctgcag agactggagt ccggggcatg atggggatgt 60
acctgaaacc tagtgagagt catcctgact ctggggaaga gccgttcaaa gatgagaaag 120
ataaagtaat ttgccacccc caacccctca caggctagac tatccatgga tttcagtggg 180
gtggtgagtc ctcatgatcc ctgaacctct cctcaaatgg tgactgttct gggggtcctt 240
tctctgcctt tctcaggggg taaccagagg tggtggtgtg gtccactgtg actcgtca 298

<210> SEQ ID NO 519
<211> LENGTH: 259
<212> TYPE: DNA
<213> ORGANISM: Homo sapiens
<220> FEATURE:
<221> NAME/KEY: misc_feature
<222> LOCATION: (143)..(144)
<223> OTHER INFORMATION: n is a, c, g, or t

<400> SEQUENCE: 519
aatgaaagct gtttgtcgta acttgaaatt ttatctttta ctatgggagt cactatttat 60
tattgcttat gtgccctgtt caaaacagag gcacttaatt tgatctttta tttttctttg 120
tttttatttt tttttttatt tanntgacca aaggtcatta caacctggct ttttattgta 180
tttgtttctg gtctttgtta agttctattg gaaaaaccac tgtctgtgtt tttttggcag 240
ttgtctgcat taacctgtt 259

<210> SEQ ID NO 520
<211> LENGTH: 192
<212> TYPE: DNA
<213> ORGANISM: Homo sapiens
<220> FEATURE:
<221> NAME/KEY: misc_feature
<222> LOCATION: (135)..(135)
<223> OTHER INFORMATION: n is a, c, g, or t

<400> SEQUENCE: 520
tgggactaga ggaaggactt aaactcatac ctaacttcac cttttgatct tgatgcccct 60
gggtgtgtag tgccagtcct gagcccttgg tcatggggcc tttcctgtac cctcaggacc 120
cctgactcat ggctncccca ccccccaacc ccatgccatt gccaattctc taaatgcatt 180
cacaaacaca aa 192

<210> SEQ ID NO 521
<211> LENGTH: 136
<212> TYPE: DNA
<213> ORGANISM: Homo sapiens

<400> SEQUENCE: 521
tgcatgcttc caatttaaga ggtataaaat agtccttcga tgtggttttt attttgcctt 60
tctttgactg tgaatgacct tggccatttc ctcatatttt ttggttattg tatttgcact 120
tgcacacctt gtctct 136

<210> SEQ ID NO 522
<211> LENGTH: 33
<212> TYPE: DNA
<213> ORGANISM: Homo sapiens

<400> SEQUENCE: 522
aggtgatgcc tggcttgaca cttctggtaa ctc 33

<210> SEQ ID NO 523
<211> LENGTH: 243
<212> TYPE: DNA
<213> ORGANISM: Homo sapiens

<400> SEQUENCE: 523
aggattgagc gcagggagca aatcattcag gaaatatgga tgaacagtgg tttggacacc 60
tcgctcccaa gaaacatggg ccagttttac tgaaaaccac atgcatcttg atgcgatcgc 120
actttttgaa gaaggaagga tcccaaatgc ccctccagtt ttggttcacc tgtaccttct 180
atgaaggaga attcgtcatg tcattcaaca ctcgtgaggc caggaagcta ttaaagggat 240
gtt 243

<210> SEQ ID NO 524
<211> LENGTH: 174
<212> TYPE: DNA
<213> ORGANISM: Homo sapiens

<400> SEQUENCE: 524
aaacaaaaca aaaggctggg cgcggtgact cacgcttgta atcccagcac tttgggaggc 60
ctaggcaggc agatcacctg aggccaggag ttcgagacca gcctggccaa catagtgaaa 120
gtctctacta aaaatacaaa aattagccgg atgtggtggc agtcacctgt aatc 174

<210> SEQ ID NO 525
<211> LENGTH: 51
<212> TYPE: DNA
<213> ORGANISM: Homo sapiens

<400> SEQUENCE: 525
cagcctccaa cacaaggctc caagacctag gctcatggac gagatgggaa g 51

<210> SEQ ID NO 526
<211> LENGTH: 208
<212> TYPE: DNA
<213> ORGANISM: Homo sapiens

<400> SEQUENCE: 526
ttggccttgg cttttctagc ctatttacct gcaggctgag ccactctttt ccctttcccc 60
agcatcactc cccaaggaag agccaatgtt ttccacccat aatcctttct gccgacccct 120
agttcccttt gctcagccaa gcttgttatc agctttcagg gccatggttc acattagaat 180
aaaaggtagt aattagaaca ctttgcaa 208

<210> SEQ ID NO 527

<211> LENGTH: 211
<212> TYPE: DNA
<213> ORGANISM: Homo sapiens

<400> SEQUENCE: 527
accgaaagta ctgaccaagt gccaggaaga ggtcagccac atccctgctg tccacccggg 60
ttcattcagg cccaagtgcg acgagaacgg caactatctg ccactccagt gctatgggag 120
catcggctac tgctggtgtg tcttccccaa cggcacggag gtccccaaca ccagaagccg 180
cgggcaccat aactgcagtg agtcactgga a 211

<210> SEQ ID NO 528
<211> LENGTH: 285
<212> TYPE: DNA
<213> ORGANISM: Homo sapiens

<400> SEQUENCE: 528
caagacctag gctcatggac gagatgggaa ggcacaggga gaagggataa ccctacaccc 60
agaccccagg ctggacatgc tgactgtcct ctcccctcca gcctttggcc ttggcttttc 120
tagcctattt acctgcaggc tgagccactc tcttcccttt ccccagcatc actccccaag 180
gaagagccaa tgttttccac ccataatcct ttctgccgac ccctagttcc ctctgctcag 240
ccaagcttgt tatcagcttt cagggccatg gttcacatta gaata 285

<210> SEQ ID NO 529
<211> LENGTH: 224
<212> TYPE: DNA
<213> ORGANISM: Homo sapiens

<400> SEQUENCE: 529
tcagtgcacg atgctccagc cacactggcc atctttcggt tcctgataca aaaaaaaaca 60
cgttcctttt ccatggaaag caggtcaccc ttgttatttt gtatcgatga caactcttta 120
aacttatttt gctttttggc tttatgtatg tgtgtgggtg ggtgggactg actgccccac 180
tagaatgtaa gctccatgag ggcagggaat cttgctttct tgtt 224

<210> SEQ ID NO 530
<211> LENGTH: 267
<212> TYPE: DNA
<213> ORGANISM: Homo sapiens

<400> SEQUENCE: 530
ggaggcagac aatgacccca cggctcctcc ttatgactcc attcaaatct acggttatga 60
aggcaggggc tcagtggccg ggtccctgag ctccctagag tcggccacca cagattcaga 120
cttggactat gattatctac agaactgggg acctcgtttt aagaaactag cagatttgta 180
tggttccaaa gacacttttg atgacgattc ttaacaataa cgatacaaat ttggccttaa 240
gaactgtgtc tggcgttctc aagaatc 267

<210> SEQ ID NO 531
<211> LENGTH: 257
<212> TYPE: DNA
<213> ORGANISM: Homo sapiens

<400> SEQUENCE: 531
ttgttactgc tgattcttgt aaatcttttt gcttctactt tcatcttaaa ctaatacgtg 60
ccagatataa ctgtcttgtt tcagtgagag acgccctatt tctatgtcat ttttaatgta 120
tctatttgta caattttaaa gttcttattt tagtatacgt ataaatatca gtattctgac 180
atgtaagaaa atgttacggc atcacactta tattttatga acattgtact gttgctttaa 240
tatgagcttc aatataa 257

<210> SEQ ID NO 532
<211> LENGTH: 256
<212> TYPE: DNA
<213> ORGANISM: Homo sapiens

<400> SEQUENCE: 532
actgcattgc tggaccctct gtgaaactga agccttctct acttgttttt atctcaagtg 60
aacctggaga agcaacaata atggaccttc tcccctagtc aaatagcctg tggacctccc 120
ctcatagtca gtctccaaaa acatgtatct ggaattaatt tattacaaag agaagtttag 180
tgtttcttct tttttacatg cgctcaatac tgactactgg ccagacacag caccatcctc 240
ttacaaacat catttc 256

<210> SEQ ID NO 533
<211> LENGTH: 260
<212> TYPE: DNA
<213> ORGANISM: Homo sapiens

<400> SEQUENCE: 533
cttgaacatg ggaaggagtt gttgcagtaa gccaagatgt gccactgtac tccagcctgg 60
gagacagagt gagactctgt ctcaaaaaat gaatgaataa ataaataaat aaataataaa 120
aaagatgatt attaacaatg ccagttaata ttaacaatat taatagtatt atttattact 180
aatgccattt tttcattttt gttaaagtat ttttattatt ttagtttaaa ttattattat 240
gagacaaagg cctccatttc 260

<210> SEQ ID NO 534
<211> LENGTH: 273
<212> TYPE: DNA
<213> ORGANISM: Homo sapiens

<400> SEQUENCE: 534
ccttgaaaag cagtgtcaga gcagaattat aaggcatttt taatattccc tgttttaata 60
aaactttttt tatgtttgat ttttttttat attttttgtc cgcacgtata tagatgtgga 120
tacataacat ttaacacggt tgcaatcaga gggtgatttg atttgttaac ttaatgtcac 180
atcataaaca ttttacatgc tgttatataa tgtacataat catttttaat gactacataa 240
catcccatcc tattgacgaa tcattatgtc ctt 273

<210> SEQ ID NO 535
<211> LENGTH: 240
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (163)..(163)
<223> OTHER INFORMATION: n is a, c, g, or t

<400> SEQUENCE: 535
aagtatacag ctgtaagtaa ccctgtcncc atggatgatc cttttctcta ggaatgtatt 60
tggattagag atgacaacta cattttcgca tttttatgtt gaagtctttt ttaaaaaggc 120

-continued tgtttacttt tcagtagtta agaatacttg tttttctttt tcnttttttt ttttttttaac 180 cttttatttt ttcgttaagc ctctattgtt tgtagaacac tcttagaaac ttggaaataa 240

<210> SEQ ID NO 536
<211> LENGTH: 221
<212> TYPE: DNA
<213> ORGANISM: Homo sapiens

<400> SEQUENCE: 536
ggcagccctg acgtgatgag ctcaaccagc agagacattc catcccaaga gaggtctgcg 60
tgacgcgtcc gggaggccac cctcagcaag accaccgtac aattggtgga aggggtgaca 120
gctgcattct cctgtgccta ccacgtaacc aaaaatgaag gagaactact gtttacaagc 180
cgccctggtg tgcctgggca tgctgtgcca cagccatgcc t 221

<210> SEQ ID NO 537
<211> LENGTH: 129
<212> TYPE: DNA
<213> ORGANISM: Homo sapiens

<400> SEQUENCE: 537
gatccagaac tgtggctggg caccgtggct cacatctgta atctcatcac tttgggaagg 60
ctaaggcggg tggatcacct aaggtaagga gttcgaaccc agcctttaca atgtaatgaa 120
accctgcct 129

<210> SEQ ID NO 538
<211> LENGTH: 108
<212> TYPE: DNA
<213> ORGANISM: Homo sapiens

<400> SEQUENCE: 538
ggtggaagac cagtaattgc tggaagactg gatttgctgg aagacttgat ttactggaag 60
acttggagct tcttggaaga catggattgt ccggaagaca tggattgt 108

<210> SEQ ID NO 539
<211> LENGTH: 45
<212> TYPE: DNA
<213> ORGANISM: Homo sapiens

<400> SEQUENCE: 539
ggaggagtga gtccctatgc tgaccccaat acttgcagag gtgat 45

<210> SEQ ID NO 540
<211> LENGTH: 106
<212> TYPE: DNA
<213> ORGANISM: Homo sapiens

<400> SEQUENCE: 540
tttaggtcag ttaagacgca agcaggaaca gccatgcttc caggattagg aattttactg 60
aatgatccat ggcaccccac tgcctctgca ggttggtgta atcagc 106

<210> SEQ ID NO 541
<211> LENGTH: 48
<212> TYPE: DNA
<213> ORGANISM: Homo sapiens

<400> SEQUENCE: 541
atgtttttta ccaaatgatc ggtagggaga tacaagggaa taaagaac 48

<210> SEQ ID NO 542
<211> LENGTH: 70
<212> TYPE: DNA
<213> ORGANISM: Homo sapiens

<400> SEQUENCE: 542
cctgccagaa tctgccgccc ctccatcttc tacctctgaa tggccaccct tagaccctgt 60
gatccatcct 70

<210> SEQ ID NO 543
<211> LENGTH: 56
<212> TYPE: DNA
<213> ORGANISM: Homo sapiens

<400> SEQUENCE: 543
tcctttgtac tggaggagtg agtccctatg ctgaccccaa tacttgcaga ggtgat 56

<210> SEQ ID NO 544
<211> LENGTH: 223
<212> TYPE: DNA
<213> ORGANISM: Homo sapiens

<400> SEQUENCE: 544
caaggtcagc gtaggtaagg atgcaactga aggtcctggg ctgcacctat gctctccagg 60
caacacctcc cactttctac agatcctaca ctccacccat cctcaatgca gccccattcc 120
ttgcacccca gaccagtcag ggatggggga agacgtgaag ttaggaatga cacggggcca 180
gaggcaggaa gctgcccaca aagaggtggt acctactctc cta 223

<210> SEQ ID NO 545
<211> LENGTH: 106
<212> TYPE: DNA
<213> ORGANISM: Homo sapiens

<400> SEQUENCE: 545
tttaggtcag ttaagacgca agcaggaaca gccatgcttc caggattagg aattttactg 60
aatgatccat ggcaccccac tgcctctgca ggttggtgta atcagc 106

<210> SEQ ID NO 546
<211> LENGTH: 209
<212> TYPE: DNA
<213> ORGANISM: Homo sapiens

<400> SEQUENCE: 546
catcctcatg actgatggat tgcacaacat gggcggggac ccaattactg tcattgatga 60
gatccgggac ttgctataca ttggcaagga tcgcaaaaac ccaagggagg attatttgga 120
tgtttatgtg tttggggtcg ggcctttggt gaaccaagtg aacatcaatg ctttggcttc 180
caagaaagac aatgagcaac atgtgttca 209

<210> SEQ ID NO 547
<211> LENGTH: 201
<212> TYPE: DNA
<213> ORGANISM: Homo sapiens

<400> SEQUENCE: 547
ctcccagtgg attcactgtc cacggcctcc caacatctcc agaccggcca ggctccacca 60
gccccttcgc tccatcagcc actgacctgc ccagcatgcc tgaacctgcc ctgacctccc 120
gagcaaacat gacagagcac aagacgtccc ccacccaatg cccggcagct ggagaggtct 180
ccaacaagct tccaaaatgg c 201

<210> SEQ ID NO 548
<211> LENGTH: 292
<212> TYPE: DNA
<213> ORGANISM: Homo sapiens

<400> SEQUENCE: 548
acagtgttgt atgaggtttg aggattttga tccaagctgg tcccactcag tccatagcag 60
agaatgaaag ggcccagaga gggtggtgac ctctgcctga agtcacacag tgagtcgagg 120
acagggaggt gaccccaggt ttctatgtgt agggcgggag gatgttttgg gacacagttc 180
aattctcatt tgtcacacac tttggctatt agagatcaac cccttcgctc ctgtgtcttg 240
caatggcagc cttggcaaac gctaaatgaa aatcgtgaca acacttgtgt ta 292

<210> SEQ ID NO 549
<211> LENGTH: 94
<212> TYPE: DNA
<213> ORGANISM: Homo sapiens

<400> SEQUENCE: 549
aattcaaagc gctcagaaag tattagctca ataagtgatg actgtgtgcc agacactgtg 60
ctaaactcct actcaagagg gataagagtc tagg 94

<210> SEQ ID NO 550
<211> LENGTH: 266
<212> TYPE: DNA
<213> ORGANISM: Homo sapiens

<400> SEQUENCE: 550
taacatgttg gctgtcatta ttacatatat ctgtgtttca ttcttgcctc tggctggaat 60
gttcttccca gctctccata tggctgattt ctcatccttc gggacttgcc ccattctcca 120
accccatcac tagttttatc tttttcactt atttatgcag tctgctcttg tcctaggaca 180
tgagctccag gagggcggga aacatctcgc tttgtacact gctgtgccct ctgtacccag 240
caaggcgcct gtgtataata ggtgct 266

<210> SEQ ID NO 551
<211> LENGTH: 112
<212> TYPE: DNA
<213> ORGANISM: Homo sapiens

<400> SEQUENCE: 551
ggaaaccgga tgagaggaaa gacctggaag ctattgtaaa atctatgctg agggtctggt 60
gactactaga ccaagggcat ggcagcagag ggcagctgaa agacttcagg aa 112

<210> SEQ ID NO 552
<211> LENGTH: 90
<212> TYPE: DNA
<213> ORGANISM: Homo sapiens

<400> SEQUENCE: 552
gggtttgagt tcataccctg ttaccatttt ggggtaccca ctgctctggt tatctaatat 60
gtaacaagcc accccaaatc atagtggctt 90

<210> SEQ ID NO 553
<211> LENGTH: 277
<212> TYPE: DNA
<213> ORGANISM: Homo sapiens

<400> SEQUENCE: 553
agacaccttg acagggcaca ccgggcactc agaagacact gatgggcaac ccccagcctg 60
ctaattcccc agattgcaac aggctgggct tcagtggcag ctgcttttgt ctatgggact 120
caatgcactg acattgttgg ccaaagccaa agctaggcct ggccagatgc accagccctt 180
agcagggaaa cagctaatgg gacactaatg gggcggtgag aggggaacag actggaagca 240
cagcttcatt tcctgtgtct tttttcacta cattata 277

<210> SEQ ID NO 554
<211> LENGTH: 289
<212> TYPE: DNA
<213> ORGANISM: Homo sapiens

<400> SEQUENCE: 554
tccaaatggt cacttttcct cgcaggcctc tctttgcata caaatgtctc cctcctgacg 60
ctcacctttt tccctggggc tctcaaatgt cttcttttca gatttcgtag cttttctttc 120
tttagcatca cttgagggca agtggtgctc caactgtctc cccccagagt tttgccgcct 180
gtactttccc acacctcagt ctcctcgcct gtagaaaggg gtcaatcgtt tgaaccctgc 240
ttcacttggt gtgtatgtga aggtgctttg aaatcaagtg ctttgcaaa 289

<210> SEQ ID NO 555
<211> LENGTH: 211
<212> TYPE: DNA
<213> ORGANISM: Homo sapiens

<400> SEQUENCE: 555
gaaaaaactt tctctttgcc atttcttctt cttctttttt aactgaaagc tgaatccttc 60
catttcttct gcacatctac ttgcttaaat tgtgggcaaa agagaaaaag aaggattgat 120
cagagcattg tgcaatacag tttcattaac tccttccctc gctcccccaa aaatttgaat 180 tttttttca acactcttac acctgttatg g 211

<210> SEQ ID NO 556
<211> LENGTH: 130
<212> TYPE: DNA
<213> ORGANISM: Homo sapiens

<400> SEQUENCE: 556 tctttttca gaatctatta aggacacttg aaagttttga aatttttggt aaatttggac 60
taccatgagg aaacttttga gattcaagtt cattctattc agagcaattc cgatattgat 120
gttaacttga 130

<210> SEQ ID NO 557
<211> LENGTH: 233
<212> TYPE: DNA
<213> ORGANISM: Homo sapiens

<400> SEQUENCE: 557
caattttgtg cctaaattgc acattagaag atggattgat tggacacatc catgtaattc 60
aaagttatta ttcaaatttg acttaattgg taatcattga aaaaactgac taatgtcatt 120
tagtgtgaag gagcactggc cagctatatg ccacactcat acatatgcat tttcagaatg 180
tgagcagctt ttctgaattt ttaatcaaac cttttcacca actttactga atg 233

<210> SEQ ID NO 558

<211> LENGTH: 152
<212> TYPE: DNA
<213> ORGANISM: Homo sapiens

<400> SEQUENCE: 558
gtaaatcact gtaaacgtgt cttcatttac tctagccaaa aggcctggct tctgatagga 60
aactggtaag aaactcttca tgaaaacaca tcactaatat tcgctattac tctcctggtc 120
tgaagtcagc ttttctgaac cattaaggta tt 152

<210> SEQ ID NO 559
<211> LENGTH: 175
<212> TYPE: DNA
<213> ORGANISM: Homo sapiens

<400> SEQUENCE: 559
gagttgtatc gtgtggtgta ttttttaaaa aatttgattt agcattcata ttttccattt 60
tattcccaat taaaagtatg cagattattt gcccaaagtt gtcctttttt tcagattcag 120
catttgtttt ttgccagttt cattttcatt tttttccatg gttccacaga agctt 175

<210> SEQ ID NO 560
<211> LENGTH: 226
<212> TYPE: DNA
<213> ORGANISM: Homo sapiens

<400> SEQUENCE: 560
taaaggtggt ttggcctcta atttaatttt gattcagact ctcctgtcag gactcaagaa 60
aatttaatta attaccaagg attaagtttt ttggttaagg tttttgggaa aaaaaaatag 120
caaagatgtt gatttcttgg aatcctttta caggttcata acagaaaaat cttcattccc 180
tgtaggcatt taattaaacc tagttgagaa gtgtgtggga ttcctc 226

<210> SEQ ID NO 561
<211> LENGTH: 270
<212> TYPE: DNA
<213> ORGANISM: Homo sapiens

<400> SEQUENCE: 561
ctgttccttt cctgggttcc aattttgtgc ctaaattgca cattagaaga tggattgatt 60
ggacacatcc atgtaattca aagttattat tcaaatttga cttaattggt aatcattgaa 120
aaaactgact aatgtcattt agtgtgaagg agcactggcc agctatatgc cacactcata 180
catatgcatt ttcagaatgt gagcagcttt tctgaatttt taatcaaacc ttttcaccaa 240
ctttactgaa tgcctactgg aattccataa 270

<210> SEQ ID NO 562
<211> LENGTH: 215
<212> TYPE: DNA
<213> ORGANISM: Homo sapiens

<400> SEQUENCE: 562
caaggccctg ctgtaagtat gatttgggga aataataaag aagatcacgg acctaggaat 60
gttttcttca gactaaacca agacaacttt gacaacccat taagttagcc ccatttcaat 120
atatcctcta aaatatctgg aaattgtcta aatgcaatgg gctgtaagtc catccctgca 180
gtgggcctgg gggctcgtta tttatttatg gtgaa 215

<210> SEQ ID NO 563
<211> LENGTH: 181

<212> TYPE: DNA
<213> ORGANISM: Homo sapiens

<400> SEQUENCE: 563
gagttgtatc gtgtggtgta ttttttaaaa aatttgattt agcattcata ttttccatct 60
tattcccaat taaaagtatg cagattattt gcccaaatct tcttcagatt cagcatttgt 120
tctttgccag tctcattttc atcttcttcc atggttccac agaagctttg tttcttgggc 180
a 181

<210> SEQ ID NO 564
<211> LENGTH: 225
<212> TYPE: DNA
<213> ORGANISM: Homo sapiens

<400> SEQUENCE: 564
ttttctgcac atttacttgc ttaaattgtg ggcaaaagag aaaaagaagg attgatcaga 60
gcattgtgca atacagtttc attaactcct tccctcgctc ccccaaaaat ttgaattttt 120
ttttcaacac tcttacacct gttatggaaa atgtcaacct ttgtaagaaa accaaaataa 180
aaattgaaaa ataaaaacca taaacatttg ccaactttct tgtac 225

<210> SEQ ID NO 565
<211> LENGTH: 211
<212> TYPE: DNA
<213> ORGANISM: Homo sapiens

<400> SEQUENCE: 565
gaaaaaactt tctctttgcc atttcttctt cttctttttt aactgaaagc tgaatccttc 60
catttcttct gcacatctac ttgcttaaat tgtgggcaaa agagaaaaag aaggattgat 120
cagagcattg tgcaatacag tttcattaac tccttccccc gctcccccaa aaatttgaat 180 tttttttca acactcttac acctgttatg g 211

<210> SEQ ID NO 566
<211> LENGTH: 68
<212> TYPE: DNA
<213> ORGANISM: Homo sapiens

<400> SEQUENCE: 566
ctggaaaaga tggtcgcact ggacatcctg gtacagttgg acctgctggc attcgaggcc 60
ctcagggt 68

<210> SEQ ID NO 567
<211> LENGTH: 83
<212> TYPE: DNA
<213> ORGANISM: Homo sapiens

<400> SEQUENCE: 567
taataacatg gcacgatgaa tgcttcttta gagtaaaaag gttttcttta acttgttaag 60
tcagagttgt ctaagtaatt gta 83

<210> SEQ ID NO 568
<211> LENGTH: 275
<212> TYPE: DNA
<213> ORGANISM: Homo sapiens

<400> SEQUENCE: 568
gttatggtgc taatgtactt tcacttttaa actctagatc agaattgttg acttgcattc 60
agaacataaa tgcacaaaat ctgtacatgt ctcccatcag aaagattcat tggcatgcca 120
caggggattt tcctccttca tcctgtaaag gtcaacaata aaaaccaaat tatggggctg 180
cttttgtcac actagcatag agaatgtgtt gaaatttaac tttgtaagct tgtatgtggt 240
tgttgatctt ttttttcctt acagacaccc ataat 275

<210> SEQ ID NO 569
<211> LENGTH: 65
<212> TYPE: DNA
<213> ORGANISM: Homo sapiens

<400> SEQUENCE: 569
ttaactccat atgtgttcct cttgttttaa ttttgtcaac cagtgcaagt gaccgacaaa 60
attcc 65

<210> SEQ ID NO 570
<211> LENGTH: 286
<212> TYPE: DNA
<213> ORGANISM: Homo sapiens

<400> SEQUENCE: 570
taaagacgca tgttatggtg ctaatgtact ttcactttta aactctagat cagaattgtt 60
gacttgcatt cagaacataa atgcacaaaa tctgtacatg tctcccatca gaaagattca 120
ttggcatgcc acaggggatt ctcctccttc atcctgtaaa ggtcaacaat aaaaaccaaa 180
ttatggggct gcttttgtca cactagcata gagaatgtgt tgaaatttaa ctttgtaagc 240
ttgtatgtgg ttgttgatct ttttttttcct tacagacacc cataat 286

<210> SEQ ID NO 571
<211> LENGTH: 111
<212> TYPE: DNA
<213> ORGANISM: Homo sapiens

<400> SEQUENCE: 571
aattgatggc tcttgatttg cagctgtatc tggagcttac cgaatctagt gcagctttaa 60
aaatagggag ccgattctgt ttccaagttc agaaggagca gcgatttggc a 111

<210> SEQ ID NO 572
<211> LENGTH: 261
<212> TYPE: DNA
<213> ORGANISM: Homo sapiens

<400> SEQUENCE: 572
agccgctgcc aagtctgtat gagaagaaca taatgaagcc tgactcagct aatgtcacaa 60
catggtgcta cttcttcttc tttttgttaa cagcaacgaa ccctagaaat atatcctgtg 120
tacctcactg tccaatatga aaaccgtaaa gtgccttata ggaatttgcg taactaacac 180
accctgcttc attgacctct acttgctgaa ggagaaaaag acagcgataa gctttcaata 240
gtggcatacc aaatggcact t 261

<210> SEQ ID NO 573
<211> LENGTH: 257
<212> TYPE: DNA
<213> ORGANISM: Homo sapiens

<400> SEQUENCE: 573
tcagcagggc atcgcatgga ccgcaggagg gcagattcgg accactaggc ctgaaatgac 60
atttcactaa aagtctccaa aacatttcta agactactaa ggccttttat gtaatttctt 120
taaatgtgta tttcttaaga attcaaattt gtaataaaac tatttgtata aaaattaagc 180
ttttattaat ttgttgctag tattgccaca gacgcattaa aagaaactta ctgcacaagc 240
tgctaataaa tttgtaa 257

<210> SEQ ID NO 574
<211> LENGTH: 139
<212> TYPE: DNA
<213> ORGANISM: Homo sapiens

<400> SEQUENCE: 574
gaaaaagaaa tacaccccat ttctggtgcc agtcagtgtc tgtctgtctc tgtatacata 60
cttatgtata aatatgtgtt tgtatatatg tttatataca tatatatttg ttcatgttat 120
tttggtttga cacttttaa 139

<210> SEQ ID NO 575
<211> LENGTH: 226
<212> TYPE: DNA
<213> ORGANISM: Homo sapiens

<400> SEQUENCE: 575
tcactgccaa ttccagcacg aagttgggcg actgccaggc aggcactccc agtcgtcaaa 60
aagtgcaaat gttactcagg gaacaattaa tgtgagttgt gtaatgtaat atgggtcaaa 120
aacatgaaaa gacgtttaaa atgtcagcgg atggctcagc ccacccatca gccagccaga 180
gagcagaaca cctgttttgc actcagtggc acagaagcca caattt 226

<210> SEQ ID NO 576
<211> LENGTH: 263
<212> TYPE: DNA
<213> ORGANISM: Homo sapiens

<400> SEQUENCE: 576
tcaggcccgg agaccgggtg ttcctccaga tgccctcaga acaggctgca ggactgtatg 60
ccgggcagta tgtccactcc tccttttcag gatatttatt gtatcccatg taaaaacaaa 120
aaaacaaaaa acaaagaaaa gaaagagatt ttatagaaga aaatgacaca ccaaaaaatc 180
caaatgaaaa acataattgc ttcaaaacac ttacacagtt ggaaagttat atgtaagtga 240
aaatttggac cattgtgtac aaa 263

<210> SEQ ID NO 577
<211> LENGTH: 245
<212> TYPE: DNA
<213> ORGANISM: Homo sapiens

<400> SEQUENCE: 577
attgtgctat aatccctatt tagttcaaaa ttaaccagaa tttttccatg tgaaatggac 60
caaactcata ttattgttat gtaaatacag agttttaatg cagtatgaca tcccacaggg 120
gaaaagaatg tctgtagtgg gtgactgtta tcaaatattt tatagaatac aatgaacggt 180
gaacagactg gtaacttgtt tgagttccca tgacagattt gagacttgtc aatagcaaat 240
cattt 245

<210> SEQ ID NO 578
<211> LENGTH: 212
<212> TYPE: DNA
<213> ORGANISM: Homo sapiens
<220> FEATURE:

<221> NAME/KEY: misc_feature
<222> LOCATION: (125)..(125)
<223> OTHER INFORMATION: n is a, c, g, or t

<400> SEQUENCE: 578
acaggccaga ttatacaata cttctgtgca caccagatgg ttgtaaagaa agatcagcga 60
gaaaggcttt ggaagtttta atccttcttt ccaccttttt tcccccgcat ttagtaaatc 120
acaancctac ctgactggca tccaattatc agagatattc agtgtttaag ctaccctctt 180
taaaagaaaa tgatctcttc ttattcctaa gg 212

<210> SEQ ID NO 579
<211> LENGTH: 221
<212> TYPE: DNA
<213> ORGANISM: Homo sapiens

<400> SEQUENCE: 579
taatgtcatc ctgtactcgg cacaaatcaa aggccaatac aagtctgaaa agcagaaata 60
aatatttttc caggtttttg ctcgggcaca tactaactgc tttgggcatt ttaatctggt 120
ctccaaacac caaagaccca tttcgagcct gctattagcc tgctgctgac tctatcactt 180
ggagcaataa tgtggggtta tggtggtgga atcttgtata t 221

<210> SEQ ID NO 580
<211> LENGTH: 224
<212> TYPE: DNA
<213> ORGANISM: Homo sapiens

<400> SEQUENCE: 580
tacccacccc taaatcattc cagtgctctc aaaaagcatg tttttcaaga tcattttgtt 60
tgttgctctc tctagtgtct tcttctctcg tcagtcttag cctgtgccct cccccttaccc 120 aggcttaggc ttaattacct gaaagattcc aggaaactgt agcttcctag ctagtgtcat 180
ttaaccttaa atgcaatcag gaaagtagca aacagaagtc aata 224

<210> SEQ ID NO 581
<211> LENGTH: 174
<212> TYPE: DNA
<213> ORGANISM: Homo sapiens

<400> SEQUENCE: 581
gatagttgta caataatgtc tgagtactta atgccactaa actgtacact taaatgtcta 60
aaatggtaaa attttatgta tattttacct caattaaaaa gaaaacacct tggcccccaa 120
aggtactttt gccaaagaac caaggctgaa atttcttgct aaatgagata atta 174

<210> SEQ ID NO 582
<211> LENGTH: 189
<212> TYPE: DNA
<213> ORGANISM: Homo sapiens

<400> SEQUENCE: 582
gatagttgta caataatgtc tgagtactta atgccactaa actgtacact taaatgtcta 60
aaatggtaaa attttatgta tattttacct caattaaaaa gaaaacacct tggcccccaa 120
aggtactttt gccaaagaac caaggctgaa atttcttgct aaatgagata attaaatgtc 180
tttcattgc 189

<210> SEQ ID NO 583
<211> LENGTH: 181

<212> TYPE: DNA
<213> ORGANISM: Homo sapiens

<400> SEQUENCE: 583
atctcaagat gaacaggtgc acctactttt gctccctctt ttttttttt ttctcttatg 60 tgtggaccca cataattcag ttcctcaaac atttgctgag cacctacttg aggaggcagt 120
attagggtca tggttaagag ccagggccct gggttcacat cccagggtag ctgtgacctt 180
g 181

<210> SEQ ID NO 584
<211> LENGTH: 145
<212> TYPE: DNA
<213> ORGANISM: Homo sapiens

<400> SEQUENCE: 584
caataaaagt ggcagacctc tttatccctg tttcacaaat aaatggaggc acagaatggg 60
gaagtggagg ccgagggaac aaagccaatt aagactgcca gcccggttcc ctggccacag 120
cactgagggt ttgaggggtg cctcc 145

<210> SEQ ID NO 585
<211> LENGTH: 249
<212> TYPE: DNA
<213> ORGANISM: Homo sapiens

<400> SEQUENCE: 585
aaagtagaac ctatggaatc cattcaaaat ctgtactgag cattgattgt atcgcactcc 60
tgtgtctagg ccctttgcat atgcactcac tcattcaaca gactttgacc ctgcctgctc 120
ttctgccagg ccgtgtgcta agggcctgcg atcccaagat aaatccctgt ctccaagcca 180
agcatgtgac tttgaagcag tgtaacttgg tgaggaacgt cttattttat ctctttacca 240
catcaacag 249

<210> SEQ ID NO 586
<211> LENGTH: 222
<212> TYPE: DNA
<213> ORGANISM: Homo sapiens

<400> SEQUENCE: 586
gtcccagggc ggtagtgaat acgcagcagc ggatcagatc agctttcagg gccccgacac 60
cccctgagca cctactgctt tgccctttta actggcacaa ggttcagtta tacaggccaa 120
gggtatcaag ctagacttcc tggttccatt ttcattgtat ttttagcatt gccttctgtg 180
tatgacaaat tttactgctt tgggtgttat atggtgacat aa 222

<210> SEQ ID NO 587
<211> LENGTH: 293
<212> TYPE: DNA
<213> ORGANISM: Homo sapiens

<400> SEQUENCE: 587
gagccttcag gccagctggg tttagcccga ggctggtttt agatgcagcg actgtttcag 60
gggtgactca gaagaaaaag aagctgagga agctgttggg gggctgaggg tgggattctc 120
gctccttcat ttcaggttac tcgttcttca gcaagttggc aaaacagaca tcatgctggt 180
gagtgccacg ttactcccct ggctggaaat gcttttctga aagtatgagt gttgtgccta 240
cttaattctg ataaacctgt ttaagcaata cttaggaggc ttacttcttt gga 293

<210> SEQ ID NO 588
<211> LENGTH: 168
<212> TYPE: DNA
<213> ORGANISM: Homo sapiens

<400> SEQUENCE: 588
gatacactat acaatcctat gaccaatctc atctacaact ttattcaaat tttatagagg 60
ctgaggtgga aggatcactt gagtttgaaa ccagcctggg caacatagtg agaccccgtc 120
tctacaaaaa gtaggaaaaa aaaaatagcg aggtgttgtg gtacacgc 168

<210> SEQ ID NO 589
<211> LENGTH: 118
<212> TYPE: DNA
<213> ORGANISM: Homo sapiens

<400> SEQUENCE: 589
agggtatgaa ggttctctct gtgtcatttc ttaaaactcc atgtgagtct atagtgagtt 60
ttaaaaagaa aaagttccag cctgggcagc atagcgagac ctattgtctc tacacata 118

<210> SEQ ID NO 590
<211> LENGTH: 238
<212> TYPE: DNA
<213> ORGANISM: Homo sapiens

<400> SEQUENCE: 590
atgctctaaa acagtgtagg atttaagaat agatggtttt taatcctgga aattgtgatt 60
gtgacccatg agtggaggaa ctttcagttc taaagctgat aaagtgtgta gccagaagag 120
tacttttttt tttgtaacca ctgtcttgat ggcaaaataa ttatggtaaa aaacaagtct 180
cgtgtttatt attccttaag aactctgtgt tatattacca tggaacgcct aataaagc 238

<210> SEQ ID NO 591
<211> LENGTH: 257
<212> TYPE: DNA
<213> ORGANISM: Homo sapiens

<400> SEQUENCE: 591
caggctgttt gggcattaat tttgcttttt gagccttaag tgtgttagta ggatggagaa 60
actgtgatgg gggactggga acctggattg tctgatttta ggtcactgtt ccctgggcct 120
gtttttgtga gcccttacac aggaagatat aaagagagtt ctttcatttc cctgctaaaa 180
tcagtatgta gtatggggaa tgtatttggg ttgtttttaa agaaaagggg aacagaatca 240
ggagagtggg caaaggc 257

<210> SEQ ID NO 592
<211> LENGTH: 238
<212> TYPE: DNA
<213> ORGANISM: Homo sapiens

<400> SEQUENCE: 592
tctttcatcg ccttccctca aaaaaacctg ctccgttgaa gtaaactaag taactcaata 60
ttctttattt tggtttggaa cctgtctcaa ttttttgtat ccatattaag aagtcaccct 120
ataatctaaa ctttgtaatt ctaatttttt tgtcccatta tcatacaaag tgcttttaaa 180
cttgttttta aaaaatgaca gataatgcca catgaatagg aagatgattc attctaaa 238

<210> SEQ ID NO 593
<211> LENGTH: 219

<212> TYPE: DNA
<213> ORGANISM: Homo sapiens

<400> SEQUENCE: 593
tgttccacaa agaacgcaac acagtcttta aactttttgg tgtaagcttt tagccttggg 60
tattttccag tggggaatgt ttaaaaatat ttgaccaaac caaagacttt ttgcctttta 120
tagcaagcat aaagactgta ctgcctggct tttgtattcc ttcagacatt attgtaaatg 180
tgcaactcct tttccctctt gtaaaccttt ataagatgt 219

<210> SEQ ID NO 594
<211> LENGTH: 173
<212> TYPE: DNA
<213> ORGANISM: Homo sapiens

<400> SEQUENCE: 594
ttcaggatgt aggaggacat gtatagtatg tcaaaaactg caagcttttc ccaactttaa 60
ccttaccagc atgttaatat ccagtttttt tatagtttaa aagttaaagt gcctcatatt 120
ttgaaaatat ccattaagga cccaggaatt agcatttcac ttgtttatac att 173

<210> SEQ ID NO 595
<211> LENGTH: 299
<212> TYPE: DNA
<213> ORGANISM: Homo sapiens

<400> SEQUENCE: 595
acaagtcata tcaggatgca gttttagaag atatttttaa gaagaatgac catgatggtg 60
atggcttcat ttttcccaag gaatacaatg tataccaacc cgatgaacta tagcatattt 120
gtatttttac ttttttttt agctatttac tgtactttat gtataaaaca aagtcacttt 180
tttccaagtt gtatttgcta tttttcccct atgagaagat attttgattt ccccaataca 240
ttgattttgg tataataaat gtgaggctgt tttgcaaact taacttgcag gaatggtca 299

<210> SEQ ID NO 596
<211> LENGTH: 237
<212> TYPE: DNA
<213> ORGANISM: Homo sapiens

<400> SEQUENCE: 596
accctatgtc ctttatttac aaagctgtgc tcctattcat gagcatggaa tgtttttcca 60
tttgtttgtg acatttttta tttctttcag gggtatcttg taattctcat tatatatatc 120
ttttgcttcc ttggttagct gtatttttag gtattttagt cttcttgtgg caattgtgaa 180
tgggattgca ttcctgattt ggctcttggc ttgaatgtta ttaacgccac atttttt 237

<210> SEQ ID NO 597
<211> LENGTH: 36
<212> TYPE: DNA
<213> ORGANISM: Homo sapiens

<400> SEQUENCE: 597
cccactaagc aacttgtgac acccacctct gcccgc 36

<210> SEQ ID NO 598
<211> LENGTH: 225
<212> TYPE: DNA
<213> ORGANISM: Homo sapiens
<220> FEATURE:
<221> NAME/KEY: misc_feature
<222> LOCATION: (140)..(143)

<223> OTHER INFORMATION: n is a, c, g, or t
<220> FEATURE:
<221> NAME/KEY: misc_feature
<222> LOCATION: (145)..(147)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (153)..(157)
<223> OTHER INFORMATION: n is a, c, g, or t
<220> FEATURE:
<221> NAME/KEY: misc_feature
<222> LOCATION: (159)..(165)
<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t

<400> SEQUENCE: 598
aaaatgaaca gttaaggctc ttaaagatcc ttgacatggc tagcaacata atgattgtca 60
ctctacctgg ggcttccaag ctacttggag tagggacaaa atatcttggc tcacgtattt 120
aagagcctga atattccagn nnngnnnana nannnnnann nnnnntnnat tttaataaca 180
taacactgtt gctcattttg taagtataag tgttatagca gtttc 225

<210> SEQ ID NO 599
<211> LENGTH: 288
<212> TYPE: DNA
<213> ORGANISM: Homo sapiens

<400> SEQUENCE: 599
ctgtcagata ccctgtttct ggagtcacat cagtgaggag ggatgtgggt aagaggagca 60
gagggcaggg gtgctgtgga catgtgggtg gagaagggag ggtggccagc actagtaaag 120
gaggaatagt gcttgctggc cacaaggaaa aggaggaggt gtctggggtg agggagttag 180
ggagagagaa gcaggcagat aagttggagc aggggttggt caaggccacc tctgcctcta 240
gtccccaagg cctctctctg cctgaaatgt tacacattaa acaggatt 288

<210> SEQ ID NO 600
<211> LENGTH: 197
<212> TYPE: DNA
<213> ORGANISM: Homo sapiens

<400> SEQUENCE: 600
tgggcctgaa taagggttat cgaatggtgg tgaatgaagg ttcagatggt ggacagtctg 60
tctatcacgt tcatctccat gttcttggag gtcggcaaat gcattggcct cctggttaag 120
cacgttttgg ggataatttt ctcttcttta ggcaatgatt aagttaggca atttccagta 180
tgttaagtaa cacactt 197

<210> SEQ ID NO 601
<211> LENGTH: 133
<212> TYPE: DNA
<213> ORGANISM: Homo sapiens

<400> SEQUENCE: 601
gtcataaaga aagcaagatg tcttgcttta ttaagaaaac ttaaacagca ctttggaagt 60

```
taaggtgggc ggattgccca agcgcaggag ttcgagacca gcctggacaa cattggagaa    120

gccccatctc aac                                                       133


<210> SEQ ID NO 602
<211> LENGTH: 359
<212> TYPE: DNA
<213> ORGANISM: Homo sapiens
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t

<400> SEQUENCE: 602

ctggtggcga cacgatcttt gggaagatca tccgnnanna nataccagcc aaaatcattt     60

ttgaggatga ccggtgcctt gctttccatg acatttcccc tcaagcacca acacattttc    120

tggtgatacc caagaaacat atatcccaga tttctgtggc agaagatgat gatgaaagtc    180

ttcttggaca cttaatgatt gttggcaaga aatgtgctgc tgatctgggc ctgaataagg    240

gttatcgaat ggtggtgaat gaaggttcag atggtggaca gtctgtctat cacgttcatc    300

tccatgttct tggaggtcgg caaatgcatt ggcctcctgg ttaagcacgt tttggggat     359


<210> SEQ ID NO 603
<211> LENGTH: 161
<212> TYPE: DNA
<213> ORGANISM: Homo sapiens
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 603

tcgctcggcc tggtggcgac acgatctttg ggaagatcat ccgnnannan ataccagcca     60

aaatcatttt tgaggatgac cggtgccttg ctttccatga catttcccct caagcaccaa    120

cacattttct ggtgataccc aagaaacata tatcccagat t                        161


<210> SEQ ID NO 604
<211> LENGTH: 206
<212> TYPE: DNA
<213> ORGANISM: Homo sapiens

<400> SEQUENCE: 604

ttctcccttc tacgtgtaca tcattaatcc ccattgccaa gggcattgtc cagaaactcc     60

cctgagacct tactccttcc agccccaaat catttacttt tctgtggtcc agccctactc    120

ctataagtca tgatctccaa agctttctgt cttccaactg cagtctccac agtcttcaga    180

agacaaatgc tcaggtagtc actgtt                                         206
```

<210> SEQ ID NO 605
<211> LENGTH: 246
<212> TYPE: DNA
<213> ORGANISM: Homo sapiens

<400> SEQUENCE: 605
ttttccagcc ctatagccac cccaagagtg gttatgcctc ctcgattgct ccatactcta 60
acatctagct ggcttccctg tctattgcct tttcctgtat ctattttcct ctatttccta 120
tcattttatt atcaccatgc aatgcctttg gaataaaaca tacaggagtc tgtttttgct 180
atggaatgcc ccatggggca tctcttgtgt acttattgtt taaggtttcc tcaaactgtg 240
attttt 246

<210> SEQ ID NO 606
<211> LENGTH: 93
<212> TYPE: DNA
<213> ORGANISM: Homo sapiens

<400> SEQUENCE: 606
ttcctgccct caactgagga cgtttacgac tgcagggtgg agcactgggg cttggatgag 60
cctcttctca agcactggga gtttgatgct cca 93

<210> SEQ ID NO 607
<211> LENGTH: 177
<212> TYPE: DNA
<213> ORGANISM: Homo sapiens

<400> SEQUENCE: 607
tggaaggagt ggctgctctc caaactatgc caaggcggcg gcagagctgg tcttctggtc 60
tccttggaga aaggttctgt tgccctgatt tatgaactct ataatagagt atataggttt 120
tgtacctttt ttacaggaag gtgactttct gtaacaatgc gatgtatatt aaacttt 177

<210> SEQ ID NO 608
<211> LENGTH: 239
<212> TYPE: DNA
<213> ORGANISM: Homo sapiens

<400> SEQUENCE: 608
cttgtctcct ccccgtgtcc ccaatgtctt cagtgggggg ccccctcttg ggtcccctcc 60
tctgccatca cctgaagacc cccacgccaa acactgaatg tcacctgtgc ctgccgcctc 120
ggtccacctt gcggcccgtg tttgactcaa ctcagctcct ttaacgctaa tatttccggc 180
aaaatcccat gcttgggttt tgtctttaac cttgtaacgc ttgcaatccc aataaagca 239

<210> SEQ ID NO 609
<211> LENGTH: 142
<212> TYPE: DNA
<213> ORGANISM: Homo sapiens

<400> SEQUENCE: 609
ggtccctgca gaagcgtggc attgtggaac aatgctgtac cagcatctgc tccctctacc 60
agctggagaa ctactgcaac tagacgcagc ccgcaggcag ccccccaccc gccgcctcct 120
gcaccgagag agatggaata aa 142

<210> SEQ ID NO 610
<211> LENGTH: 296
<212> TYPE: DNA
<213> ORGANISM: Homo sapiens

<400> SEQUENCE: 610
agcacactag cacacagcac acacacaaag acacagcaca cacatgcaca cacagcacac 60
acacgcgaac acagcacaca cgaacacagc acacacagca cacacacaaa cacagcacac 120
acatgcacac agcacatgca cacacagcac acacatgaac acagcacaca gcacacacat 180
gcacacagca cacacgcatg cacagcacac atgaacacag cacacacaaa cacacagcac 240
acacatgcac acacagcaca cacactcatg cgcagcacat acatgaacac agctca 296

<210> SEQ ID NO 611
<211> LENGTH: 238
<212> TYPE: DNA
<213> ORGANISM: Homo sapiens

<400> SEQUENCE: 611
agcagaattt cagccggccg tgcgcgccag ggcgctccgc gctacctgcc cgcgccgccc 60
gcgctcgggt tcccggggag ggcgccagtg ctccgcgcgc gccccagcca aggtgaatcc 120
ccggcagcgc cttccttccg ctgcccggga agcttgagct caacaattag cccttgatcc 180
tcgggggatt ccaatccacg gaacaacttc cctgctttcc ccgaactcgg acatttta 238

<210> SEQ ID NO 612
<211> LENGTH: 198
<212> TYPE: DNA
<213> ORGANISM: Homo sapiens

<400> SEQUENCE: 612
tgctttcccc aaatgtactg atcacactcc aggctccccc aaaatctaga cagtgctttc 60
ttccatctct gaagggtgtt aaaacctttc cctgaagcca cagtaattat gaaggttatt 120
ttttccccgg ctgctgccag cgtccaggcc actaacttat attcttaaga tgtgaaaatt 180
aatctcagct tcccctaa 198

<210> SEQ ID NO 613
<211> LENGTH: 209
<212> TYPE: DNA
<213> ORGANISM: Homo sapiens

<400> SEQUENCE: 613
aacaacccag actggctcct cactcccttt tccatcacta aaaatcacag agcagtcaga 60
gggacccagt aagaccaaag gaggggagga cagagcatga aaaccaaaat ccatgcaaat 120
gaaatgtaat tggcacgacc ctcacccccca aatcttacat ctcaattccc atcctaaaaa 180
gcactcatac tttatgcatc cccgcagct 209

<210> SEQ ID NO 614
<211> LENGTH: 150
<212> TYPE: DNA
<213> ORGANISM: Homo sapiens

<400> SEQUENCE: 614
agggacccag taagaccaaa ggaggggagg acagagcatg aaaaccaaaa tccatgcaaa 60
tgaaatgtaa ttggcacgac cctcaccccc aaatcttaca tctcaattcc catcctaaaa 120
agcactcata ctttatgcat ccccgcagct 150

<210> SEQ ID NO 615
<211> LENGTH: 295
<212> TYPE: DNA

-continued

<213> ORGANISM: Homo sapiens

<400> SEQUENCE: 615
ggcaagttct tccaatatga cacctggaag cagtccaccc agcgcctgcg caggggcctg 60
cctgccctcc tgcgtgcccg ccggggtcac gtgctcgcca aggagctcga ggcgttcagg 120
gaggccaaac gtcaccgtcc cctgattgct ctacccaccc aagaccccgc ccacgggggc 180
gcccccccag agatggccag caatcggaag tgagcaaaac tgccgcaagt ctgcagcccg 240
gcgccaccat cctgcagcct cctcctgacc acggacgttt ccatcaggtt ccatc 295

<210> SEQ ID NO 616
<211> LENGTH: 183
<212> TYPE: DNA
<213> ORGANISM: Homo sapiens

<400> SEQUENCE: 616
catcaggttc catcccgaaa atctctcggt tccacgtccc cctggggctt ctcctgaccc 60
agtccccgtg ccccgcctcc ccgaaacagg ctactctcct cggccccctc catcgggctg 120
aggaagcaca gcagcatctt caaacatgta caaaatcgat tggctttaaa cacccttcac 180
ata 183

<210> SEQ ID NO 617
<211> LENGTH: 170
<212> TYPE: DNA
<213> ORGANISM: Homo sapiens

<400> SEQUENCE: 617
tttgctttcc ccaaatgtac tgatcacact ccaggctccc ccaaaatcta gacagtgctt 60
tcttccatct ctgaagggtg ttaaaacctt tccctgaagc cacagtaatt atgaaggtta 120
ttttttcccc ggctgctgcc agcgtccagg ccactaactt atattcttaa 170

<210> SEQ ID NO 618
<211> LENGTH: 262
<212> TYPE: DNA
<213> ORGANISM: Homo sapiens

<400> SEQUENCE: 618
tggctggtat ggctctgagg ctccctgggg cctgctcaag ctcctcctgc tccttgctgt 60
tttctgatga tttgggggct tgggagtccc tttgtcctca tctgagactg aaatgtgggg 120
atccaggatg gccttccttc ctcttaccct tcctccctca gcctgcaacc tctatcctgg 180
aacctgtcct ccctttctcc ccaactatgc atctgttgtc tgctcctctg caaaggccag 240
ccagcttggg agcagcagag aa 262

<210> SEQ ID NO 619
<211> LENGTH: 165
<212> TYPE: DNA
<213> ORGANISM: Homo sapiens

<400> SEQUENCE: 619
ctcagggagc gaacgtggat gaaaaccaca gggattccgg acgccagacc ccattttata 60
cttcactttt ctctacagtg ttgttttgtt gttgttggtt tttatttttt atactttggc 120
cataccacag agctagattg cccaggtctg ggctgaataa aacaa 165

<210> SEQ ID NO 620
<211> LENGTH: 191

<212> TYPE: DNA
<213> ORGANISM: Homo sapiens

<400> SEQUENCE: 620
ctttttaatg ttagtgatcc acctgcctca gcctcccaaa gtgctgggat tacaggcttg 60
aaagtctaac ttttttttac ttatatattt gatacatata attcttttgg ctttgaaact 120
tgcaactttg agaacaaaac agtcctttaa attttgcact gctcaattct gtttttcgtt 180
tgcattgtct t 191

<210> SEQ ID NO 621
<211> LENGTH: 220
<212> TYPE: DNA
<213> ORGANISM: Homo sapiens

<400> SEQUENCE: 621
gcctgtggcc acctctgggg cacaatgggg gctccccact gcccagtctg cccctcgggt 60
tgggggagta tcccaggcct ctctgtggga cctgggcccc tgacgggcct tttcagcccg 120
ttttgaggac agacagtccc ccgaggtagg ctacatcccc ccacccccagc tggtctgctt 180 ggatttccta cagcccccgt gggcatggac cacctttatt 220

<210> SEQ ID NO 622
<211> LENGTH: 92
<212> TYPE: DNA
<213> ORGANISM: Homo sapiens

<400> SEQUENCE: 622
ggacagacag tcccccgagg taggctacat ccccccaccc cagctggtct gcttggattt 60
cctacagccc ccgtgggcat ggaccacctt ta 92

<210> SEQ ID NO 623
<211> LENGTH: 203
<212> TYPE: DNA
<213> ORGANISM: Homo sapiens

<400> SEQUENCE: 623
ggtaaaaatc caaattgtat cacagaaaat acagtgaata aaaccatcct cttaagaggg 60
tgtgtacatt tataaatttg cctatgattg cctataaagt caaagaagtt gcaccagtat 120
gcatgactgc caaaagtaca taaactgagc atatccattt ccctacattc ttgcaaacat 180
tgtgccttcg aactttttgg cct 203

<210> SEQ ID NO 624
<211> LENGTH: 294
<212> TYPE: DNA
<213> ORGANISM: Homo sapiens

<400> SEQUENCE: 624
cagggttcct ttgcctgcta acaagcccac gtggaccagt ttgaatgtct ttcctttaca 60
cctatgtttt taagtagtca aacttcaaga aacaatttaa acaagttttt gttgcatatg 120
tgtttgtgaa cttgtatttg tatttagtag gcttctatat tgcatttaac ttgtttttgt 180
aactcctgat ttttcctttt cggatactat tgatgaataa agaaattaaa gtgatagttt 240
tattggtttc ctttccccca attaaggcca aataaagtcg tgagaacatt accc 294

<210> SEQ ID NO 625
<211> LENGTH: 106
<212> TYPE: DNA

<213> ORGANISM: Homo sapiens

<400> SEQUENCE: 625
atgtgtttgt gaacttgtat ttgtatttag taggcttcta tattgcattt aacttgtttt 60
tgtaactcct gattcttcct tttcggatac tattgatgaa taaaga 106

<210> SEQ ID NO 626
<211> LENGTH: 114
<212> TYPE: DNA
<213> ORGANISM: Homo sapiens

<400> SEQUENCE: 626
aggaggcaca gaccagtgtc tggatcccag catcttctcc acttcagcgc tgagttcagt 60
atacacaagt gtctgctaca gtcgccaaat caccagtatt tgcttatata gcaa 114

<210> SEQ ID NO 627
<211> LENGTH: 195
<212> TYPE: DNA
<213> ORGANISM: Homo sapiens

<400> SEQUENCE: 627
actttctctc gccatgtagt gagtggaata taaacagtac ggcatgtggc acctgaacag 60
tcttcatgcc caggaatccc aaatgctgtt tactctacag aaaggaatca cttgattttc 120
cacttcagaa gccaaccgct caacaacact ggggaagaaa tgaagaatcc tgggtctcct 180
tgtagtcgat caaga 195

<210> SEQ ID NO 628
<211> LENGTH: 172
<212> TYPE: DNA
<213> ORGANISM: Homo sapiens

<400> SEQUENCE: 628
agcccaccca ttgaagtctc cttgggccac caaaggtggt ggccatggta ccggggactt 60
gggagagtga gacccagtgg agggagcaag aggagaggga tgtcgggggg gtggggcacg 120
gggtagggga aatggggtga acggtgctgg cagttcggct agatttctgt ct 172

<210> SEQ ID NO 629
<211> LENGTH: 157
<212> TYPE: DNA
<213> ORGANISM: Homo sapiens

<400> SEQUENCE: 629
tatgaattcc attcaaatcg ttcctttttg ttaacaaggg gcatggggag gggtgggggt 60 ggggggcag aggcgtctga ccccaggaac ctgcagggcg gggctgggtc ggtgcccttt 120
aaggacaatt ttgaccttgt tcaacctttc cacaaag 157

<210> SEQ ID NO 630
<211> LENGTH: 36
<212> TYPE: DNA
<213> ORGANISM: Homo sapiens

<400> SEQUENCE: 630
tgggggggca gaggcgtctg accccaggaa cctgca 36

<210> SEQ ID NO 631
<211> LENGTH: 299
<212> TYPE: DNA
<213> ORGANISM: Homo sapiens

<400> SEQUENCE: 631
gcctgtggat cccttttcag tataacgctt ttattttagt ttttagagag acgaggtctt 60
gctctgttgc ccaggctggg tgcagcggtg cgatcttggg tcactgcagc ctccaactcc 120
ttggctcaag ctgtcctctg gcctcagcct cctgagtagc tgggaccaca ggcgagtgtc 180
accatgctgg gcagtataaa gttttaaatg cataaaataa aatccacaag atgaccaagg 240
aaggcaatta tgttgaaata cagatcaaaa tattaaaaaa acacacatct tatgctctt 299

<210> SEQ ID NO 632
<211> LENGTH: 245
<212> TYPE: DNA
<213> ORGANISM: Homo sapiens

<400> SEQUENCE: 632
gatgtgcctt aaattatacc aaagattact aattattcct ctttgcccaa aatacttgca 60
tccaaggttc tagtctctgt tgctgtgctg gtctttagcc ccactgctgg cactgatgtc 120
cctccttttt cacggagacc tatctgaggt acaggatggg gctggcacca gatgatgtcc 180
caccacagtc cctcacctcc ggcctccaca tgacagaacc aatttacact caaccatgac 240
ctcac 245

<210> SEQ ID NO 633
<211> LENGTH: 252
<212> TYPE: DNA
<213> ORGANISM: Homo sapiens

<400> SEQUENCE: 633
gattcgagga ccatgtaggt cttttacgta gcccaaatcc ataaattagt ctcacttttt 60
gtatttatcg tttcatatta aaccctctat atcaaatgtt catcatgatt ttgtatgatt 120
tttataacta ttttattcat tttattagat ttattttaaa attttttaat ggtaaatttt 180
taaactgtgg aaaccactga aggtgcttat taactgtttt cccagatttg tacaagtatt 240
ggatgattcc tt 252

<210> SEQ ID NO 634
<211> LENGTH: 247
<212> TYPE: DNA
<213> ORGANISM: Homo sapiens

<400> SEQUENCE: 634
atttatacta atggttcata tcctttattg ctcaatgatc taattaaagg gatcattgcc 60
acatttcatg tttatatttc tacaatttgt ttagaaaaca tctcctgacc atatcagtag 120
ctcgtgttat ctttttatca actgcttccc agagtcctaa aacaatagaa attttggatt 180
gaaaagttca gcataaggag tttgagtcag taaaggatgg gataaaggag tcgagatgat 240
tcaatga 247

<210> SEQ ID NO 635
<211> LENGTH: 202
<212> TYPE: DNA
<213> ORGANISM: Homo sapiens

<400> SEQUENCE: 635
tttatttatt ggtctgaaag gcatttcaaa ggtattataa taatatattg gtgtaattta 60
attggtgcaa catgctttat ggctcctgtc aaaattggtt ttcactcatt tgattggttt 120
gagcccagaa cagcctacag gggaaaaaca agctggataa ccacccaaag tgtttgtatt 180
ttcgttggaa actgattttt gt 202

<210> SEQ ID NO 636
<211> LENGTH: 300
<212> TYPE: DNA
<213> ORGANISM: Homo sapiens

<400> SEQUENCE: 636
cttagtttac acatctgcca aaggggtaga attacacttc tttttacagg taaatgtcaa 60
ggcacaatca gttttcagga agtgcttcaa gaccccaggt gaaatgaaaa tgctaagtac 120
cctctgaatg gccatgcctg ttaccaggtg ctgcttcttc agatgatggg gagcactttt 180
cagggtgaaa ttcaggcgag ttttgcccag gcctgctgtc ttgagtacaa atgtgaatga 240
tcgactgact gcttgttgcc aaactggaaa tgttctgtag ggatttactg gcatggtatc 300

<210> SEQ ID NO 637
<211> LENGTH: 167
<212> TYPE: DNA
<213> ORGANISM: Homo sapiens

<400> SEQUENCE: 637
ctgaacagga gttgggataa tggccatctt ttctttccta tcctttcttc ccccctcact 60
gtgaaaaata acagtccacc ccaagtcata cactggaccc agtgcctgcg gggacaggac 120
tgtgggtttc ttggtcacac ctgtgttggt gctcaatgca gtgtaga 167

<210> SEQ ID NO 638
<211> LENGTH: 271
<212> TYPE: DNA
<213> ORGANISM: Homo sapiens

<400> SEQUENCE: 638
gactgtgctc tcttaaaaat aagaaagagc ctcttcatct tcaaaaggac tacatctgaa 60
gtttccccag aaggacaaat gtctacttag accttataaa tttccaaaat aagagagtca 120
gagccagagg tggcttgtaa gttgacttct gttgagatct gaccacattt gatctcttgt 180
tttaattttc caactaactg aacttggaag aaaacccaaa ccaagtttta atctgatgcc 240
taatcagccc gtctccaacc atcagagaaa a 271

<210> SEQ ID NO 639
<211> LENGTH: 234
<212> TYPE: DNA
<213> ORGANISM: Homo sapiens

<400> SEQUENCE: 639
ctccacttcc ctcagatgat gaggagccag ggctaagggg gcagccttct ctcttcccag 60
tgatgcacat ccttcacatt ggctgctttg ttctggaata tggatatctc agcctggatg 120
ccgaggaagc tgctggatgc ttaatggtgc tagaggctca agtgtgtttg aaaccaagag 180
ccagttgtcc cccatgcaga aagaaatcct gtgtgagcct ctggtatgag aaat 234

<210> SEQ ID NO 640
<211> LENGTH: 261
<212> TYPE: DNA
<213> ORGANISM: Homo sapiens

<400> SEQUENCE: 640
gggagaagat gacccgtgga acacttgcct ggcccactca gaatccacgg tgacctttcc 60

-continued gcttgccaaa ataaccgaag gaaagaccgt tcaccagact tggctccttt aaacatttgc 120
tgttcaaaca tgtttttgaa tatacattct ataaaagatt atttgaaaga caaaattcat 180
agaaaatgga gcaaaactgt ataaactgat ttgtaactaa cactggacca ttggatcgat 240
attatatgct gtaaccatgt g 261

<210> SEQ ID NO 641
<211> LENGTH: 92
<212> TYPE: DNA
<213> ORGANISM: Homo sapiens

<400> SEQUENCE: 641
ctcaaaaaag tggttttgac cagagaggcc cagatggagg ctgttcattc cctgcagtgt 60
cggcattgta aataaagcct gagcacttgc tg 92

<210> SEQ ID NO 642
<211> LENGTH: 238
<212> TYPE: DNA
<213> ORGANISM: Homo sapiens

<400> SEQUENCE: 642
gagcaggagc ctctacacag cctctggctc ttaggtccca gtcatgtttg cacccccctca 60 aaggggcagg accagccctt cctttcagtg tccataccag gggccttcca tgtgctgatg 120
ggtgatgtga ctgtggtcag caggcttggg aagtgctgct gctgtagctt gagttgggct 180
ggggtcttgg taggacgctg atctcagaag tccccaaagt tcactgtgta ggtctcta 238

<210> SEQ ID NO 643
<211> LENGTH: 128
<212> TYPE: DNA
<213> ORGANISM: Homo sapiens

<400> SEQUENCE: 643
gaccagacag tgctgttggt gactgtccct gacttcagtg ccacgcagac cgcctgcctt 60
gtgaacctgc gcagcctggc ctgccagccc atcagcttct cgggcttcgg ggcagaggac 120
gatgacct 128

<210> SEQ ID NO 644
<211> LENGTH: 152
<212> TYPE: DNA
<213> ORGANISM: Homo sapiens

<400> SEQUENCE: 644
gccatttaag ttaatgccgg gcctggtaca cttttaagag tgaaaagggg caggacaaat 60
gcaaagctca atggggctct tggcaatac ggataaacca gggctgtttt gagtaaatca 120
aatgaggata cacagtcact gtgagaacca gt 152

<210> SEQ ID NO 645
<211> LENGTH: 270
<212> TYPE: DNA
<213> ORGANISM: Homo sapiens

<400> SEQUENCE: 645
taaactctct agggccaaaa cctggtatgg tcattgggaa atgagtgctc agggagatgg 60
agcttagggg aggtgggtgc ttccctccta gatgtcagca tacactcttt cttcttttgt 120
cccaggtcta aaacatcttt cctagagaaa acaaaaggga ctaaactaga aatataaaga 180

-continued gccctataca tgacaggtga tcacgtactg aatgattttg aagtagtaca aacaataaaa 240
attctcattc cgcatcatca tgcggtccat 270

<210> SEQ ID NO 646
<211> LENGTH: 216
<212> TYPE: DNA
<213> ORGANISM: Homo sapiens

<400> SEQUENCE: 646
aatgctgact cgacagcctt ttgccattgg tggctccggc agcaccttta tctatggtta 60
tgtggatgca gcatataagc caggcatgtc tcccgaggag tgcaggcgct tcaccacaga 120
cgctattgct ctggccatga gccgggatgg ctcaagcggg ggtgtcattt acctggtcac 180
tattacagct gccggtgtgg accatcgagt catctt 216

<210> SEQ ID NO 647
<211> LENGTH: 214
<212> TYPE: DNA
<213> ORGANISM: Homo sapiens

<400> SEQUENCE: 647
tatcggtatc ttagaaacta tctatattct aggccaggag cagtggctca tgcctgtaat 60
cccaacattt tgggaggtca aggtgggcag atccctagag cccaggagtt tgagaccagc 120
ctgggcaaca tggcaaaacc ccgtctctac aaaaaattta gctggatggg gtgcacctgt 180
aatcccaact agtcagaagg ctagacggga ggat 214

<210> SEQ ID NO 648
<211> LENGTH: 45
<212> TYPE: DNA
<213> ORGANISM: Homo sapiens

<400> SEQUENCE: 648
gaggtggaaa gatcatctga gccggggaga tcaaggctgt agtga 45

<210> SEQ ID NO 649
<211> LENGTH: 242
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t

<400> SEQUENCE: 649
gagatgaaac tatgggcccc agactntact gcagcagctg tgatttcctc catagttggc 60
ttctgggtca ggcactaggc aatattttct tgaagacttc ttccaaatac ctgtggctct 120
tgtcccactg cagccaccag cctgtgcagg tagcggtgct catattgggg aaggggcttc 180
ccatccaaca gcagctgtnc ccccggtggg ctggtacaga ttctgcaaca gggcagccac 240
tg 242

<210> SEQ ID NO 650
<211> LENGTH: 214
<212> TYPE: DNA
<213> ORGANISM: Homo sapiens

<400> SEQUENCE: 650
tatcggtatc ttagaaacta tctatattct aggccaggag cagtggctca tgcctgtaat 60
cccaacattt tgggaggtca aggtgggcag atccctagag cccaggagtt tgagaccagc 120
ctgggcaaca tggcaaaacc ccgtctctac aaaaaattta gctggatggg gtgcacctgt 180
aatcccaact agtcagaagg ctagacggga ggat 214

<210> SEQ ID NO 651
<211> LENGTH: 76
<212> TYPE: DNA
<213> ORGANISM: Homo sapiens

<400> SEQUENCE: 651
ggcattggct aaatgtttta taaattttat ctcttaaaat tcaaaccaaa aaaccccctg 60
tattcacacc tgtaat 76

<210> SEQ ID NO 652
<211> LENGTH: 224
<212> TYPE: DNA
<213> ORGANISM: Homo sapiens

<400> SEQUENCE: 652
tccacacctg attagaacat tcataagcca catttagaaa cagatttgct ttcagctgtc 60
acttgcacac atactgccta gttgtgaacc aaatgtgaaa aaacctcctt catcccattg 120
tgtatttgat acctgccgag ggccaagggt gtgtgttgac aacgccgctc ccagccggcc 180
ctggttgcgt ccacgtcctg aacaagagcc gcttccggat ggct 224

<210> SEQ ID NO 653
<211> LENGTH: 222
<212> TYPE: DNA
<213> ORGANISM: Homo sapiens

<400> SEQUENCE: 653
gaatcaccag tttgatactc tctgtaatca gaacagtggg cagtgcctgg gtgaacgtgt 60
ctagcagcca ctgtgcggga tcgctgtaac aggagtggaa tgtacatatt tatttacttt 120
tctaactgct ccaacagcca aatgcctttt ttatgaccat tgtattcagt tcattaccaa 180
agaaatgttt gcactttgta atgatgcctt tcagttcaaa ta 222

<210> SEQ ID NO 654
<211> LENGTH: 279
<212> TYPE: DNA
<213> ORGANISM: Homo sapiens

<400> SEQUENCE: 654
tggccacggc gcttggaatc ctggttgttg ctggatgctc ttttgcgatt aggagatacc 60
aaaaaaaagc gacagcctga agcagccaca aaatcctgtg ttagaagcag ctgtgggggt 120
cccagtggag atgagcctcc cccatgcctc cagcagcctg accctcgtgc cctgtctcag 180
gcgttctcta gatcctttcc tctgtttccc tctctcgctg gcaaaagtat gatctaattg 240
aaacaagact gaaggatcaa taaacagcca tctgcccct 279

<210> SEQ ID NO 655
<211> LENGTH: 106
<212> TYPE: DNA
<213> ORGANISM: Homo sapiens

<400> SEQUENCE: 655

-continued atagccctaa atgtactctt gaacttttta ctggaacaat gtttgatact ttagtatgta 60
agctgtattt atgtaatatt tagaacgaca tgttaataaa caaagt 106

<210> SEQ ID NO 656
<211> LENGTH: 125
<212> TYPE: DNA
<213> ORGANISM: Homo sapiens

<400> SEQUENCE: 656
attggaaaag aaaaggaagc caggcgtggt ggctcatgcc tgtggtccta gcactttggg 60
agtccaaggc aggcagatca cgaggtcagg agatcgagac catcctggcc ggcagggtaa 120
aaccc 125

<210> SEQ ID NO 657
<211> LENGTH: 70
<212> TYPE: DNA
<213> ORGANISM: Homo sapiens

<400> SEQUENCE: 657
ggaagactaa gttagctaca aagaaaacta agtattatac caaaaaaact tatccgggcg 60
tggtgacagg 70

<210> SEQ ID NO 658
<211> LENGTH: 129
<212> TYPE: DNA
<213> ORGANISM: Homo sapiens

<400> SEQUENCE: 658
agctttattg tactggatat ctgtatttac tgagtatacc tatatgggag tcccttatat 60
tactttggaa taacagtttt tcatatataa aaaatgttgt gaaacttact gggagtgtat 120
gtaatatgc 129

<210> SEQ ID NO 659
<211> LENGTH: 121
<212> TYPE: DNA
<213> ORGANISM: Homo sapiens

<400> SEQUENCE: 659
atataccata ggctaaaact aaggctttca ctctagaatg caaagctgtt ttgcagctgt 60
tttcccttaa agatgtcctg ttgctttagt gatatttaga cccctctcag ttaagaaatg 120
c 121

<210> SEQ ID NO 660
<211> LENGTH: 265
<212> TYPE: DNA
<213> ORGANISM: Homo sapiens

<400> SEQUENCE: 660
agatcactgc atccgcctat acaatcttta ccaataaaga ctcgaggcac cgttcttgct 60
cccgtgagct gttgcaaata atcttgaatc tcgttagtgt ggttggtggc tgtgatatcg 120
acaaattcca gaagcccttg tttgatgggc aattgactga ggatctcttg ggccctcctg 180
cagtacgggc aggtgggctt gatgaacaca accaccttcc caggctggat tttgcagttc 240
acaaactctt gagccatgcc gatgg 265

<210> SEQ ID NO 661
<211> LENGTH: 82

<212> TYPE: DNA
<213> ORGANISM: Homo sapiens

<400> SEQUENCE: 661
ttatagtata atattgggac cccataccgt tagcccttgt atgtatacca acactgccaa 60
agtaaaacat taggtcaggc at 82

<210> SEQ ID NO 662
<211> LENGTH: 253
<212> TYPE: DNA
<213> ORGANISM: Homo sapiens

<400> SEQUENCE: 662
gtcctcaggt gacatttggt tgtgaaaagt gatattttag ttctaactac ctaagtcagc 60
agcaaagttt aaacagtaca gatttaaaaa ttttttataa aggaatttaa ctcttgttaa 120
ctatattata tttagcttta ttgtactgga tatctgtatt tactgagtat acctatatgg 180
gagtccctta tattactttg gaataacagt ttttcatata taaaaaatgt tgtgaaactt 240
actgggagtg tat 253

<210> SEQ ID NO 663
<211> LENGTH: 81
<212> TYPE: DNA
<213> ORGANISM: Homo sapiens

<400> SEQUENCE: 663
gtcctcaggt gacatttggt tgtgaaaagt gatattttag ttctaactac ctaagtcagc 60
agcaaagttt aaacagtaca g 81

<210> SEQ ID NO 664
<211> LENGTH: 237
<212> TYPE: DNA
<213> ORGANISM: Homo sapiens

<400> SEQUENCE: 664
cagttccagt aattattgct gctgttggta ccagacaaaa tgaagagtta ccttgtacat 60
gcccactatg tacctcagac agagggagct gtgttagtac aactgaaggg atccaacttg 120
caaaagaact aggagcgacc tatcttgaac tccacagcct tgatgacttt tacataggaa 180
agtattttgg aggagtgttg gagtatttta tgattcaagc cttaaatcag aagacaa 237

<210> SEQ ID NO 665
<211> LENGTH: 95
<212> TYPE: DNA
<213> ORGANISM: Homo sapiens

<400> SEQUENCE: 665
tgccaaagta aaacattagg tcaggcatgg tggctcaggc ctgtaatccc agcattttgg 60
gaggctgagg caagtggata acttgaggtc atgag 95

<210> SEQ ID NO 666
<211> LENGTH: 182
<212> TYPE: DNA
<213> ORGANISM: Homo sapiens

<400> SEQUENCE: 666
catggtggct tcatattaag tagtaacaga agtttgaaca attggataaa tttgacttcc 60
aagacagcta aacttttcaa ctgcaatttt aaaaactaca ctacactgtt atagttaatc 120
tgacaaaaat gtcctcaaag agtactttat tttatttaaa gcatctgttt aattcaacct 180
tt 182

<210> SEQ ID NO 667
<211> LENGTH: 208
<212> TYPE: DNA
<213> ORGANISM: Homo sapiens

<400> SEQUENCE: 667
gatgaaaata ggcttgccac tttctcttat tttaattcca tggtagtcaa tgaactggct 60
gccactttaa tataactgaa aattcatttt gagaccaagc aggatcaagt ttgtagaata 120
aacactggtt tcctagccat cctctgaaaa cagtatgaaa catgaccaag tacataatgg 180
atttagtaat aaatattgtc gaattgct 208

<210> SEQ ID NO 668
<211> LENGTH: 210
<212> TYPE: DNA
<213> ORGANISM: Homo sapiens

<400> SEQUENCE: 668
ttagggccca gtcgagaccc agatccactg aacatctgtg tctttatttt gctgcttgta 60
tttattgtag tcaaatgctt tacatcagaa tgatgaaaat aggcttgcca ctttctctta 120
ttttaattcc atggtagtca atgaactggc tgccacttta atataactga aaattcattt 180
tgagaccaag caggatcaag tttgtagaat 210

<210> SEQ ID NO 669
<211> LENGTH: 289
<212> TYPE: DNA
<213> ORGANISM: Homo sapiens

<400> SEQUENCE: 669
atattgtccg ggtggataag aaccaggatt ttgtaacagg gaggcaacaa gctcaaaatc 60
agaaaaaaga gatttgtcaa tggaacaaga ggttgaagtg ctttgaagtt ggaggaagag 120
gtcacaggca aaaaagtaca ggcagccttt agaaaaccaa aaggacaaag gaacagattt 180
tcccctggag tctgcagaag gaaccagccc tgcctgcaca tggctttagc ccagtgacac 240
tgattttgga catttgacct tcagaactgc ttgctcataa acttgtctt 289

<210> SEQ ID NO 670
<211> LENGTH: 285
<212> TYPE: DNA
<213> ORGANISM: Homo sapiens

<400> SEQUENCE: 670
atattgtccg ggtggataag aaccaggatt ttgtaacagg gaggcaacaa gctcaaaatc 60
agaaaaaaga gatttgtcaa tggaacaaga ggttgaagtg ctttgaagtt ggaggaagag 120
gtcacaggca aaaaagtaca ggcagccttt agaaaaccaa aaggacaaag gaacagattt 180
tcccctggag tctgcagaag gaaccagccc tgcctgcaca tggctttagc ccagtgacac 240
tgattttgga catttgacct tcagaactgc ttgctcataa acttg 285

<210> SEQ ID NO 671
<211> LENGTH: 185
<212> TYPE: DNA
<213> ORGANISM: Homo sapiens

<400> SEQUENCE: 671

-continued

```
attcaaactc aagtccttgg agtgtcacaa aggactaaca acgctggctg ggacaaaacc     60

tacagcttct ttaaatgctg aggggcccct atggagaaat ggcccagtgt gtttctcatg    120

ggtgtctcct ccacttcccc acagaatgca atgaactcct gattccccag gtcacctaca    180

ggata                                                                185
```

<210> SEQ ID NO 672
<211> LENGTH: 65
<212> TYPE: DNA
<213> ORGANISM: Homo sapiens

<400> SEQUENCE: 672

```
aactcaagaa atggcatcga aaagcaagtc aaaaccgtga gatttcagaa ttacagccct     60

cctcc                                                                 65
```

<210> SEQ ID NO 673
<211> LENGTH: 262
<212> TYPE: DNA
<213> ORGANISM: Homo sapiens

<400> SEQUENCE: 673

```
atgacaaggc aggacatcca atgccttcga gctctgtggt ctggcctgtc tctccagatc     60

agatttagag tgaggtagca gatgacataa tattctcttt ggtgttcaat ccgaagaggc    120

caatgcttca gcacaatgtc ccctagccat cacccccagc ccgactcccc accaagcatc    180

ctgcatccct ctgccacatc ttcattcttt tccattctgt cttttccccg ataccttctg    240

accccaggga tttctaatag ag                                             262
```

<210> SEQ ID NO 674
<211> LENGTH: 242
<212> TYPE: DNA
<213> ORGANISM: Homo sapiens

<400> SEQUENCE: 674

```
aggatagatg gcgtggcctt ccaaacatac aaacataatg atttgatgcc acaaagctcg     60

cttactcaga ccaaggagtg aaaaattgtc gtgcccactt tatgccccag catggagtat    120

gtggcctctt gtcatccccg tgttactgtg tagaatttct atggtgtcct aaagggggct    180

gcagcagggg tgtgacaacg gtgggattgt tggcgttgct tctttgacct tacaatatcc    240

tc                                                                   242
```

<210> SEQ ID NO 675
<211> LENGTH: 251
<212> TYPE: DNA
<213> ORGANISM: Homo sapiens

<400> SEQUENCE: 675

```
ctctttaccg cgagactgat cagaagaagc aaaaggggaa agggggctag aggtccactc     60

gcacctttta catcagacaa gaggaggact gtgccagaaa tctgtgcatg aaacaccatc    120

tgctcttcat gcagggaggg gtcaaccgtg tgaacgtgca gagattactc gagccttctt    180

tgccaaaaat atgcattctt cccagctgta agggtgtgaa gccaaatatg tcttttagca    240

tgaaacaata a                                                         251
```

<210> SEQ ID NO 676
<211> LENGTH: 277
<212> TYPE: DNA

<213> ORGANISM: Homo sapiens

<400> SEQUENCE: 676
tgttgcccac tccatattcc aaaagtaggg gagggccagc accagcatcg gagcacagca 60
ccatcctcac ccccatccac aagcagacca aggcggactg ttcctggctt cctaaaggct 120
tcctaaagac aatgaggtga attttgccac agctctgaag agatgctcgt ttgcactaca 180
gatattccct gctagggatc aacagtctac aacagtgagg cactgctaac tgtacaaagg 240
cagttccatt cagtacctta gatccattct gggccca 277

<210> SEQ ID NO 677
<211> LENGTH: 269
<212> TYPE: DNA
<213> ORGANISM: Homo sapiens

<400> SEQUENCE: 677
agctgaacta gaactatgag gggttggggg gagggcttgg aattatgggc tatttttact 60
gggggcaagg gagggagatg acagcctggg tcacagtgcc tgttttcaaa tagtccctct 120
gctcccaaga tcccagccag gaaggctggg gccctactgt ttgtcccctc tgggctgggg 180
tggggggagg gaggaggttc cgtcagcagc tggcagtagc cctcctctct ggctgcccca 240
ctggccacat ctctggcctg ctagattaa 269

<210> SEQ ID NO 678
<211> LENGTH: 171
<212> TYPE: DNA
<213> ORGANISM: Homo sapiens

<400> SEQUENCE: 678
agcttgttgc caaagtctgt tgagcagcac tgttgccaag ggtcctggtg aagtcatccc 60
aggaggaaac cacagtctgt attctttgaa gggctgctgc acattgttga atccatcgac 120
ctttaactgc aatgggatct ctaatacatt ttgaggtcag ccacttctcc a 171

<210> SEQ ID NO 679
<211> LENGTH: 246
<212> TYPE: DNA
<213> ORGANISM: Homo sapiens

<400> SEQUENCE: 679
gaagctattg tccacagatt gatgcttcca taatggaatc agctttaatt gcaaggaatg 60
aagaaaaaca agagtggacc ttcaaagcta caacattttc ctcctcccct ccctccccac 120
cagccccttc cccaccaaga actgttatga tgtcccaaag tgaggtggtg ttgattccag 180
tctcaatggg attttctgac tttaatgttt gcaaggcatt tcaccagaat acagctataa 240
acggcc 246

<210> SEQ ID NO 680
<211> LENGTH: 276
<212> TYPE: DNA
<213> ORGANISM: Homo sapiens

<400> SEQUENCE: 680
tacccatgtt ggtctaaatg tgcttaaaag ttttccaata actgaaatga gtatcagttt 60
taaatttaaa aatttgttac ttggttactc catatttcag gtattagtgg ctaccatatt 120
ggtcagagca gattcatagg atgatttccc aggtttgaag tgtgtgtata tttctggtat 180
tataagatgt cagactggtt tttggagaaa tatgttgtct taatttttac ctgctttgat 240
atgacctttc tgtgtgtacg tgtgacattt ctttat 276

<210> SEQ ID NO 681
<211> LENGTH: 285
<212> TYPE: DNA
<213> ORGANISM: Homo sapiens

<400> SEQUENCE: 681
ccttctgttt gtgtacaaga gtaatttaaa agaaaaagct atgtgaaaat agttggggtt 60
ttttgtgtgt tttgtttttt gtggtggtga aggaggaggc ctaatgtcca gaggactgtt 120
tatccctgaa gtatgatata ctaaaatatt ttttattatt tgtatcaatt ttccttggag 180
ctcaatgtgc ccttgcagtt ttcagacttt attttaggaa aatatatttg catgttttcc 240
ccccattttc aatgtttggt gtcctggttc atcatacccc acaga 285

<210> SEQ ID NO 682
<211> LENGTH: 211
<212> TYPE: DNA
<213> ORGANISM: Homo sapiens

<400> SEQUENCE: 682
gaggcctgag gaaggtagta cttccacaaa agggagggac ccgggcccca gcctcaagct 60
agtgggggag gcagatagcc tgaatccagg ggattttttg ggctttttaa aatgtccatt 120
gtgagttccc tgtgtttggg attccactca ttttggcatt cacagtgcct ggaatgtttt 180
agattttcag caatgcgtgt tgaataaatg a 211

<210> SEQ ID NO 683
<211> LENGTH: 98
<212> TYPE: DNA
<213> ORGANISM: Homo sapiens

<400> SEQUENCE: 683
catccagaaa aaggcagact aagaatcaga agccatgtga ttgatgtctg acgtgagtct 60
gtctcaggta gattccgggt gtcagtgtgg tttataat 98

<210> SEQ ID NO 684
<211> LENGTH: 62
<212> TYPE: DNA
<213> ORGANISM: Homo sapiens

<400> SEQUENCE: 684
tggaccaatg atgacaactg ccggcgtatg agtgttgggt gatgaataat acgtgtctag 60
aa 62

<210> SEQ ID NO 685
<211> LENGTH: 41
<212> TYPE: DNA
<213> ORGANISM: Homo sapiens

<400> SEQUENCE: 685
ggcgtatgag tcatacatga tgaatatgtg tctggaactc t 41

<210> SEQ ID NO 686
<211> LENGTH: 34
<212> TYPE: DNA
<213> ORGANISM: Homo sapiens

<400> SEQUENCE: 686
atgacaactg ccggcgtatg agtgttgggt gatg 34

<210> SEQ ID NO 687
<211> LENGTH: 250
<212> TYPE: DNA
<213> ORGANISM: Homo sapiens

<400> SEQUENCE: 687
atctagcatg cagagtgtag tgtgttgaaa cggtgtatga cattgctgta tcaaagttgt 60
aaaattaagc attatttatt gaaaactatg tatttttttg taaaaacctg atcacataga 120
gaatatcagt ggcttgtgct tgtgcttcga tctaaccagc ttcttgaccc acccccccctt 180 ggtatgcagt gttaatgctc agggttgaaa atagtacact ccaatgtctc ttttgcaaga 240
gtttttcaca 250

<210> SEQ ID NO 688
<211> LENGTH: 259
<212> TYPE: DNA
<213> ORGANISM: Homo sapiens

<400> SEQUENCE: 688
gcgaggacgc cgacgacctg atgttcgacc tgagcttgaa tttctctcaa agcgcgcaca 60
gcgccagcga gcagcagctg gggggcggcg cggcggccgg gaacctgtcc ctgtcgctgg 120
tggataagga tttggattcg ttcagcgagg gcagcctggg ctcccacttc gagttccccg 180
actactgcac gccggagctg agcgagatga tcgcgggggga ctggctggag gcgaacttct 240
ccgacctggt gttcacata 259

<210> SEQ ID NO 689
<211> LENGTH: 228
<212> TYPE: DNA
<213> ORGANISM: Homo sapiens

<400> SEQUENCE: 689
tgttgaaacg gtgtatgaca ttgctgtatc aaagttgtaa aattaagcat tatttattga 60
aaactatgta tttttttgta aaaacctgat cacatagaga atatcagtgg cttgtgcttg 120
tgcttcgatc taaccagctt cttgacccac ccccccttgg tatgcagtgt taatgctcag 180
ggttgaaaat agtacactcc aatgtctctt ttgcaagagt ttttcaca 228

<210> SEQ ID NO 690
<211> LENGTH: 247
<212> TYPE: DNA
<213> ORGANISM: Homo sapiens

<400> SEQUENCE: 690
gcacggactg tcagttctct gggaagtggt cagcgcatcc tgcagggctt ctcctcctct 60
gtcttttgga gaaccagggc tcttctcagg ggctctaggg actgccaggc tgtttcagcc 120
aggaaggcca aaatcaagag tgagatgtag aaagttgtaa aatagaaaaa gtggagttgg 180
tgaatcggtt gttctttcct cacatttgga tgattgtcat aaggttttta gcatgttcct 240
ccttttc 247

<210> SEQ ID NO 691
<211> LENGTH: 95
<212> TYPE: DNA
<213> ORGANISM: Homo sapiens

<400> SEQUENCE: 691
ctattggaca gtgctcttct agatcatcat aagactacag agcacttttc aaagctcatg 60
catgttcatc atgttagtgt cgtattttga gctgg 95

<210> SEQ ID NO 692
<211> LENGTH: 114
<212> TYPE: DNA
<213> ORGANISM: Homo sapiens

<400> SEQUENCE: 692
tcatccccat ggagcattgc accacccgct ttttcgagac ctgtgacctg gacaatgaca 60
agtacatcgc cctggatgag tgggccggct gcttcggcat caagcagaag gata 114

<210> SEQ ID NO 693
<211> LENGTH: 170
<212> TYPE: DNA
<213> ORGANISM: Homo sapiens

<400> SEQUENCE: 693
acacaaattt cagcaccatt ctgcctgaaa tggcaccatc acaacctcag tcttgggtta 60
ggtgttgttc ctgtcctgag ttccttggga tggtaaacac aggcagtagc ccttagttta 120
tctagatctg aaaacccaga catcagatat cgtcaaccaa gacatgggtg 170

<210> SEQ ID NO 694
<211> LENGTH: 131
<212> TYPE: DNA
<213> ORGANISM: Homo sapiens

<400> SEQUENCE: 694
ggtcagaagt agaatctttt catcatcaca gaaagttcta ttggacagtg ctcttctaga 60
tcatcataag actacagagc acttttcaaa gctcatgcat gttcatcatg ttagtgtcgt 120
attttgagct g 131

<210> SEQ ID NO 695
<211> LENGTH: 153
<212> TYPE: DNA
<213> ORGANISM: Homo sapiens

<400> SEQUENCE: 695
atgggatggt cggatctcac aggctgagaa ctcgttcacc tccaagcatt tcatgaaaaa 60
gctgcttctt attaatcata caaactctca ccatgatgtg aagagtttca caaatctttc 120
aaaataaaaa gtaatgactt agaaactgcc caa 153

<210> SEQ ID NO 696
<211> LENGTH: 222
<212> TYPE: DNA
<213> ORGANISM: Homo sapiens

<400> SEQUENCE: 696
tgttttcctc taattctcct cactcccaaa caccaccttc cgtcccccca atacacaaat 60
ttcagcacca ttctgcctga aatggcacca tcacaacctc agtcttgggt taggtgttgt 120
tcctgtcctg agttccttgg gatggtaaac acaggcagta gcccttagtt tatctagatc 180
tgaaaaccca gacatcagat atcgtcaacc aagacatggg tg 222

<210> SEQ ID NO 697
<211> LENGTH: 175
<212> TYPE: DNA

<213> ORGANISM: Homo sapiens

<400> SEQUENCE: 697
aaaattagca tgctgctttt tgtacttgga agtgtttcaa aaaattatat gaccatattt 60
actctttcta actttcttta ctccatcatg gctggttgat tttgtagaga aattagaacc 120
cataaccata cacaggctat caacatgtta ttcaatgtga cacctaactc ttttc 175

<210> SEQ ID NO 698
<211> LENGTH: 194
<212> TYPE: DNA
<213> ORGANISM: Homo sapiens

<400> SEQUENCE: 698
ttccaagctc ctcgtgataa tgcagacttc ctggagtaca aacacaggat ttgtaattcc 60
ttactgtaac ggagtttaga gccagggctg atgctttggt gtggccagca ctctgaaact 120
gagaaatgtt cagaatgtac ggaaagatga tcagctattt tcaacataac tgaaggcata 180
tgctggccca taaa 194

<210> SEQ ID NO 699
<211> LENGTH: 166
<212> TYPE: DNA
<213> ORGANISM: Homo sapiens

<400> SEQUENCE: 699
tgagtttccc tagagctgtg cggccagata gctgttcctg agttgcaagc acgatggaga 60
tttggacact gtgtgctttt ggtggggtgg agaggtgggg tggggtgggg tgtggtgggg 120
tggaggctgt ctgtgtccag gaaacttaat tccctggtga ctagag 166

<210> SEQ ID NO 700
<211> LENGTH: 225
<212> TYPE: DNA
<213> ORGANISM: Homo sapiens
<220> FEATURE:
<221> NAME/KEY: misc_feature
<222> LOCATION: (119)..(119)
<223> OTHER INFORMATION: n is a, c, g, or t

<400> SEQUENCE: 700
ctgtttcctt ctactgatgg ctagttaggt tattggaagt cttttgctgt tgctagttag 60
tcttgtatag acattgtaat gcacatgtgc aaaaatacaa gtatgataca atcttaaang 120
ggagttgctg agtccaatat atacattaca aatattgata gatattgcaa aattgccttc 180
atagaggcta tattaattta tagttccagc agcaacatat gagtt 225

<210> SEQ ID NO 701
<211> LENGTH: 275
<212> TYPE: DNA
<213> ORGANISM: Homo sapiens

<400> SEQUENCE: 701
tccacctatc ccaaagtcgt atcaaagaag tggctgcaga ttggagccca aagcctttgg 60
ttcctcagtt tccaaatgga ttctcactag gtgggatcat gagtttgctt tggacacccc 120
aaattctaac tatttctttt gtttcttaca tcctttccct cttccccagc cccttcccct 180
catgttacac ctcttgctgg tttgagacgt caatcaccac tgagaaagaa ttaaaccagt 240
attttgagct ggcaaaattc ttagcctagt acaat 275

<210> SEQ ID NO 702
<211> LENGTH: 97
<212> TYPE: DNA
<213> ORGANISM: Homo sapiens

<400> SEQUENCE: 702
tccagctttg tgtttatctt tccagagaag tttactgtgt attaagcaaa tatgtatatc 60
tttattcttg ctcagtattt tcgcaaacag cagctgt 97

<210> SEQ ID NO 703
<211> LENGTH: 272
<212> TYPE: DNA
<213> ORGANISM: Homo sapiens

<400> SEQUENCE: 703
tccccggacg agtgcctctg gatggactgg gtcacagaga agaacatcaa cgggcaccag 60
gccaagtttt tcgcctgcat caagagaagt gacggctcct gtgcgtggta ccgcggcgcg 120
gcgcccccca agcaggagtt tttggacatc gaggacccat aagcaggcct ccaacgcccc 180
tgtggccaac tgcaaaaaaa gcctccaagg gtttcgactg gtccagcttt gacatccctt 240
cctggaaaca gcatgaataa aacactcatc cc 272

<210> SEQ ID NO 704
<211> LENGTH: 151
<212> TYPE: DNA
<213> ORGANISM: Homo sapiens

<400> SEQUENCE: 704
tggacttgct gccgtaattt aaagctctgt tgattttgtt tccgtttgga tttttggggg 60
aggggagcac tgtgtttatg ctggaatatg aagtctgaga ccttccggtg ctgggaacac 120
acaagagttg ttgaaagttg acaagcagac t 151

<210> SEQ ID NO 705
<211> LENGTH: 205
<212> TYPE: DNA
<213> ORGANISM: Homo sapiens

<400> SEQUENCE: 705
tgagctttga gtcaaatatg ggatgcagac caggtgtggt ggctcacgcc tgtcatccca 60
gcactttggg aggccaaggc gggtggattg tttgtgccca ggagttcgag actagcctgg 120
ccaacttcgc aaaaccctgt ttttgcaaaa aataggcgtg gtggcatgta cctgtggtcc 180
cagctattca aaaggctgag atagg 205

<210> SEQ ID NO 706
<211> LENGTH: 162
<212> TYPE: DNA
<213> ORGANISM: Homo sapiens

<400> SEQUENCE: 706
tgtttttgac atcagctgta atcattcctg tgctgtgttt tttattaccc ttggtaggta 60
ttagacttgc cctttttttaa aaaaaggttt ttgcatcgtg gaagcatttg acccagagtg 120
gaacgcgtgg cctatgcagg tggattcctt caggtctttc ct 162

<210> SEQ ID NO 707
<211> LENGTH: 260
<212> TYPE: DNA
<213> ORGANISM: Homo sapiens

<400> SEQUENCE: 707
gagtaggttc ggtctgaaag gtgtggcctt tatatttgat ccacacacgt tggtctttta 60
accgtgctga gcagaaaaca aaacaggtta agaagagccg ggtggcagct gacagaggaa 120
gccgctcaaa taccttcaca ataaatagtg gcaatatata tatagtttaa gaaggctctc 180
catttggcat cgtttaattt atatgttatg ttctaagcac agctctcttc tcctattttc 240
atcctgcaag caactcaaaa 260

<210> SEQ ID NO 708
<211> LENGTH: 84
<212> TYPE: DNA
<213> ORGANISM: Homo sapiens
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t

<400> SEQUENCE: 708
tccctcaaag actgacagcc atcgttctgc acggggcttt ctgcatgtna cgncagctaa 60
gcatagtaag aagtccagcc tagg 84

<210> SEQ ID NO 709
<211> LENGTH: 217
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t

<400> SEQUENCE: 709
tgaaaacaag catgagtaga tcctgcttnc caatgggggc cttcccgtct gcttactgct 60
taggtttnct gcggtgggtc tgagcaatgc agaaagtttc ttacaatttc tctggattga 120
aacaagaaat agctccctcg ctcctcttca taaatttctc agagaaaatc taagttncca 180
ggaagtagcc aaagaccagg agattgtgga atcaaaa 217

<210> SEQ ID NO 710
<211> LENGTH: 254
<212> TYPE: DNA
<213> ORGANISM: Homo sapiens

<400> SEQUENCE: 710
tgagcttccc ttggacacta actcttccca gatgatgaca atgaaattag tgcctgtttt 60
cttgcaaatt tagcacttgg aacatttaaa gaaaggtcta tgctgtcata tggggtttat 120
tgggaactat cctcctggcc ccaccctgcc ccttcttttt ggttttgaca tcattcattt 180
ccacctggga atttctggtg ccatgccaga aagaatgagg aacctgtatt cctcttcttc 240
gtgataatat aatc 254

<210> SEQ ID NO 711
<211> LENGTH: 225
<212> TYPE: DNA
<213> ORGANISM: Homo sapiens

<400> SEQUENCE: 711
tagaggcttc ttagattctc ccagcatccg cctttccctt tagccagtct gctgtcctga 60
aacccagaag tgatggagag aaaccaacaa gagatctcga accctgtcta gaaggaatgt 120
atttgttgct aaatttcgta gcactgttta cagttttcct ccatgttatt tatgaatttt 180
atattccgtg aatgtatatt gtcttgtaat gttgcataat gttca 225

<210> SEQ ID NO 712
<211> LENGTH: 257
<212> TYPE: DNA
<213> ORGANISM: Homo sapiens

<400> SEQUENCE: 712
gaaagcctga gtttgcaacc agttgtaggg tttttgttgt gttttttttt tttttttgaa 60
ataaaactat aatataaatt ctcctattaa ataaaattat tttaagtttt agtgtcaaaa 120
gtgagatgct gagagtaggt gataatgtat attttacaga gtgggggttg gcaggatggt 180
gacattgaac atgattgctc tctgtctctt ttttcagctt atgggtattt atcttctatt 240
agtatttgta tcttcag 257

<210> SEQ ID NO 713
<211> LENGTH: 267
<212> TYPE: DNA
<213> ORGANISM: Homo sapiens

<400> SEQUENCE: 713
tcctgtaaaa tacagtgcag gccaggcgcg gtgactcacg cctgtaatcc cagcattttg 60
ggaggccaag ggtggcggat catgaggtca ggagatcgag accatcctgg ctaacacggt 120
gaaaccccat ctttactaaa aatacaaaaa attaaccagg tgtggtggcg cacatctgaa 180
gtcccagcta cttgggaggc tgaggcagga taatcactta aacttgggag gtggaggttg 240
cagtgagacg acacctcgcc actgcac 267

<210> SEQ ID NO 714
<211> LENGTH: 169
<212> TYPE: DNA
<213> ORGANISM: Homo sapiens

<400> SEQUENCE: 714
atccacagat atagccaagt agattgggta gaggatacta tttccagaat agtgtttagc 60
tcacctaggg ggatatgttg tatacacatt tgcatatacc cacatggggg acataagcta 120
atctttttac aggacacaga attctgttca atgctgttaa atatgccaa 169

<210> SEQ ID NO 715
<211> LENGTH: 163
<212> TYPE: DNA
<213> ORGANISM: Homo sapiens

<400> SEQUENCE: 715
gatactttca ttttgcacat catgcacatc atggtattca ggggctagag tgattttttt 60
ccagattatc taaagttgga tgcccacact atgaaagaaa tatttgtttt atttgcctta 120
tagatatgct caaggttact gggcttgcta ctatttgtaa ctc 163

<210> SEQ ID NO 716
<211> LENGTH: 216
<212> TYPE: DNA
<213> ORGANISM: Homo sapiens

<400> SEQUENCE: 716
ccagctgttt gcgcgtttga cttttgtggc ctcagcagga caggccccgg gcactgcctc 60
acagccaagg ctggactggg ttggctgcag tgtggtgttt agtggatacc acatcggaag 120
tgatttttta aattggattt gaattcggct cctgtttttt atttgtcatg aaacagtgta 180
tttggggaga tgctgtggga ggatgtaaat atcttg 216

<210> SEQ ID NO 717
<211> LENGTH: 204
<212> TYPE: DNA
<213> ORGANISM: Homo sapiens

<400> SEQUENCE: 717
aggaggagcg ccagttgccc ctcgctcaca gaccacacac ccagccctcc tgggccagcc 60
cagagggccc ttcagacccc agctgtctgc gcgtctgact cttgtggcct cagcaggaca 120
ggccccgggc actgcctcac agccaaggct ggactgggtt ggctgcagtg tggtgtttag 180
tggataccac atcggaagtg attt 204

<210> SEQ ID NO 718
<211> LENGTH: 219
<212> TYPE: DNA
<213> ORGANISM: Homo sapiens

<400> SEQUENCE: 718
ccagctgttt gcgcgtttga cttttgtggc ctcagcagga caggccccgg gcactgcctc 60
acagccaagg ctggactggg ttggctgcag tgtggtgttt agtggatacc acatcggaag 120
tgatttttta aattggattt gaattcggct cctgtttttt atttgtcatg aaacagtgta 180
tttggggaga tgctgtggga ggatgtaaat atcttgttt 219

<210> SEQ ID NO 719
<211> LENGTH: 36
<212> TYPE: DNA
<213> ORGANISM: Homo sapiens

<400> SEQUENCE: 719
caccactaaa agatcgcagt ttgcctggtg cagtgg 36

<210> SEQ ID NO 720
<211> LENGTH: 138
<212> TYPE: DNA
<213> ORGANISM: Homo sapiens

<400> SEQUENCE: 720
tcatgtttgc tgtagtgctc atatttattg ttgtttttgt tttagtactc acttgtttca 60
taatatcaag attactaaaa atgggggaaa ggacttttaa tcttttttttc ataatatctt 120 tgacacatat tacagaag 138

<210> SEQ ID NO 721
<211> LENGTH: 283
<212> TYPE: DNA
<213> ORGANISM: Homo sapiens

<400> SEQUENCE: 721
gatcaagacc atagtgacca acatagtgaa accccatctc tactgaaagt acaaaaatta 60
gctgggtgtg ttggcacatg cctgtagtcc cagctacttg agaggctgag gcaagagaat 120
tgtttgaacc cgggaggcag aggttgcagt gtggtgagat catgccacta cactccagcc 180
tggcgacaga gcgagacttg gtttcaaaaa aaaaaaaaaa aaaaacttca gtaagtacgt 240
gttatttttt tcaataaaat tctattacag tatgtcaaaa aaa 283

<210> SEQ ID NO 722
<211> LENGTH: 265
<212> TYPE: DNA
<213> ORGANISM: Homo sapiens

<400> SEQUENCE: 722
aacaaaatat ttctccccta gtgagagaaa gaggtcctca gagagtagca gctcacataa 60
ctgggaccag aggaagaagc aacacattgt cttctccaaa ctccaagaat gaaaaggctc 120
tgggccgcaa aataaactcc tgggaatcat caaggagtgg gcattcattc ctgagcaact 180
tgcacttgag gaatggtgaa ctggtcatcc atgaaaaagg gttttactac atctattccc 240
aaacatactt tcgatttcag gagga 265

<210> SEQ ID NO 723
<211> LENGTH: 51
<212> TYPE: DNA
<213> ORGANISM: Homo sapiens

<400> SEQUENCE: 723
gactggccca ctggcatttt tgtaagaaga gggaaatttg ggccgggcgc g 51

<210> SEQ ID NO 724
<211> LENGTH: 201
<212> TYPE: DNA
<213> ORGANISM: Homo sapiens

<400> SEQUENCE: 724
tattgttgat gaaaagtgct agaaatagtt gttggtctaa agatgcagaa tatggactct 60
attccatcta tcaaggggga atatttgagc ttaaggaaaa tgacagaatt tttgtttctg 120
taacaaatga gcacttgata gacatggacc atgaagccag ttttttcggg gccttttttag 180 ttggctaact gacctggaaa g 201

<210> SEQ ID NO 725
<211> LENGTH: 173
<212> TYPE: DNA
<213> ORGANISM: Homo sapiens

<400> SEQUENCE: 725
agttaaaacg tcacaaaggt gctgctttta cagggaagct tattctgttt taaacattga 60
aaagttgtgg tctgatcagt taatttgtat gtagcagtgt atgctctcat atacaattac 120
tgacctatgc tctaaaacat gaatgctttg ttacagaccc aagctgtcca ttt 173

<210> SEQ ID NO 726
<211> LENGTH: 216
<212> TYPE: DNA
<213> ORGANISM: Homo sapiens

<400> SEQUENCE: 726
aaacaaaact cacgtatcat ctcaatagat acagaaaagg cttttgataa aattcaactt 60

-continued gacttcatgt taaaaaccct caacaaacca ggcgtcgaag gaacatacct caaaataata 120
agagccatct atgacaaaac cacagccaac atcatactga atgagcaaaa gctggagcat 180
tactcttgag aagtagaaca aggcacttca gtccta 216

<210> SEQ ID NO 727
<211> LENGTH: 296
<212> TYPE: DNA
<213> ORGANISM: Homo sapiens

<400> SEQUENCE: 727
aaagaaaatg tggtggcagg gagtggtggc tcatgtctgt aatcccagca ctttgggagg 60
ctgaggcggg tggttcacct gaggtcagga gtttgagacc agcctggcca acatggcgaa 120
actccgtctc cgctaaaaat acgaaaatta gccaggcgtg gtggcgagca cctgtcatcc 180
cagctacttg ggaggcctag gcgtgagaat cgcttgaacc tggaaggtgg tggttgcagt 240
gagccgagat cctgccactg cactccagcc tgggcaacca agcgagactc tgcctt 296

<210> SEQ ID NO 728
<211> LENGTH: 205
<212> TYPE: DNA
<213> ORGANISM: Homo sapiens

<400> SEQUENCE: 728
aatgttgtgg ctgaaaaggc cgtttttttt gactcccact tctttgggtg cccaaatgca 60
ctatttcgta gcacttacca cctggtttat ttgcatcacc tccgagagac tgagtcacct 120
ttgactcaag ccaggtcttt gaaggtagag ccaggtccct tttttctgtg tctccagctt 180
ttaggccagg gattgatttg gagca 205

<210> SEQ ID NO 729
<211> LENGTH: 173
<212> TYPE: DNA
<213> ORGANISM: Homo sapiens

<400> SEQUENCE: 729
tattttccct ctttcgaaca aagacattgg tttgcccaag gactacaaat aaaccaacgg 60
gaaaaaagaa aggttccagt tttgtctgaa aattctgatt aagcctctgg gccctacagc 120
ctggagaacc tggagaatcc tacacccaca gaacccggct ttgtccccaa aga 173

<210> SEQ ID NO 730
<211> LENGTH: 230
<212> TYPE: DNA
<213> ORGANISM: Homo sapiens

<400> SEQUENCE: 730
atccaagacc tgaaagatgt tcacaaatgt tgtggctgaa aaggccgttt tttttgactc 60
ccacttcttt gggtgcccaa atgcactatt tcgtagcact taccacctgg tttatttgca 120
tcacctccga gagactgagt cacctttgac tcaagccagg tctttgaagg tagagccagg 180 tcccttttt ctgtgtctcc agcttttagg ccagggattg atttggagca 230

<210> SEQ ID NO 731
<211> LENGTH: 278
<212> TYPE: DNA
<213> ORGANISM: Homo sapiens

<400> SEQUENCE: 731
ggaagccatt atcctaaatg aactcactca gaaacagaaa accaaatacc acatgttctc 60

-continued

```
acttataagt agaagctaaa cattgagtac acatggatac aaagaaggga accgcagaca    120

ctggggccta cctgaggtcg gagcatggaa ggagggtgag gatcaaaaaa ctacctatct    180

ggtactatgc tttttatctg gatgatgaaa taatctgtac aacaaaccct ggtgacatgc    240

aatttaccta tatagcaagc ctacacatgt gcccctga                            278


<210> SEQ ID NO 732
<211> LENGTH: 67
<212> TYPE: DNA
<213> ORGANISM: Homo sapiens

<400> SEQUENCE: 732

gcatttttat acaccaacga catccaagct gagagccaaa tcaagaatgc aatcctattc     60

acaattg                                                               67


<210> SEQ ID NO 733
<211> LENGTH: 223
<212> TYPE: DNA
<213> ORGANISM: Homo sapiens

<400> SEQUENCE: 733

gtgttgagta agttggtctt tcccggtgct atacttgcct cctctccacg gaagaattgt     60

tcaggagatg cgcttggggt gatgacttcc ttaaatacac gctgtagggg gtgaagagct    120

tggaggacca ggcactttga ggaagggcag ttcgtgggct ggggtgggaa caggatggcg    180

ggcaatagac tagggtaggc cgcgatggcc tgtagaaggt tgc                      223


<210> SEQ ID NO 734
<211> LENGTH: 236
<212> TYPE: DNA
<213> ORGANISM: Homo sapiens
<220> FEATURE:
<221> NAME/KEY: misc_feature
<222> LOCATION: (159)..(159)
<223> OTHER INFORMATION: n is a, c, g, or t

<400> SEQUENCE: 734

aaggacctgt gttcatagac aatctaaact gtgtttctga agtttgtgca catttttctt     60

cactgtaatg ttattttaca gctgtttgtt aaaatagtga ataatttaat gatcctaaaa    120

gtaacaggtt tcgtgtgagt gtgcttgtat acgtgagant tgccttattt tcaggttgtt    180

ttatttaacg atggttcctt ggacagcatt ctggtgttca gcaaccaata tggaat        236
```